(12) United States Patent
Gelvan et al.

(10) Patent No.: US 8,343,733 B2
(45) Date of Patent: Jan. 1, 2013

(54) METHODS AND COMPOSITIONS FOR IDENTIFYING A CELL PHENOTYPE

(75) Inventors: Dan Jacob Gelvan, Ramat-HaSharon (IL); Lev Goltsman, Rechovot (IL); Alexander Chausovsky, Jerusalem (IL)

(73) Assignee: Zetiq Technologies Ltd., Ramat-Gan (IL)

( * ) Notice: Subject to any disclaimer, the term of this patent is extended or adjusted under 35 U.S.C. 154(b) by 1030 days.

(21) Appl. No.: 12/224,792

(22) PCT Filed: Mar. 6, 2007

(86) PCT No.: PCT/IL2007/000281
§ 371 (c)(1),
(2), (4) Date: Sep. 5, 2008

(87) PCT Pub. No.: WO2007/102146
PCT Pub. Date: Sep. 13, 2007

(65) Prior Publication Data
US 2009/0117610 A1 May 7, 2009

Related U.S. Application Data

(60) Provisional application No. 60/778,902, filed on Mar. 6, 2006, provisional application No. 60/778,900, filed on Mar. 6, 2006, provisional application No. 60/778,944, filed on Mar. 6, 2006, provisional application No. 60/778,839, filed on Mar. 6, 2006.

(51) Int. Cl.
*C12Q 1/02* (2006.01)
*C12N 5/06* (2006.01)
(52) U.S. Cl. ......................... 435/40.5; 435/375
(58) Field of Classification Search ............... None
See application file for complete search history.

(56) References Cited

U.S. PATENT DOCUMENTS

| 2002/0058028 A1 | 5/2002 | Malmros et al. |
| 2005/0181429 A1 | 8/2005 | Fejgin et al. |
| 2009/0117610 A1 | 5/2009 | Gelvan et al. |

FOREIGN PATENT DOCUMENTS

| WO | WO 96/16334 | 5/1996 |
| WO | WO 03/091729 | 11/2003 |
| WO | WO 2004/086937 | 10/2004 |
| WO | WO 2007/015926 | 2/2007 |
| WO | WO 2007/102146 | 9/2007 |
| WO | WO 2009/055052 | 4/2009 |

OTHER PUBLICATIONS

Ye et al Mol Cell Biochem 1999, 196, pp. 99-108.*
Office Action Dated Aug. 7, 2011 From the Israel Patent Office Re. Application No. 211963 and Its Translation Into English.
Molnár et al. "Predictive Molecular Pathological Testing in the Diagnosis of High-Grade Tumors of Glial Origin", Magyar Onkologia, 53: 33-38, 2009.
International Search Report and the Written Opinion Dated Oct. 18, 2007 From the International Searching Authority Re. Application No. PCT/IL2007/000281.
Office Action Dated Nov. 7, 2010 From the Israel Patent Office Re. Application No. 193805 and Its Translation Into English.
Search Report and Written Opinion Dated Nov. 11, 2010 From the Intellectual Property Office of Singapore Issued by the Austrian Patent Office Re. 200806458-6.
Wikipedia "Staining", Wikipedia, the Free Encyclopedia, Retrieved From the Internet, 9 P., Nov. 8, 2010.
Response Dated Mar. 24, 2011 to Search Report and Written Opinion of Nov. 11, 2010 From the Intellectual Property Office of Singapore Issued by the Austrian Patent Office Re. 200806458-6.
Response Dated Mar. 27, 2011 to Office Action of Nov. 7, 2010 From the Israel Patent Office Re. Application No. 193805.
International Preliminary Report on Patentability Dated Sep. 18, 2008 From the International Bureau of WIPO Re.: Application No. PCT/IL2007/000281.
Desmedt et al. "Quantitation of HER2 Expression or HER2: HER2 Dimers and Differential Survival in a Cohort of Metastatic Breast Cancer Patients Carefully Selected for Trastuzumab Treatment Primarily by FISH", Diagnostic Molecular Pathology, 18: 22-29, 2009. Abstract!
Idelevich et al. "Novel Histochemical Stain for Tinctorial Detection of Cancer and Neoplastic Cells", The Journal of Histotechnology, 32(3): 97-105, Sep. 2009.
Komen et al. "Viability Analysis and Apoptosis Induction of Breast Cancer Cells in a Microfluidic Device: Effect of Cytostatic Drugs", Biomedical Microdevices, 10: 727-737, 2008.
Molnár et al. "Predictive Molecular Pathological Testing in the Diagnosis of High-Grade Tumors of Glial Origin", Magyar Onkologia, 53: 33-38, 2009. Abstract!
Kortegangas-Savolainen et al. "Allergens of Ficus Benjamina (Weeping Fig): Unique Allergens in Sap", Allergy, 61(3): 393-394, 2006. p. 393, col. 2, Line 5-col. 3, Line 8.
Sackeyfio et al. "The Anti-Inflammatory Effect of a Crude Aqueous Extract of the Root Bark of Ficus-Elastica in the Rat", Archives Internationales de Pharmacodynamie et de Therapie, 281(1): 169-176, 1986, Database Accession No. PREV198682095850. Abstract.
Steven et al. "Fluorescent Location of Cells of Cytological Interest in Cervical Smears Prestained With Thionin", Anticancer Research, 16(3A): 1193-1196, 1996. Abstract.

* cited by examiner

*Primary Examiner* — Tekchand Saidha
*Assistant Examiner* — Md. Younus Meah
(74) *Attorney, Agent, or Firm* — Rothwell, Figg, Ernst & Manbeck, P.C.

(57) ABSTRACT

A method of staining or pre-staining at least one cell is provided. The method comprising contacting the at least one cell with a staining agent selected from the group consisting of an extract of a *Ficus elastica* plant, a $C_{23}H_{44}O_4$ and a proanthocyanidin, thereby staining or pre-staining the at least one cell. Also provided are methods of detecting cells of different differentiation stages and methods of diagnosing cancer and metabolic diseases.

26 Claims, 61 Drawing Sheets
(56 of 61 Drawing Sheet(s) Filed in Color)

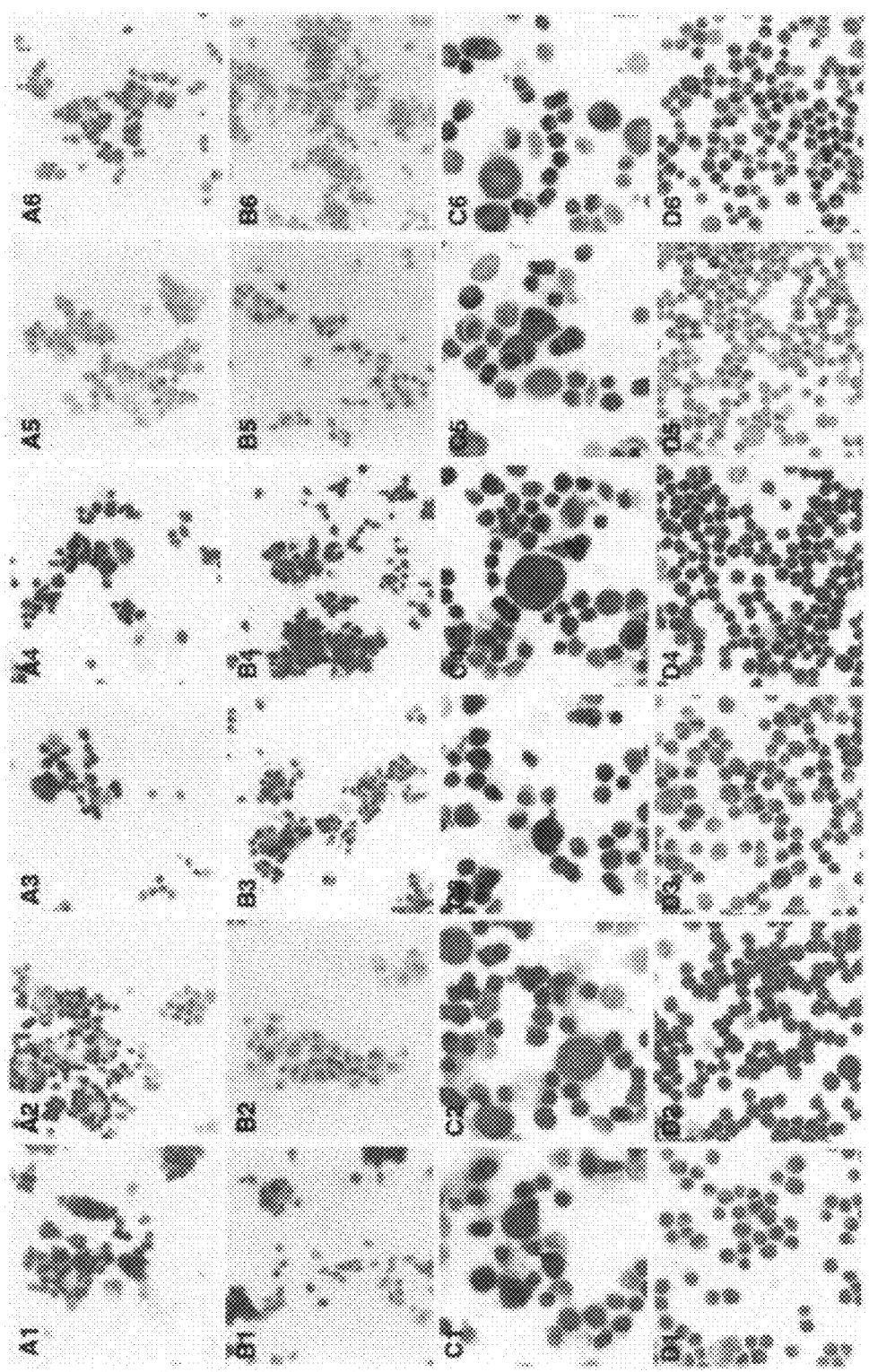

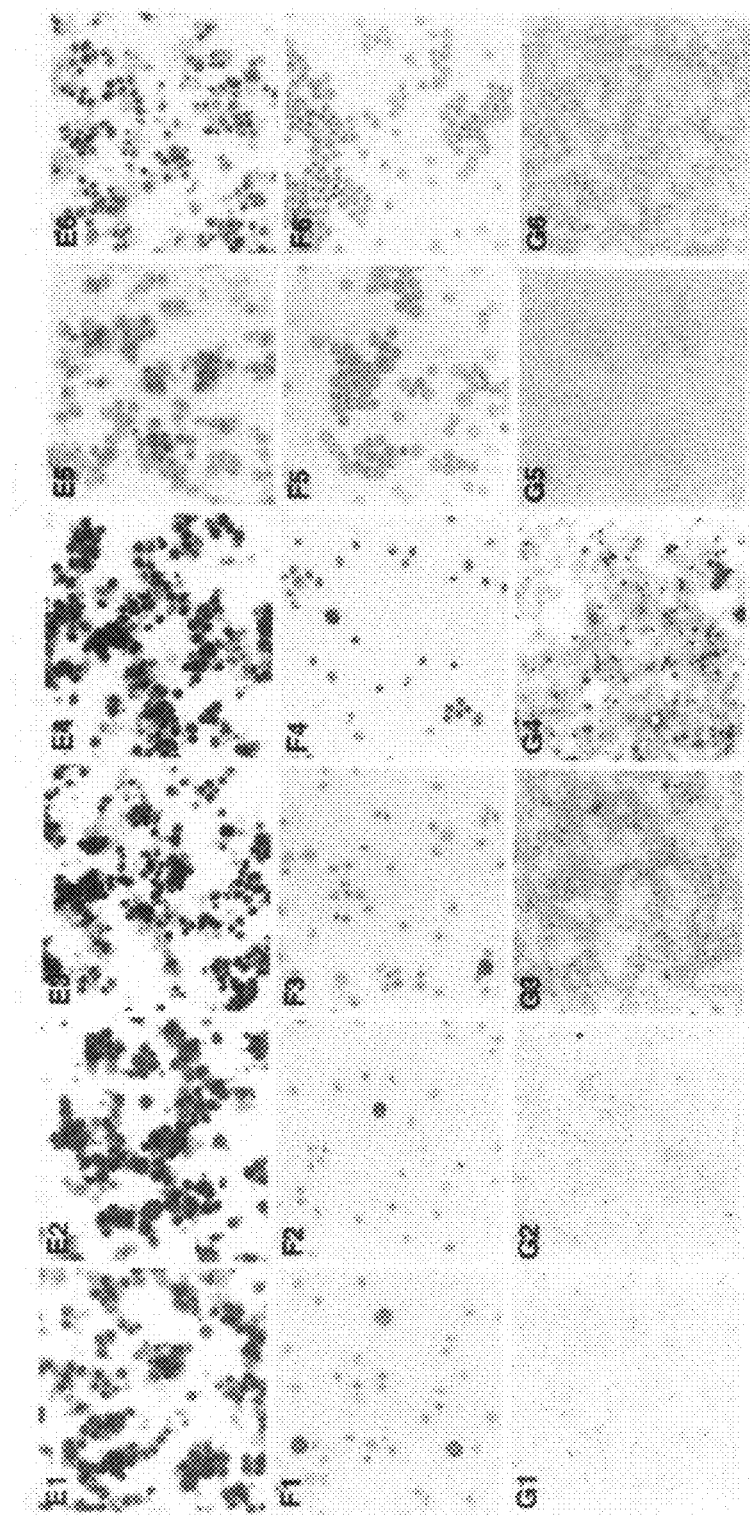

Colon cancer

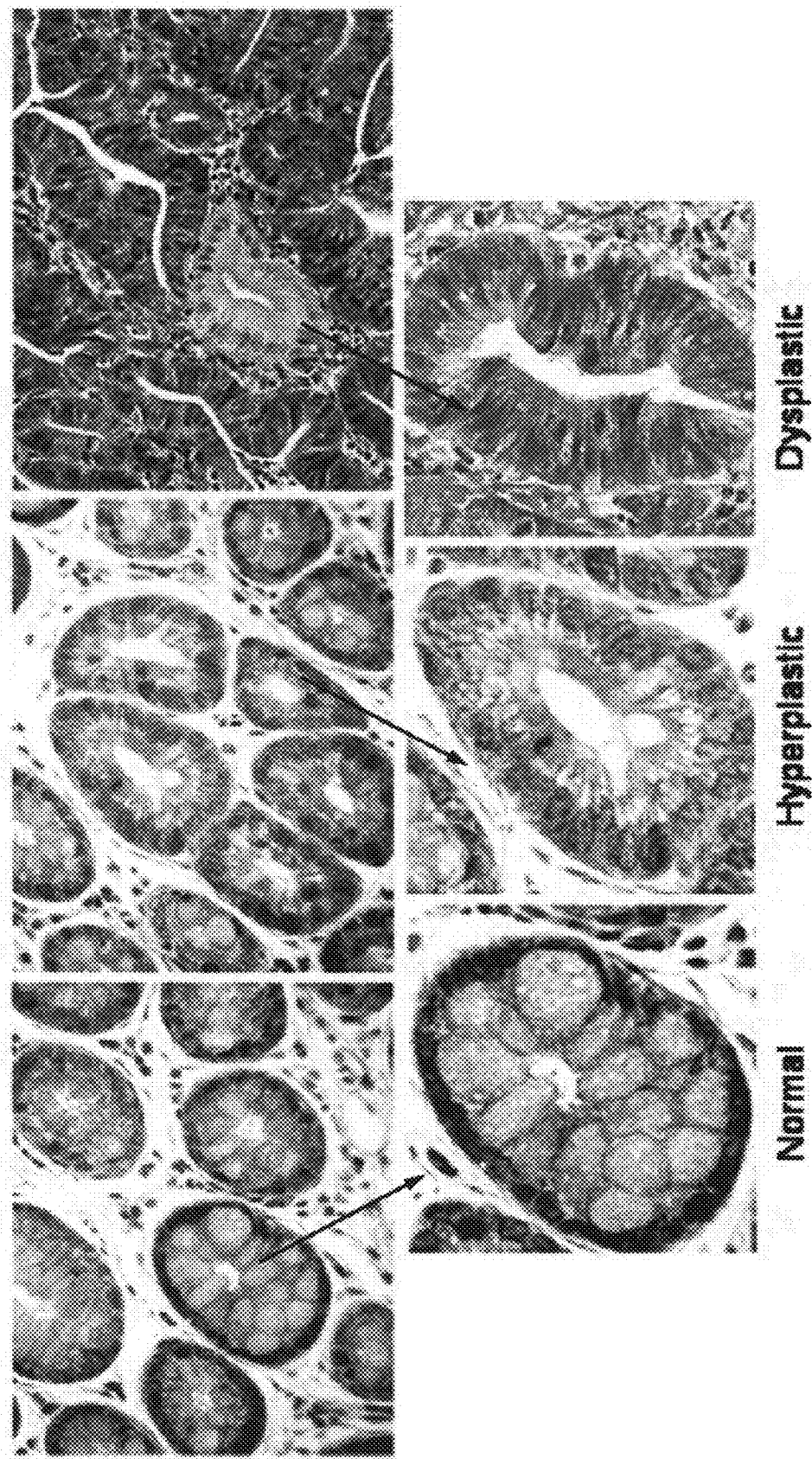

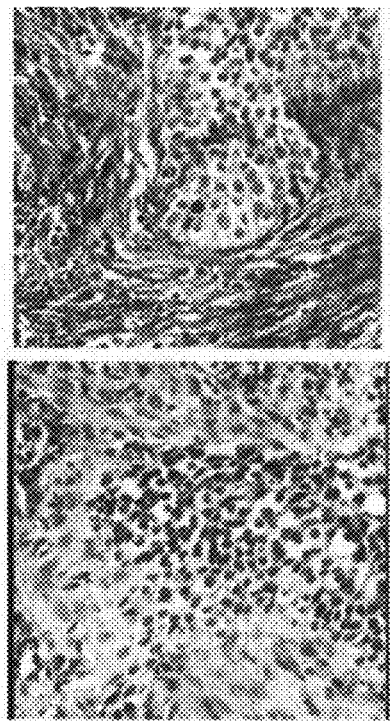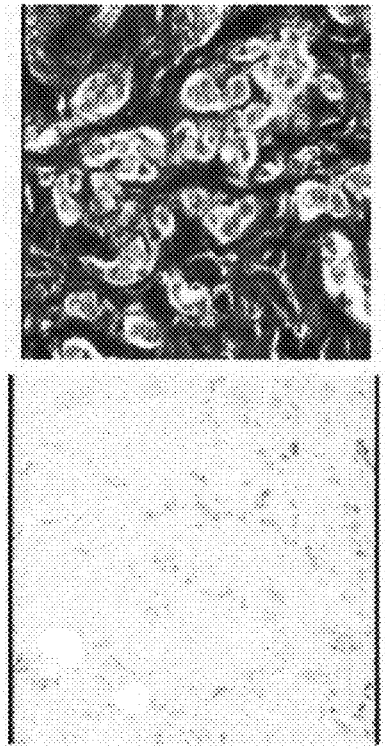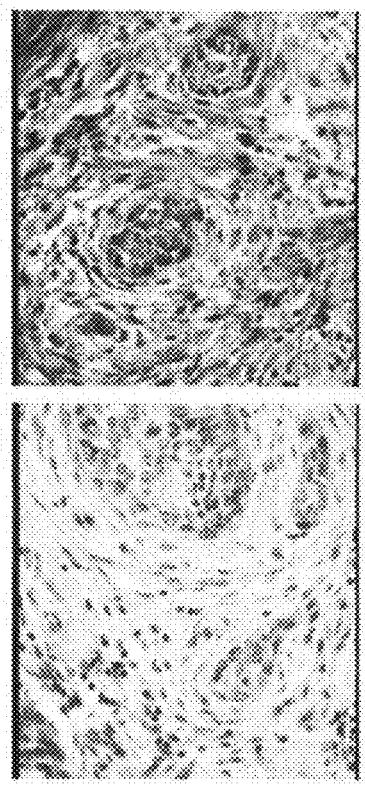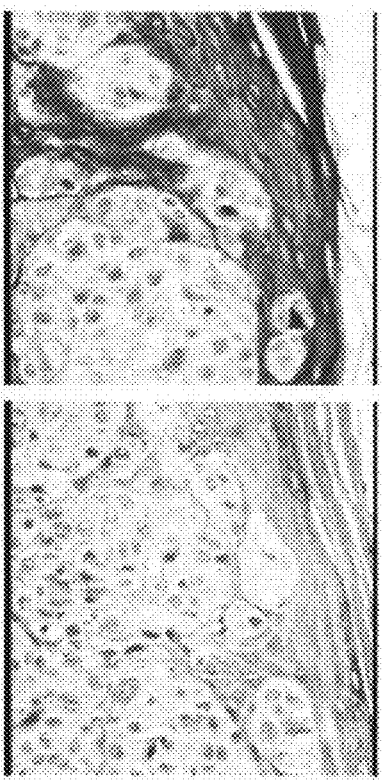

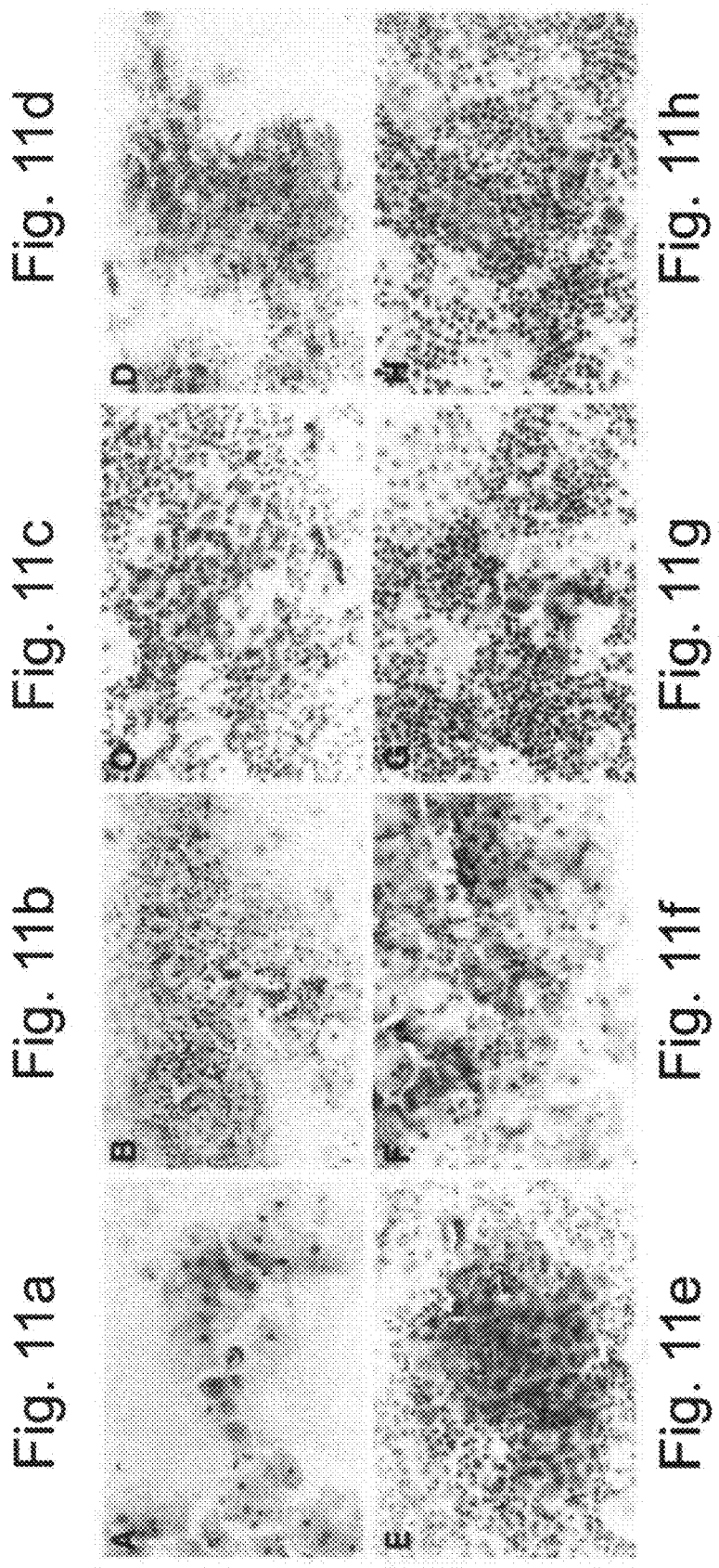

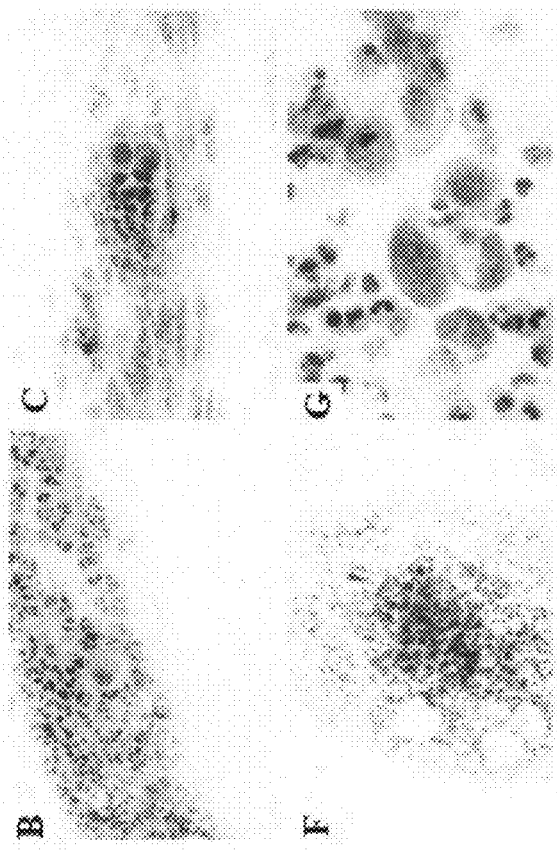
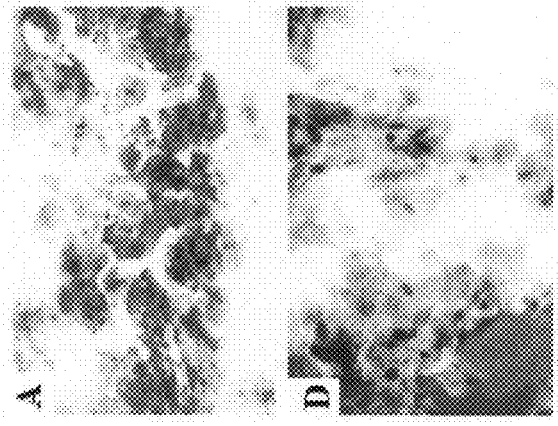

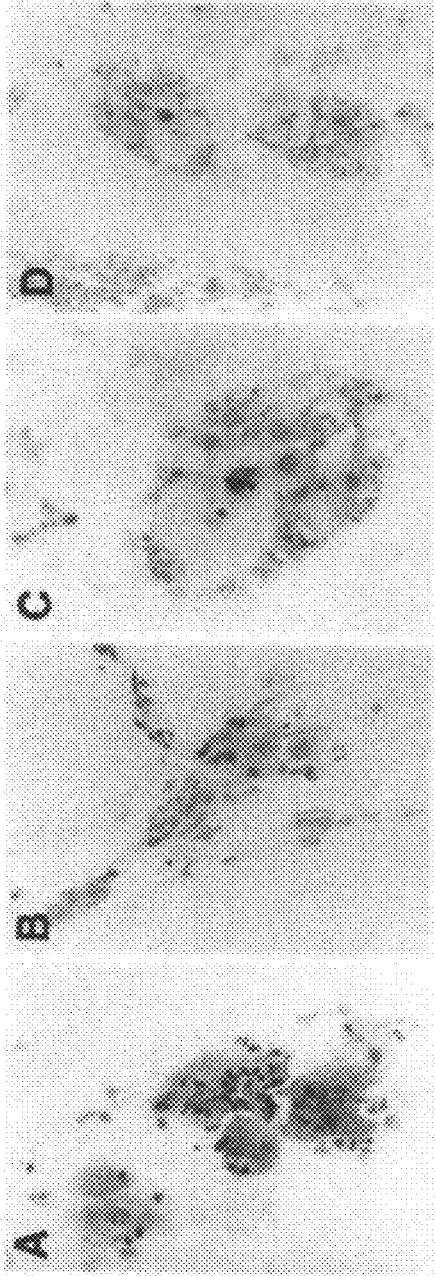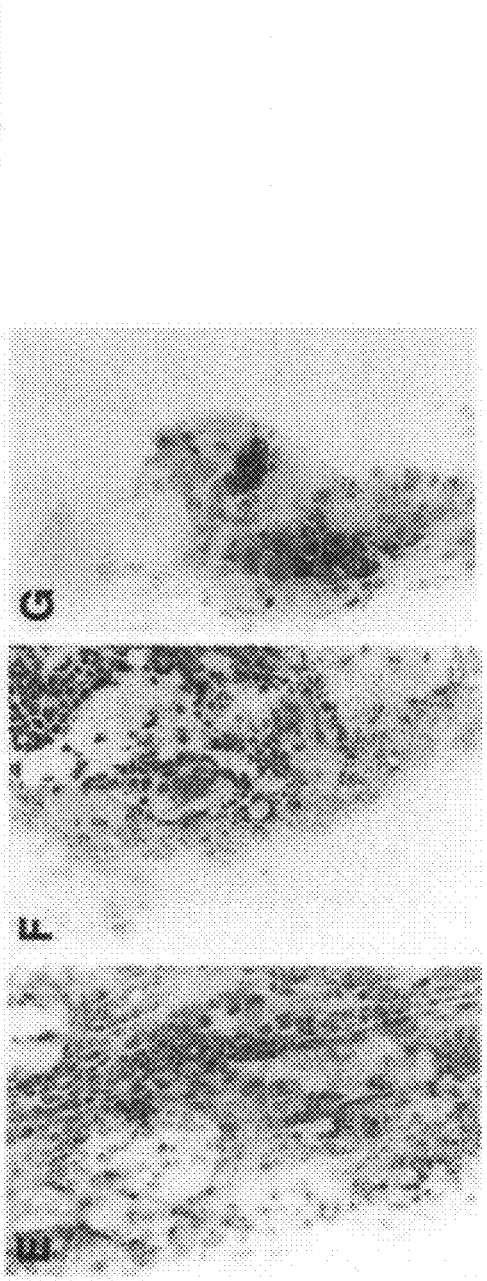

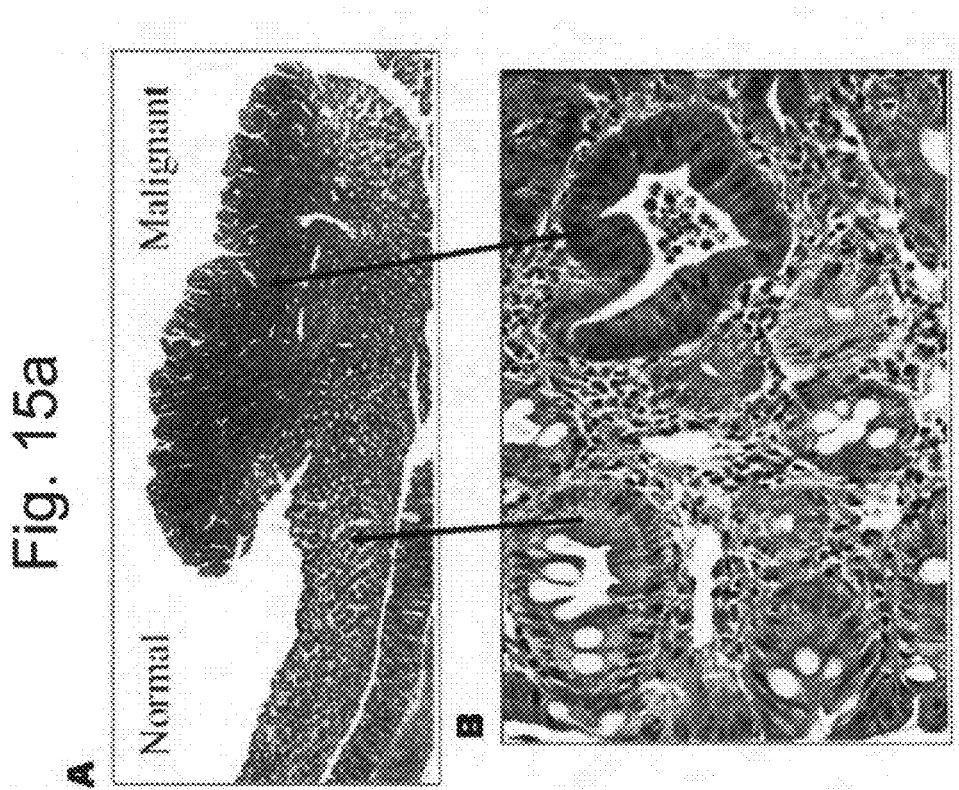
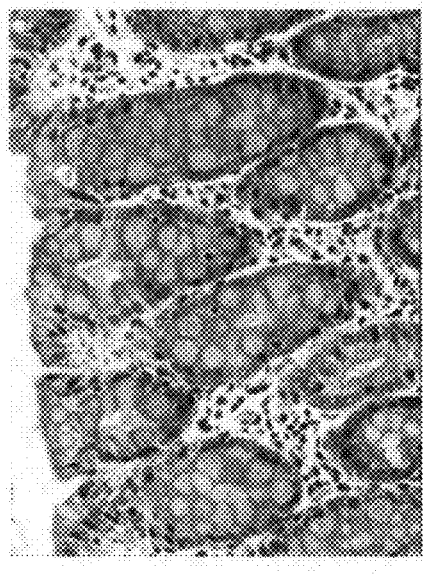
Fig. 15a  Fig. 15b  Fig. 15c

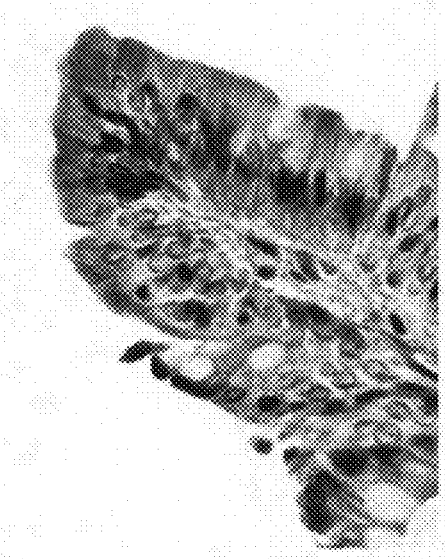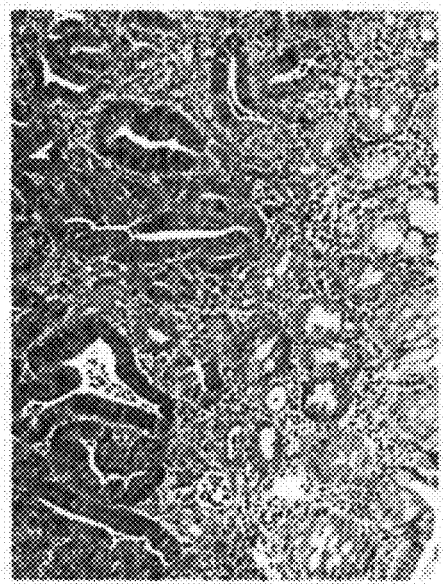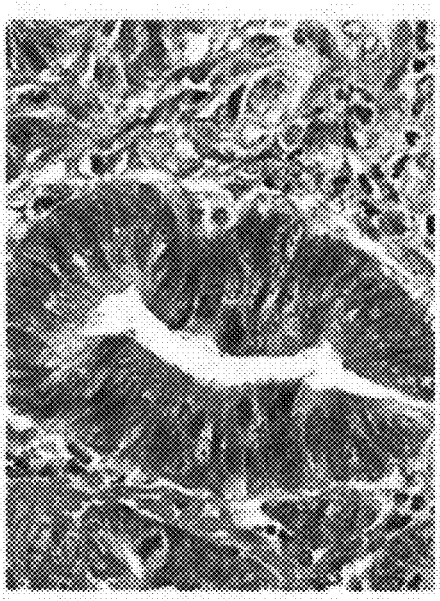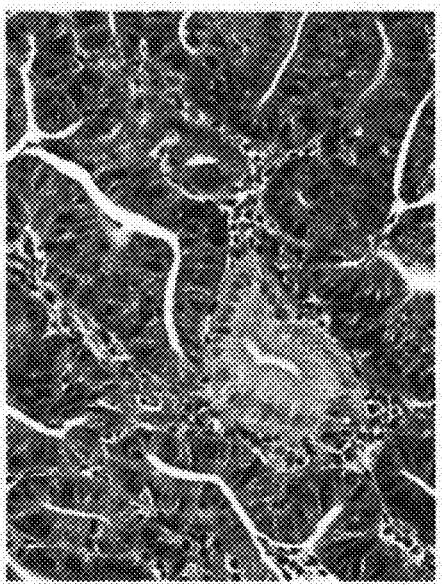
Dimethylhydrazine-induction of colon carcinogenesis in rats
Fig. 16a
Fig. 16b
Fig. 16c
Fig. 16d

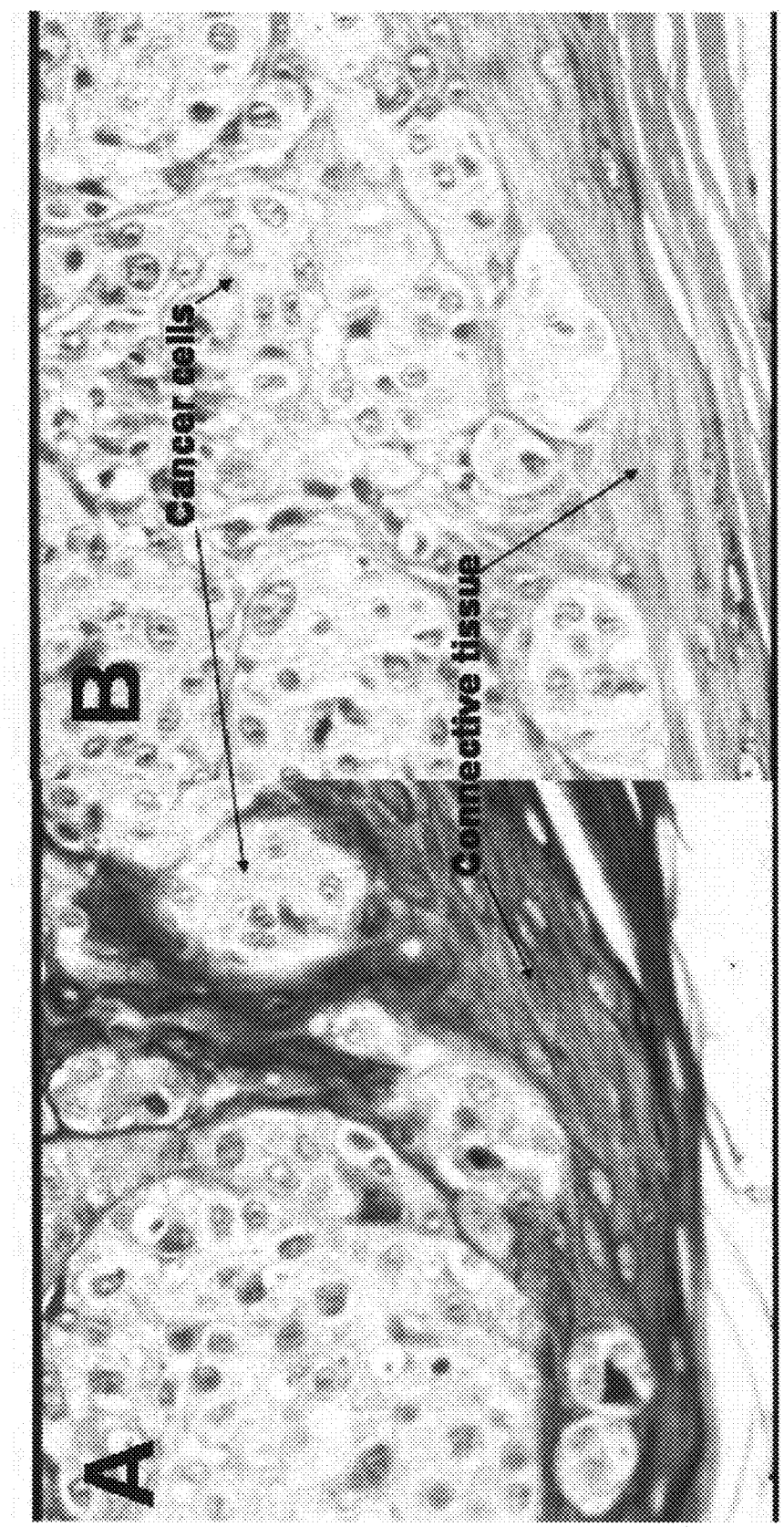

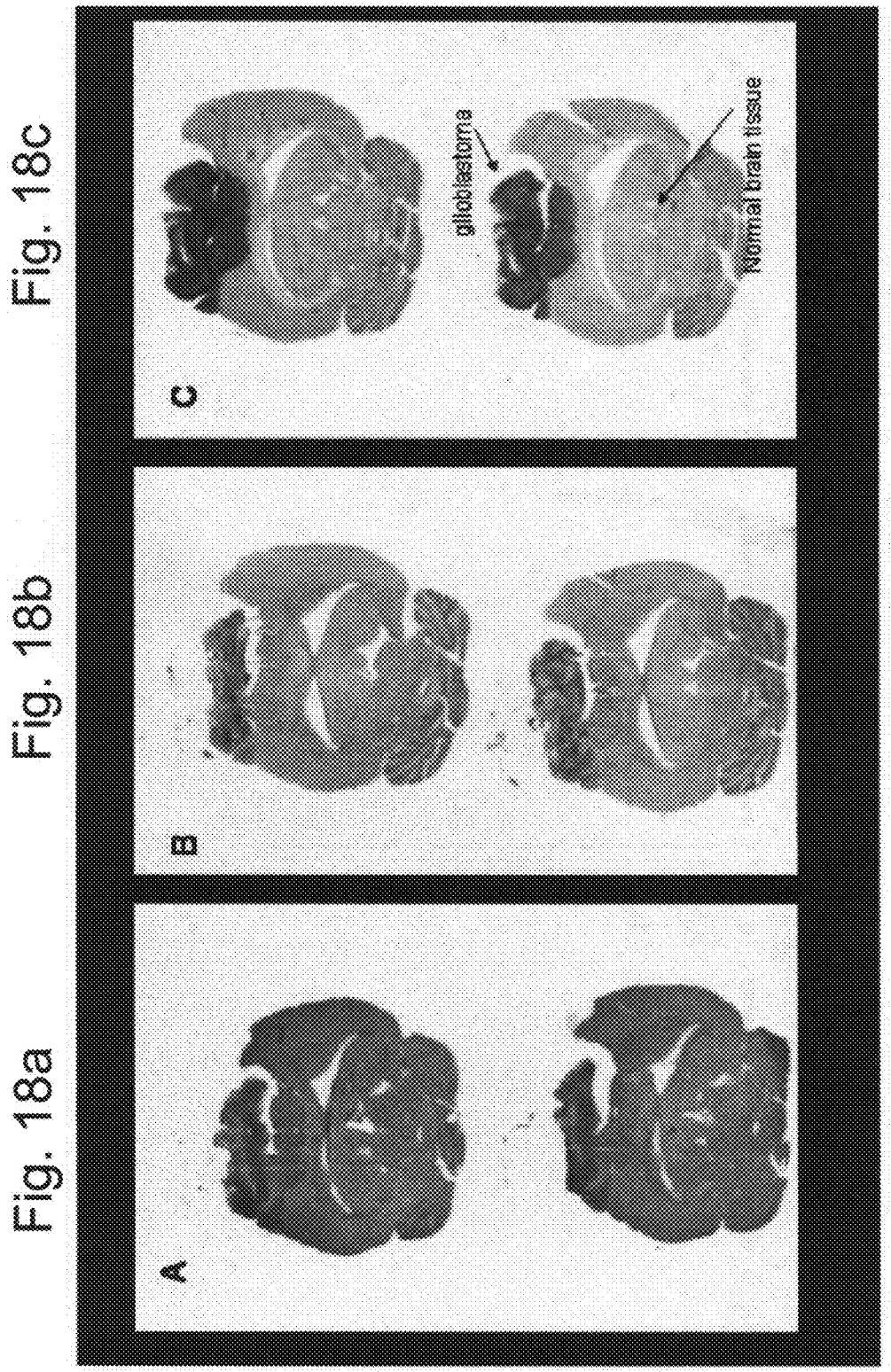

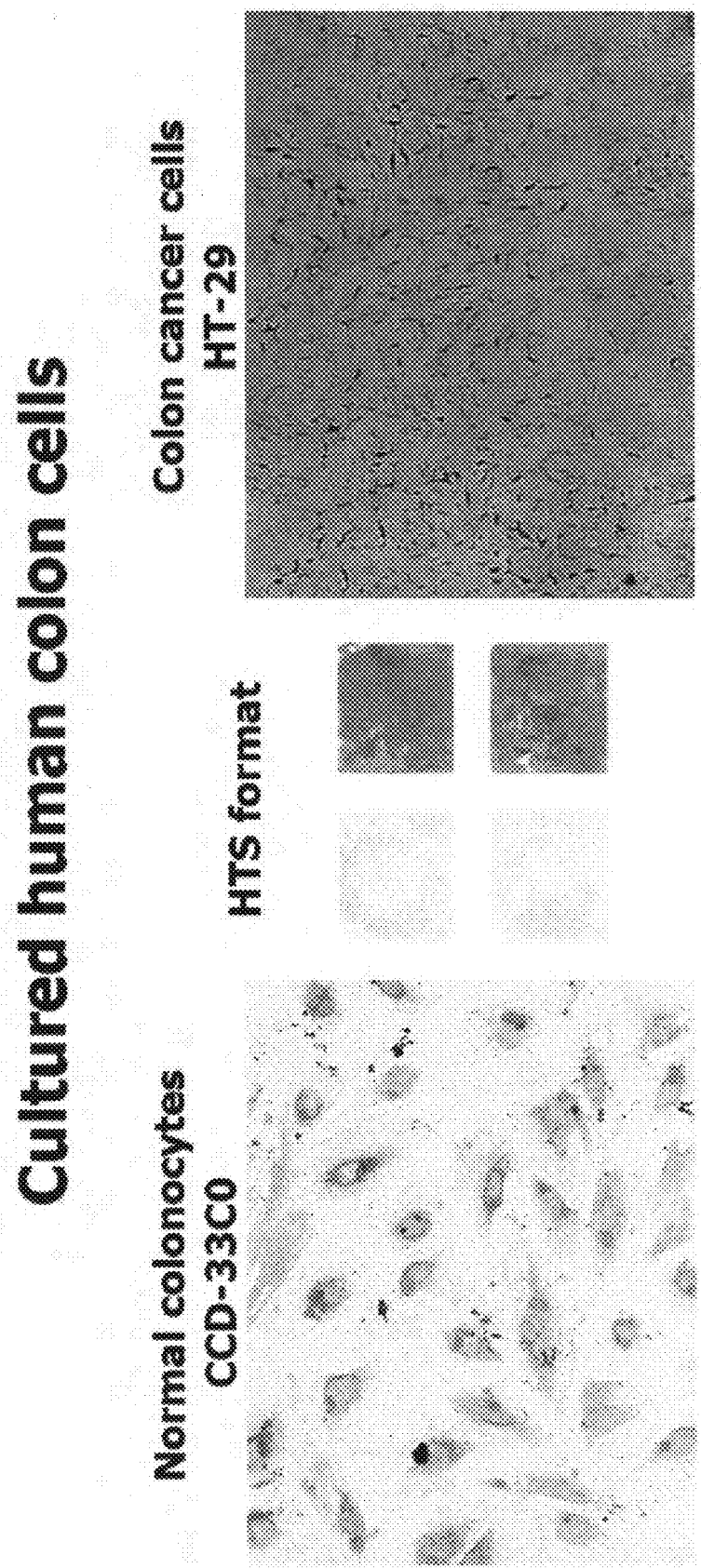

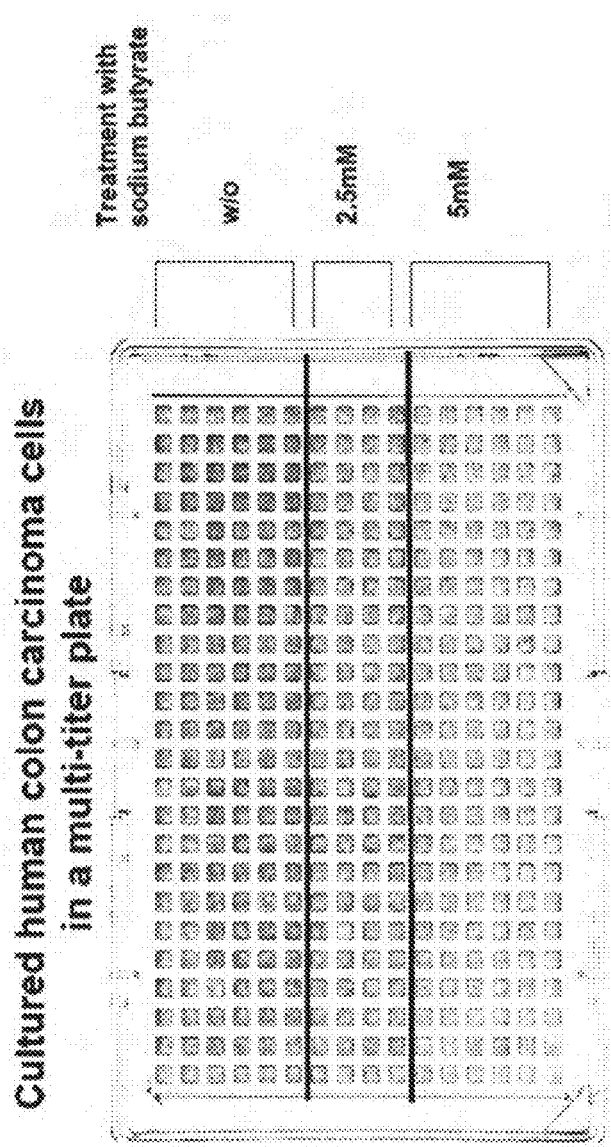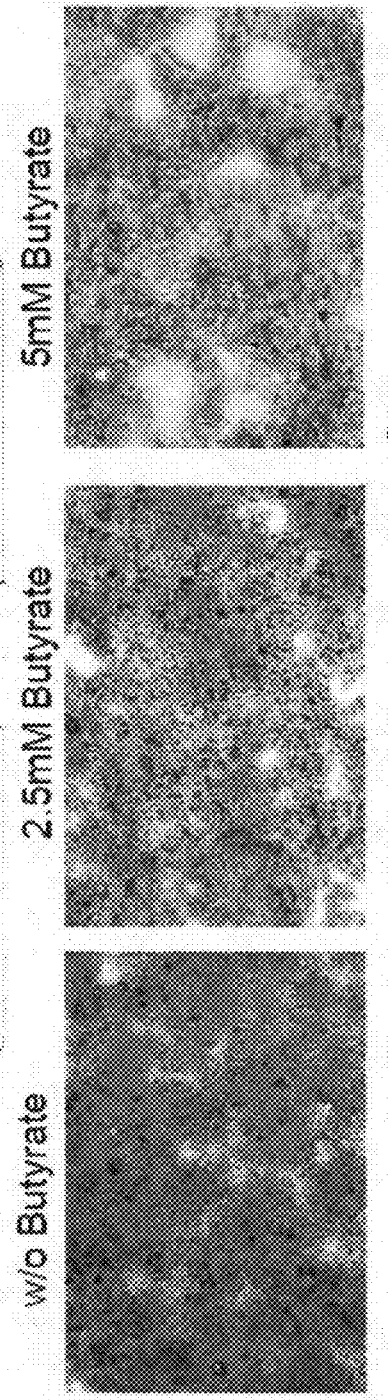
Fig. 22a
Fig. 22b  Fig. 22c  Fig. 22d

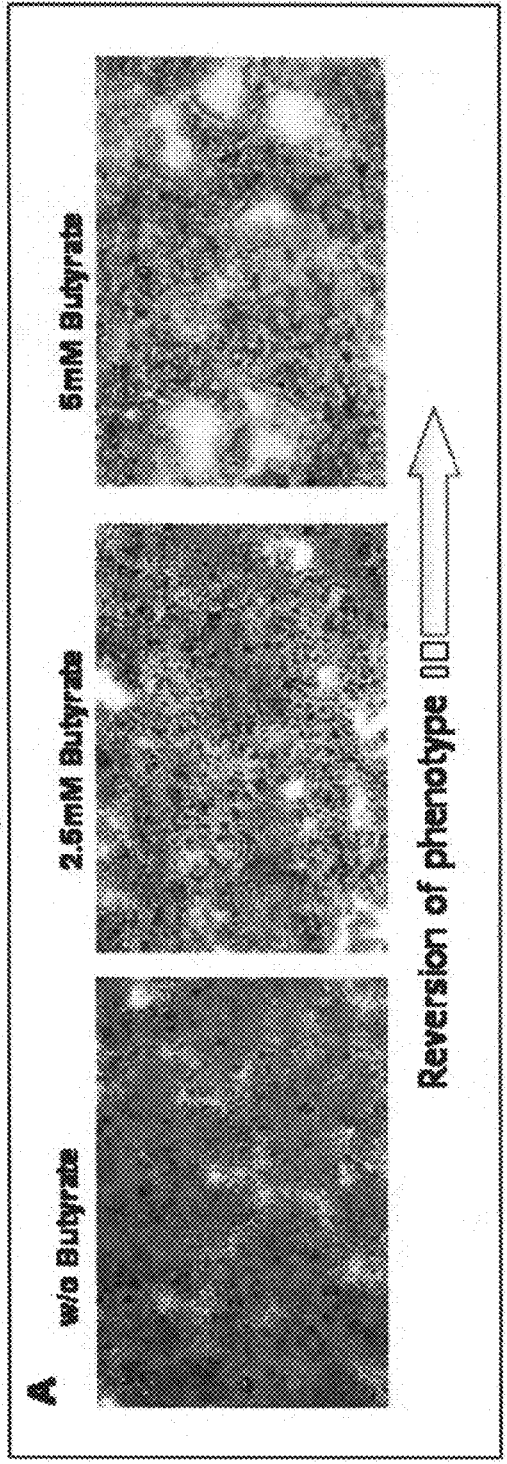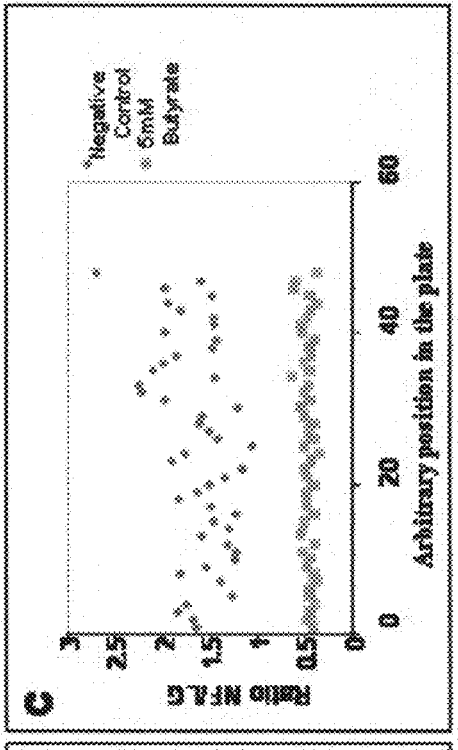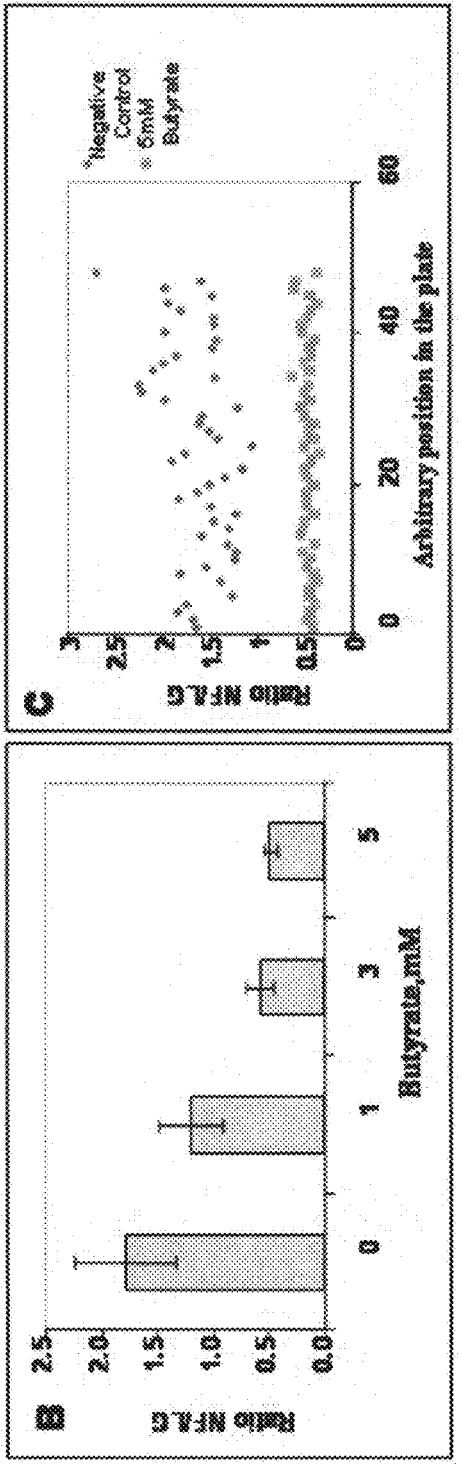
Fig. 23a
Fig. 23b
Fig. 23c

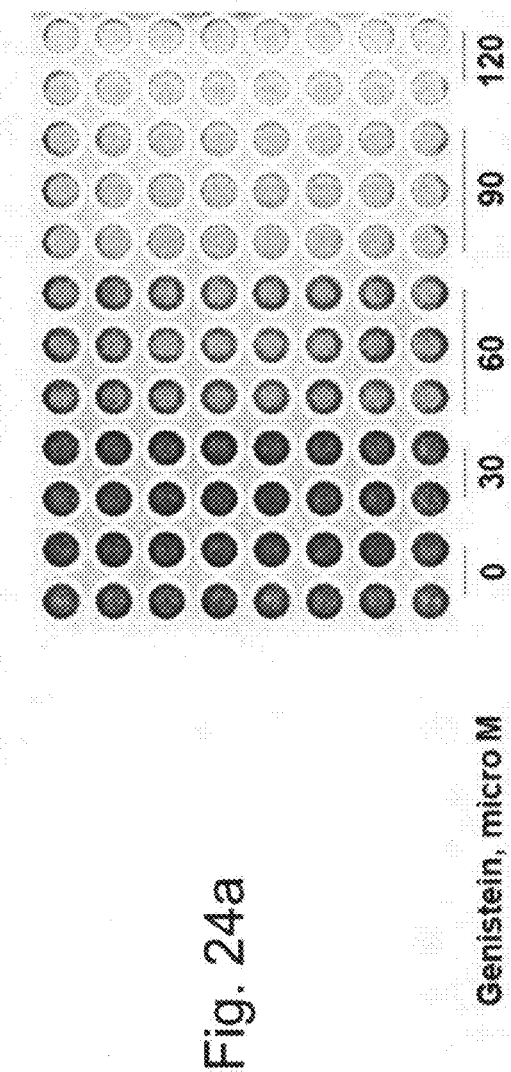
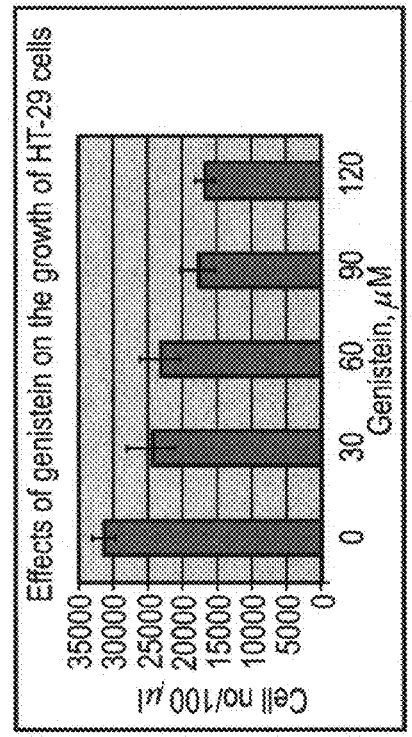
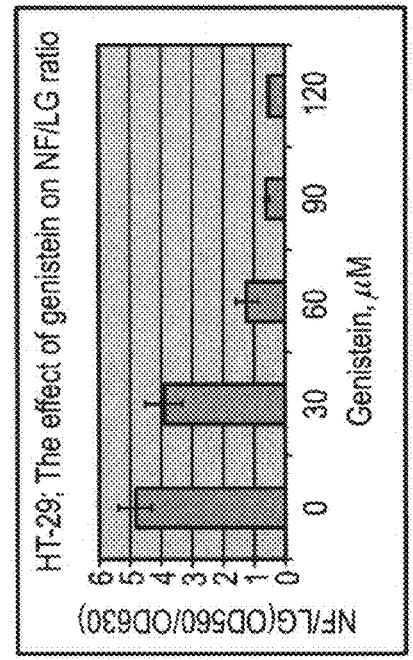
Fig. 24a
Fig. 24b
Fig. 24c

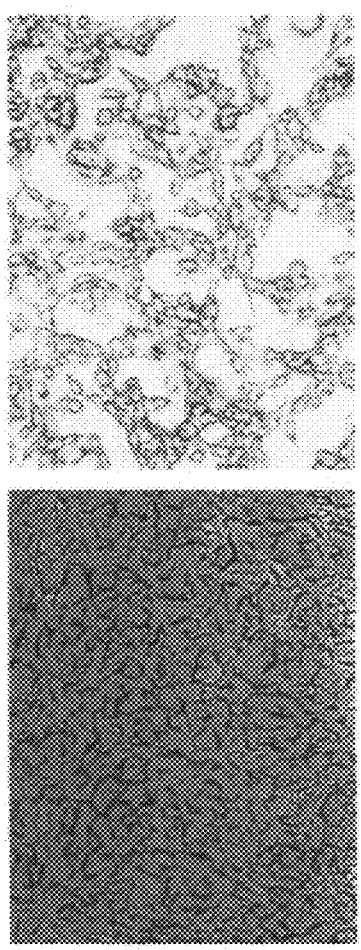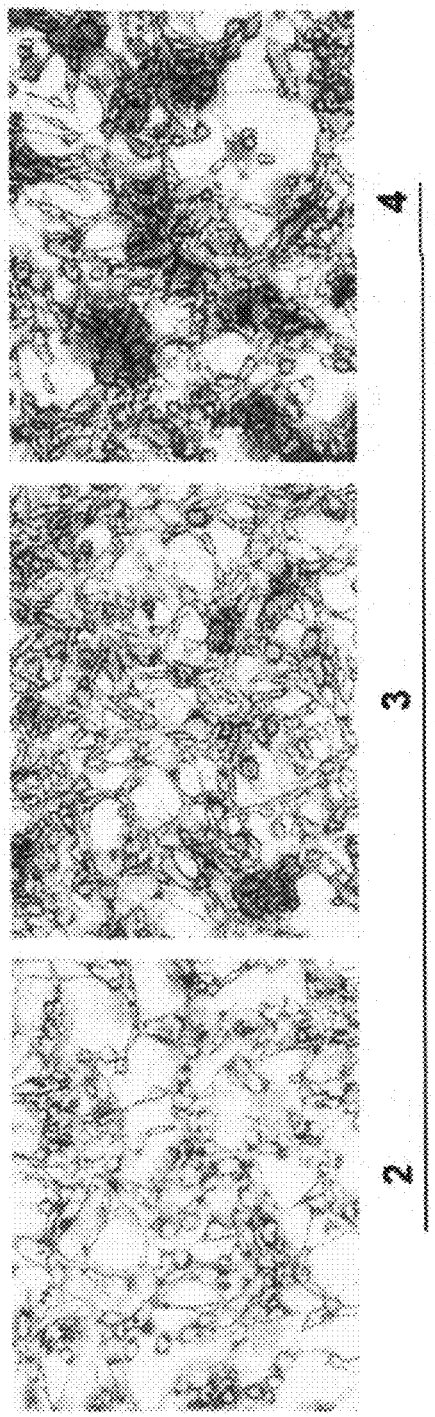
Fig. 26a Fig. 26b Fig. 26c Fig. 26d Fig. 26e

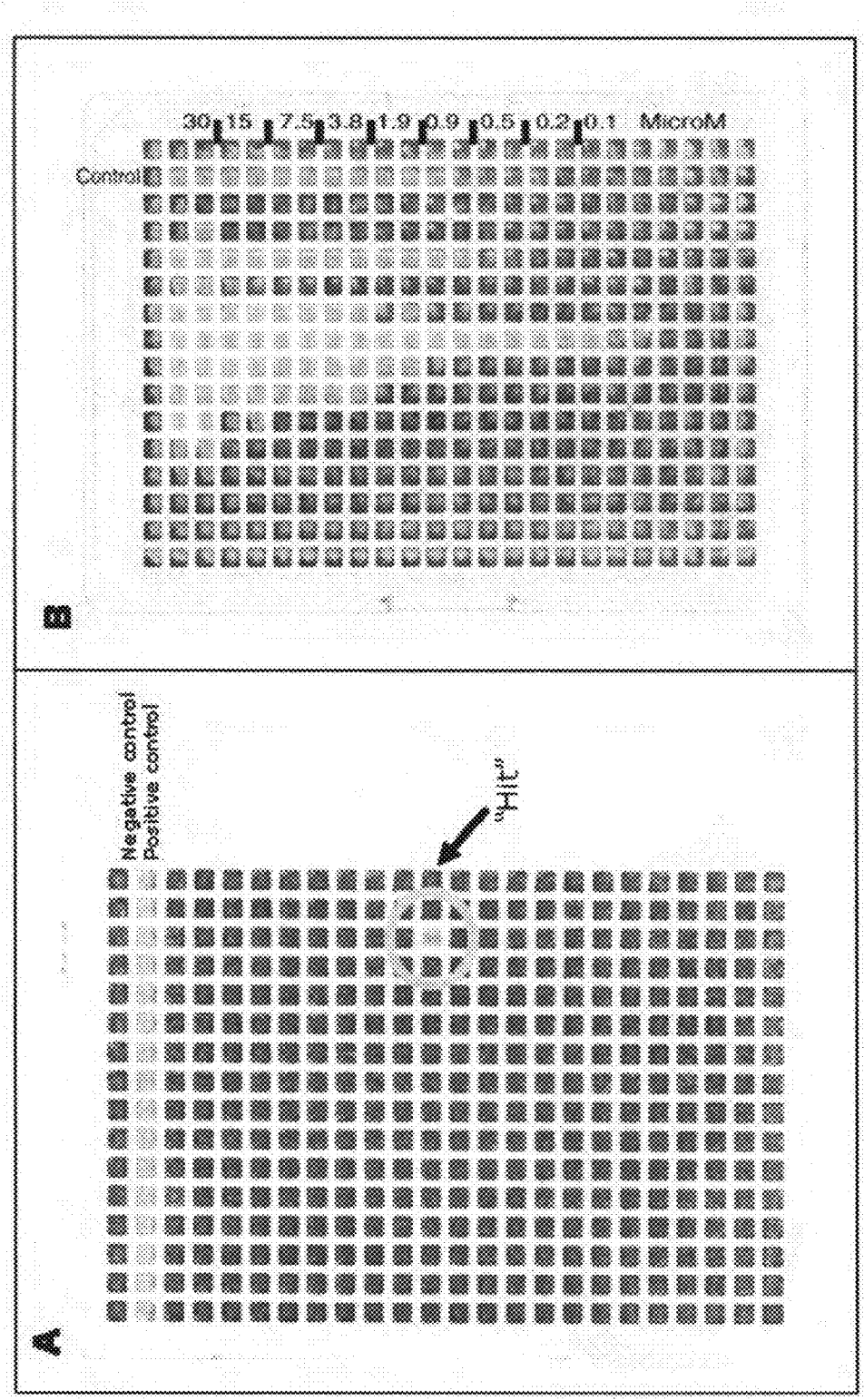

PCMV-Ras Vector – Wild type (wt) Ha-Ras protein

PCMV-Ras V12 Vector – Active form of the Ras (containing a glycine to valine mutation at residue 12)

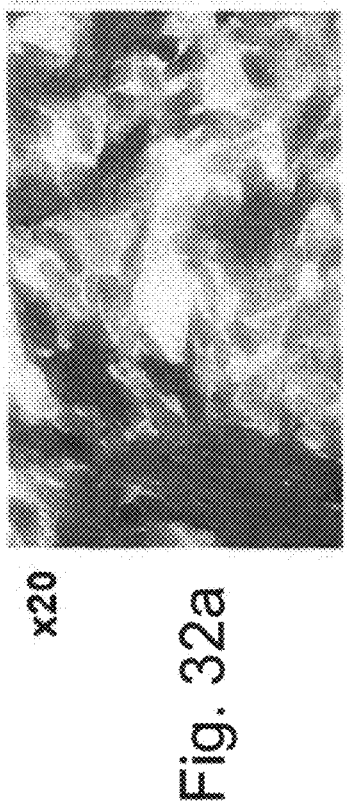
Fig. 32a, Fig. 32b, Fig. 32c, Fig. 32d
*Ras-transformed* cells treated with MEK1/2 inhibitor (PD98059) show changes in Cell morphology and CamaRx staining

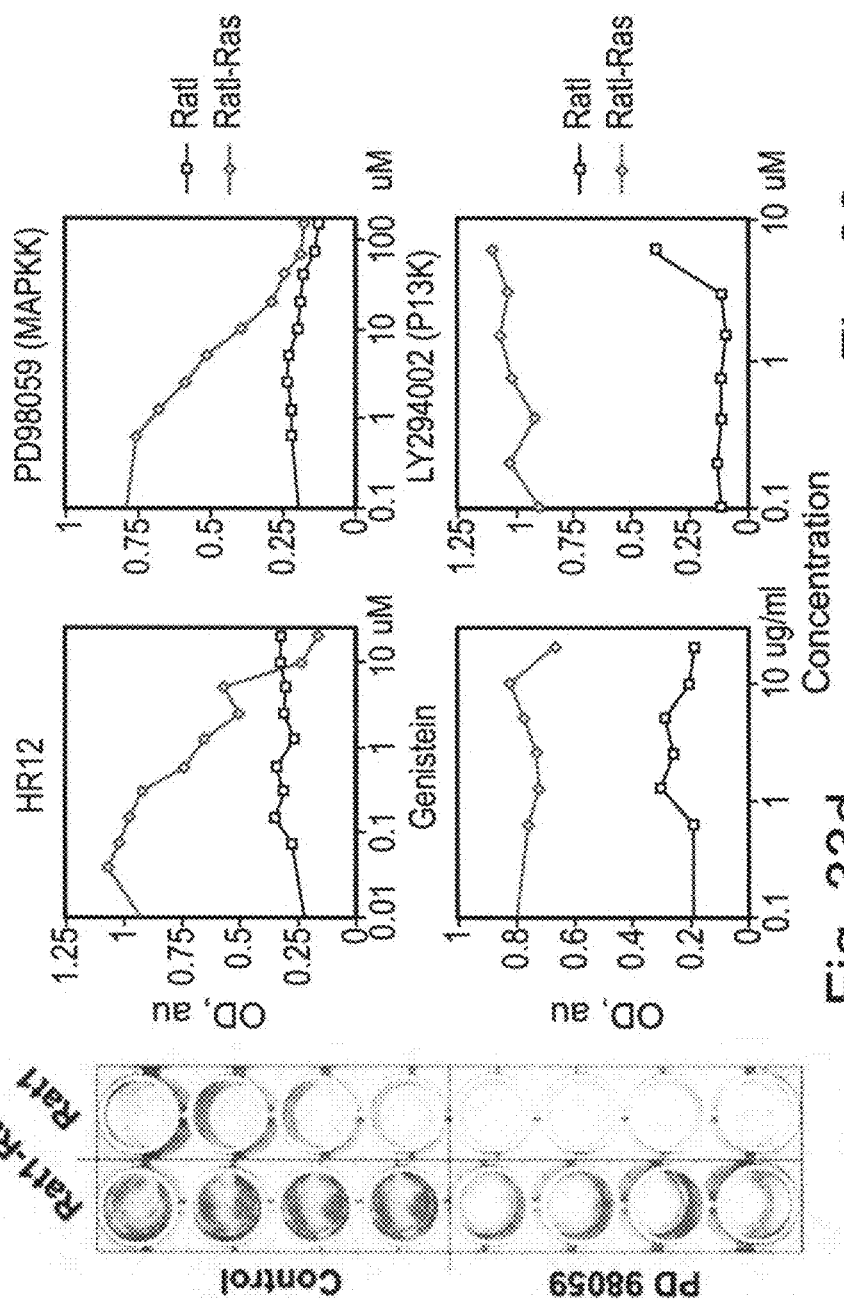

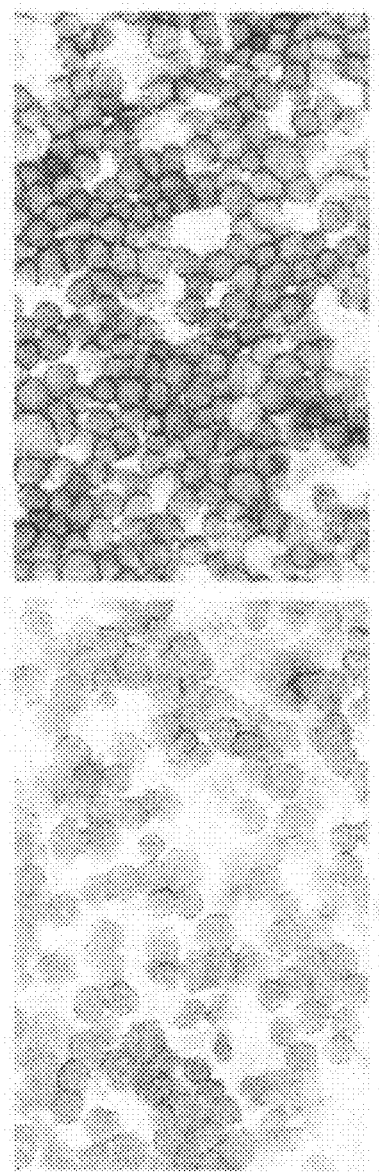
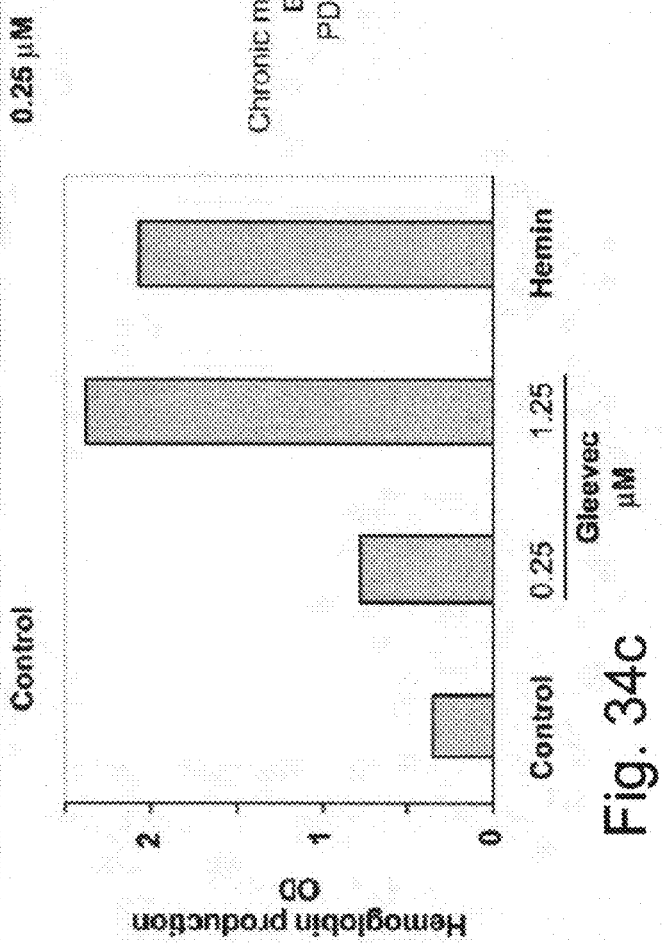
Fig. 34a
Fig. 34b
Fig. 34c

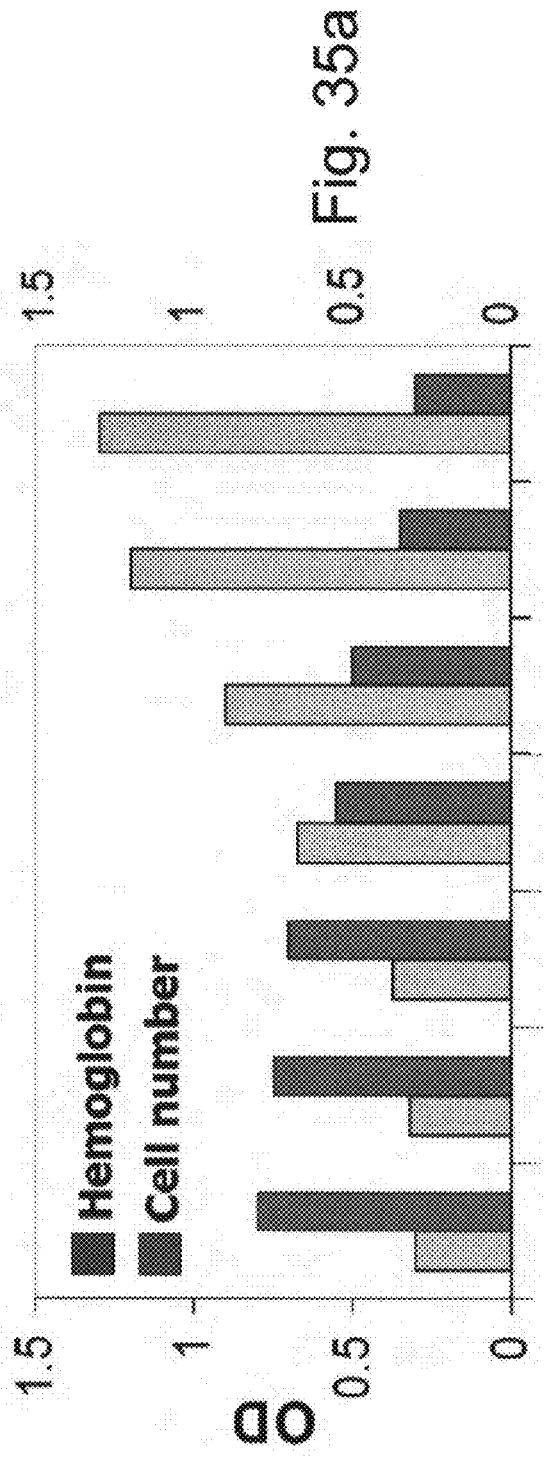
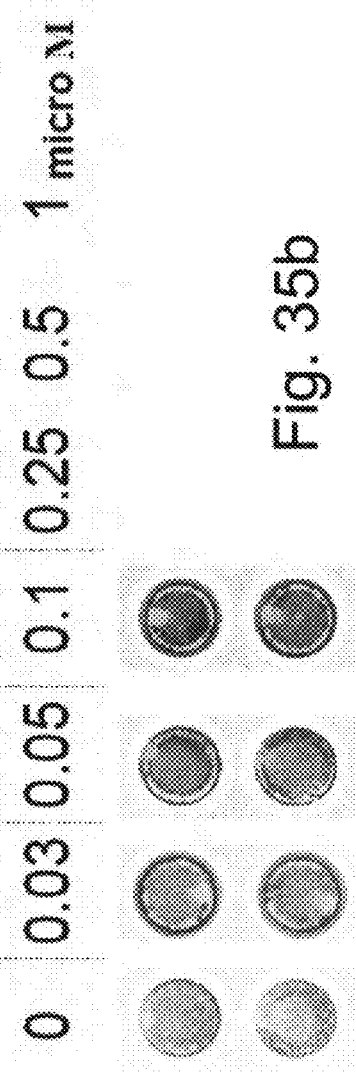
Fig. 35a
Fig. 35b

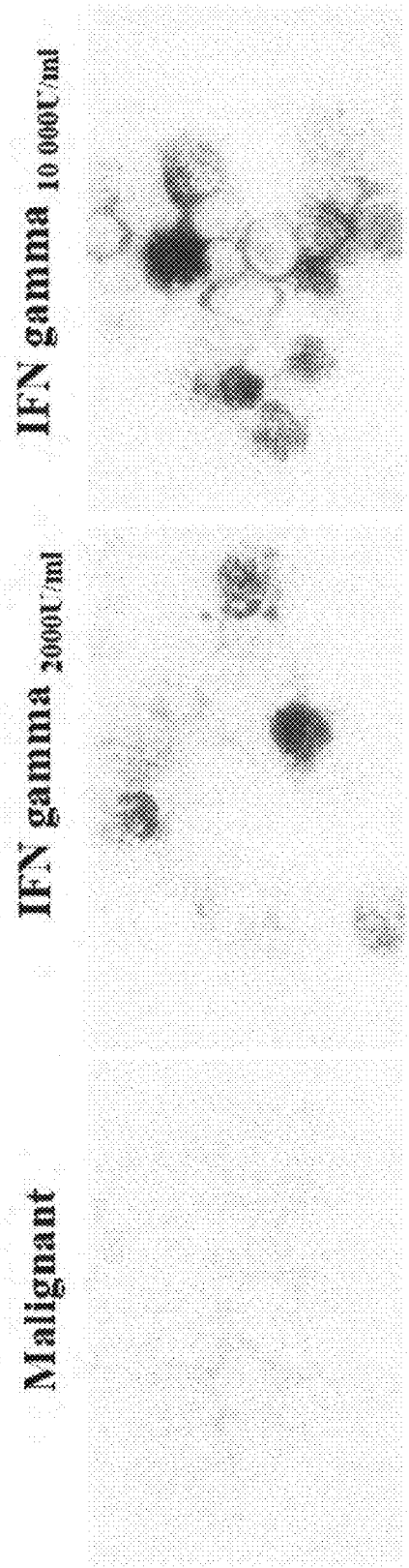

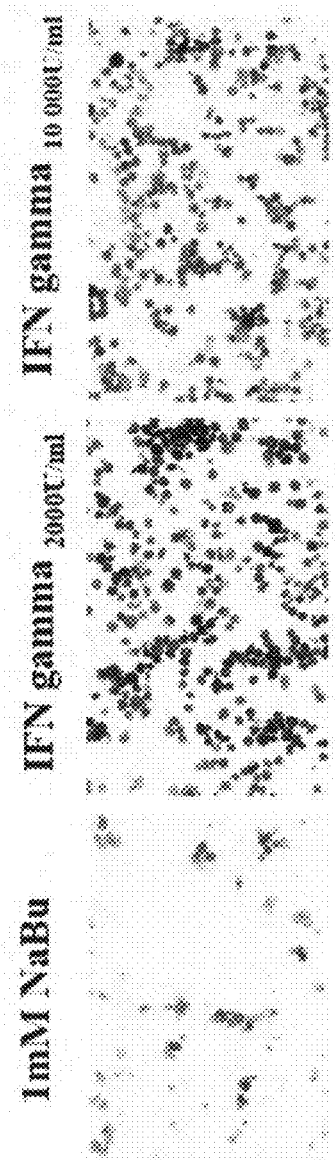
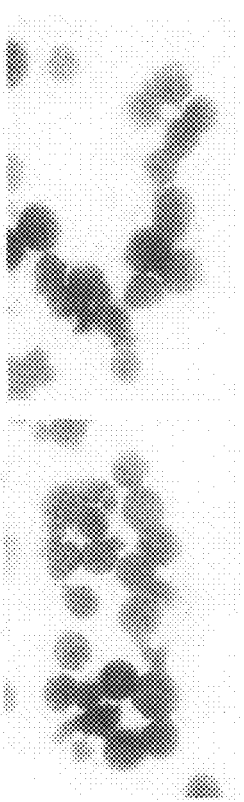
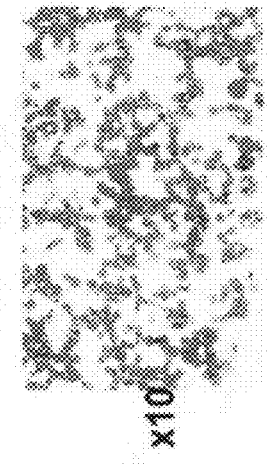
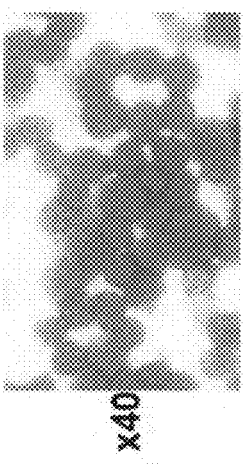
Fig. 38a  Fig. 38c  Fig. 38e  Fig. 38g
Fig. 38b  Fig. 38d  Fig. 38f  Fig. 38h
CamaRx staining of U-937 cells treated with Interferon gamma

Fig. 39

| Typhostin | Known activity | Effect |
|---|---|---|
| AG17 | Universal cell proliferation blocker | Toxic |
| AG18 | | No |
| AG494 | Analog to AG555 | Yes/No |
| AG879 | | Yes |
| AG974 | | No |
| AG1295 | | No |
| AG1387 | | Yes/No |
| AG555 | Cdk 2 activity blocker | No |
| AG1478 | EGFR kinase inhibitor | Yes |
| 0.1% DMSO | Control | ? |
| No treatment | Control | ? |
| No treatment | Control | ? |

HF1 – Plate overview

HPV 16 immortalized Human Keratinocytes

Fluorescence fingerprint of CST-2001

OLIGOMER-2 CST-2001

(MW 874.82)

$-CH_2-CHOH-CHOH-CHOH-CH_2OH$

MS: 438 and 877

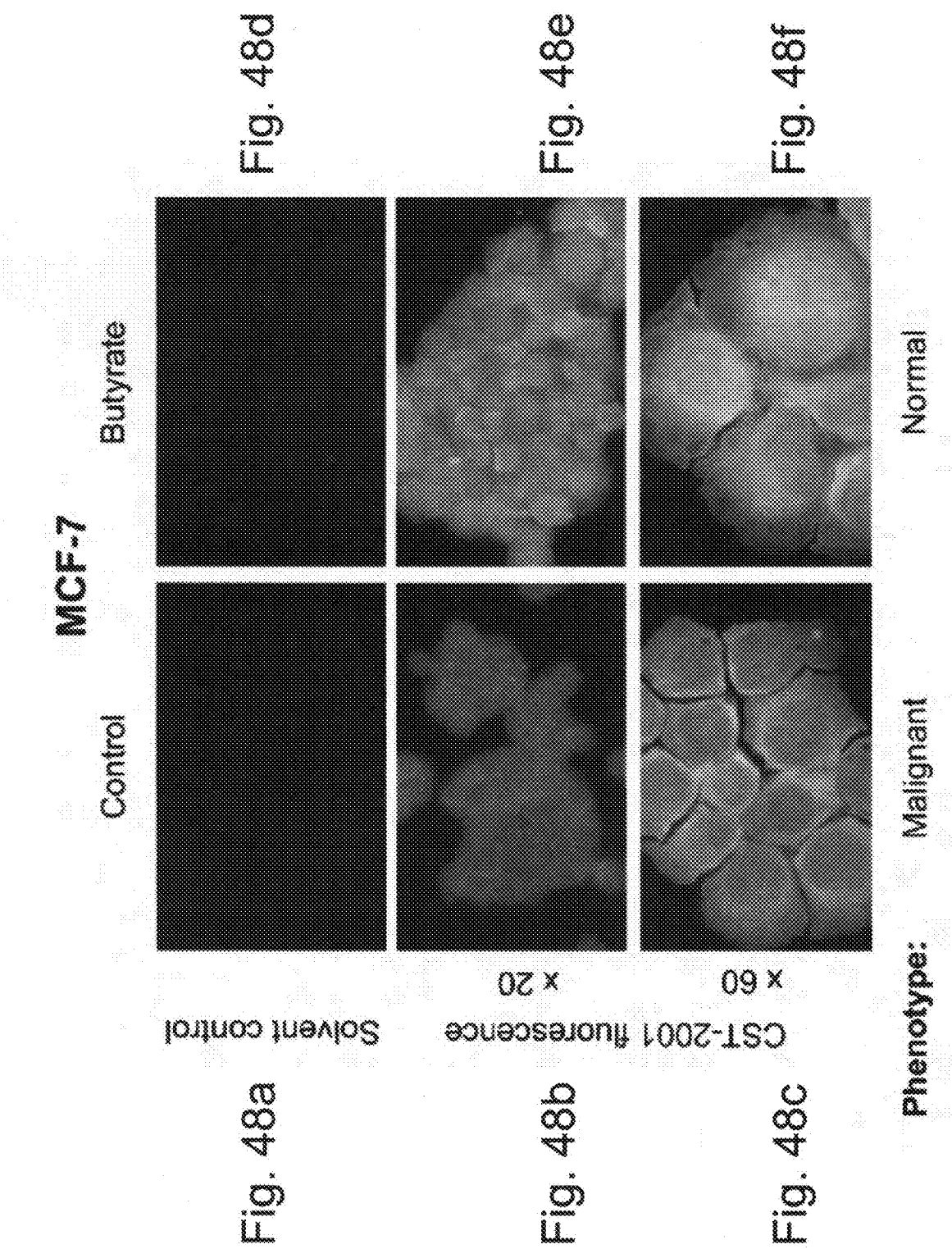

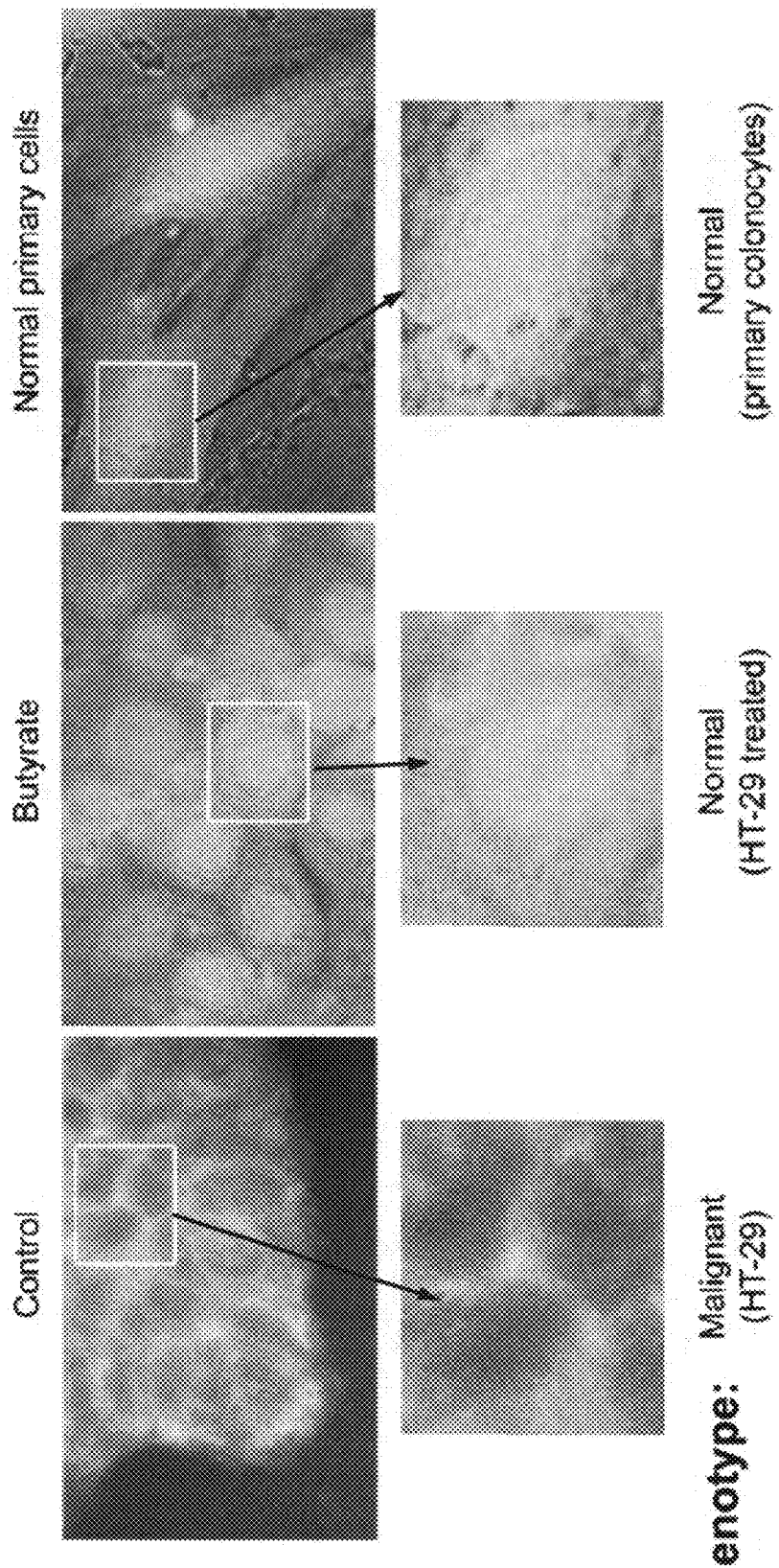

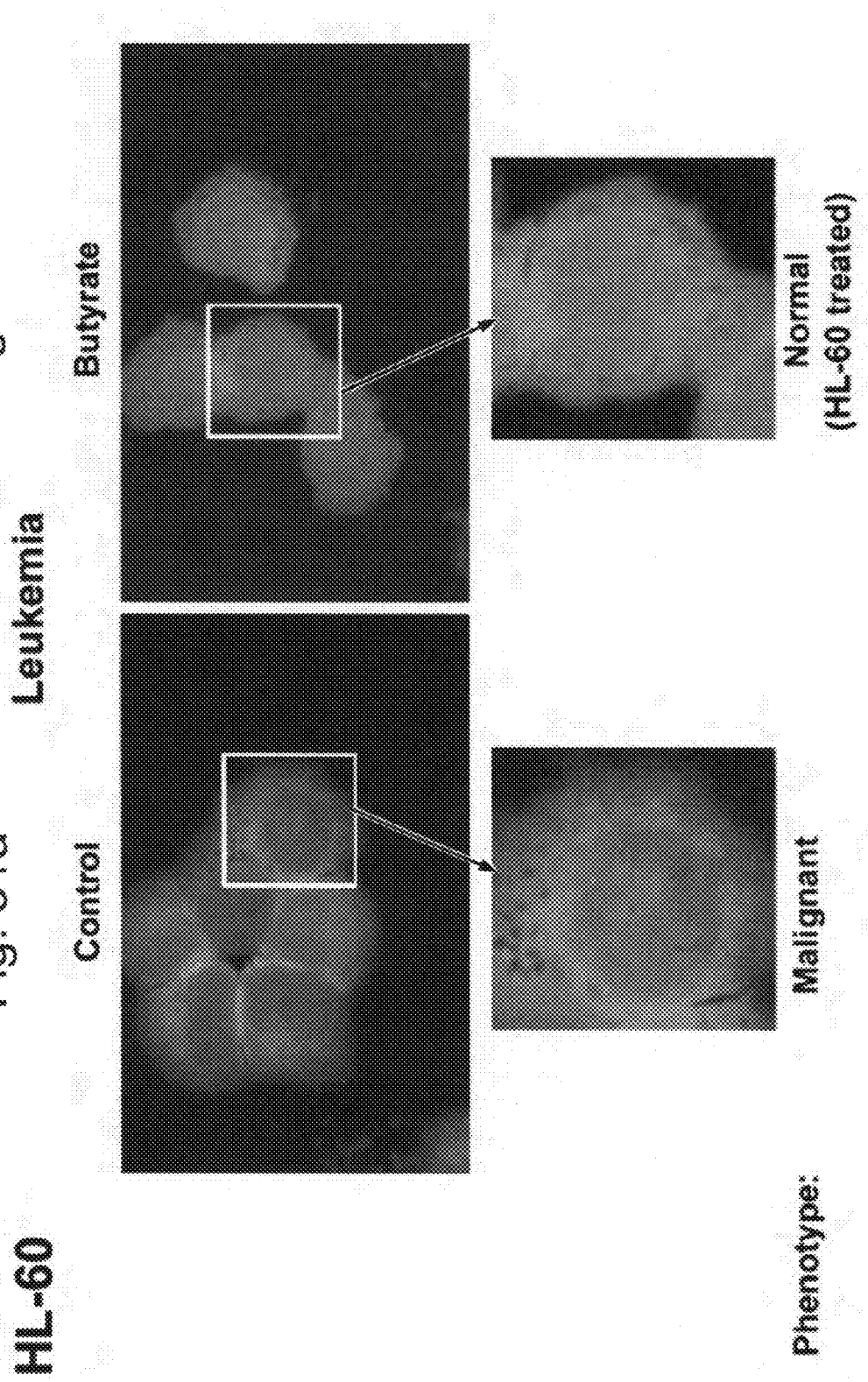

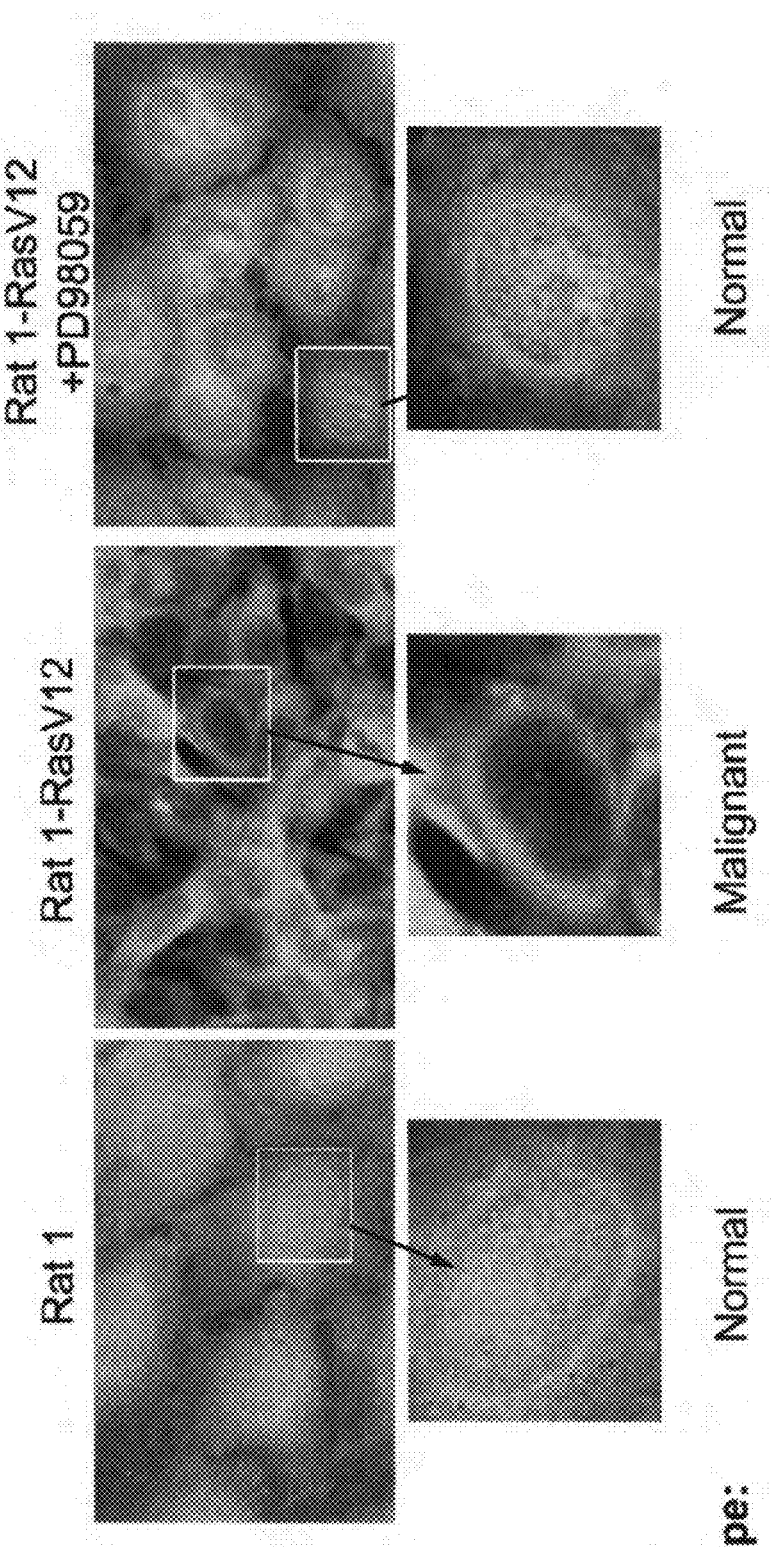

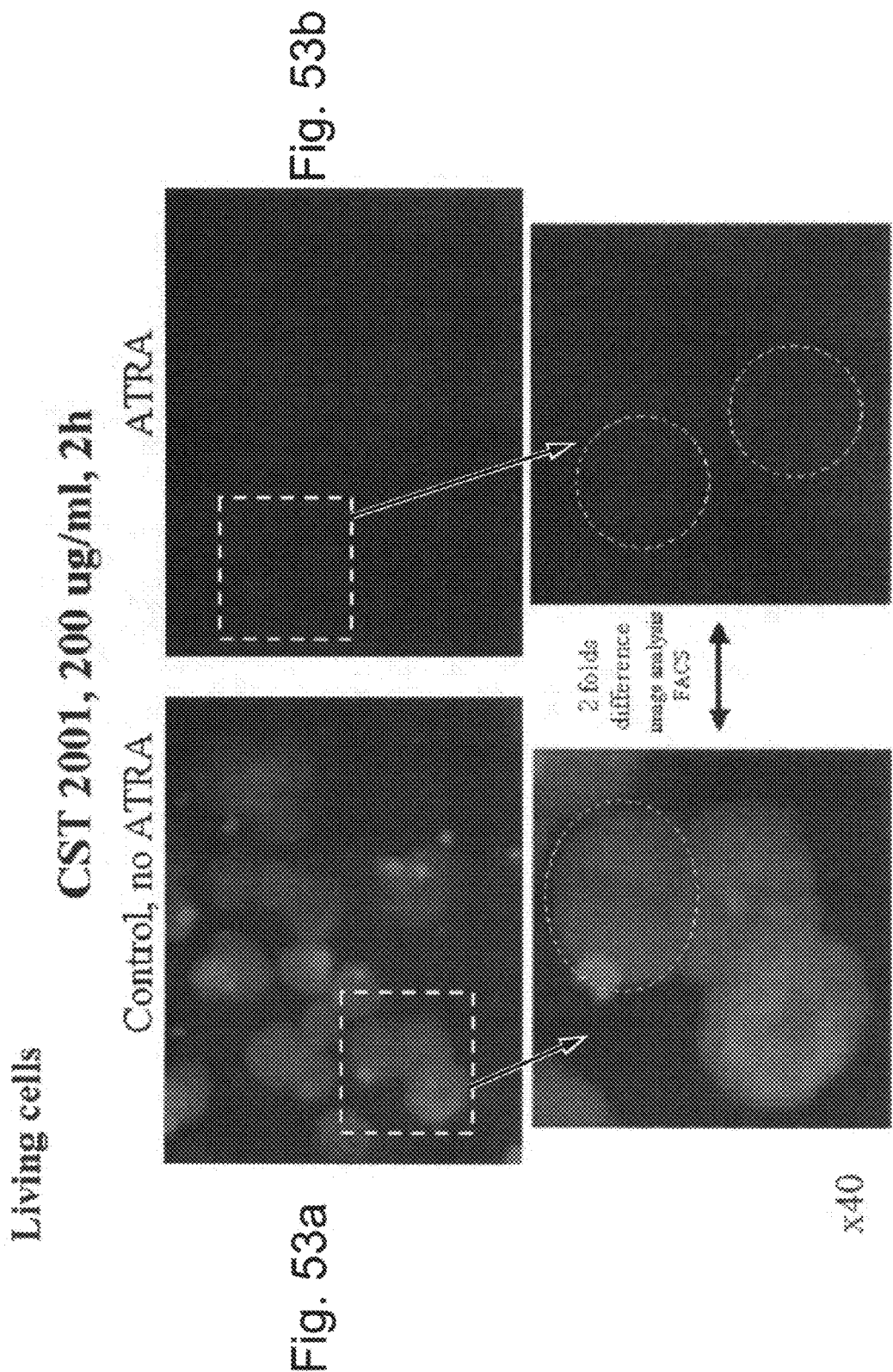

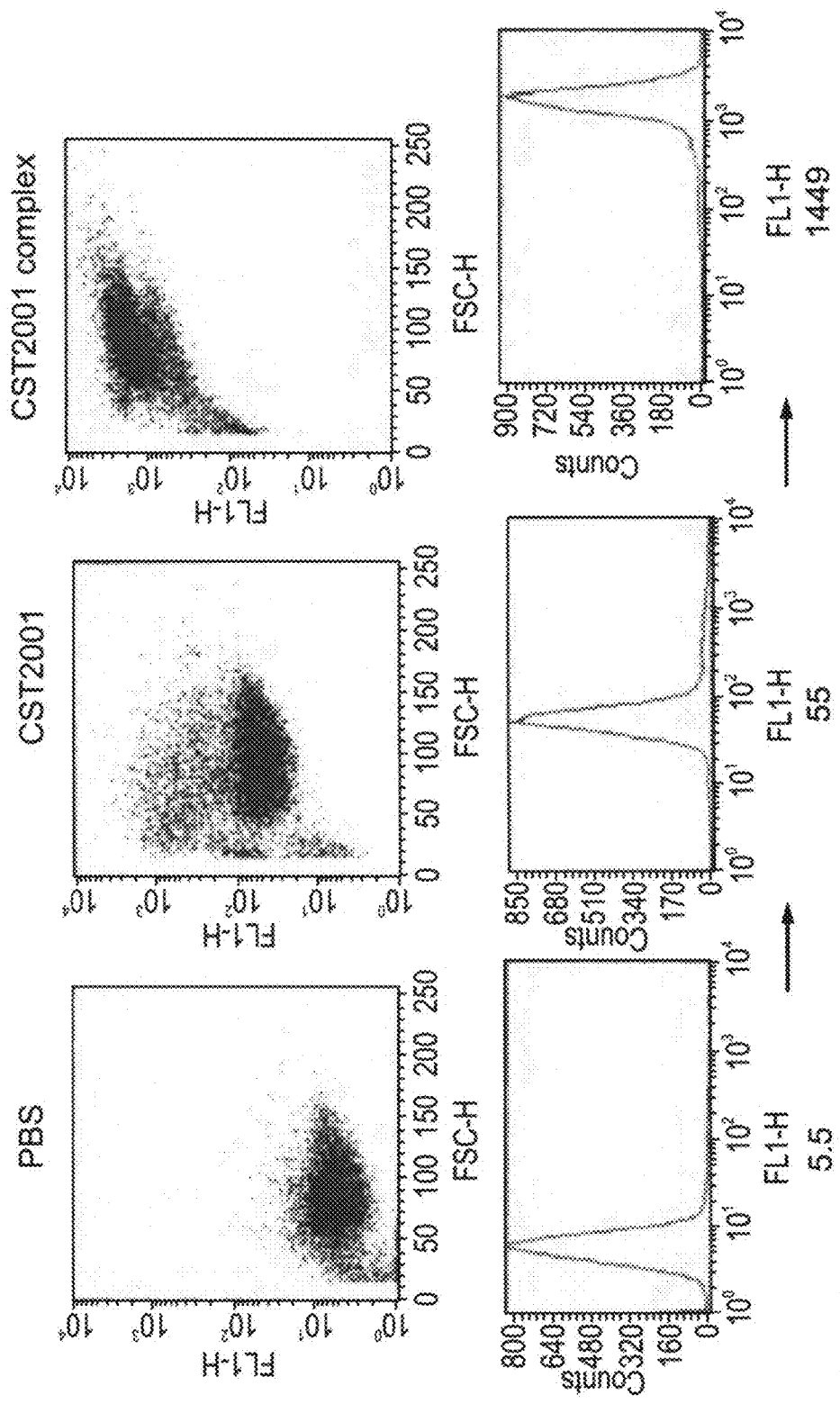

CST 2001 forms complex with biotinylated BSA

Cells → CST 2001 → BSA-Bio or + BSA-Native → Streptavidin Cy3 → Visualization

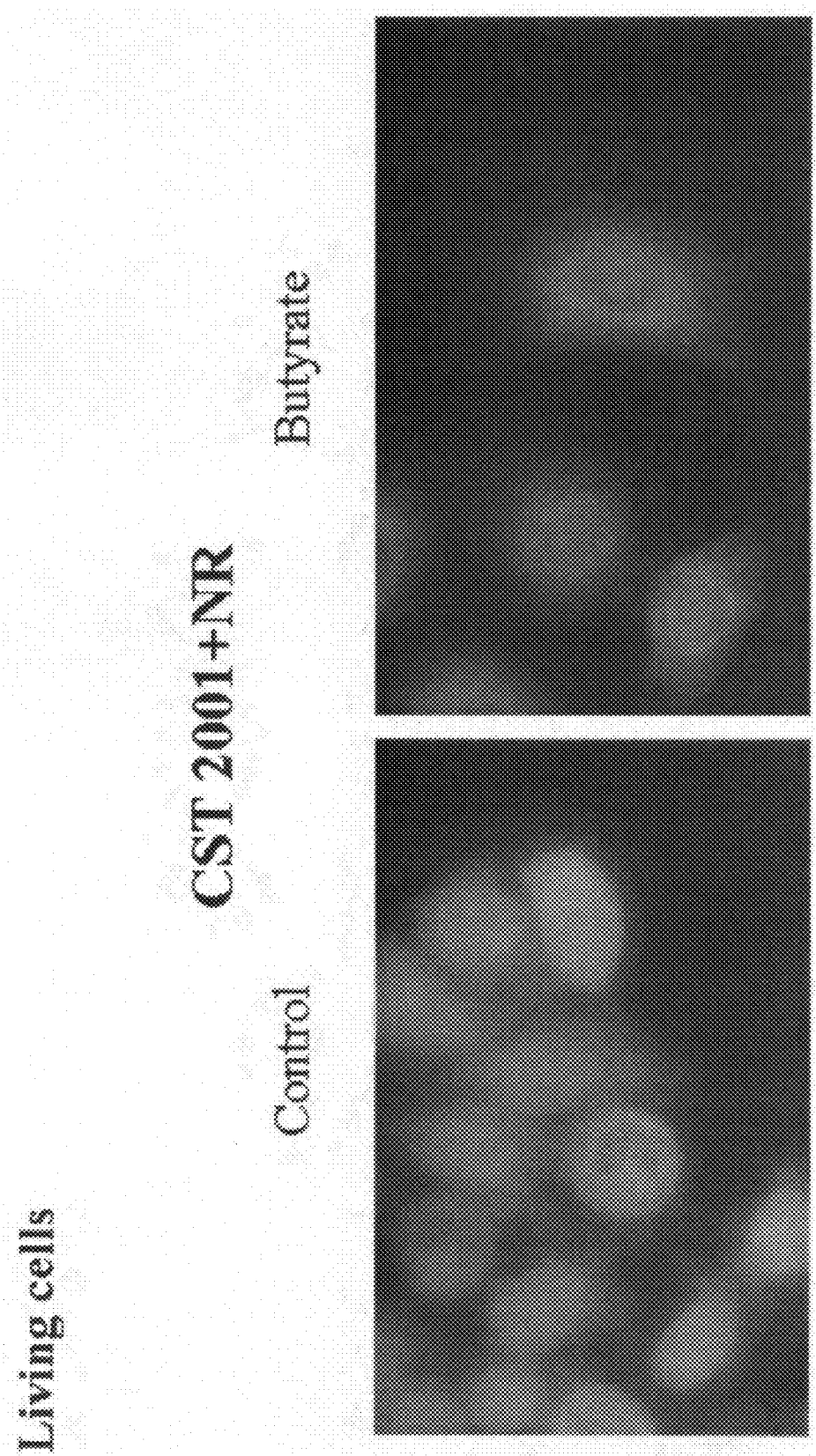

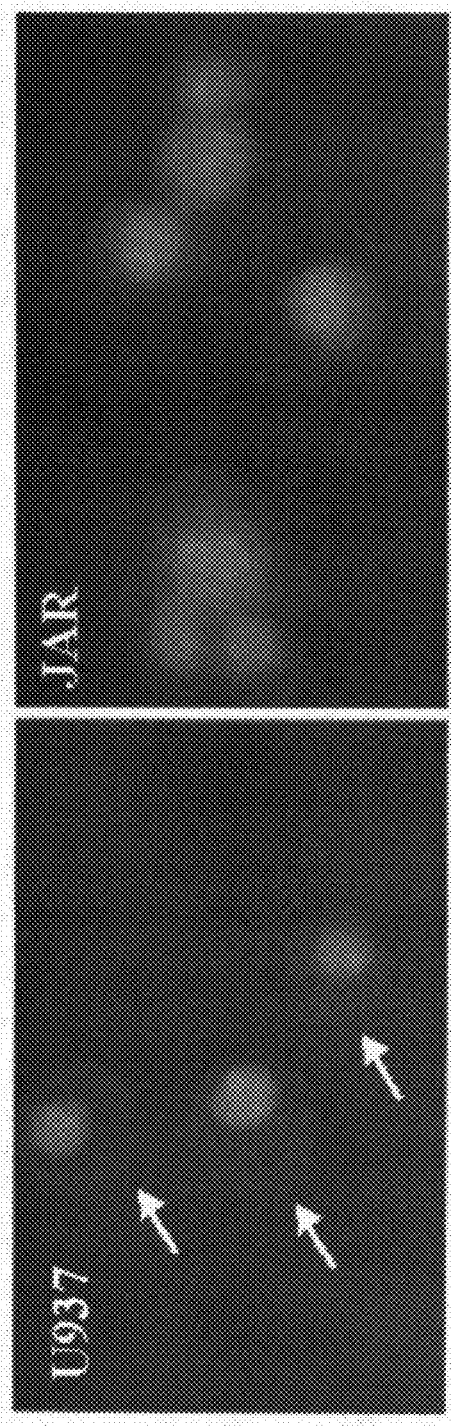
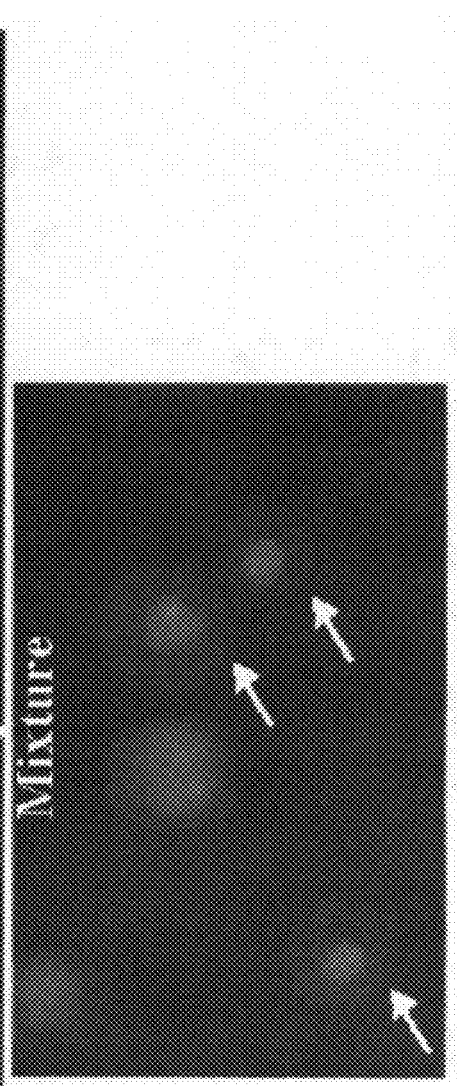
Fig. 61a Fig. 61b Placenta-originated cell line (choriocarcinoma)
Fig. 61c CST 2001 complex with Naturstoff reagent

METHODS AND COMPOSITIONS FOR IDENTIFYING A CELL PHENOTYPE

RELATED APPLICATIONS

This Application is a National Phase of PCT Patent Application No. PCT/IL2007/000281 having International filing date of Mar. 6, 2007, which claims the benefit of U.S. Provisional Patent Application Nos. 60/778,839, 60/778,944, 60/778,900 and 60/778,902 all filed on Mar. 6, 2006. The contents of the above Applications are all incorporated herein by reference.

FIELD AND BACKGROUND OF THE INVENTION

The present invention generally relates to compounds, methods and compositions useful in identifying a cell phenotype, and more specifically to compounds, methods and compositions useful in differentiating between a cell having a malignant phenotype, a cell having a pre-malignant phenotype and a cell having a non-malignant phenotype, or a metabolically impaired cell and a metabolically normal cell or a maternal versus a fetal cell. More particularly the invention relates to differential staining of cells in a biological sample, cytological or histological preparation. The present invention further relates to use of the compounds, methods and compositions for drug discovery, target validation, diagnosis, drug therapy monitoring and monitoring of disease progress.

For oncological diagnosis it is necessary to determine the presence of tumor cells, malignant or pre-malignant, among other normal or reactive cells in a tested specimen, and if possible, to determine the type of tumor and the organ from which it was derived.

The assessment of pathologically relevant traits in living cells is commonly performed by means of interpretation of cellular morphology or by testing of functional aspects such as motility [Alberts et al., Molecular Biology of the Cell. 3rd ed. New York and London (1994)], vitality, anchorage independent growth [Hamburger and Salmon, Science (1976) 197:461-463] and others. By contrast, fixed cells and tissue samples render themselves to histological assessment. For example, malignancy or cancer give rise to morphological changes that give rise to phenotypic changes. Traditionally, these assessments are performed by means of light microscopy following staining of the specimen with a dye or a combination of dyes in order to make the cells visible to the human eye. Thereafter, oncodiagnosis is established based on morphological features, such as, tissue organization, structure of nuclei and cytoplasm, nuclei to cytoplasm ratio, etc. as suggested by Boyd [Boyd, "A textbook of Pathology" Philadelphia: Lea & Febiger, $8^{th}$ edition (1970)] "the chief characteristics of the neoplastic cell, as revealed by the light microscope, are nuclear and chromosomal aberrations, decreased cytoplasmic-nuclear ratio, a coarse irregular chromatin network, and larger nucleoli than normal". In addition, metabolic disorders are characterized by the presence of metabolically impaired cells having an altered (impaired) phenotype as compared with the phenotype of a metabolically normal cell.

Yet, cytological assessments do not allow precise identification of cancer cells among the normal cellular population in a given preparation. One reason is that, in some cases, non-malignant cells mimic morphologic characteristics of cancer cells. For example, reactive mesothelium cells, present in serous effusions, often display atypical features such as multinucleation, nuclear hyperchromatism, eccentric position of the nucleus and cytoplasmic basophilia, features which are typically characteristic of cancer cells [Brownlow et al., Equine Vet. J. (1982) 14(1):86-88; Hansen et al., Am. J. Med. (1984) 77:887; Petrova et al., Lab. Delo. (1989) 6:9-11; Bibbo et al. (1976A) in Wied et al., "Compendium on Diagnostic Cytology" Chicago: Tutorial of Cytology, $7^{th}$ Edition (1976)]. In sputum cytology, for example, vacuolated cells could indicate cancer, but also reactive glandular cells, in particular in patients with pneumonia [Bibbo (1976B) in Wied et al., "Compendium on Diagnostic Cytology" Chicago: Tutorial of Cytology, 7th Edition (1976)]. In addition, some malignant cells appear to have normal morphology therefore oncocytology suffers from false negative and false positive diagnoses [Morell et al., Obstet. Gynecology. (1982) 60:41-45].

Thus, despite the long list of classical cytological methods, the efficiency of cytological diagnosis is largely determined by the qualification and experience of the cytopathologist, and by his abilities to analyze the obtained data.

The classical cytological techniques are in many cases supplemented by a group of technologies, which are based on compounds of high affinity and specificity, known as immunohistochemistry, immunocytochemistry and in situ hybridization. These technologies are used for phenotypic characterization of tumors (e.g., by implication of antibodies to intermediate filaments), detection of tumor markers of prognostic value (e.g., detection of p53 antigen), as well as the detection of other oncogenic expression features and nucleic acid sequences. Despite the high specificity of these techniques to detect malignancies, none of these techniques provides a pan-malignant tool for oncodiagnosis.

The three most common types of clinical specimens used in modern diagnostic cytology are exfoliated cytology specimens, fine needle aspiration biopsy (FNAB) specimens, and cervical vaginal smears.

Exfoliative cytology deals with the phenomenon of exfoliation of cancer cells from the surface of tumors early in the progression of the disease, even in the pre-invasive stages thereof [Boyd, "A textbook of Pathology" Philadelphia: Lea & Febiger, $8^{th}$ edition (1970)]. The exfoliated cells can be found in numerous body fluids such as pleural, peritoneal, pericardial, cerebrospinal, ocular, joint, gastrointestinal fluids, as well as in respiratory specimens, skin and mucosal samples and urine. These exfoliated cells can be collected by means of brushings, washings, direct puncture, drainage, touch preparations, scrapings, etc.

Fine needle aspiration (FNA) biopsy is a form of diagnostic biopsy that uses thin (fine) needles (22-gauge or narrower) to obtain cellular samples from within the body using a minimal invasive mode of body penetration. Fine needle aspirated cellular samples are then examined microscopically to detect the presence of various disease processes [NMLLS, "Fine Needle Aspiration Biopsy (FNAB) Techniques; Approved Guideline", NMLLS document GP20-A (1996)]. As opposed to exfoliate cytology, FNAB is directed towards the analysis of lesions or masses and is therefore regarded as a more direct diagnostic approach. FNAB typically encompasses lesions and masses from the breast, thyroid glands, head, neck, prostate, chest, lungs, abdomen, etc.

Cervical vaginal smears are scrapings from the female reproductive tract aimed at enabling the diagnosis of numerous types of atypia, some of neoplastic nature, others of pre-malignant nature, or other pathological processes.

All types of cellular samples must be transferred to a slide, processed and stained in order to enable visualization by means of light microscopy.

At present, diagnostic cytology is typically based on a rather narrow set of staining methods and compositions, some of which appeared many years ago, but are still being extensively used in present clinical cytology [Kjeldsberg and Kniger, Body fluids, Chicago (1987); Koss, Diagnostic cytology and its histopathologic basis. Third edition, Philadelphia (1979)]. This refers primarily to the alcohol-fixed Papanicolaou stain and the air-dried May-Grunwald-Giemsa (a version of which is known as Romanowsky) stain, while staining with hematoxylin and eosin, Shorr's staining for endocrine cytology and the Pappenheim method are more rarely used.

The May-Grunwald-Giemsa (MGG) staining method is widely used in clinical laboratories for the diagnosis of cells of hematopoietic origin and others. However, this method does not express tinctorial selectivity for malignant cells.

The Papanicolaou staining method was initially developed for analysis of vaginal smears [Papanicolaou and Traut, Am. Y. Obst. Gynecol. (1941) 42:193-206; Papanicolaou "Atlas of Exfoliative Cytology" Cambridge, Mass.: Harvard University Press (1954)] and allows the differentiation of cell types of stratified and simple epithelia present in alcohol-fixed smears. The Papanicolaou method (Pap smears) allows one to obtain detailed morphology of the nucleus and cytoplasm in normal and tumor cells. This approach has been also widely used in other fields of clinical cytology. It should be emphasized that the Papanicolaou staining procedure, as well as all other staining procedures, do not reveal any tinctorial selectivity for malignant cells.

Thus, none of these prior art cytological staining protocols provide selective heterochromatic or tinctorial selectivity of pre-malignant and malignant cells, metabolically impaired cells and fetal cells. There is thus a widely recognized need for, and it would be highly advantageous to have reliable and efficient cytological staining methods which detect, monitor and validate phenotypical changes in cancer cells as compared to normal cells, in metabolically impaired cells as compared to metabolically normal cells and in fetal cell as compared to maternal cell. While existing practice is reliable, it is both time consuming and in most cases not amenable to high throughput testing of cellular phenotype. Moreover, as a result of the increasing number of new genes with unknown function, as well as the need to determine the function of known genes, there is a great demand for rapid and simple methods for detecting oncogenes and tumor suppressor genes. There is a recognized need to test chemicals and drugs for mutagenicity, particularly with techniques which are readily adapted to automation for high throughput screening. Furthermore, there is a need for new type/generation of anti-cancer treatments changing the behavior/phenotype of cells from malignant to normal. Also there is a need for the correct combination of drugs in anti-cancer treatment. These requests are not fulfilled due to the lack of the screening assays and platforms.

SUMMARY OF THE INVENTION

According to one aspect of the present invention there is provided a method of staining or pre-staining at least one cell, the method comprising contacting the at least one cell with a staining agent selected from the group consisting of an extract of a *Ficus elastica* plant, a $C_{23}H_{44}O_4$ and a proanthocyanidin, thereby staining or pre-staining the at least one cell.

According to another aspect of the present invention there is provided a method of staining at least one cell, the method comprising: (a) contacting the at least one cell with a staining agent selected from the group consisting of an extract of a *Ficus elastica* plant, a $C_{23}H_{44}O_4$ and a proanthocyanidin, so as to obtain a pre-stained cell or cells; and (b) contacting the pre-stained cell or cells with at least one dye.

According to further features in preferred embodiments of the invention described below, the at least one cell comprises a heterogeneously differentiated population of cells.

According to still further features in the described preferred embodiments, the at least one dye is a single dye.

According to still further features in the described preferred embodiments, the at least one dye is selected from the group consisting of a basic dye and an acidic dye.

According to still further features in the described preferred embodiments, when: (i) the at least one dye is an acidic dye a staining intensity above a predetermined threshold is indicative of a differentiated cell; (ii) the at least one dye is a basic dye a staining intensity above a predetermined threshold is indicative of an undifferentiated cell; (iii) the at least one dye comprises the acidic dye and the basic dye a staining intensity above a predetermined threshold with the acidic dye is indicative of a differentiated cell and a staining intensity above a predetermined threshold with the basic dye is indicative of an undifferentiated cell.

According to still further features in the described preferred embodiments, the heterogeneously differentiated population of cells comprises a solid tissue section.

According to still further features in the described preferred embodiments, the heterogeneously differentiated population of cell comprises isolated cells.

According to still further features in the described preferred embodiments, the heterogeneously differentiated population of cells comprises malignant or pre-malignant cells.

According to still further features in the described preferred embodiments, the heterogeneously differentiated population of cells comprises fetal cells.

According to still further features in the described preferred embodiments, the heterogeneously differentiated population of cells comprises metabolically impaired cells.

According to still further features in the described preferred embodiments, the extract of *Ficus elastica* plant comprises a leaf extract.

According to still further features in the described preferred embodiments, the extract of *Ficus elastica* plant comprises an ethanol extract.

According to still further features in the described preferred embodiments, the ethanol extract comprises a 70% ethanol extract.

According to still further features in the described preferred embodiments, the extract of *Ficus elastica* plant comprises a crude plant extract.

According to still further features in the described preferred embodiments, the extract of *Ficus elastica* plant comprises a purified plant extract.

According to still further features in the described preferred embodiments, the extract of *Ficus elastica* plant comprises a diluted extract.

According to still further features in the described preferred embodiments, the extract of *Ficus elastica* plant comprises NMR spectra as detailed in FIGS. 43-44.

According to still further features in the described preferred embodiments, the staining agent is fluorescent.

According to still further features in the described preferred embodiments, the staining agent emits fluorescence at 430 nm upon excitation at 375 nm.

According to still further features in the described preferred embodiments, the staining agent is biotinylated.

According to still further features in the described preferred embodiments, at least one of the $C_{23}H_{44}O_4$ and the proanthocyanidin is naturally occurring.

According to still further features in the described preferred embodiments, at least one of the $C_{23}H_{44}O_4$ and the proanthocyanidin is synthetic.

According to still further features in the described preferred embodiments, the ethanol extract of Ficus elastica plant is supplemented with positively charged ions.

According to still further features in the described preferred embodiments, the positively charged ions are selected from the group consisting of magnesium and calcium.

According to still further features in the described preferred embodiments, the at least one dye comprises two dyes.

According to still further features in the described preferred embodiments, the at least one dye is selected from the group consisting of a basic dye, an acidic dye, a triamnotriphenylmethane derivative, a diazo derivative and a combination of same.

According to still further features in the described preferred embodiments, the two dyes comprise dyes selected from the group consisting of a basic dye, an acidic dye, a triamnotriphenylmethane derivative, a diazo derivative and a combination of same.

According to still further features in the described preferred embodiments, staining with the two dyes is effected sequentially.

According to still further features in the described preferred embodiments, the basic dye is selected from the group consisting of Dahlia and new Fuchsin.

According to still further features in the described preferred embodiments, the acidic dye is Light Green.

According to still further features in the described preferred embodiments, the differentiated cell is a normal healthy cell and the undifferentiated cell is a malignant or pre-malignant cell.

According to yet another aspect of the present invention there is provided a method of identifying a cell of a differentiation state of interest, the method comprising: (a) staining the cell; and (b) analyzing the staining, wherein when: (i) the at least one dye is an acidic dye, a staining intensity above a predetermined threshold is indicative of a differentiated cell; (ii) the at least one dye is a basic dye, a staining intensity above a predetermined threshold is indicative of an undifferentiated cell; (iii) the at least one dye comprises the acidic dye and the basic dye, a staining intensity above a predetermined threshold with the acidic dye is indicative of a differentiated cell and a staining intensity above a predetermined threshold with the basic dye is indicative of an undifferentiated cell.

According to still further features in the described preferred embodiments, the undifferentiated cell is a malignant or pre-malignant cell.

According to an additional aspect of the present invention there is provided a method of diagnosing a cancer in a subject, the method comprising: (a) staining cells of the subject, so as to obtain stained population of cells; and (b) analyzing a staining of the stained population of cells, wherein when: (i) the at least one dye is an acidic dye, a staining intensity above a predetermined threshold is indicative of differentiated cells; (ii) the at least one dye is a basic dye, a staining intensity above a predetermined threshold is indicative of undifferentiated cells; (iii) the at least one dye comprises the acidic dye and the basic dye, a staining intensity above a predetermined threshold with the acidic dye is indicative of differentiated cells and a staining intensity above a predetermined threshold with the basic dye is indicative of undifferentiated cells, whereby a presence or level of the undifferentiated cells in indicative of malignant or pre-malignant cells thereby diagnosing the cancer in the subject.

According to yet an additional aspect of the present invention there is provided a method of determining an-anti cancer treatment course in a subject in need thereof, the method comprising: (a) administering to the subject an anti-cancer therapy; (b) analyzing a presence or level of malignant or pre-malignant cells in a biopsy sample of the subject following step (a) according to the above method, whereby the presence or level of the malignant or pre-malignant cells is indicative of the treatment course.

According to still further features in the described preferred embodiments, the method further comprising obtaining an additional biopsy sample of the subject prior to step (a) and/or concomitant with step (b).

According to still further features in the described preferred embodiments, the method further comprising comparing the level of the malignant or pre-malignant cells in the biopsy sample with the additional biopsy sample.

According to a further aspect of the present invention there is provided a method of determining an anti-cancer treatment regimen in a subject in need thereof, the method comprising: (a) analyzing a presence or level of malignant or pre-malignant cells in a biopsy sample of the subject; (b) administering to the subject a therapeutic effective amount of an anti cancer therapy according to the presence or level of malignant cells in the biopsy sample of the subject.

According to still further features in the described preferred embodiments, the method further comprising repeating step (a) following (b).

According to yet a further aspect of the present invention there is provided a method of identifying an agent capable of reversing a pre-malignant or malignant phenotype of a cell, the method comprising: (a) subjecting the cell to an agent; (b) analyzing a malignant phenotype of the cell following (a) and optionally prior to (a) according to the above method, wherein a reversion of phenotype is indicative of an agent capable of reversing a pre-malignant or malignant phenotype of a cell According to still further features in the described preferred embodiments, the agent comprises a test composition.

According to still further features in the described preferred embodiments, the test composition is selected from the group consisting of a polynucleotide a polypeptide, a small molecule chemical, a carbohydrate, a lipid and a combination of same.

According to still further features in the described preferred embodiments, the agent comprises a test condition.

According to still further features in the described preferred embodiments, the test condition is selected from the group consisting of a growth condition and a radiation condition.

According to still further features in the described preferred embodiments, the cell comprises a plurality of cells.

According to still further features in the described preferred embodiments, the method is performed using means for high output.

According to still further features in the described preferred embodiments, the means comprises an automated sampling device, a liquid handling equipment, an automated stainer, a dispenser, a robot, or any combination thereof.

The present invention successfully addresses the shortcomings of the presently known configurations by providing methods for cell staining which can be used to distinguish between cells of different differentiation levels.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

Figures 1A, 1B:
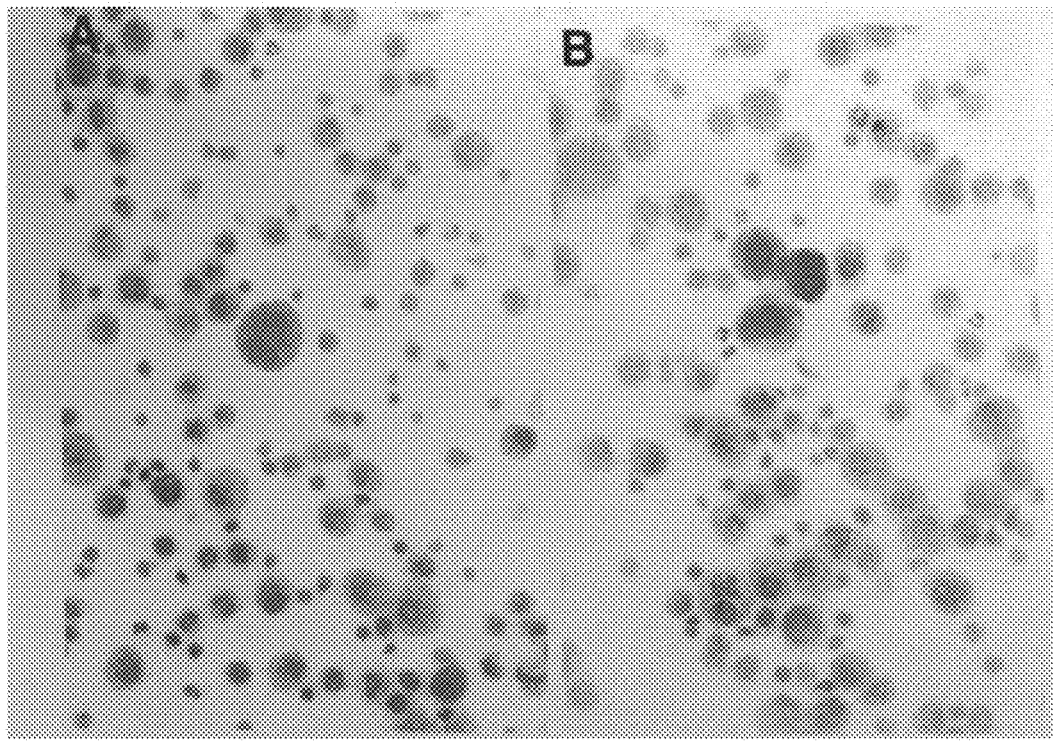

FIGS. 1A-B show smears prepared from a pleural fluid derived from a male patient diagnosed, by means of histopathology, with carcinoma of unknown origin, stained using the staining procedure according to the present invention.

Figures 2A, 2B:
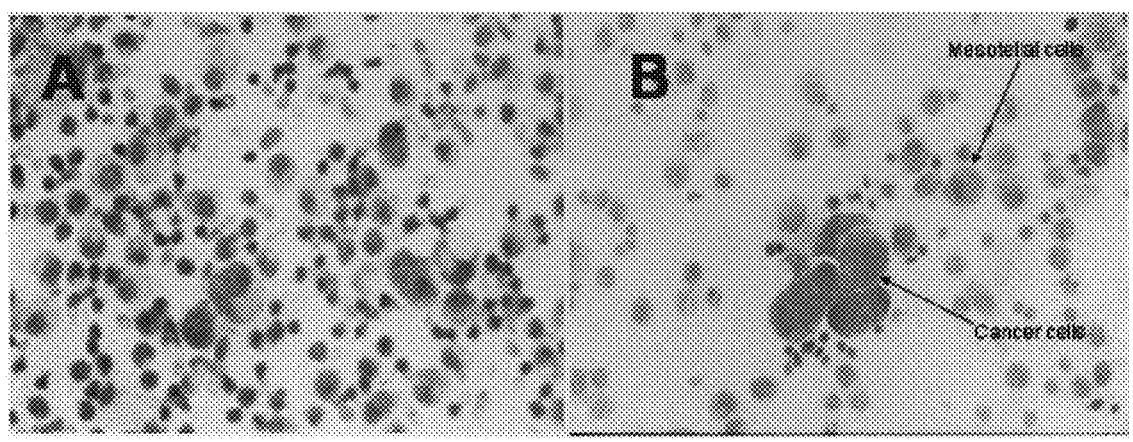

FIGS. 2A-B show smears prepared from pleural effusions. FIG. 2A depicts pleural effusions stained with May-Grunwald-Giemsa protocol. Specimens were stained by means of such as in order to allow for visualization of cells. These conventional techniques were not differential; and FIG. 2B depicts pleural effusions stained with the novel staining procedure according to the present invention. While the cytoplasm of cells with malignant properties was stained red, the cytoplasm of normal epithelial cells, macrophages and leukocytes of all types were stained green.

Figure 3:
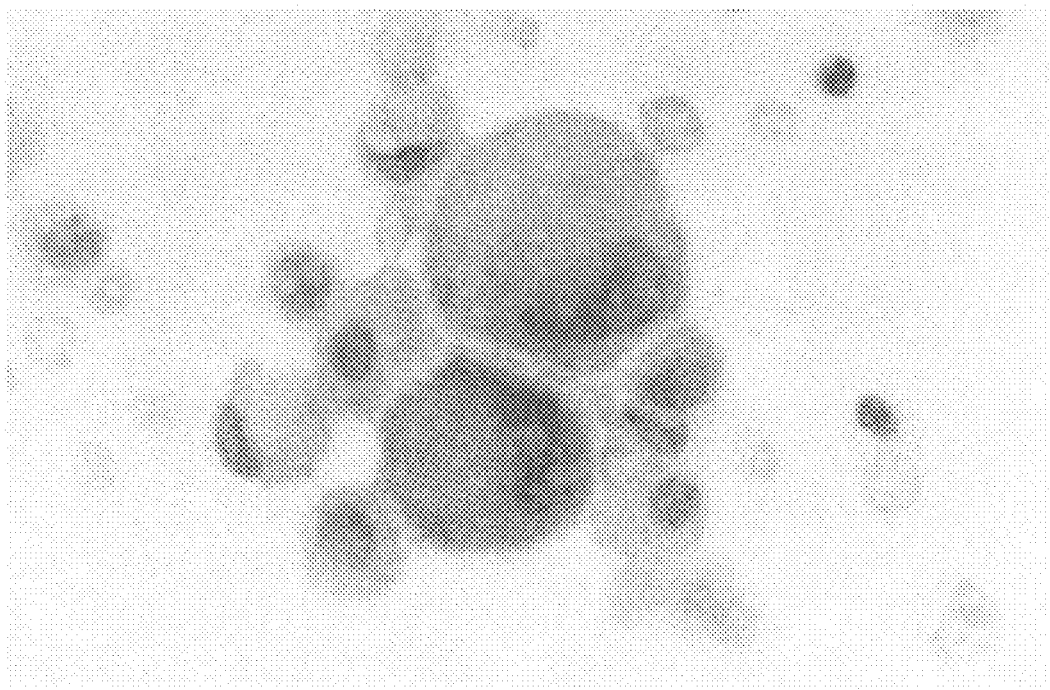

FIG. 3 shows a smear prepared from a pleural fluid derived from a female patient diagnosed, by means of histopathology, with carcinoma of the breast, stained using the staining procedure according to the present invention.

Figure 4:
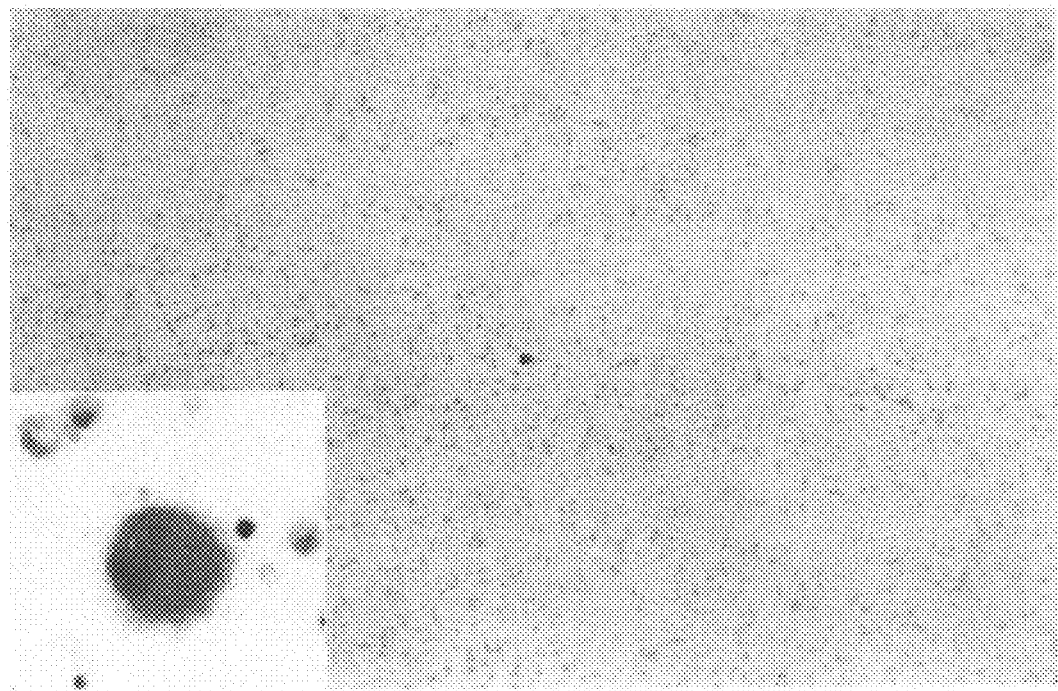

FIG. 4 shows a smear prepared from a pleural fluid derived from a male patient diagnosed, by means of histopathology, with carcinoma of unknown origin, stained using the staining procedure according to the present invention. The inset shows a magnification of the single stained cell. A total of three malignant cells were found on this specific slide.

FIGS. 5A-G show seven panels (A-G) of six (1-6) staining situations as presented in Table 5. FIG. 5A depicts 3LL lung carcinoma; FIG. 5B depicts C6 Astrocytoma; FIG. 5C depicts A375 Human Melanoma; FIG. 5D depicts Friend Erythroleukemia; FIG. 5E depicts NIH3T3; FIG. 5F depicts Rat peritoneal inflammatory exudate; and FIG. 5G depicts a normal clinical case.

Figure 6A:
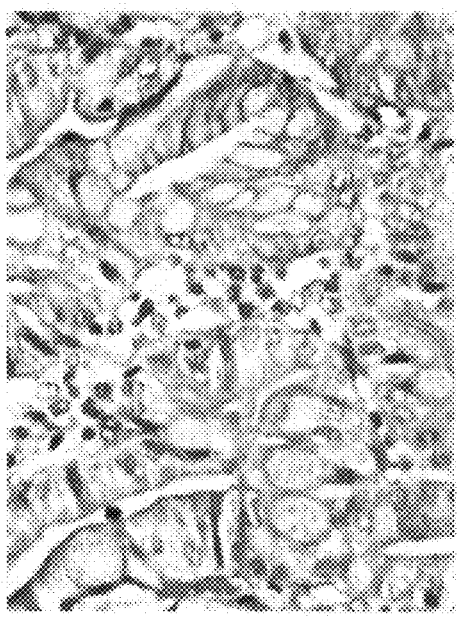
Figure 6B:
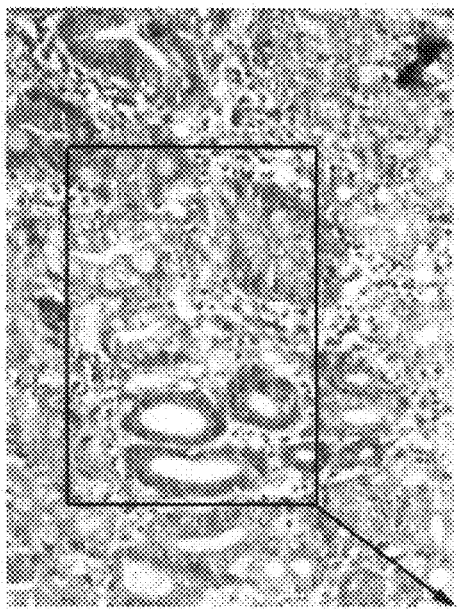
Figure 6C:
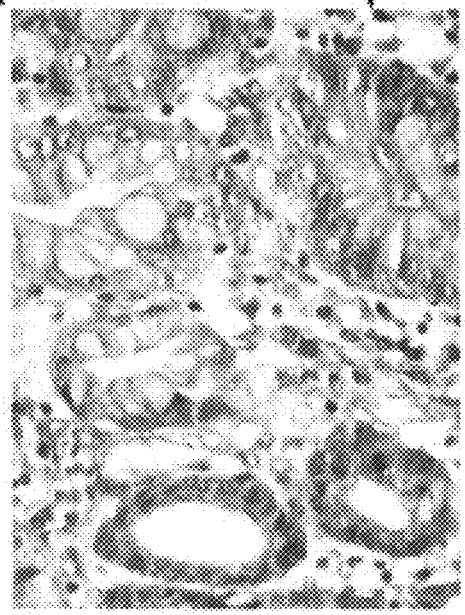
Figure 6D:
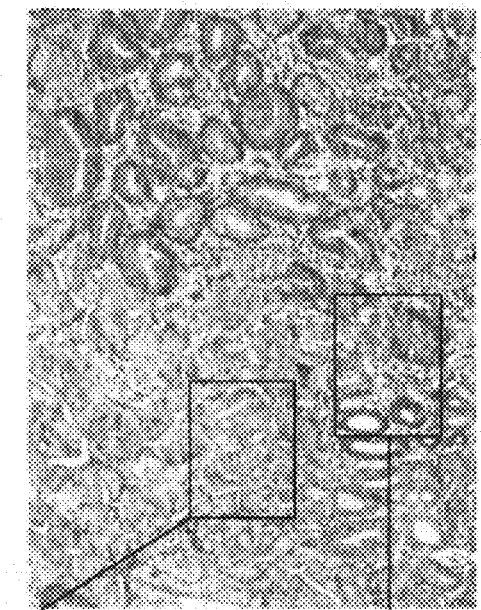

FIGS. 6A-D show a histological section from a patient diagnosed with colon carcinoma stained using the staining procedure according to the present invention. FIG. 6D depicts the entire histological section; and FIGS. 6A-C depict magnification of certain fields of FIG. 6D according to the indicated arrows. Note that the pictures show a clear association between morphology and color.

FIGS. 7A-C show histological sections prepared from dimethylhydrazane-induced colon cancer animal model and stained with the novel staining protocol. FIG. 7A depicts regions corresponding to the morphologically normal phenotype; FIG. 7B depicts regions corresponding to the morphologically hyperplastic tissue; and FIG. 7C depicts regions corresponding to the morphologically dysplastic tissue.

Figure 8:
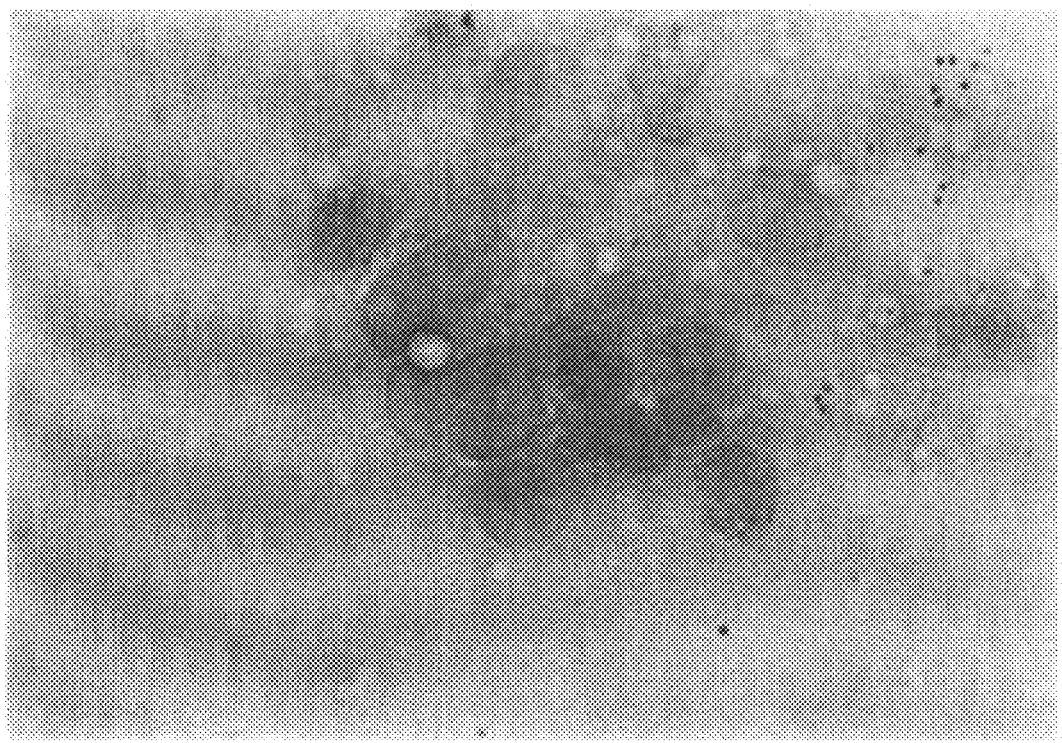

FIG. 8 shows a smear prepared from a female patient diagnosed, by means of histopathology, with ovary sarcoma, stained using the staining procedure according to the present invention.

FIGS. 9A-D show four pairs of histology sections. The right panel of each pair contains a slide stained with the staining procedure according to the present invention and the left panel shows a slide stained with the conventional Hematoxylin-Eosin technique. FIG. 9A depicts Cervix Carcinoma; FIGS. 9B and 9D depict Breast Carcinoma; and FIG. 9C depicts skin melanoma.

Figure 10:
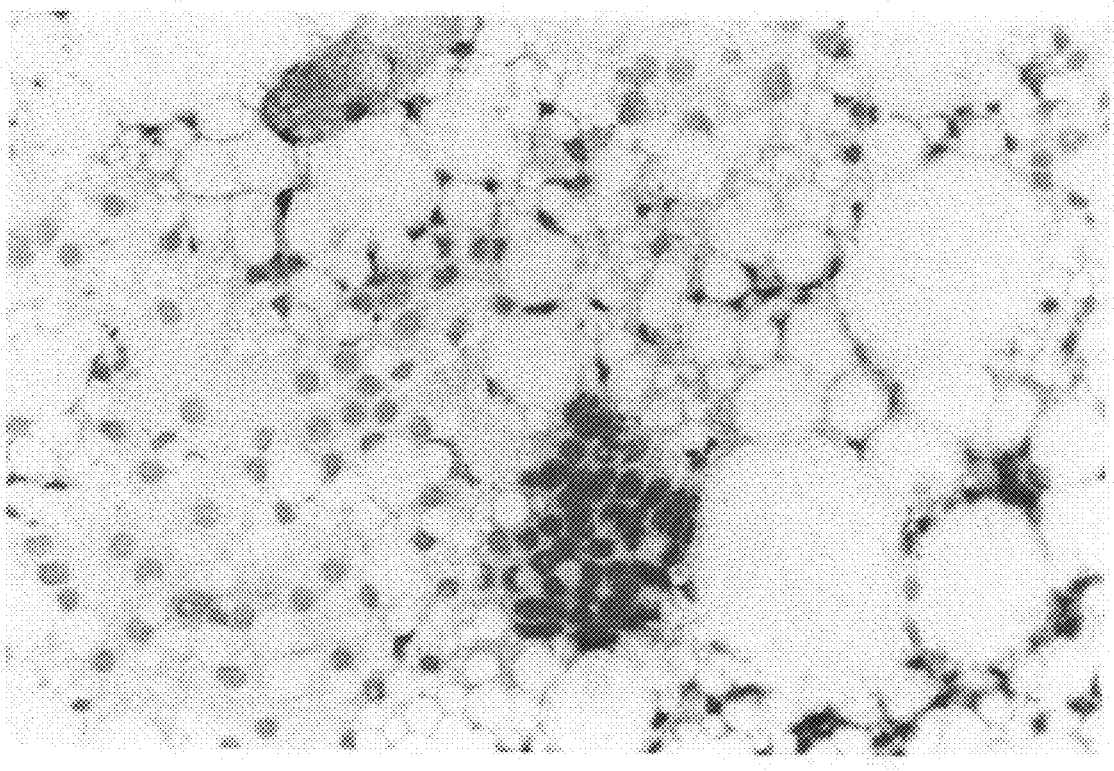

FIG. 10 shows a tumor imprint prepared from a sample of breast tissue containing carcinoma foci, stained using the staining procedure according to the present invention.

FIGS. 11A-H show Pap-smears from a woman diagnosed with High Grade Squamous Intraepithelial Lesion (HGSIL). FIGS. 11A-D show a slide stained with the conventional Papanicolaou stain, while FIGS. 11E-H show a slide from the same patient stained using the staining procedure according to the present invention.

FIGS. 12A-G show various pre-malignant and other conditions of clinical significance in cervical smears, stained using the staining procedures according to the present invention. FIG. 12A depicts normal smear; FIGS. 12B-C depict Atypical Squamous Cells of Undetermined Significance; FIGS. 12D-E depict Low Grade Squamous Intraepithelial Cells (LGSIL); and FIGS. 12F-G depict High Grade Squamous Intraepithelial Lesion (HGSIL).

FIGS. 13A-G show Pap smears stained using the staining procedure according to the present invention. Shown are cases in which the staining procedure according to the present invention yielded positive results as opposed to conventional diagnosis that yielded negative results. FIGS. 13A-B depicts a 41 years old, conventional Normal diagnosis; FIGS. 13C-D depicts a 52 years old, conventional Inflammation diagnosis; FIG. 13E depicts a 36 years old, conventional Inflammation diagnosis; FIG. 13F depicts a 52 years old, conventional Normal diagnosis; and FIG. 13G depicts a 54 years old, conventional Inflammation diagnosis.

Figures 14A, 14B, 14C:
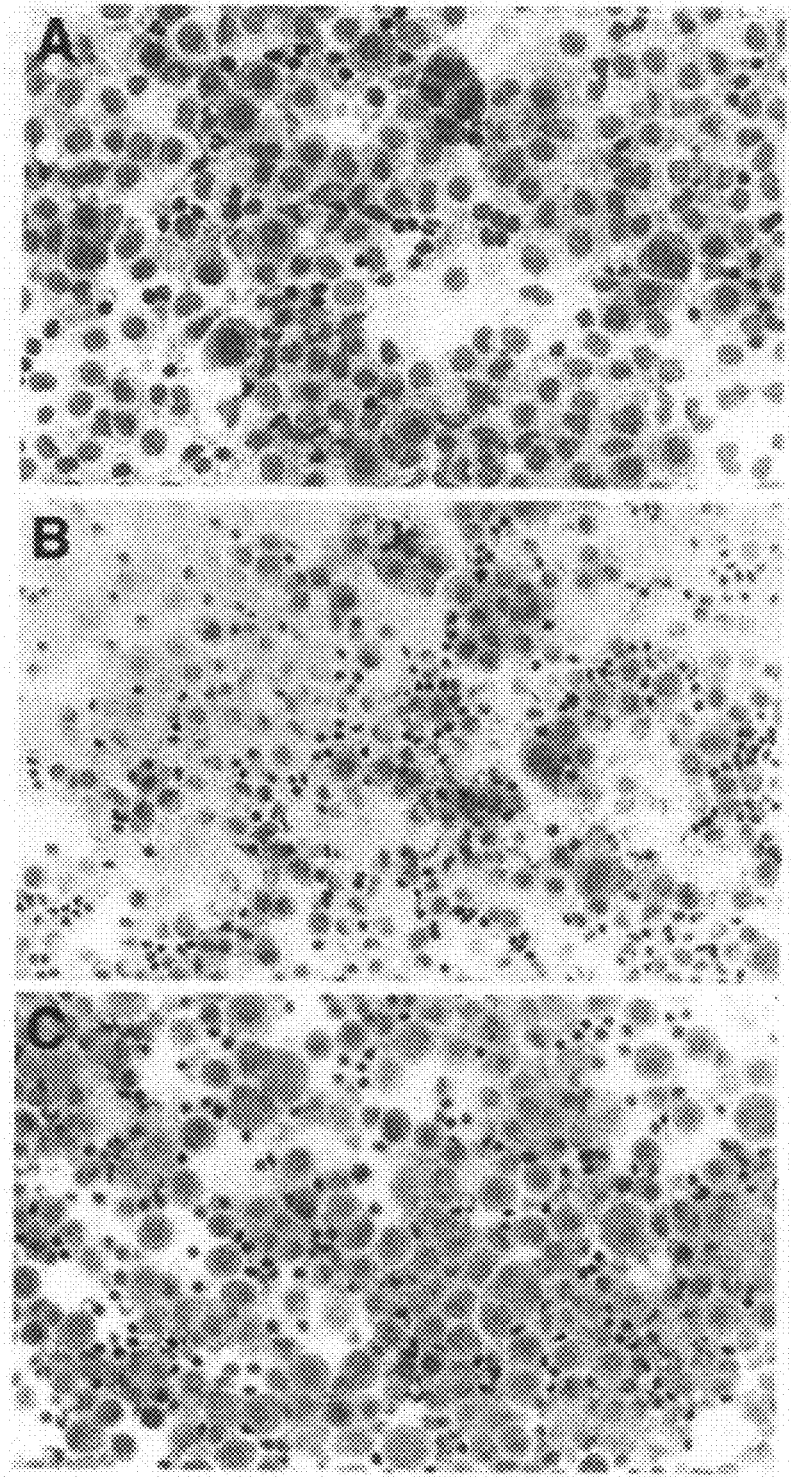

FIGS. 14A-C show air-dried cytospin smears prepared from pleural fluid of a 65 year old male patient diagnosed with breast cancer. FIG. 14A depicts May-Grunwald-Giemsa staining; and FIGS. 14B-C depict variations of the staining procedure according to the present invention.

FIGS. 15A-C show histology section staining of dimethylhydrazane-induced colon cancer in rat animal model. FIG. 15A depicts the full histology section and shows a mixed tissue that includes malignant and normal colon tissue together; FIG. 15B depicts magnification of FIG. 15A according to the indicated arrows; and FIG. 15C depicts normal colon tissue. Note that regions corresponding to the morphologically normal and malignant tissue are distinguishable by the green/red staining pattern, indicated by arrows.

FIGS. 16A-D show histology section staining of dimethylhydrazane-induced colon cancer in rat animal model. Note that the morphological differences between normal and malignant tissue are associated with changes in the color.

FIGS. 17A-B show histological section staining of a melanoma tumor FIG. 17A depicts staining according to the teachings of this invention; and FIG. 17B depicts staining by Hematoxylin-Eosin.

FIGS. 18A-C show Rat brain model with glioblastoma. FIG. 18A depicts tumor in full section of the brain staining by Giemsa; FIG. 18B depicts tumor in full section of the brain staining by Hematoxylin-Eosin; and FIG. 18C depicts tumor in full section of the brain staining by the novel staining protocol of the present invention. Note that only the staining protocol of this invention differentiated between tumor and normal tissue.

Figure 19B:
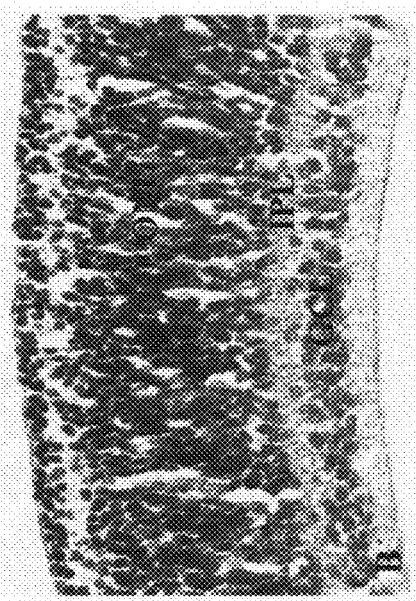
Figure 19D:
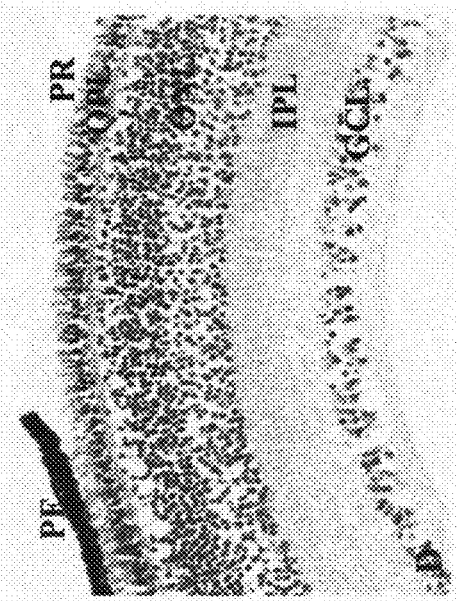
Figure 19A:
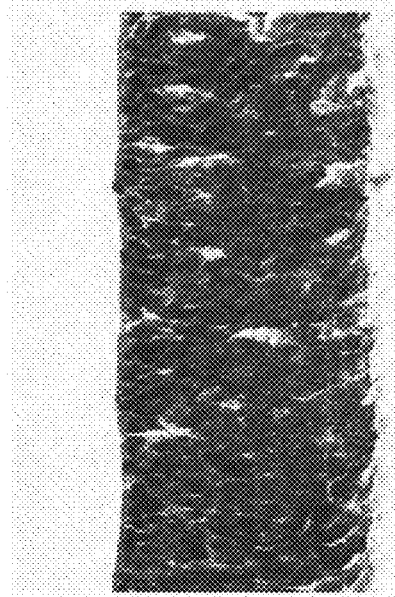
Figure 19C:
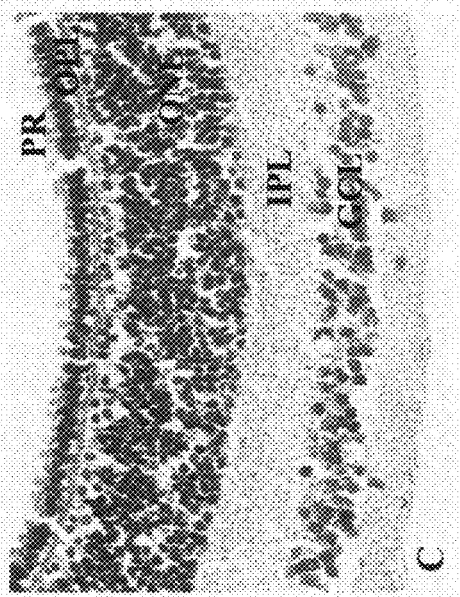

FIGS. 19A-D show changes in the staining during the normal physiological embryogenesis. Vertical sections of chick embryonic retina from different differentiation stages were dissected out of chick embryos. Paraffin blocks were prepared, cut and mounted on glass slides. The retina sections were stained according to the respective protocol. FIG. 19A depicts retina of 7 day embryo [stages 30-31 according to Hamburger & Hamilton (Hamburger and Hamilton, J. Morphol. (1951) 88:49-92)]; FIG. 19B depicts retina of 9 day embryo (differentiation stage 35); FIG. 19C depicts retina of 14 day embryo (differentiation stage 40); and FIG. 19D depicts retina of 18 day embryo (differentiation stage 44). Abbreviations: GCL=Ganglion Cell Layer, IPL=Inner Plexiform Layer, ONL=Outer nuclear Layer, OPL=Outer Plexiform Layer, PR=Photoreceptors, PE=Pigmented Epithelium.

FIGS. 20A-C show differential staining of normal and adenocarcinoma cells. FIG. 20A depicts normal primary colonocytes (CCD-33C0) which were plated in chamber slides; FIG. 20B depicts macroscopic images of 4 wells (in 384 well plate) plated with normal colonocytes (CCD-33C0) on the left panels or colon cancer cells (HT-29) on the right panels; and FIG. 20C depicts human colorectal adenocarcinoma cell line HT-29 which were plated in chamber slides. At the end of the plating period the air-dried specimens were stained.

Figure 21:
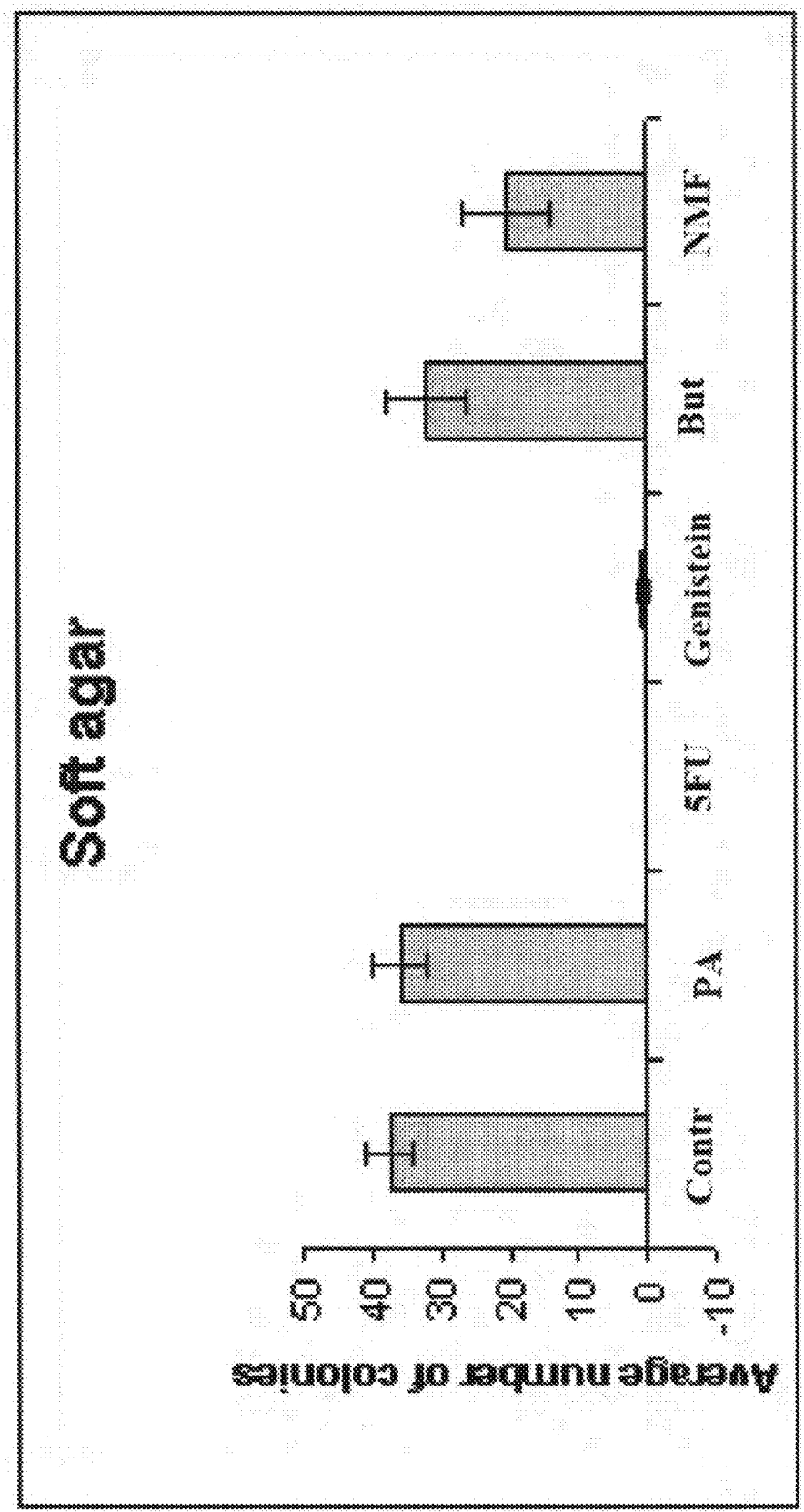

FIG. 21 shows anchorage-independent growth of HT-29 cells after pre-treatment with reference chemical compounds. HT-29 cells were incubated for three days with medium alone (Contr), 30 micro M Phytic acid (PA), 10 micro M 5 FU, 100 micro M Genistein, 5 mM Butyrate (But), or 30 micro M N-methylformamide (NNE) according to the soft agar protocol.

FIGS. 22A-D show the phenotype drug screening result in HT-29 (human colon carcinoma cells). FIG. 22A depicts HT-29 cells plated in 384 well plate; FIG. 22B depicts untreated HT-29 cells; FIG. 22C depicts HT-29 cells treated with 2.5 mM Sodium Butyrate; and FIG. 22D depicts HT-29 cells treated with 5 mM Sodium Butyrate. The phenotypic changes were detected by means of dose depend, gradual color changes from red (malignant) to blue/green (normal).

FIGS. 23A-C show the phenotype drug screening result in HT-29 (human colon carcinoma cells). FIG. 23A depicts HT-29 cells untreated, treated with 2.5 mM or 5 mM Sodium Butyrate visualized under a microscope; and FIGS. 23B-C depict optical density of cells as was measured in a spectrophotometer The ratio between absorbance at 560 nm (red) to 630 nm (green) was calculated.

FIGS. 24A-C show the effect of Genistein on HT-29 cell staining. HT-29 cells were plated in 96 well plates for one day, treated with 0-120 micro M Genistein, air fixed and stained. FIG. 24A depicts dose-dependent change of the staining; FIG. 24B depicts quantification of the staining type and was performed using the ratio (R) of NF/LG (OD 560 to OD 630). This ratio corresponds to the Red and Green balance in the well. Normal cells were stained green with R less than 1, malignant cells were stained red exhibited R higher than 1; and FIG. 24C depicts the effect of Genistein on the number of cells.

Figure 25:
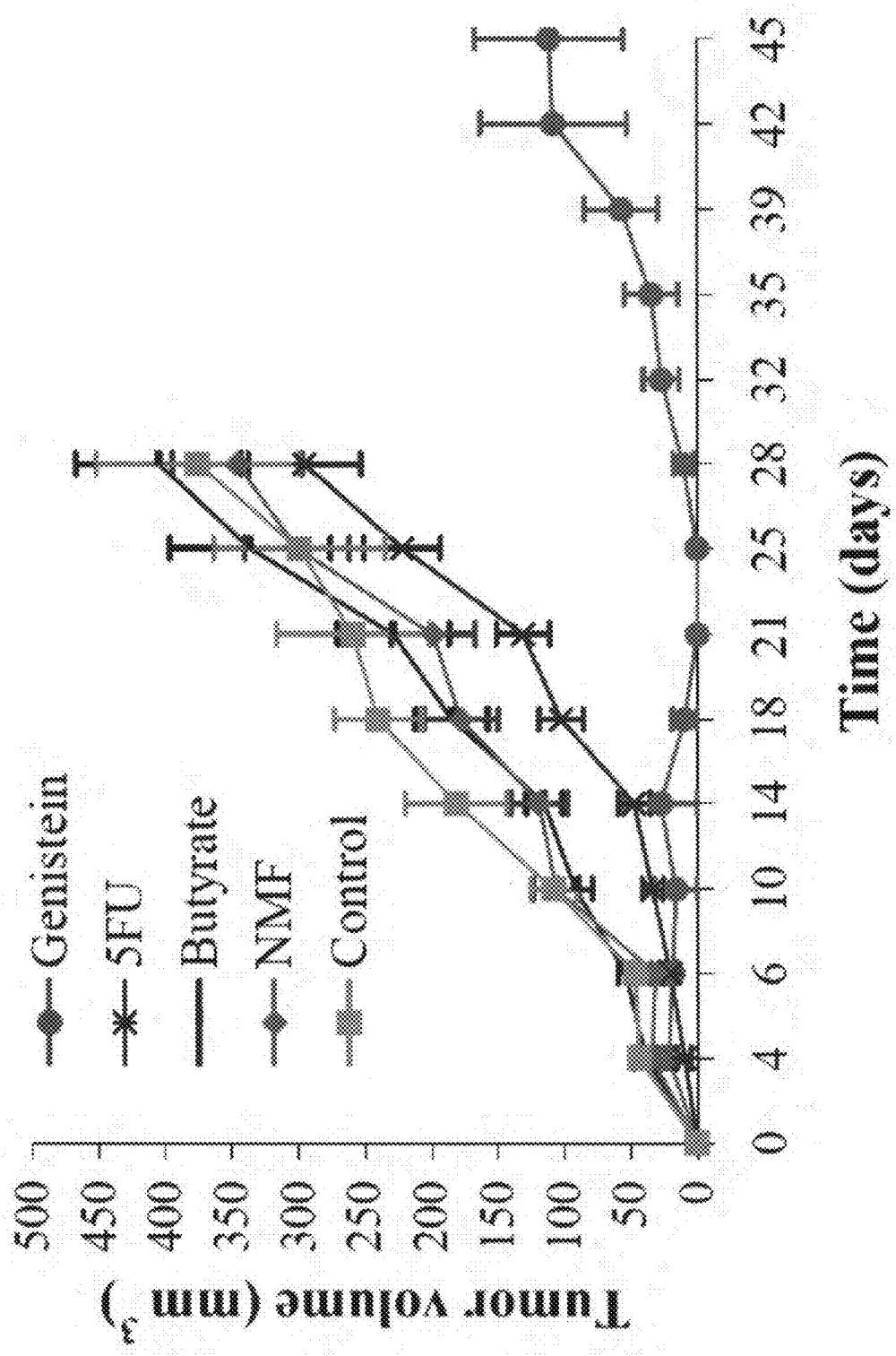

FIG. 25 shows the effect of the cell treatment on the tumorgenicity of HT-29 cells in Nude mice. The experiment was completed according to the Nude mice experimental protocol explained in detail in the materials and experimental procedures section hereinbelow.

FIGS. 26A-E show Butyrate-induced transient phenotype change of HT-29 cells. HT-29 cells were treated by 5 mM Butyrate for 4 days. At the end of the treatment period, growth medium with butyrate was replaced with butyrate-free medium for 2, 3 or 4 days. Air-dried cells were stained according to protocol I. FIG. 26A depicts untreated control HT-29 cells; FIG. 26B depicts HT-29 cells treated by 5 mM Butyrate for 4 days; FIG. 26C depicts HT-29 cells which at the end of the treatment period were grown in butyrate-free medium for 2 days; FIG. 26D depicts HT-29 cells which at the end of the treatment period were grown in butyrate-free medium for 3 days; and FIG. 26E depicts HT-29 cells which at the end of the treatment period were grown in butyrate-free medium for 4 days. Note the transient nature of the staining type change that is in the correlation with the soft agar results (FIG. 21).

FIGS. 27A-B show high throughput screening (HTS) results. FIG. 27A depicts HT-29 cells which were plated in 384 well plates and treated with different compounds. Sodium butyrate was used as the positive control and media alone (no treatment) served as the negative control. Staining of the cells indicated the visual difference between positive and negative controls and the visualization of a positively active compound (Hit); and FIG. 27B depicts dose dependency of active compounds detected earlier in a screen. Compound activity was measure from a concentration of 30 µM and descending.

Figure 28:
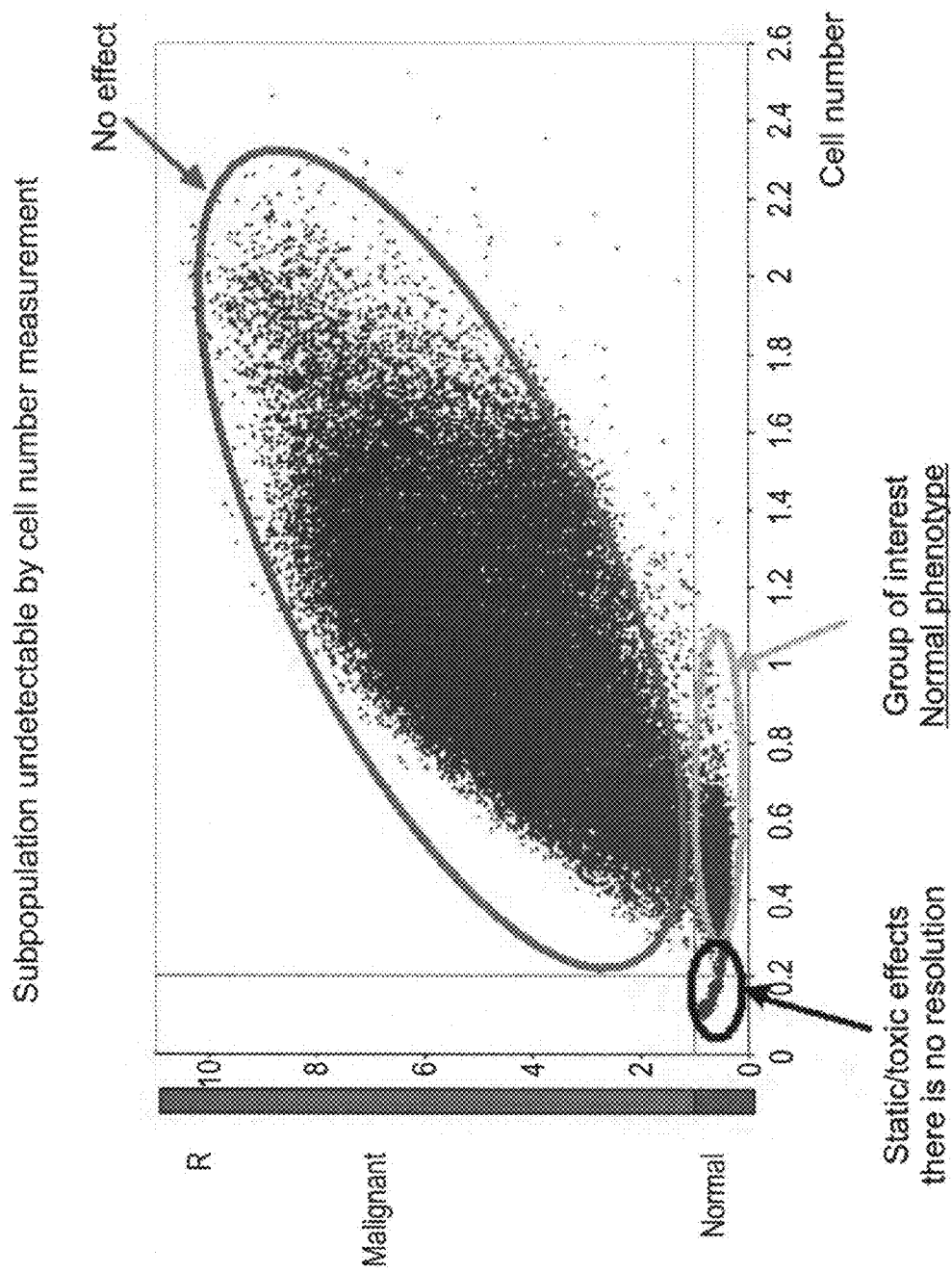

FIG. 28 shows high throughput screening (HTS) results. HT-29 cells were plated in 384 well plates and treated with drug-like chemical library (ChemBridge Corporation) at 30 micro M concentrations. At the end of this process air dried plates were stained using protocol III. The screen gave rise to three distinct archetypes of responses: Toxic/static effect (marked black), change of phenotype (based on the Red-to-Green color change, normal phenotype, marked turquoise) and no obvious change of phenotype (Red staining, marked red). Staining results were registered using optical density measurement (OD 560 and OD 630) in each well by multiwell scanner. Quantification of the staining type was performed using the ratio (R) of NF/LG (OD 560 to OD 630). This ratio corresponded to the Red and Green balance in the well. The group of interest stained green and exhibited R less than 1 and cell number index higher than 0.2. Malignant cells stained red regardless cell number index.

Figure 29:
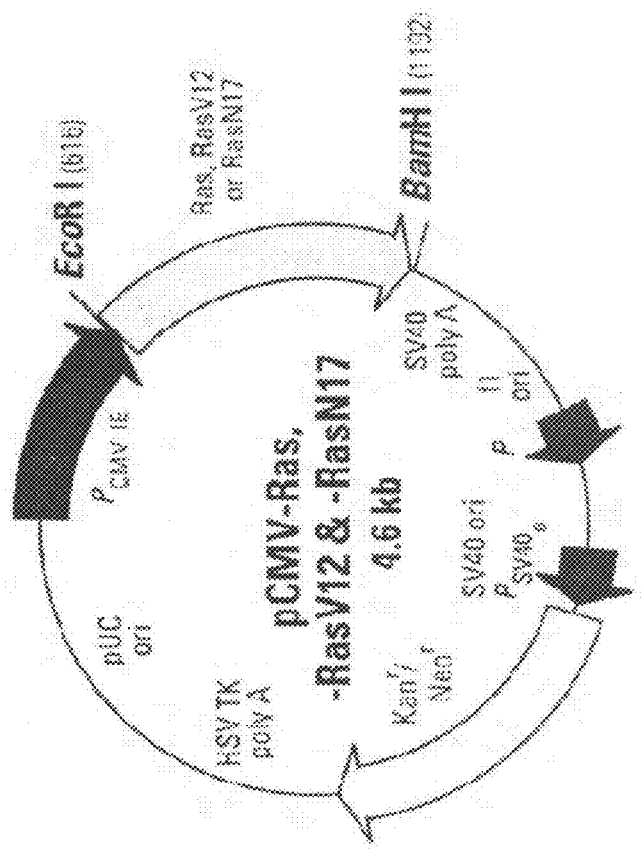

FIG. 29 shows constructs design. PCMV-Ras Vector (wild type Ha-Ras protein) and PCMV-Ras V12 Vector (active form of Ras) were purchased from Clontech.

Figure 30B:
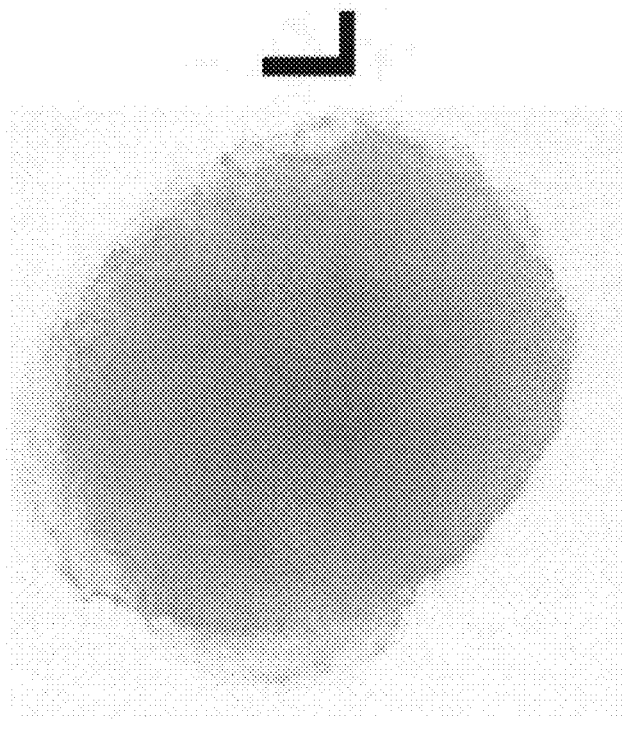
Figure 30A:
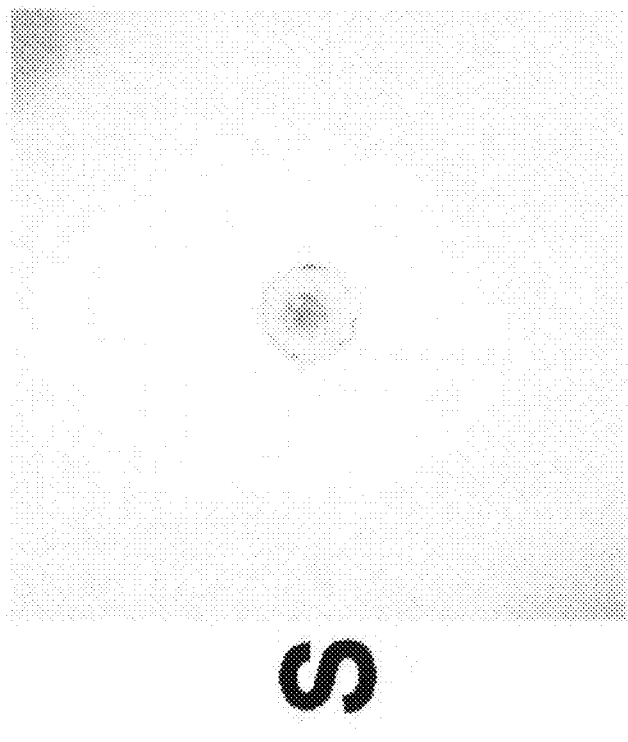

FIGS. 30A-B show anchorage-independent growth in soft agar. Stable Ras-expressing Rat2 clones were established characterized and plated into soft agar according to the protocols (see materials and experimental procedures section hereinbelow and Table 13). At the end of three week incubation period, the colonies were counted. FIG. 30A depicts empty vector (Vec) or Wild type of Ras (Ras Vec) which induced small colonies formation (S); and FIG. 30B depicts expression of transforming/oncogenic form of Ras (Ras V12) which induced large colonies formation (L).

Figures 31A, 31B, 31C, 31D:
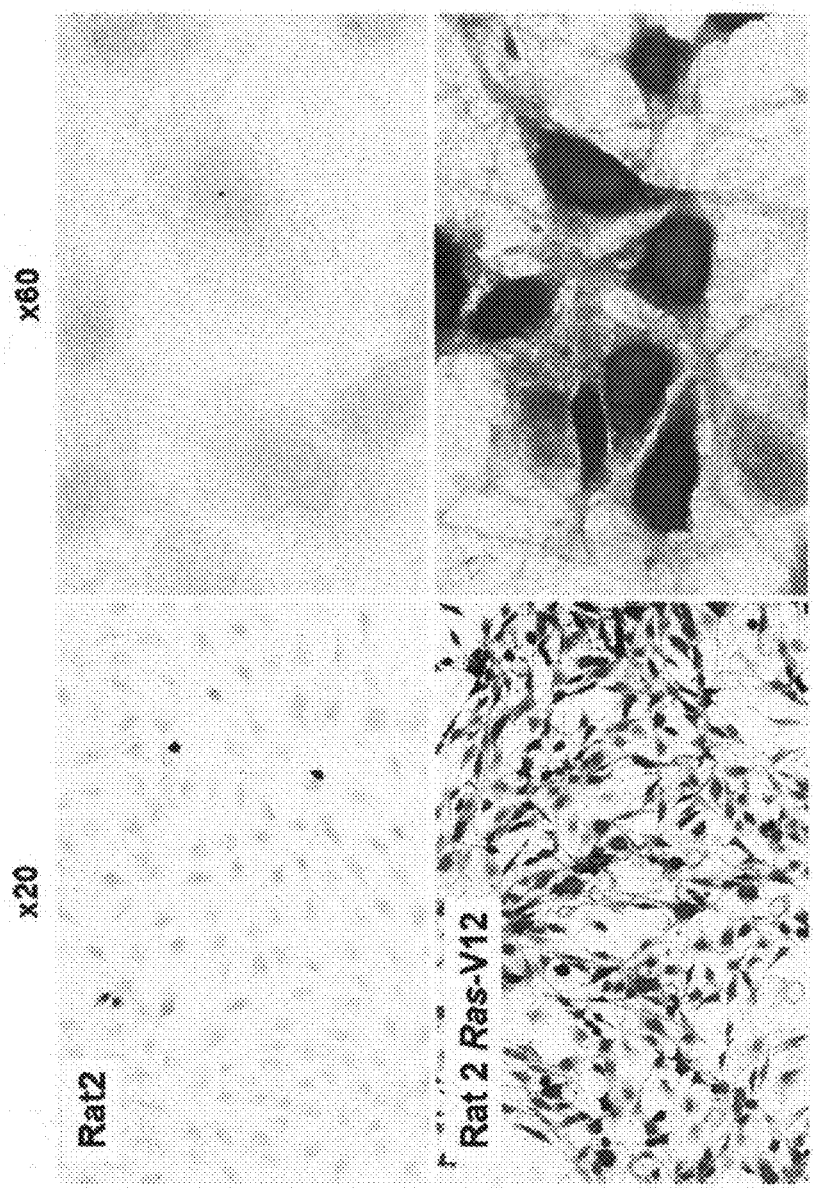

FIGS. 31A-D show the effect of Ras V12-induced transformation on the staining type. FIGS. 31A-B depict Rat2 cells plated and stained on microscopic cover slips (magnified by ×20 and ×60, respectively); and FIGS. 31C-D depict Rat2 Ras V12 cells plated and stained on microscopic cover slips (magnified by ×20 and ×60, respectively). At the end of the plating period the air-dried specimens were stained according to Protocol IV.

FIGS. 32A-D show the effect of Ras V12 oncogene signaling inhibition on the staining type. FIGS. 32A-B depict Rat2 Ras V12 cells incubated without treatment (magnified by ×20 and ×60, respectively); and FIGS. 32C-D depict Rat2 Ras V12 cells incubated with 50 micro M PD98059 (MAPKK inhibitor) for 3 days (magnified by ×20 and ×60, respectively). Note that the phenotype change was observed (cell spreading and contact inhibition restoration) as well as cellular staining (Red-to-Green staining).

FIGS. 33A-E show the Ras/MAPK pathway phenotype drug screening in Rat1 Ras and Rat1 cells treated by different concentrations of signaling pathway inhibitors. FIG. 33A depicts the phenotype of Rat1 Ras and Rat1 cells untreated and treated by PD98059; FIG. 33B depicts Rat1 Ras and Rat1 cells treated by farnesylation inhibitor (HR12); FIG. 33C depicts Rat1 Ras and Rat1 cells treated by MAPK inhibitor (PD98059); FIG. 33D depicts Rat1 Ras and Rat1 cells treated by Genistein (tyrosine phosphorylation inhibitor); and FIG. 33E depicts Rat1 Ras and Rat1 cells treated by LY294002 (PI3 kinase inhibitor).

FIGS. 34A-C show K562 erythroleukemic cells differentiation induced by Gleevec and its effect on staining and hemoglobin production. FIG. 34A depicts K562 untreated cells; FIG. 34B depicts K562 cells treated with 0.25 µM Gleevec (according to the protocol); and FIG. 34C depicts detection of hemoglobin production. K562 cells were treated with 0.25 µM or 1.25 µM Gleevec (according to the protocol), hemoglobin production was determined by Benzidine assay. Note that as a result of the differentiation, Red-to-Green staining type change has been detected. Gleevec-induced differentiation was supported by the dose-dependent increase in hemoglobin production.

FIGS. 35A-B show the differentiation induced by different doses of Gleevec and its effect on staining, cell number and hemoglobin production. FIG. 35A depicts K562 cell number and hemoglobin production following treatment with 0-1 µM Gleevec (according to the protocol); and FIG. 35B depicts K562 cell phenotype following treatment with 0-0.1 µM Gleevec. Note that the staining assay exhibits the sensitivity at the low nano molar range, where there is no effect on the hemoglobin production or cell number.

Figures 36A, 36B:
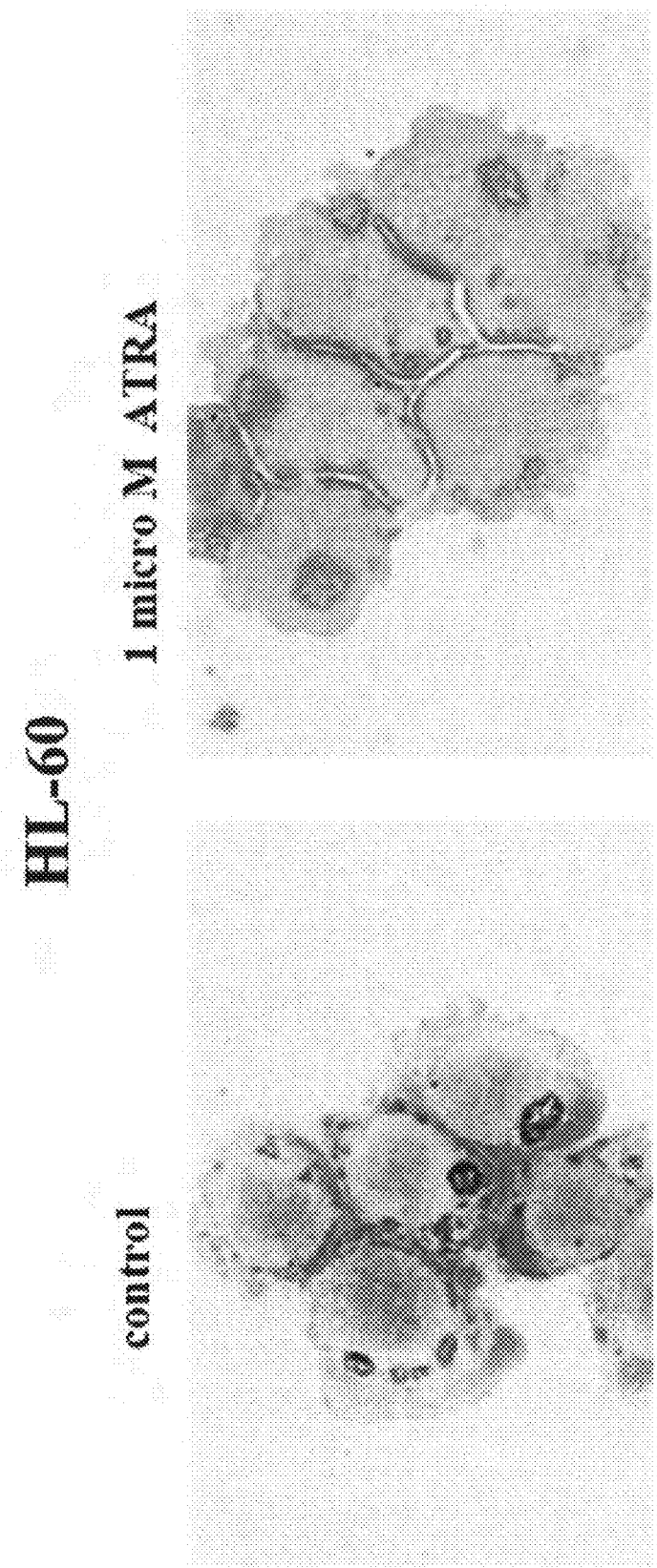

FIGS. 36A-B show all-trans-retinoic acid (ATRA)-induced differentiation of HL-60 cells (human acute myeloid leukemia cell line). FIG. 36A depicts untreated HL-60 cells; and FIG. 36B depicts HL-60 cells which were triggered to differentiate by 1 µM ATRA for 3 days.

FIGS. 37A-C show IFN-gamma-induced differentiation of U937 cells (monocytic leukemia/histiocytic lymphoma cell line). FIG. 37A depicts untreated, malignant U937 cells; FIG. 37B depicts U937 cells treated for 4 days with 2000 U/ml recombinant human IFN-gamma; and FIG. 37C depicts U937 cells treated for 4 days with 10000 U/ml recombinant human IFN-gamma. Nitrobluetetrazolium test (NBT) was performed as a biochemical marker detecting the differentiation of U937 cells. Note the dose-dependent increase in the biochemical marker of differentiation.

FIGS. 38A-H show IFN-gamma or sodium butyrate (NaBu) induced differentiation of U937 cells. FIGS. 38A-B depict untreated, malignant U937 cells (magnified by ×10 and ×40, respectively); FIGS. 38C-D depict U937 cells treated for 4 days with 1 mM NaBu (magnified by ×10 and ×40, respectively); FIGS. 38E-F depict U937 cells treated for 4 days with 2000 U/ml recombinant human IFN-gamma (magnified by ×10 and ×40, respectively); and FIGS. 38G-H depict U937 cells treated for 4 days with 10000 U/ml recombinant human IFN-gamma (magnified by ×10 and ×40, respectively). CamaRx staining was performed.

FIG. 39 shows the potential of the phenotype drug screening method. The experiment was performed in HPV 16 immortalized human keratinocytes, treated with different inhibitors as indicated in the Table. Note that AG494 is a chemical modification of AG555.

Figure 40:
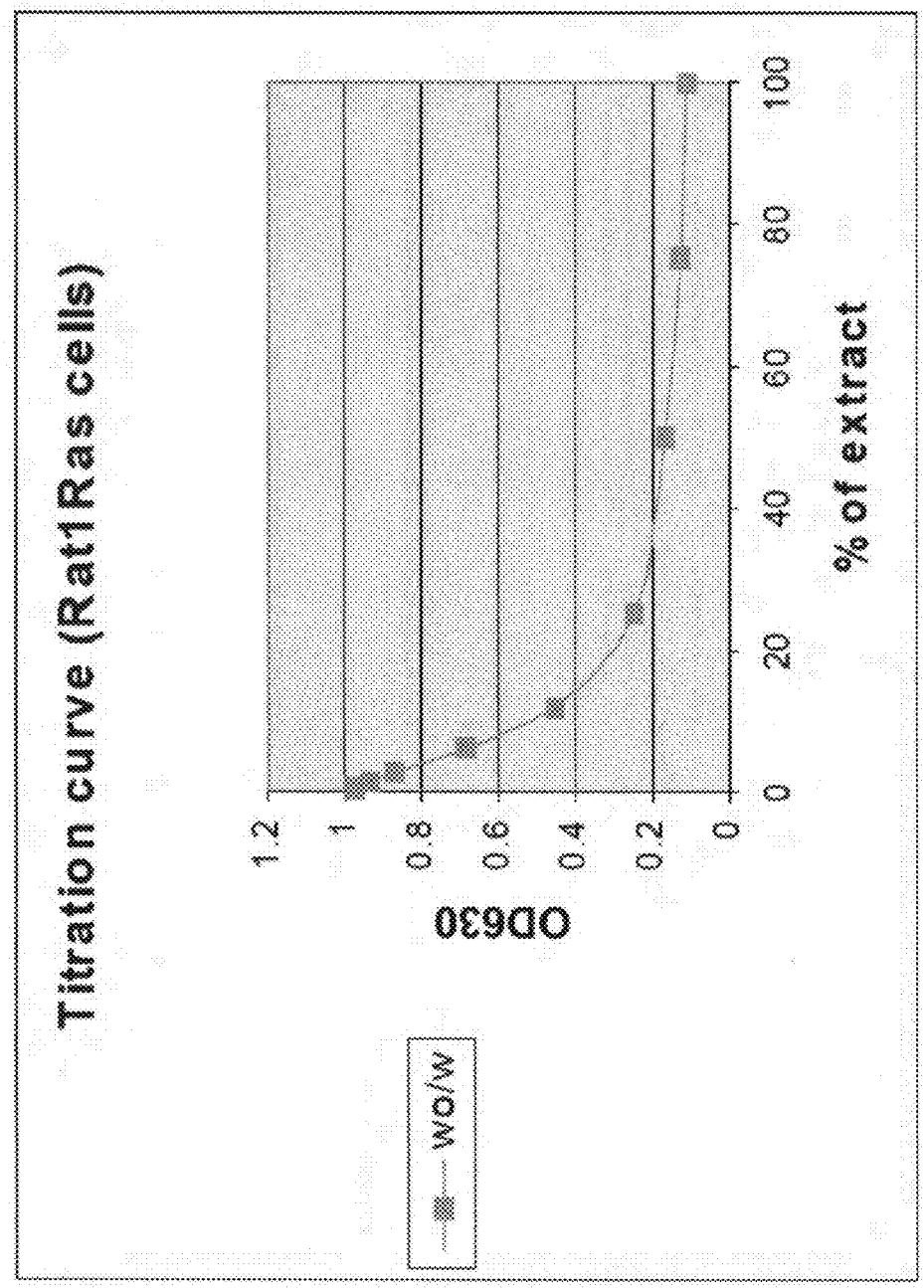

FIG. 40 shows the concentration-dependent inhibition of staining by extract. Rat1 Ras V12 cells were stained according to LG rapid assay (protocol VIII). The extract dilution was performed in 70% EtOH. The staining intensity was quantified by an ELISA reader with 630 nm filter. Note the concentration-dependent gradual decrease in inhibition potency of the extract.

Figure 41:
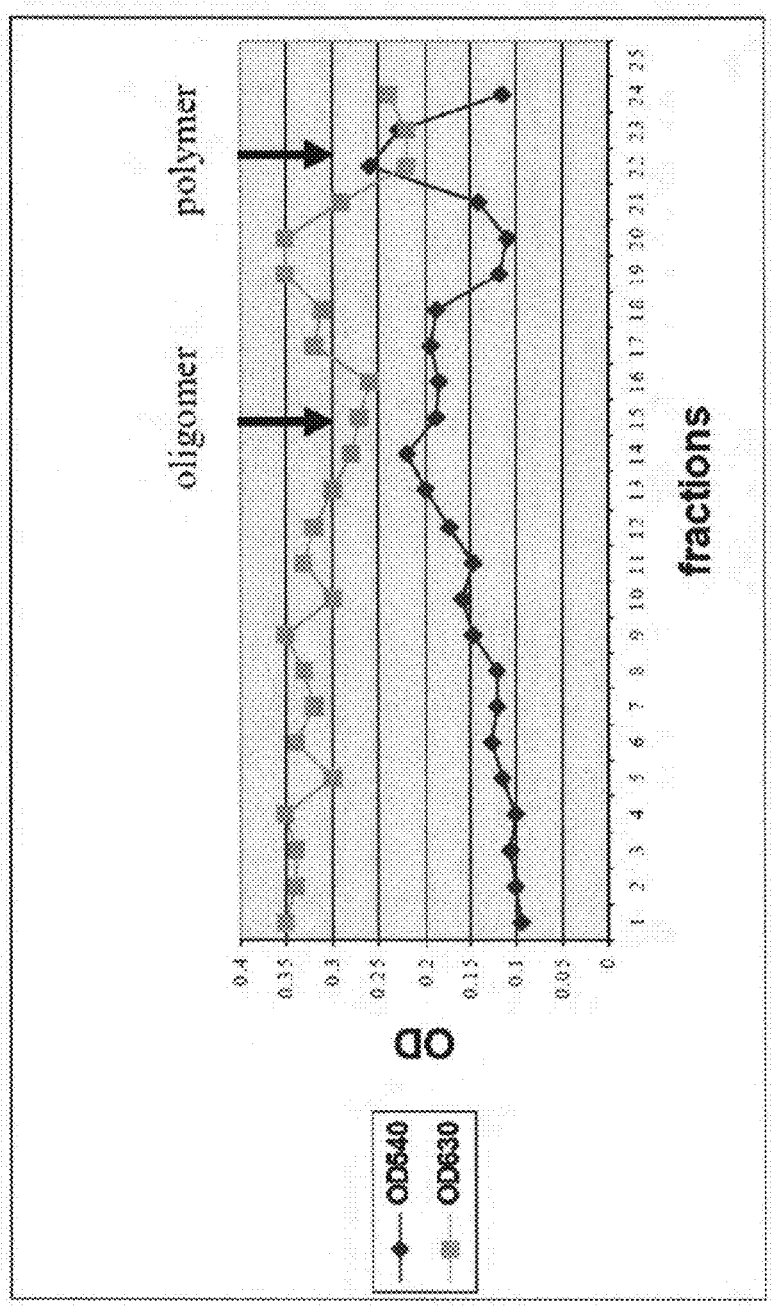

FIG. 41 shows the biological effect of Sephadex LH-20-purified crude extract fractions on LG inhibition in Rat2-RasV12 cells. Note the correlation between staining modulation and the amount of proanthocyanidins.

Figure 42:
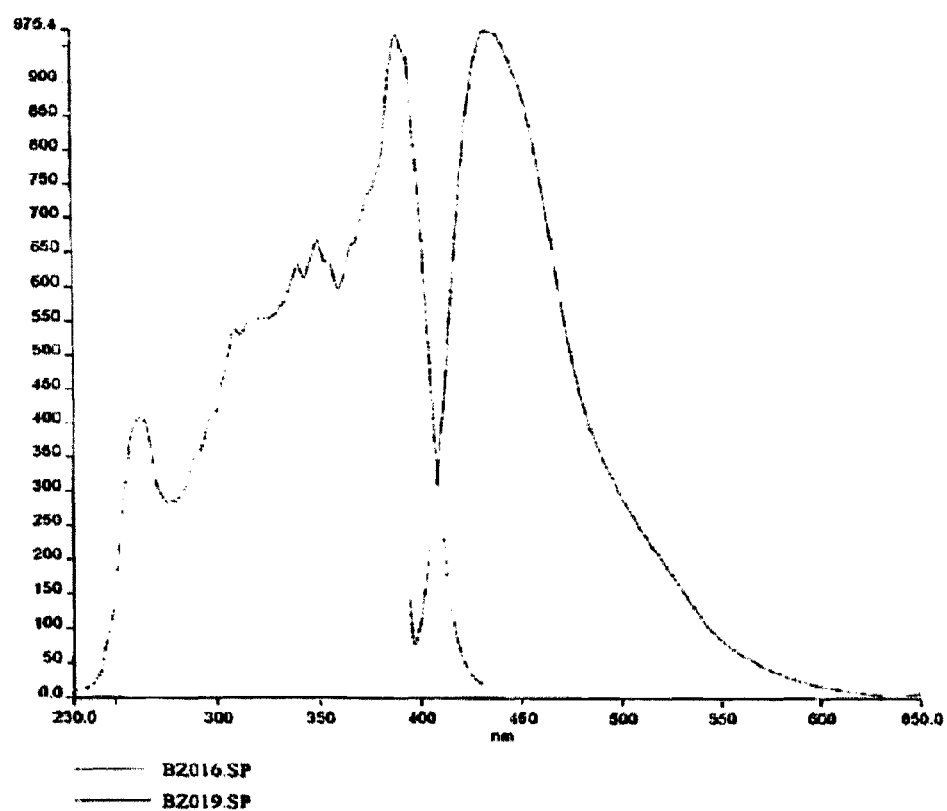

FIG. 42 shows the fluorescence fingerprint of extract activity (CST 2001) in acetic acid.

Figure 43:
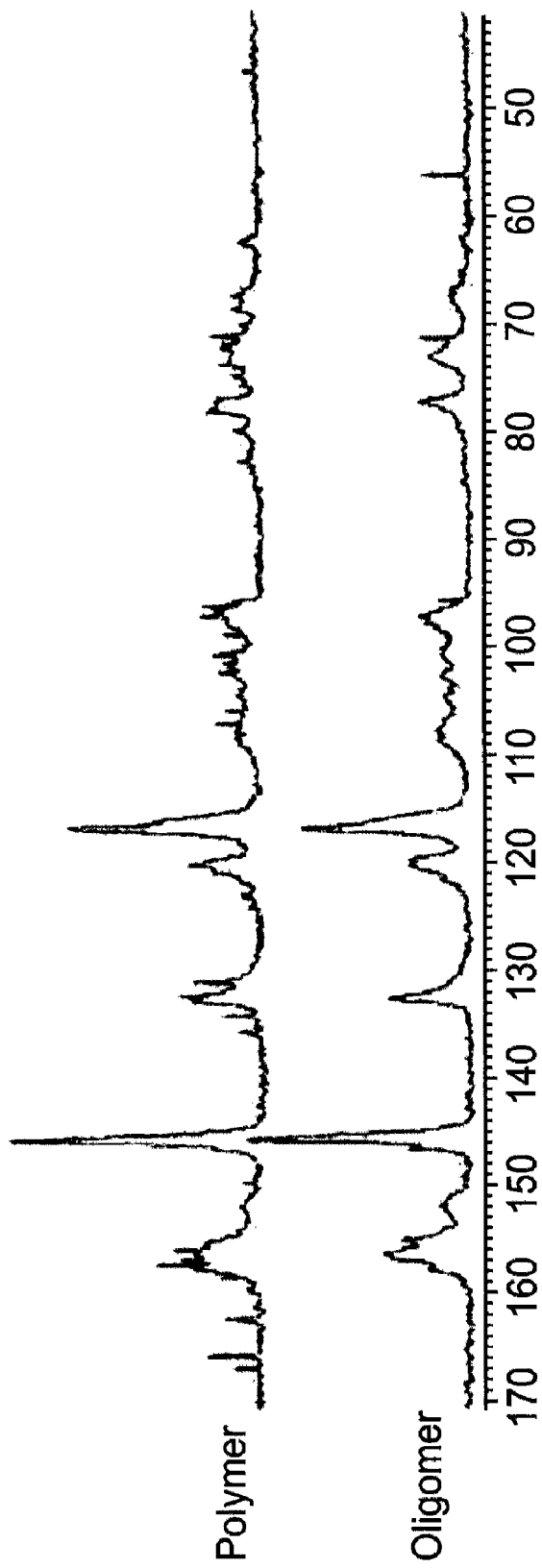

FIG. 43 shows NMR fingerprints of CST 2001 polymer and oligomer fractions.

Figure 44:
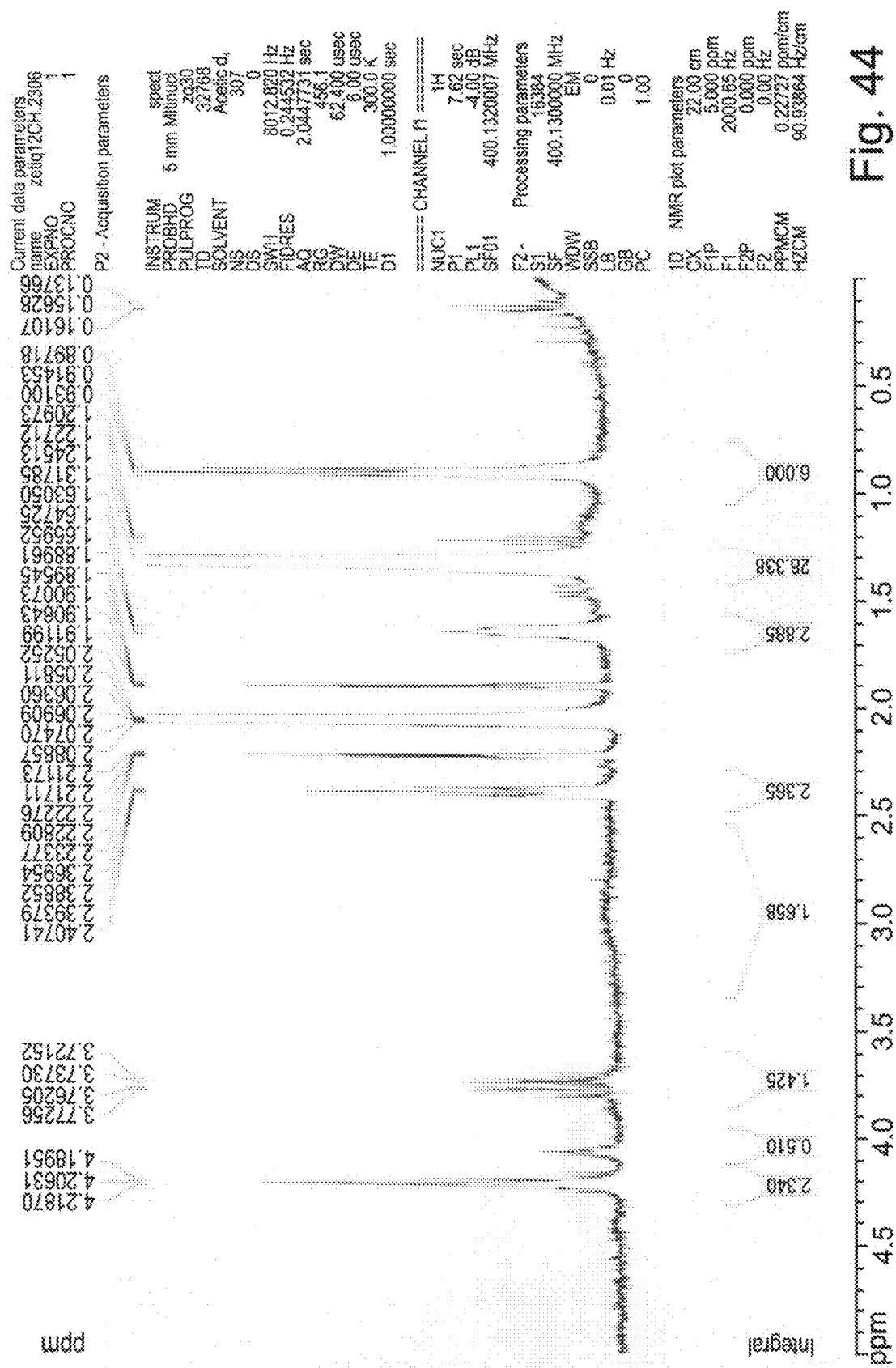

FIG. 44 shows NMR fingerprint of CST 2001.

Figure 45:
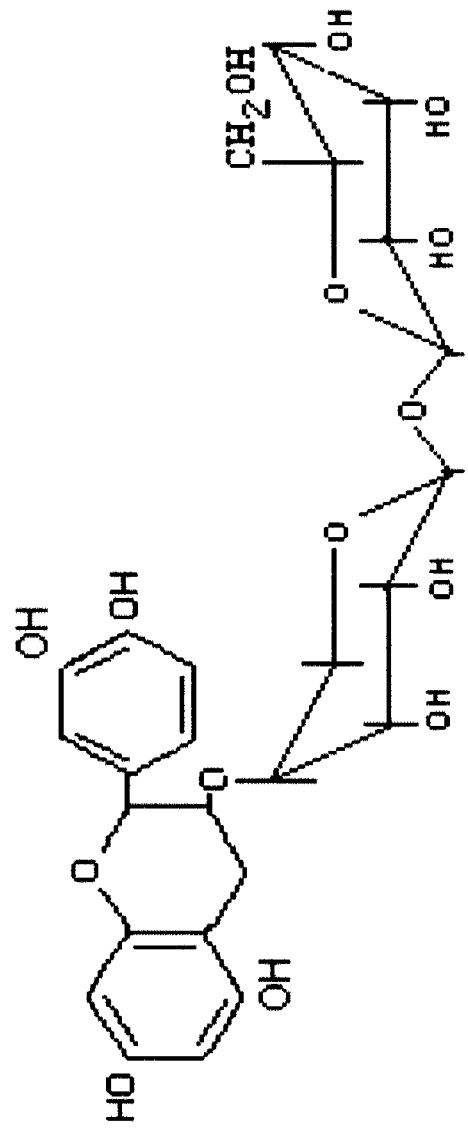

FIG. 45 shows chemical structure of oligomeric form of CST 2001.

Figure 46:
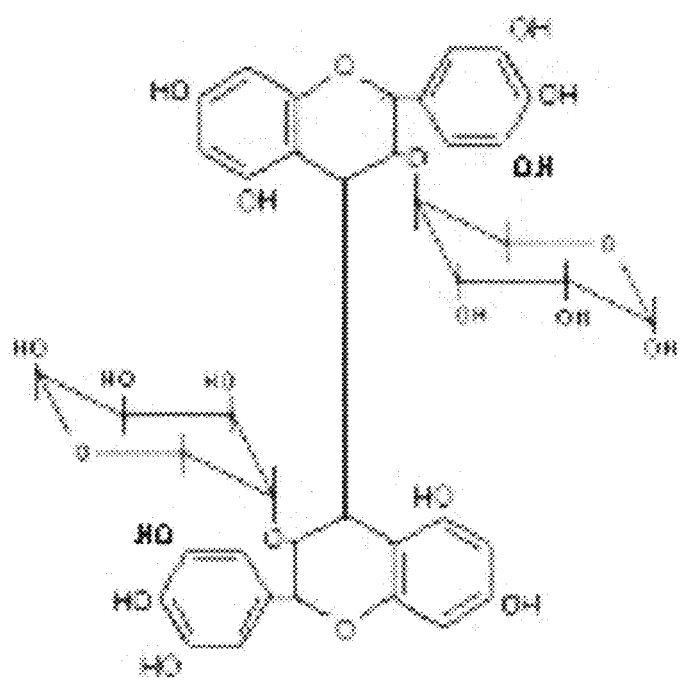

FIG. 46 shows chemical structure of alternative oligomeric form of CST 2001.

Figures 47A, 47B, 47C:
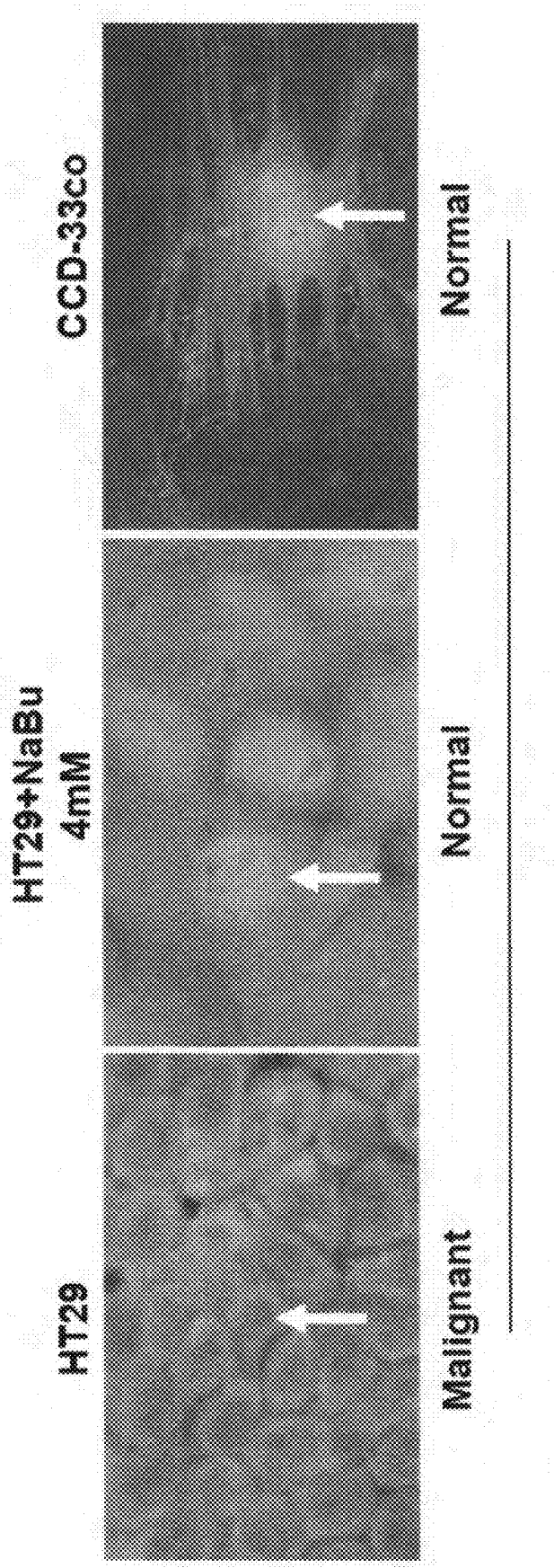

FIGS. 47A-C show the differential interaction of crude plant extract with malignant and normal cells. FIG. 47A depicts HT-29 cells which represent malignant cellular phenotype; FIG. 47B depicts HT-29 cells treated with 4 mM sodium butyrate which exhibit normal phenotype; and FIG. 47C depicts primary colonocytes (CCD-33CO) which exhibit normal phenotype. Cells were stained according to protocol IX and fluorescence detection was performed using an Olympus microscope equipped with the digital image processing work station. Note the difference in the intensity of nuclear staining. Malignant nuclei tend to be less stained compared to normal cell's nuclei.

FIGS. 48A-F show differential interaction of CST 2001 with human breast carcinoma (MCF-7) cells. FIG. 48A depicts MCF-7 untreated cells incubated in 70% ethanol as solvent control; FIGS. 48B and 48C depict untreated MCF-7 cells (magnified by ×20 and ×60, respectively); FIG. 48D depicts MCF-7 treated cells (with Butyrate) incubated in 70% ethanol as solvent control; and FIGS. 48E and 48F depict MCF-7 treated with 2.5 mM of sodium butyrate (magnified by ×20 and ×60, respectively). Note that MCF-7 untreated cells represented phenotypically malignant cells while Butyrate-treated MCF-7 cells represented phenotypically normal cells. Nucleus from the phenotypically normal cells stained stronger with CST 2001 than the respective malignant counterpart.

FIGS. 49A-C show the differential interaction of CST 2001 with human colon cells. FIG. 49A depicts malignant, human colon carcinoma (HT-29) cells (Control, phenotypically malignant); FIG. 49B depicts HT-29 cells treated with 4 mM sodium butyrate (Butyrate, phenotypically normal); and FIG. 49C depicts normal primary colonocytes (Normal primary cells, phenotypically normal). The panels presented below show magnifications as indicated by the arrows. Note that nucleus from the phenotypically normal cells stained stronger with CST 2001 than the respective malignant counterpart.

Figure 50A:
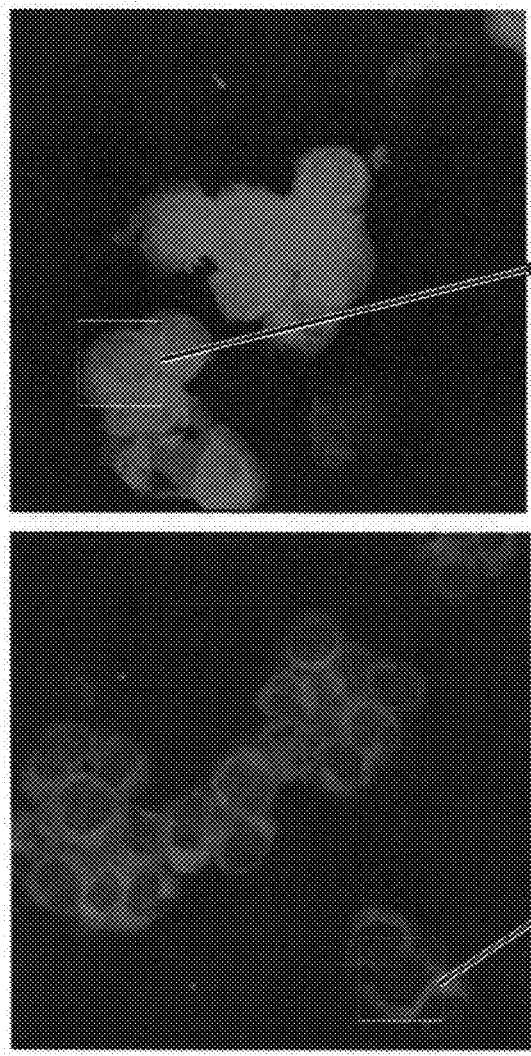
Figure 50B:
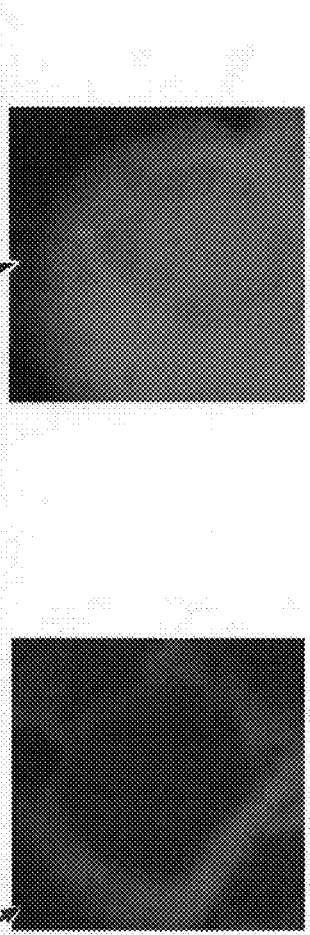

FIGS. 50A-B show differential interaction of CST 2001 with human leukemia K562 cell line. FIG. 50A depicts untreated K562 cells (phenotypically malignant); and FIG. 50B depicts K562 cells treated with 1 mM sodium butyrate (phenotypically normal). The panels presented below show magnifications as indicated by the arrows.

FIGS. 51A-B show differential interaction of CST 2001 with human leukemic HL-60 cell line. FIG. 51A depicts untreated HL-60 cells (phenotypically malignant); and FIG. 51B depicts HL-60 cells treated with 1 mM sodium butyrate (phenotypically normal). The panels presented below show magnifications as indicated by the arrows.

FIGS. 52A-C show differential interaction of CST 2001 in a Rat1 system. FIG. 52A depicts Rat1 fibroblasts (phenotypically normal); FIG. 52B depicts Ras V12-transformed Rat1 (Rat1-Ras V12) cells (phenotypically malignant); and FIG. 52C depicts Rat1-Ras cells treated with PD98059 (MAPKK specific inhibitor) blocking the malignant transformation initiated by Ras V12 (phenotypically normal). The panels presented below show magnifications as indicated by the arrows.

FIGS. 53A-B show differential interaction of CST 2001 (native) with living U937 leukemia cells. FIG. 53A depicts untreated U937 cells (control); and FIG. 53B depicts U937 cells treated with 1.5 µM ATRA for 72 hours to induce phenotype normalization. The CST 2001-originated fluorescence was detected by Olympus microscope equipped with the digital image processing work station.

Figure 54:
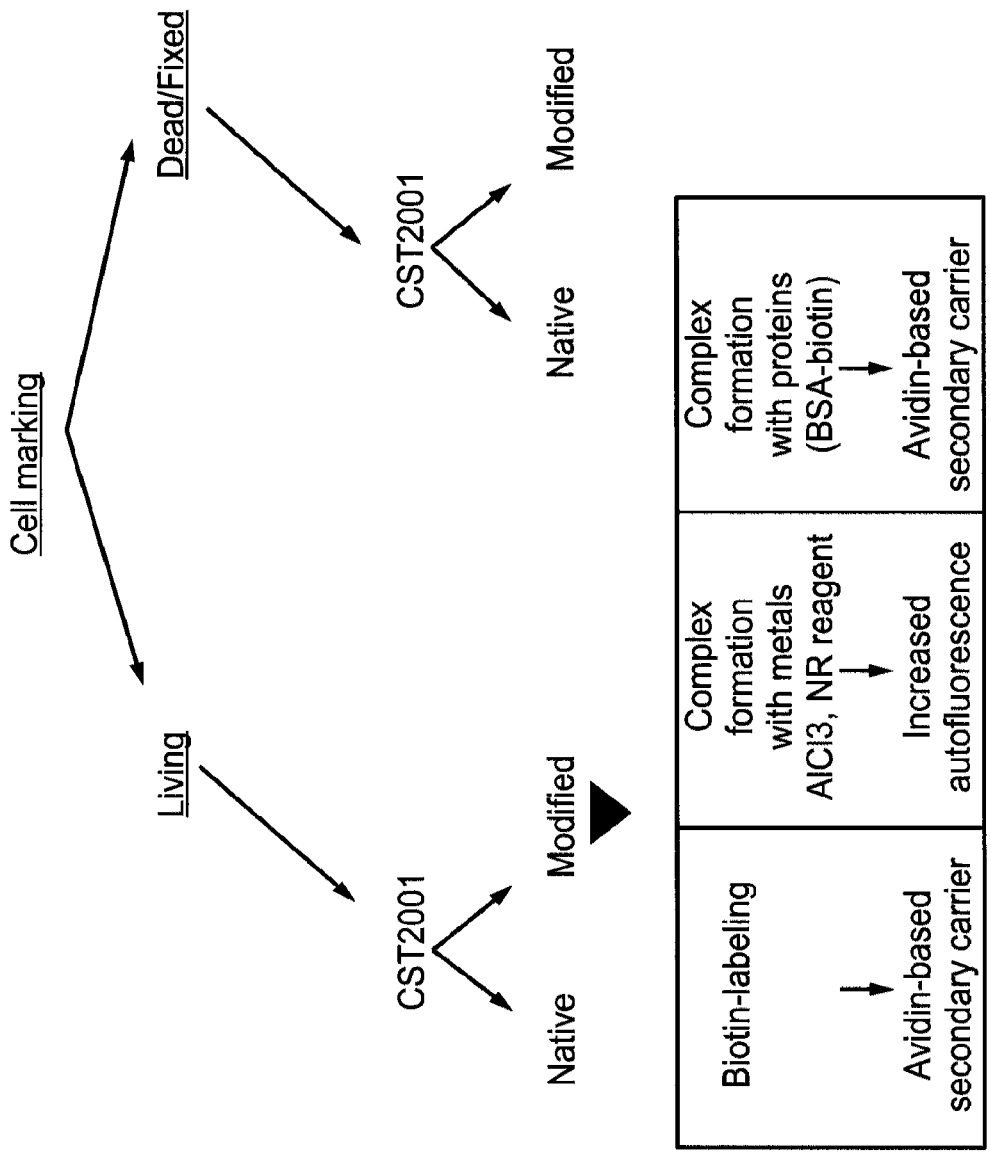

FIG. 54 shows a flow chart illustration of different possibilities for the CST-2001 labeling. Cells could be living or fixed and CST 2001 could be intact or modified. Limited numbers of CST 2001 modification options are described in the figure.

Figures 55A, 55B:
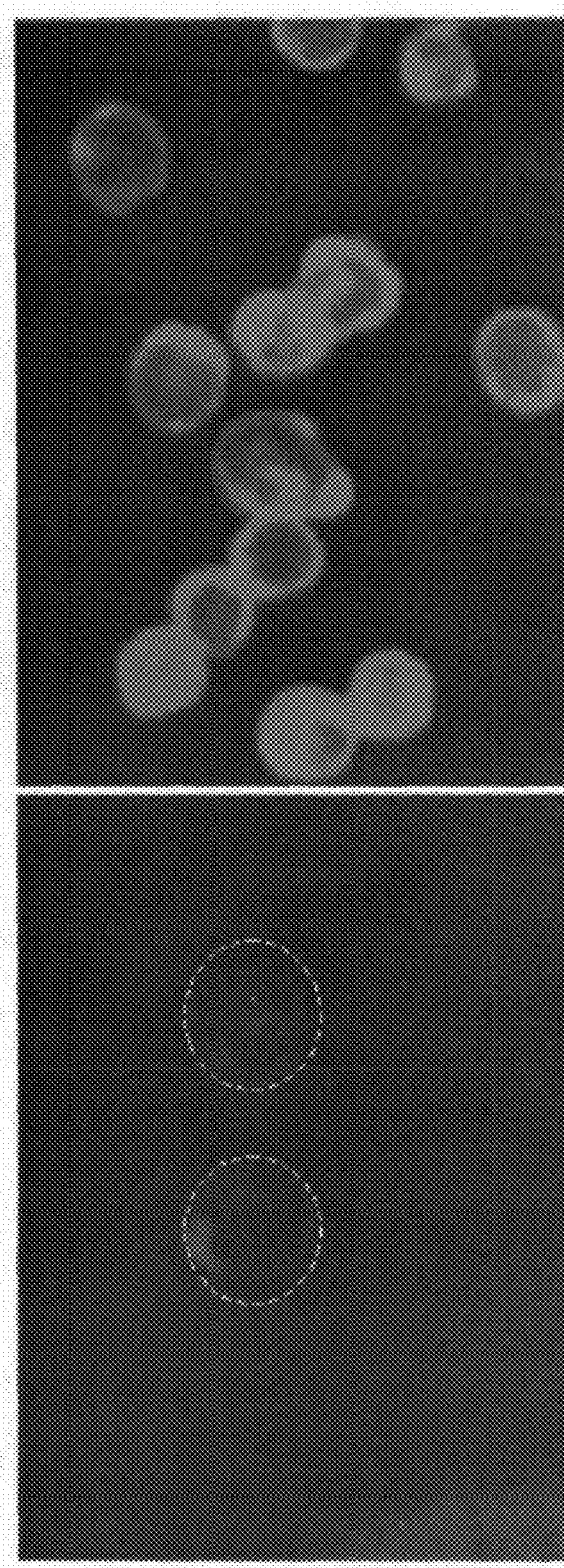

FIGS. 55A-B show biotinylated CST 2001 visualization in U937 leukemia cells. FIG. 55A depicts an example of native CST 2001 stained U937 cells; and FIG. 55B depicts an example of biotinylated CST 2001 stained U937 visualized with Streptavidin Cy3.

FIGS. 56A-C show a fluorescent signal of CST 2001 in complex with metals using Naturstoff reagent (NR) in U937 cells. FIG. 56A depicts fluorescent signal of U937 cells originated from PBS; FIG. 56B depicts fluorescent signal of U937 cells originated from CST 2001; and FIG. 56C depicts fluorescent signal of U937 cells originated from CST 2001 in complex with NR. The results were detected by FACS (Fluorescence-activated cell sorter). Mean fluorescent intensity of the major peaks is indicated in the graphs below each figure.

Figure 57:
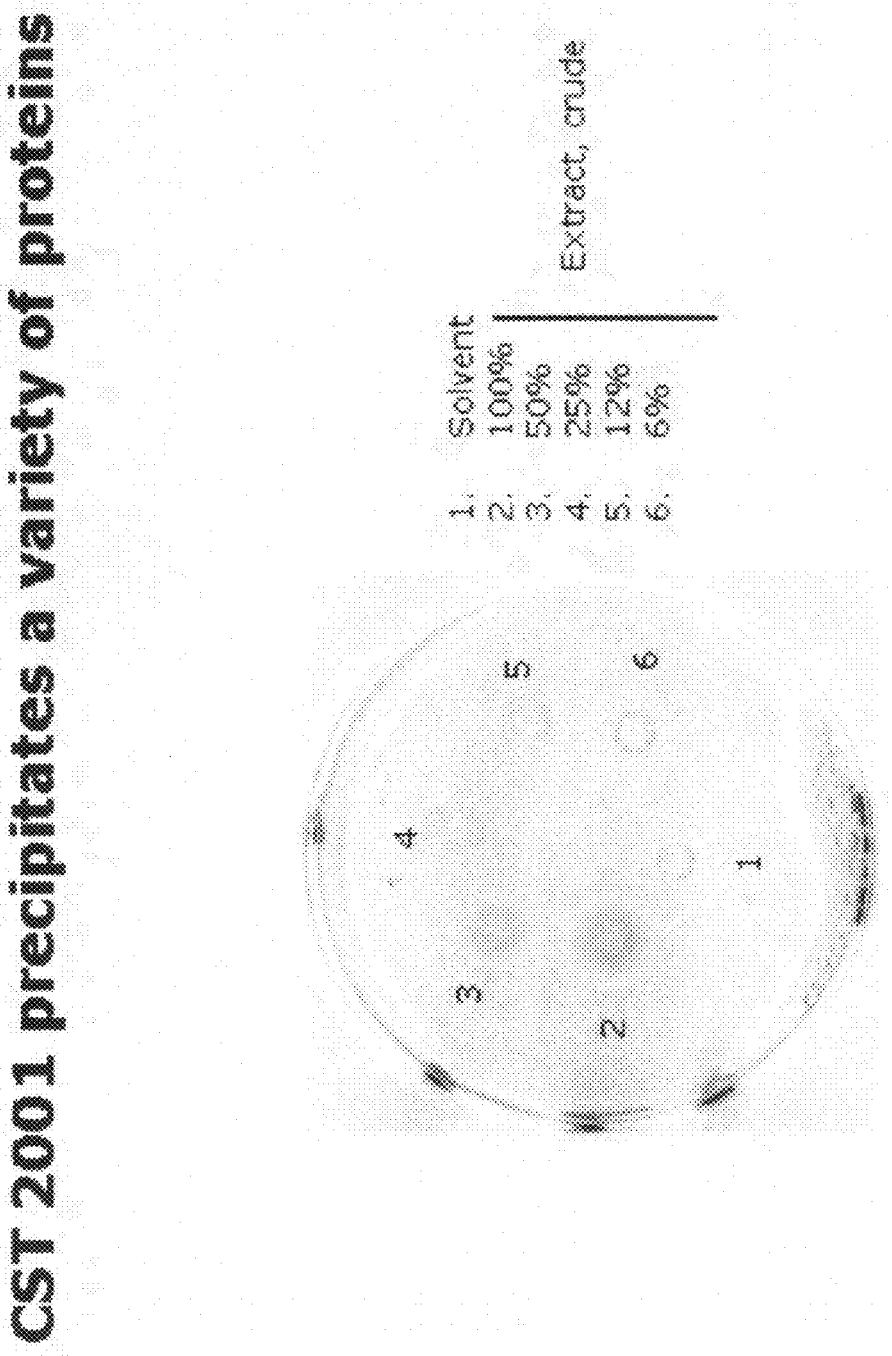

FIG. 57 shows a radial diffusion assay of the complex formed between CST 2001 and BSA which is visualized by precipitation.

Figure 58A:
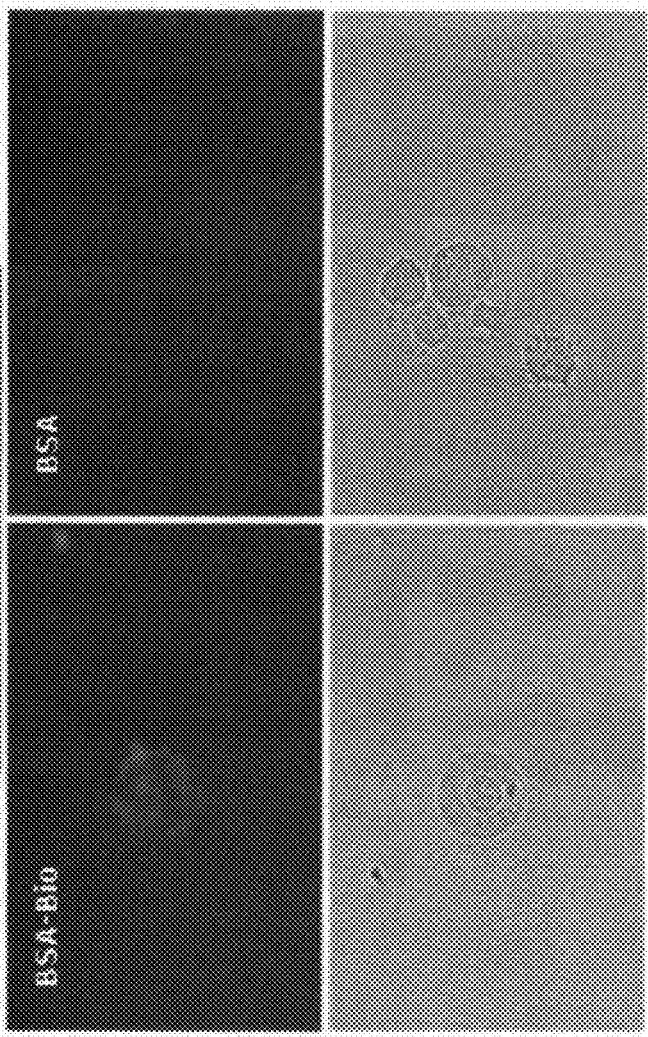
Figure 58B:
Figure 58C:
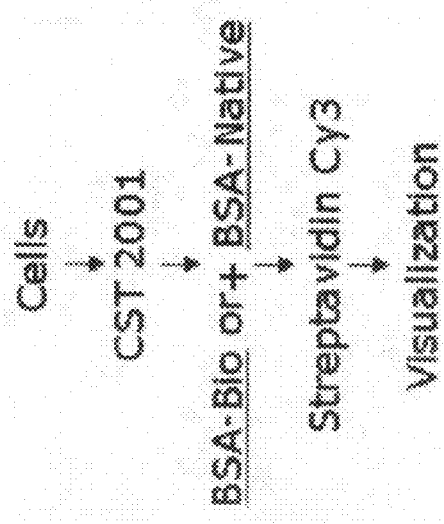

FIGS. 58A-C show staining of cells with biotinylated CST using Cy3-bound avidin. BSA—designates native BSA (control). BSA-Bio designates biotinylated BSA. The lower panels show the cells in the sample.

FIGS. 59A-B show differential fluorescent staining by CST 2001+Naturstoff reagent (NR) of living MCF-7 adenocarcinoma cells. FIG. 59A depicts untreated MCF-7 cells (malignant, control); and FIG. 59B depicts MCF-7 cells treated with Butyrate (normalized).

Figures 60A, 60B:
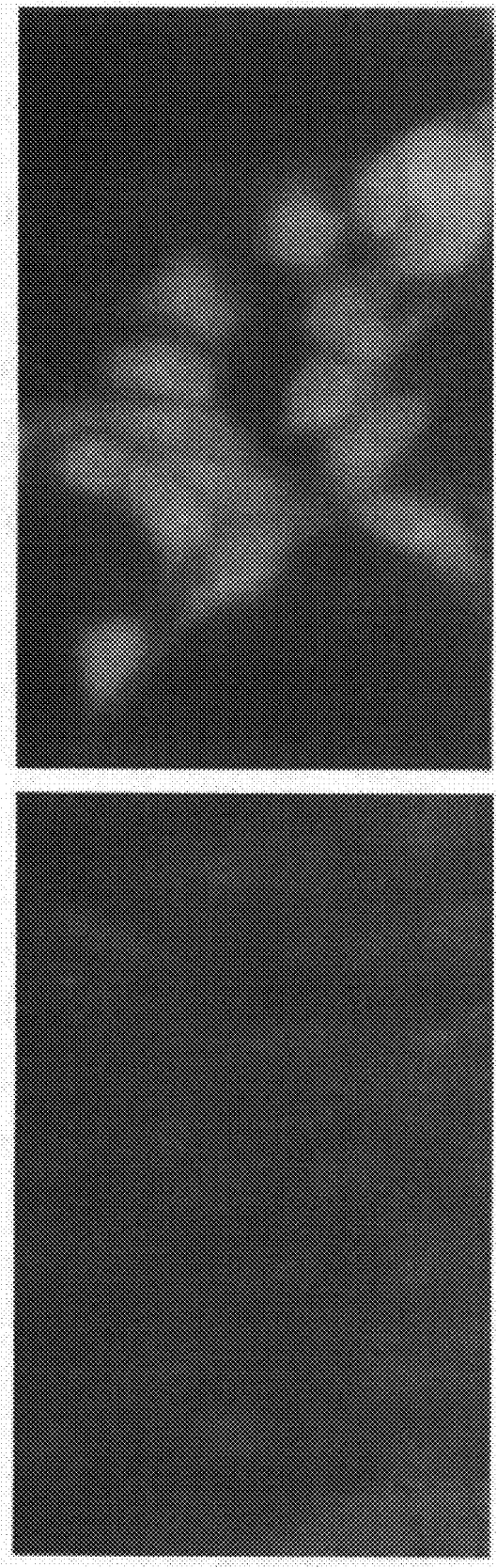

FIGS. 60A-B show differential fluorescent staining by CST 2001+Naturstoff reagent (NR) of living Rat2 cells. FIG. 60A depicts untreated (normal) Rat2 cells; and FIG. 60B depicts Rat2 Ras V12 transformed cells (malignant).

FIGS. 61A-C show differential staining by CST 2001. FIG. 61A depicts CST 2001 staining of U937 cells (leukemic cells); FIG. 61B depicts CST 2001 staining of Jar (human choriocarcinoma cells); and FIG. 61C depicts a mixture of U937 and Jar cells stained by a complex of CST 2001-Naturstoff reagent. Arrows indicate U937 cells stained by CST 2001+NR complex.

Figure 62B:
Figure 62D:
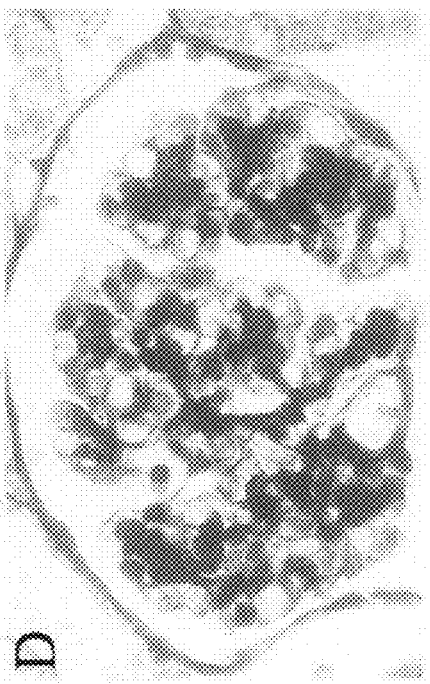
Figure 62A:
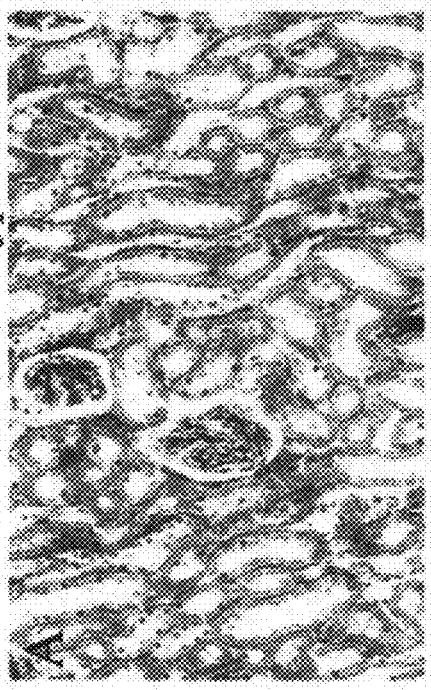
Figure 62C:

FIGS. 62A-D show histology sections staining prepared from diabetes type II-induced animal model. FIGS. 62A and 62C depict sections of kidneys from normal gerbils; and FIGS. 62B and 62D depict sections of kidneys from diabetic gerbils. All sections were CAMA stained according to protocol X. High magnification images (lower panels) focus on glomerulus structures and accentuate the green staining associated with diabetic tissue, visualized by this protocol.

DESCRIPTION OF THE PREFERRED EMBODIMENTS

The present invention is of compositions and methods of analyzing cellular phenotype which can be for the detection of cell differentiation. Specifically, the present invention can be used to diagnose cancer, monitor treatment, determining treatment regimen and develop novel treatment modalities for the disease.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

For decades, oncology research has focused on the search for detectable cancer specific markers, which can be used to verify the presence or absence of cancerous cells of various germlines in a tested biological specimen. Numerous cancer specific markers, including proteins, carbohydrates and nucleic acids, were found and characterized. However, none were shown to be pan-malignant, expressed by or secreted from all or even most cancer cell types. Hence, the quest is ongoing for a universal marker enabling effective oncodetection.

Normal and malignant cells have remarkably different phenotypes. The differences include the ability to form tumors in animal models, colony formation in soft agar, lost of contact inhibition and spreading alterations, a faster metabolic rate and expression of tumor-specific markers. It would be of utmost importance to discriminate between the normal and malignant phenotype by a simple method, not limited to any particular cell type.

One possible approach to distinguish malignant and normal cells is based on differences in their metabolic state [also known as the "Warburg effect", Warburg O. Metabolism of Tumors. London: Arnold Constable, 1930; Semenza G. L., Artemov D., Bedi A., Bhujwalla Z., Chiles K., Feldser D., Laughner E., Ravi R., Simons J., Taghavi P., Zhong H. 2001. 'The metabolism of tumours': 70 years later. Novartis Found Symp.; 240:251-60; discussion 260-4; Kannagi R. 2004. Molecular mechanism for cancer-associated induction of sialyl Lewis X and sialyl Lewis A expression—The Warburg effect revisited. *Glycoconj J.* 20(5):353-64].

The Warburg effect describes the high rate of anaerobic glycolysis that characterizes rapidly-growing cancer cells. The shift in energy production from oxidative phosphorylation to glycolysis is a fundamental property of cancer cells.

Although Warburg thought that cancer is caused by defects in oxidative phosphorylation in the mitochondria, it is now known that this shift occurs even in the presence of oxygen] Lu H., Forbes R. A., and Verma A., 2002. Hypoxia-inducible Factor 1 Activation by Aerobic Glycolysis Implicates the Warburg Effect in Carcinogenesis. *J. of Biol Chem* 277(26), 23111-23115]. Yet the validity of the hyper-glycolytic phenomenon in rapidly growing cancers remains [Weinhouse S. Glycolysis, 1972. Respiration and anomalous gene expression in experimental hepatomas. *Cancer Research;* 32:2007-2016].

While reducing the present invention to practice, the present inventors have uncovered a novel detection assay, capable of distinguishing between different metabolic or differentiation cell phenotypes, by differential staining, without compromising morphological evaluation. Without being bound by theory, it is suggested that the ability to distinguish between different differentiation states or metabolic states (proliferation capacities) is based on the above-described Warburg effect. The method is capable of producing a clear tinctorial distinction between cells having a differential metabolic state or at a different stage of differentiation, and thus can be a useful tool in early cancer cell detection.

As is illustrated hereinbelow and in the Examples section which follows, the present methodology is based on the use of a plant extract (Zetiq™ solution) for accentuating the differential cell staining by acidic (e.g., green) and/or basic dyes (e.g., red). It is believed that normally differentiated cells have higher affinity to acidic dyes than less differentiated cells (e.g., metabolically impaired or malignant). Likewise those less differentiated cells exhibit higher affinity to basic dyes than normally differentiated cells. The present staining technique accentuates these differences in staining (i.e., differential staining).

The result is a binary chromogenic response, with rapid metabolizing cells such as malignant or non-differentiated cells, staining red/purple, and normal or highly differentiated cells with a slower metabolism, staining green or bluish green. Most importantly, this differential staining is achieved without compromising the acuity of visualization of the morphological differences of cell substructures detectable under the microscope using conventional staining methods, thus allowing also traditional morphological based analysis of the stained cells.

The method was successfully validated for oncodetection of a wide variety of malignancies including carcinomas, sarcomas, and others in both rodents and human biological samples. The neoplastic sensitivity of the method was confirmed on cytological samples, histological samples and samples of carcinogen-induced cancer models in animals. Moreover, the method clearly distinguishes normal from malignant, as well as differentiated from non-differentiated cells, in various in vitro systems.

Specifically, using the present methodology, the present inventors have successfully detected cancer cells from peritoneal, pleural and pericardial aspirates, and distinctly differentiated between malignant and non-malignant cells. Using a two-step dying procedure, the cytoplasm of normal cells stained green or remained unstained while the cytoplasm of cancer cells stained red in color (FIGS. 1A, B thru FIG. 4 and FIG. 8). This was evident especially in difficult cases in which the May-Grunwald-Giemsa (MGG) staining procedure could not differentiate between malignant and normal cells.

The present inventors have also shown differential staining of cervical smears. These results demonstrate differential staining of normal cells in green tones in sharp contrast to cancer cells staining in red tones (FIGS. 11A-H thru FIGS. 13A-G).

The present inventors have also shown that the staining procedure of the present invention is not limited to cytological smears prepared from fluids, but may also be applied to touch preparations (FIG. 10) and to other types of cell or tissue preparations (histological) such as paraffin embedded tissue (FIGS. 6A-D and FIGS. 9A-D). The present invention clearly distinguishes between normal cells and malignant cells in the same tissue, such as in colon cancer (FIGS. 6A-D, FIGS. 7A-C, FIGS. 15A-C and FIGS. 16A-D) and in melanoma (FIGS. 17A-B).

The methods and compositions of the present invention allow the challenging task of boundary detection of a malignant tissue after surgical excision (FIGS. 18A-C) as well as discriminating between stages of differentiation, such as in embryogenesis (FIGS. 19A-D).

Thus, according to one aspect of the present invention there is provided a method of staining or pre-staining at least one cell, the method comprising contacting the at least one cell with a staining agent selected from the group consisting of an extract of a *Ficus elastica* plant, a $C_{23}H_{44}O_4$ and a proanthocyanidin, thereby staining or pre-staining the at least one cell.

As used herein the term "staining" refers to visually highlighting cells or subcellular structures thereof. The staining agent of the present invention is characterized by auto-fluorescence which may be detected by appropriate means. Thus, the staining agent of the present invention emits fluorescence at 430 nm upon excitation at 375 nm. Basically, the staining agent of the present invention stains cells of normal metabolism or differentiation state, but less so (or not at all) cells of impaired metabolism or differentiation state (as will be further described hereinbelow). Such a differential staining can be detected by means designed for fluorescence detection (e.g., fluorescent microscope).

As used herein the term "pre-staining" refers to preparing or conditioning cells for staining for the purpose of accentuating the staining. Typically, a pre-stain procedure facilitates achieving better visualization of the stained structures once exposed to a dye. In accordance with the present invention the pre-staining procedure facilitates classification of stained cells of different metabolic or differentiation states by accentuating their differential affinities to acidic and basic dyes.

As used herein the term "cell" refers to a eukaryotic cell of multicellular organisms, preferably a human being. Single cells may be used in accordance with the teachings of the present invention as well as plurality of cells. Thus, homogeneous or heterogeneous populations (e.g., of different differentiation states) of cells may be stained. Typically, biological samples (e.g., biopsies) comprise heterogeneous populations of cells.

Such heterogeneous populations may comprise heterogeneously differentiated cells (such as of a solid tissue (e.g., tumor) sample or section or isolated cells e.g., in suspension e.g., blood). For example the population of cells may comprise malignant or pre-malignant cells as well as normal healthy cells. Alternatively, such a population of cells may comprise metabolically normal and metabolically impaired cells. Additionally or alternatively, the population may comprise fetal and/or embryonic cells as well as maternal cells.

Cells of the present invention may be cell-lines, primary cultures and cellular samples such as from biopsies (surgical biopsies, fine needle aspirates and the like). Methods of biopsy retrieval are well known in the arts and much depend on the kind of cancer or any other medical condition to be detected.

As mentioned hereinabove, the staining agent of the present invention is isolated from plants and active fractions thereof can be naturally occurring or synthetic.

Preferred plants for extract isolation include, but are not limited to *Ficus*, *Aloe* and *Lantana* plants, preferably from *Ficus elastica*, *Lantana Camara* and *Aloe arborescens* plants. According to a currently known most preferred embodiment the extract is from *Ficus elastica*.

The extract may be prepared from various portions of the plant e.g., leaves. Guidelines for extract preparation from leaves are provided in the experimental details section of Example 1 of the Examples section which follows.

Various preparation protocols of an ethanol extract of the present invention are described in the experimental details section of the examples section which follows. The extract may be a purified plant extract which essentially comprises the active ingredients but devoid of contaminants, or a crude plant extract, as long as it's characteristic staining abilities are maintained. Indeed as shown in Example 15 hereinbelow, an active extract fraction, CST2001, showed enhanced contrast and intensity of the signal when staining malignant cells. FIGS. 43 and 44 describe the characterization of an active fraction which comprises $C_{23}H_{44}O_4$ or proanthocyanidins. The latter, also known as a specific class of flavinoids is typically in an oligomeric form (which may comprise 2-10 mers, e.g., $C_{26}H_{32}O_{15}$ see FIG. 45, and FIG. 46) or polymeric form.

The ethanol extract of the present invention comprises a 50% ethanol extract, 60% ethanol extract, 70% ethanol extract, 80% ethanol extract 90% ethanol extract or a hundred % ethanol extract. Preferably used is a diluted or non-diluted extract. Measures should be taken however not to over dilute the extract, as this may affect the subsequent staining (see Table 14 below).

The staining agent of the present invention (e.g., extract) may be supplemented with positively charged ions including but not limited to magnesium and calcium (see Example 15 hereinbelow).

The staining agent of the present invention is contacted with the cells under conditions which allow fluorescent staining or same or satisfactory pre-staining. Examples of such conditions include, but are not limited to, fixation conditions; rinses, air drying, paraffin embedding and the like (see Examples section hereinbelow).

Stained cells of the present invention may be detected using fluorescent detection methods which are well known in the art and further described hereinbelow.

To accentuate the difference between cells of different metabolic or differentiation states, the cells are contacted with at least one dye.

Examples of such dyes are provided in Table 1a and further hereinbelow. According to a preferred embodiment the acidic dye is Light Green and the basic dye is New Fuchsin or Dahlia.

TABLE 1a

| Name | C.I. # | Class | Common name |
| --- | --- | --- | --- |
| Acetyl yellow | 13015 | Nitro | Fast yellow |
| Acid black 1 | 20470 | Azo | Amido black 10B |
| Acid blue 22 | 42755 | Triarylmethane | Water blue I |
| Acid blue 93 | 42780 | Triarylmethane | Methyl blue |
| Acid fuchsin | 42685 | Triarylmethane | Acid fuchsin |
| Acid green | 42095 | Triarylmethane | Light green SF yellowish |
| Acid green 1 | 10020 | Nitroso | Naphthol green B |

TABLE 1a-continued

| Name | C.I. # | Class | Common name |
| --- | --- | --- | --- |
| Acid green 5 | 42095 | Triarylmethane | Light green SF yellowish |
| Acid magenta | 42685 | Triarylmethane | Acid fuchsin |
| Acid orange 10 | 16230 | Azo | Orange G |
| Acid red 4 | 14710 | Azo | Azo-eosin |
| Acid red 26 | 16150 | Azo | Xylidine ponceau |
| Acid red 29 | 16570 | Azo | Chromotrope 2R |
| Acid red 44 | 16250 | Azo | Ponceau 6R |
| Acid red 51 | 45430 | Fluorone | Erythrosin B |
| Acid red 66 | 26905 | Azo | Biebrich scarlet |
| Acid red 73 | 27290 | Azo | Woodstain scarlet |
| Acid red 87 | 45380 | Fluorone | Eosin Y ws |
| Acid red 91 | 45400 | Fluorone | Eosin B |
| Acid red 92 | 45410 | Fluorone | Phloxine B |
| Acid red 94 | 45440 | Fluorone | Rose bengal |
| Acid red 101 | 50085 | Quinone-Imine | Azocarmine G |
| Acid red 103 | 50090 | Quinone-Imine | Azocarmine B |
| Acid roseine | 42685 | Triarylmethane | Acid fuchsin |
| Acid rubin | 42685 | Triarylmethane | Acid fuchsin |
| Acid violet 19 | 42685 | Triarylmethane | Acid fuchsin |
| Acid yellow 1 | 10316 | Nitro | Naphthol yellow S |
| Acid yellow 9 | 13015 | Nitro | Fast yellow |
| Acid yellow 23 | 19140 | Azo | Tartrazine |
| Acid yellow 24 | 10315 | Nitro | Martius yellow |
| Acid yellow 36 | 13065 | Azo | Metanil yellow |
| Acid yellow 73 | 45350 | Fluorone | Fluorescein |
| Acid yellow S | 10316 | Nitro | Naphthol yellow S |
| Acid yellow T | 19140 | Azo | Tartrazine |
| Acridine orange | 46005 | Acridine | Acridine orange |
| Acriflavine | 46000 | Acridine | Acriflavine |
| Alcian blue | 74240 | Phthalocyanine | Alcian blue 8GX |
| Alcian yellow | 12840 | Azo | Alcian yellow |
| Alcohol soluble eosin | 45386 | Fluorone | Ethyl eosin |
| Alizarin | 58000 | Anthraquinone | Alizarin |
| Alizarin blue | 67410 | Anthraquinone | Alizarin blue |
| Alizarin blue 2RC | 58605 | Anthraquinone | Anthracene blue SWR |
| Alizarin carmine | 58005 | Anthraquinone | Alizarin red S |
| Alizarin cyanin BBS | 58610 | Anthraquinone | Alizarin cyanin BBS |
| Alizarol cyanin R | 43820 | Triarylmethane | Chromoxane cyanin R |
| Alizarin red S | 58005 | Anthraquinone | Alizarin red S |
| Alizarin purpurin | 58205 | Anthraquinone | Purpurin |
| Aluminon | 43810 | Triarylmethane | Chrome violet CG |
| Amido black 10B | 20470 | Azo | Amido black 10B |
| Amidonaphthol red | 18050 | Azo | Azophloxine |
| Amidoschwarz | 20470 | Azo | Amido black 10B |
| Aniline blue WS | — | Triarylmethane | Aniline blue WS |
| Aniline purple | — | Azin | Mauveine |
| Anthracene blue SWR | 58605 | Anthraquinone | Anthracene blue SWR |
| Anthracene blue SWX | 58610 | Anthraquinone | Alizarin cyanin BBS |
| Auramine O | 41000 | Diarylmethane | Auramine O |
| Azo-eosin | 14710 | Azo | Azo-eosin |
| Azocarmine B | 50090 | Quinone-Imine | Azocarmine B |
| Azocarmine G | 50085 | Quinone-Imine | Azocarmine B |
| Azoeosin G | 14710 | Azo | Azo-eosin |
| Azoic diazo 5 | 37125 | Diazonium salt | Fast red B |
| Azoic diazo 48 | 37235 | Diazonium salt | Fast blue B |
| Azophloxine | 18050 | Azo | Azophloxine |
| Azovan blue | 23860 | Azo | Evans blue |
| Azure A | 52005 | Thiazin | Azure A |
| Azure B | 52010 | Thiazin | Azure B |
| Azure C | 52002 | Thiazin | Azure C |
| Basic blue 8 | 42563 | Triarylmethane | Victoria blue 4R |
| Basic blue 9 | 52015 | Thiazin | Methylene blue |
| Basic blue 12 | 51180 | Oxazin | Nile blue A |
| Basic blue 15 | 44085 | Triarylmethane | Night blue |
| Basic blue 17 | 52040 | Thiazin | Toluidine blue O |
| Basic blue 20 | 42585 | Triarylmethane | Methyl green |
| Basic blue 26 | 44045 | Triarylmethane | Victoria blue B |
| Basic brown 1 | 21000 | Azo | Bismarck brown Y |
| Basic fuchsin | — | Triarylmethane | Basic fuchsin |
| Basic green 4 | 42000 | Triarylmethane | Malachite green |
| Basic green 5 | 52020 | Thiazine | Methylene green |
| Basic orange 14 | 46005 | Acridine | Acridine orange |
| Basic red 2 | 50240 | Safranin | Safranin O |
| Basic red 5 | 50040 | Eurhodin | Neutral red |
| Basic red 9 | 42500 | Triarylmethane | Pararosanilin |
| Basic violet 2 | 42520 | Triarylmethane | New fuchsin |

TABLE 1a-continued

| Name | C.I. # | Class | Common name |
|---|---|---|---|
| Basic violet 3 | 42555 | Triarylmethane | Crystal violet |
| Basic violet 4 | 42600 | Triarylmethane | Ethyl violet |
| Basic violet 10 | 45170 | Rhodamine | Rhodamine B |
| Basic violet 14 | 42510 | Triarylmethane | Rosanilin |
| Basic yellow 1 | 49005 | Thiazole | Thioflavine T |
| Basic yellow 2 | 41000 | Diarylmethane | Auramine O |
| Biebrich scarlet | 26905 | Azo | Biebrich scarlet |
| Biebrich scarlet R | 26105 | Azo | Sudan IV |
| Bismarck brown Y | 21000 | Azo | Bismarck brown Y |
| Brazilein | 75280 | Natural | Brazilein |
| Brazilin | 75280 | Natural | Brazilin |
| Brilliant crocein | 27290 | Azo | Woodstain scarlet |
| Brilliant crystal scarlet 6R | 16250 | Azo | Ponceau 6R |
| Calcium red | 60760 | Anthraquinone | Nuclear fast red |
| Carmine | 75470 | Natural | Carmine |
| Carminic acid | 75470 | Natural | Carmine |
| Carmoisine 6R | 16570 | Azo | Chromotrope 2R |
| Celestine blue B | 51050 | Oxazin | Celestine blue B |
| China blue | — | — | Aniline blue |
| Chlorantine fast red 5B | 28160 | Azo | Sirius red 4B |
| Cochineal | 75470 | Natural | Carmine |
| Coelestine blue | 51050 | Oxazin | Celestine blue B |
| Chicago blue 4B | — | azo | Pontamine sky blue 5B |
| Chrome violet CG | 43810 | Triarylmethane | Chrome violet CG |
| Chromotrope 2R | 16570 | Azo | Chromotrope 2R |
| Chromoxane cyanin R | 43820 | Triarylmethane | Chromoxane cyanin R |
| Congo corinth | 22145 | Azo | Congo corinth |
| Congo red | 22120 | Azo | Congo red |
| Cotton blue | 42780 | Triarylmethane | Methyl blue |
| Cotton red | 22120 | Azo | Congo red |
| Croceine scarlet | 26905 | Azo | Biebrich scarlet |
| Crocein scarlet 3B | 27290 | Azo | Woodstain scarlet |
| Crocein scarlet MOO | 27290 | Azo | Woodstain scarlet |
| Crocin | 75100 | Natural | Saffron |
| Crystal ponceau 6R | 16250 | Azo | Ponceau 6R |
| Crystal scarlet | 16250 | Azo | Ponceau 6R |
| Crystal violet | 42555 | Triarylmethane | Crystal violet |
| Dahlia | 42530 | Triarylmethane | Hoffman's violet |
| Diamond green B | 42000 | Triarylmethane | Malachite green |
| Direct blue 14 | 23850 | Azo | Trypan blue |
| Direct blue 58 | 23860 | Azo | Evans blue |
| Direct red | 22120 | Azo | Congo red |
| Direct red 10 | 22145 | Azo | Congo corinth |
| Direct red 28 | 22120 | Azo | Congo red |
| Direct red 80 | 35780 | Azo | Sirius red F3B |
| Direct red 81 | 28160 | Azo | Sirius red 4B |
| Direct yellow 7 | 49010 | Thiazole | Thioflavine S |
| Durazol blue 4R | — | Azo | Durazol blue 4R |
| Durazol blue 8G | — | Phthalocyanine | Durazol blue 8G |
| Eosin B | 45400 | Fluorone | Eosin B |
| Eosin Bluish | 45400 | Fluorone | Eosin B |
| Eosin | 45380 | Fluorone | Eosin Y ws |
| Eosin Y | 45380 | Fluorone | Eosin Y ws |
| Eosin yellowish | 45380 | Fluorone | Eosin Y ws |
| Eosinol | — | Fluorone | Eosinol |
| Erie garnet B | 22145 | Azo | Congo corinth |
| Eriochrome cyanin R | 43820 | Triarylmethane | Chromoxane cyanin R |
| Erythrosin B | 45430 | Fluorone | Erythrosin B |
| Ethyl eosin | 45386 | Fluorone | Ethyl eosin |
| Ethyl green | 42590 | Triarylmethane | Ethyl green |
| Ethyl violet | 42600 | Triarylmethane | Ethyl violet |
| Evans blue | 23860 | Azo | Evans blue |
| Fast blue B | 37235 | Diazonium salt | Fast blue B |
| Fast green FCF | 42053 | Triarylmethane | Fast green FCF |
| Fast red B | 37125 | Diazonium salt | Fast red B |
| Fast yellow | 13015 | Nitro | Fast yellow |
| Fast yellow extra | 13015 | Nitro | Fast yellow |
| Fast yellow G | 13015 | Nitro | Fast yellow |
| Fat black HB | 26150 | Azo | Sudan black B |
| Fluorescein | 45350 | Fluorone | Fluorescein |
| Food green 3 | 42053 | Triarylmethane | Fast green FCF |
| Gallein | 45445 | Fluorone | Gallein |
| Gallamine blue | 51045 | Oxazin | Gallamine blue |
| Gallocyanin | 51030 | Oxazin | Gallocyanin |
| Gentian violet | — | Triarylmethane | Methyl violet 2B |
| Haematein | 75290 | Natural | Hematein |
| Haematine | 75290 | Natural | Hematein |
| Haematoxylin | 75290 | Natural | Hematoxylin |
| Helio fast rubin BBL | 60760 | Anthraquinone | Nuclear fast red |
| Helvetia blue | 42780 | Triarylmethane | Methyl blue |
| Hematein | 75290 | Natural | Hematein |
| Hematine | 75290 | Natural | Hematein |
| Hematoxylin | 75290 | Natural | Hematoxylin |
| Hoffman's violet | 42530 | Triarylmethane | Hoffman's violet |
| Hydrazine yellow | 19140 | Azo | Tartrazine |
| Imperial red | 45400 | Fluorone | Eosin B |
| Ingrain blue 1 | 74240 | Phthalocyanine | Alcian blue 8GX |
| Ingrain yellow 1 | 12840 | Azo | Alcian yellow |
| INT | — | Tetrazolium salt | Iodonitrotetrazolium |
| Kermes | 75460 | Natural | Kermes |
| Kermesic acid | 75460 | Natural | Kermes |
| Kernechtrot | 60760 | Anthraquinone | Nuclear fast red |
| Lac | 75450 | Natural | Laccaic acid |
| Laccaic acid | 75450 | Natural | Laccaic acid |
| Lauth's violet | 52000 | Thiazin | Thionin |
| Light green | 42095 | Triarylmethane | Light green SF yellowish |
| Lissamine fast yellow | 18965 | Azo | Lissamine fast yellow |
| Lissamine green SF | 42095 | Triarylmethane | Light green SF yellowish |
| Luxol fast blue | — | Phthalocyanine | Luxol fast blue MBS |
| Magenta 0 | 42500 | Triarylmethane | Pararosanilin |
| Magenta I | 42510 | Triarylmethane | Rosanilin |
| Magenta II | — | Triarylmethane | Magenta II |
| Magenta III | 42520 | Triarylmethane | New fuchsin |
| Malachite green | 42000 | Triarylmethane | Malachite green |
| Manchester brown | 21000 | Azo | Bismarck brown Y |
| Martius yellow | 10315 | Nitro | Martius yellow |
| Mauve | — | Azin | Mauveine |
| Mauveine | — | Azin | Mauveine |
| Merbromin | — | Fluorone | Mercurochrome 220 |
| Mercurochrome | — | Fluorone | Mercurochrome 220 |
| Metanil yellow | 13065 | Azo | Metanil yellow |
| Methylene azure A | 52005 | Thiazin | Azure A |
| Methylene azure B | 52010 | Thiazin | Azure B |
| Methylene azure C | 52002 | Thiazin | Azure C |
| Methylene blue | 52015 | Thiazin | Methylene blue |
| Methylene green | 52020 | Thiazine | Methylene green |
| Methyl blue | 42780 | Triarylmethane | Methyl blue |
| Methyl green | 42585 | Triarylmethane | Methyl green |
| Methyl violet | 42535 | Triarylmethane | Methyl violet 2B |
| Methyl violet 2B | 42535 | Triarylmethane | Methyl violet 2B |
| Methyl violet 10B | 42555 | Triarylmethane | Crystal violet |
| Milling yellow 3G | — | Azo | Milling yellow 3G |
| Mordant blue 3 | 43820 | Triarylmethane | Chromoxane cyanin R |
| Mordant blue 10 | 51030 | Oxazin | Gallocyanin |
| Mordant blue 14 | 51050 | Oxazin | Celestine blue B |
| Mordant blue 23 | 58610 | Anthraquinone | Alizarin cyanin BBS |
| Mordant blue 32 | 58605 | Anthraquinone | Anthracene blue SWR |
| Mordant blue 45 | 51045 | Oxazin | Gallamine blue |
| Mordant red 3 | 58005 | Anthraquinone | Alizarin red S |
| Mordant red 11 | 58000 | Anthraquinone | Alizarin |
| Mordant violet 25 | 45445 | Fluorone | Gallein |
| Mordant violet 39 | 43810 | Triarylmethane | Chrome violet CG |
| Naphthalene blue black | — | Azo | Naphalene blue black |
| Naphthol blue black | 20470 | Azo | Amido black 10B |
| Naphthol green B | 10020 | Nitroso | Naphthol green B |
| Naphthol yellow S | 10316 | Nitro | Naphthol yellow S |
| Natural black 1 | 75290 | Natural | Hematein |
| Natural red | 58205 | Anthraquinone | Purpurin |
| Natural red 3 | 75460 | Natural | Kermes |
| Natural red 4 | 75470 | Natural | Carmine |
| Natural red 8 | 58205 | Anthraquinone | Purpurin |
| Natural red 16 | 58205 | Anthraquinone | Purpurin |
| Natural red 24 | 75280 | Natural | Brazilin |
| Natural red 25 | 75450 | Natural | Laccaic acid |
| Natural red 28 | — | Natural | Orcein |
| Natural yellow 6 | 75100 | Natural | Saffron |
| NBT | — | Tetrazolium salt | Nitro blue tetrazolium |

TABLE 1a-continued

| Name | C.I. # | Class | Common name |
|---|---|---|---|
| Neutral red | 50040 | Eurhodin | Neutral red |
| New fuchsin | 42520 | Triarylmethane | New fuchsin |
| Niagara blue 3B | 23850 | Azo | Trypan blue |
| Night blue | 44085 | Triarylmethane | Night blue |
| Nile blue | 51180 | Oxazin | Nile blue A |
| Nile blue A | 51180 | Oxazin | Nile blue A |
| Nile blue sulphate | 51180 | Oxazin | Nile blue A |
| Nile red | — | Oxazone | Nile red |
| Nitro BT | — | Tetrazolium salt | Nitro blue tetrazolium |
| Nitro blue tetrazolium | — | Tetrazolium salt | Nitro blue tetrazolium |
| Nuclear fast red | 60760 | Anthraquinone | Nuclear fast red |
| Oil red O | 26125 | Azo | Oil red O |
| Orange G | 16230 | Azo | Orange G |
| Orcein | — | Natural | Orcein |
| Pararosanilin | 42500 | Triarylmethane | Pararosanilin |
| Perkin's violet | — | Azin | Mauveine |
| Phloxine B | 45410 | Fluorone | Phloxine B |
| Picric acid | 10305 | Nitro | Picric acid |
| Ponceau 2R | 16150 | Azo | Xylidine ponceau |
| Ponceau 6R | 16250 | Azo | Ponceau 6R |
| Ponceau B | 26905 | Azo | Biebrich scarlet |
| Ponceau de Xylidine | 16150 | Azo | Xylidine ponceau |
| Ponceau S | 27195 | Azo | Ponceau S |
| Pontamine sky blue 5B | — | azo | Pontamine sky blue 5B |
| Primula | 42530 | Triarylmethane | Hoffman's violet |
| Primuline | 49000 | Thiazole | Primuline |
| Purpurin | 58205 | Anthraquinone | Purpurin |
| Pyronin B | 45010 | Pyronin | Pyronin B |
| Pyronin G | 45005 | Pyronin | Pyronin Y |
| Pyronin Y | 45005 | Pyronin | Pyronin Y |
| Rhodamine B | 45170 | Rhodamine | Rhodamine B |
| Rosanilin | 42510 | Triarylmethane | Rosanilin |
| Rose bengal | 45440 | Fluorone | Rose bengal |
| Saffron | 75100 | Natural | Saffron |
| Safranin O | 50240 | Safranin | Safranin O |
| Scarlet R | 26105 | Azo | Sudan IV |
| Scarlet red | 26105 | Azo | Sudan IV |
| Scharlach R | 26105 | Azo | Sudan IV |
| Shellac | 75450 | Natural | Laccaic acid |
| Sirius red F3B | 35780 | Azo | Sirius red F3B |
| Sirius red 4B | 28160 | Azo | Sirius red 4B |
| Sirius supra blue F3R | — | Azo | Durazol blue 4R |
| Solochrome cyanin R | 43820 | Triarylmethane | Chromoxane cyanin R |
| Soluble blue | — | — | Aniline blue |
| Solvent black 3 | 26150 | Azo | Sudan black B |
| Solvent blue 38 | — | Phthalocyanine | Luxol fast blue MBS |
| Solvent red 23 | 26100 | Azo | Sudan III |
| Solvent red 24 | 26105 | Azo | Sudan IV |
| Solvent red 27 | 26125 | Azo | Oil red O |
| Solvent red 45 | 45386 | Fluorone | Ethyl eosin |
| Solvent yellow 94 | 45350 | Fluorone | Fluorescein |
| Spirit soluble eosin | 45386 | Fluorone | Ethyl eosin |
| Sudan III | 26100 | Azo | Sudan III |
| Sudan IV | 26105 | Azo | Sudan IV |
| Sudan black B | 26150 | Azo | Sudan black B |
| Sudan red BK | 26100 | Azo | Sudan III |
| Sulfur yellow S | 10316 | Nitro | Naphthol yellow S |
| Swiss blue | 52015 | Thiazin | Methylene blue |
| Tartrazine | 19140 | Azo | Tartrazine |
| Thioflavine S | 49010 | Thiazole | Thioflavine S |
| Thioflavine T | 49005 | Thiazole | Thioflavine T |
| Thionin | 52000 | Thiazin | Thionin |
| Toluidine blue | 52040 | Thiazin | Toluidine blue O |
| Toluyline red | 50040 | Eurhodin | Neutral red |
| Tropaeolin G | 13065 | Azo | Metanil yellow |
| Trypaflavine | 46000 | Acridine | Acriflavine |
| Trypan blue | 23850 | Azo | Trypan blue |
| Uranin | 45350 | Fluorone | Fluorescein |
| Victoria blue 4R | 42563 | Triarylmethane | Victoria blue 4R |
| Victoria blue B | 44045 | Triarylmethane | Victoria blue B |
| Victoria blue R | 44040 | Triarylmethane | Victoria blue R |
| Victoria green B | 42000 | Triarylmethane | Malachite green |
| Water blue I | 42755 | Triarylmethane | Water blue I |
| Water soluble eosin | 45380 | Fluorone | Eosin Y ws |
| Woodstain scarlet | 27290 | Azo | Woodstain scarlet |
| Xylidine ponceau | 16150 | Azo | Xylidine ponceau |
| Yellowish eosin | 45380 | Fluorone | Eosin Y ws |

Catalog numbers indicated are from StainsFile (http://stainsfile.info/StainsFile/jindex.html)

According to a preferred embodiment the dye is a basic or an acidic dye, such that when:

(i) the at least one dye is an acidic dye a staining intensity above a predetermined threshold is indicative of a differentiated cell;

(ii) the at least one dye is a basic dye a staining intensity above a predetermined threshold is indicative of an undifferentiated cell;

(iii) the at least one dye comprises the acidic dye and the basic dye a staining intensity above a predetermined threshold with the acidic dye is indicative of a differentiated cell and a staining intensity above a predetermined threshold with the basic dye is indicative of an undifferentiated cell.

As used herein the phrase "staining above a predetermined intensity" refers to at least 10%, 20%, 30%, 40%, 50%, 80%, 100% (i.e., two-fold), 3 fold, 5 fold or 10 fold or higher staining intensity as compared to a reference cell. The reference cell can be a normally differentiated cell, preferably of the same tissue and specimen as the tested cell suspicious of an undifferentiated phenotype. Alternatively, the reference cell is an undifferentiated cell (of impaired metabolic state or malignant/pre-malignant phenotype), when the tested cell is a cell of a normal terminally differentiated phenotype (preferably of the same tissue and specimen).

To better improve the visual difference between cells of different differentiation or metabolic states, two different dyes are used in sequence (e.g., an acidic dye and a basic dye). Thus, for example, the cells may be first stained with an acidic dye (e.g., green) and subsequently with a basic dye (e.g., red). In line with the above exemplification, normally differentiated cells will be stained green (or not at all) while less differentiated cells will be stained red. Other dyes are further described hereinbelow.

Staining detection modalities are further described hereinbelow. Additional staining modalities or morphological analyses can be effected in parallel, since as mentioned hereinabove, the present teachings do not compromise cell morphology.

Thus, it is apparent that the present teachings can be used to identify cells of different differentiation states (or a differentiation state of interest) in a cellular sample.

Thus, according to an additionally aspect of the present invention there is provided a method of identifying a cell of a differentiation state of interest, the method comprising: staining the cell as described above; and analyzing the staining, wherein when the at least one dye is an acidic dye, a staining intensity above a predetermined threshold is indicative of a differentiated cell; the at least one dye is a basic dye, a staining intensity above a predetermined threshold is indicative of an undifferentiated cell; the at least one dye comprises the acidic dye and the basic dye, a staining intensity above a predetermined threshold with the acidic dye is indicative of a differentiated cell and a staining intensity above a predetermined threshold with the basic dye is indicative of an undifferentiated cell.

The above-described methodology can be used in the clinic for diagnosing (in the very broad sense of the term as will be further described hereinbelow) a variety of medical conditions which are associated with cells of impaired differentiation states (i.e., such cells contribute to the onset or are the outcome of the medical condition). While the following mostly addresses malignant diseases, the present invention can be used to diagnose or monitor treatment of numerous medical conditions as will be further detailed hereinbelow.

Thus, according to another aspect of the present invention there is provided a method of diagnosing a cancer in a subject in need thereof.

As used herein the term "diagnosing" refers to classifying a pathology (e.g., a cancer or a pre-malignant lesion) or a symptom, determining a severity of the pathology (grade or stage), monitoring pathology progression, forecasting an outcome of a pathology and/or prospects of recovery.

As used herein the phrase "subject in need thereof" refers to an animal or human subject who is at risk of having cancer [e.g., a genetically predisposed subject, a subject with medical and/or family history of cancer, a subject who has been exposed to carcinogens, occupational hazard, environmental hazard] and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness]. Additionally or alternatively, the subject in need thereof can be a healthy human subject undergoing a routine well-being check up.

Analyzing presence of malignant or pre-malignant cells can be effected in-vivo or ex-vivo, whereby a biological sample (e.g., biopsy) is retrieved. Such biopsy samples comprise cells and may be an incisional or excisional biopsy. Alternatively the cells may be retrieved from a complete resection.

Biopsy specimens are often taken from part of a lesion when the cause of a disease is uncertain or its extent or exact character is in doubt. The margins or boundaries of a biopsy specimen are also carefully examined to see if the disease may have spread beyond the area biopsy. "Clear boundaries," or "negative boundaries," means that no disease was found at the edges of the biopsy specimen. "Positive boundaries" means that disease was found, and additional treatment may be needed. The present inventors were able to demonstrate the ability of the present teachings to detect the boundaries of a rat brain's tumor (see Example 4).

While employing the present teachings, additional information may be gleaned pertaining to the determination of treatment regimen, treatment course and/or to the measurement of the severity of the disease.

Thus according to yet another aspect of the present invention there is provided a method of determining an anti-cancer treatment regimen in a subject in need thereof. Thus the method is well suited for subjects who are diagnosed with cancer, or can be applied concomitantly with diagnosis. The method is effected by analyzing a presence or level of malignant or pre-malignant cells in a biopsy sample of the subject according to the teachings of the present invention; and administering to the subject a therapeutic effective amount of an anti cancer therapy according to the presence or level of malignant cells in the biopsy sample of the subject.

As used herein the phrase "treatment regimen" refers to a treatment plan that specifies the type of treatment, dosage, schedule and/or duration of a treatment provided to a subject in need thereof (e.g., a subject diagnosed with a pathology). The selected treatment regimen can be an aggressive one which is expected to result in the best clinical outcome (e.g., complete cure of the pathology) or a more moderate one which may relieve symptoms of the pathology yet results in incomplete cure of the pathology. It will be appreciated that in certain cases the treatment regimen may be associated with some discomfort to the subject or adverse side effects (e.g., a damage to healthy cells or tissue). The type of treatment can include a surgical intervention (e.g., removal of lesion, diseased cells, tissue, or organ), a cell replacement therapy, an administration of a therapeutic drug (e.g., receptor agonists, antagonists, hormones, chemotherapy agents) in a local or a systemic mode, an exposure to radiation therapy using an external source (e.g., external beam) and/or an internal source (e.g., brachytherapy) and/or any combination thereof. The dosage, schedule and duration of treatment can vary, depending on the severity of pathology and the selected type of treatment, and those of skills in the art are capable of adjusting the type of treatment with the dosage, schedule and duration of treatment.

Examples of routinely used cancer therapy include, but are not limited to, radiation therapy, chemotherapy (e.g., CHOP, Cisplatin, carboplatin, oxaliplatin, azathioprine, mercaptopurine, vinca alkaloids, etoposide, teniposide, paclitaxel, docetaxel, irinotecan, topotecanamsacrine, etoposide, etoposide phosphate, teniposide and dactinomycin), antibody therapy [e.g., trastuzumab (Herceptin) and rituximab (Rituxan)] or a combination of any of the above.

As mentioned the same teachings described herein can be effectively used to determine an-anti cancer treatment course in a subject in need thereof, the method comprising: administering to the subject an anti-cancer therapy (such as described above); and analyzing a presence or level of malignant or pre-malignant cells in a biopsy sample of the subject following administration according to the above-described method, whereby the presence or level of said malignant or pre-malignant cells is indicative of the treatment course.

Preferably, a number of biopsy samples are obtained such as prior to treatment and following treatment (can be repeated routinely, such as at any treatment cycle). In this case, the level of malignant or pre-malignant cells is compared in the different biopsies and a reduction in the level following treatment is indicative of treatment (alleviation and ultimately curing).

The present teachings allow identifying cellular phenotypes easily. This may be harnessed for identification of anti-cancerous agents which may be used as therapeutic leads. Indeed, the present inventors have employed the teachings of the present invention for drug screening (FIGS. 22A-D, FIGS. 23A-C, FIGS. 24A-C, FIGS. 27A-B and FIG. 28), establishment of in-vitro cell systems (FIGS. 20A-C) and target validation (FIGS. 30A-B, FIGS. 31A-D and FIGS. 32A-D). As is illustrated hereinbelow in the example section, drugs affectability can be tested in model systems, such as for Chronic Myelogenous Leukemia (CML) using the staining methods of the present invention (FIGS. 34A-C and FIGS. 35A-B).

Thus, according to still another aspect of the present invention there is provided a method of identifying an agent capable of reversing a pre-malignant or malignant phenotype of a cell, the method comprising, subjecting the cell to an agent; and analyzing a malignant phenotype of the cell thereafter according to the present teachings, wherein at least a partial reversion of phenotype is indicative of an agent capable of reversing a pre-malignant or malignant phenotype of the cell.

As used herein the phrase "malignant" also known as "cancerous" refers to uncontrolled cell proliferation which causes the formation of tumors with the capability of invasion, also referred to as metastasis.

As used herein the phrase "pre-malignant" refers to cellular transformation that may, but do not always, become malignant, cancerous. Also called precancerous (e.g., pre-malignant lesion).

As used herein the phrase "reversing a pre-malignant or malignant phenotype" refers to at least partially reversing the proliferative and/or invasive characteristics of the pre-malignant or malignant cell.

As used herein, the term "agent" refers to a molecule(s) or a condition capable of reversing or partially reversing the malignant or pre-malignant cellular phenotype.

Examples of molecules which can be utilized as agents according to the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone and/or bass structures or other chemical modifications); proteins, polypeptides (e.g. peptides, e.g. IFN-gamma see FIGS. 37A-C and FIGS. 38A-H), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

Examples of conditions suitable for use as agents according to the present invention include, but are not limited to culturing conditions, such as, for example, temperature, humidity, atmospheric pressure, gas concentrations, growth media, contact surfaces, radiation exposure (such as, gamma radiation, uv radiation, X-radiation) and the presence or absence of other cells in a culture. Another condition suitable for use as an agent according to the present invention includes an infection by intracellular invading microorganisms such as, but not limited to: (i) intracellular bacteria: *Myobacterium, tuberculosis, Myobacterium leprae, Listeria monocytogenes, Brucella abortus*, (ii) intracellular fungi: *Pneumocystis carinii, Candida albicans, Histoplasma capsulatum, Cryptococcus neoformans*, (iii) intracellular parasites: *Leishmania* sp., (iv) intracellular viruses: Herpes simplex virus, Variola, Measles virus, Retrovirus.

Cells that can be utilized by this aspect of the present invention include, cell-lines, primary cultures, permanent cell culture, organotypic cultures or tissues. Examples of cancer cells are provided in the Examples section which follows.

As mentioned hereinabove, reversion of phenotype is detected according to the present teachings. For example, the cell will no longer stain red following exposure to the reversing agent.

For further confirmation of abnormal phenotype reversion, the cells are microscopically examined for specific changes, such as, for example, physiological changes including apoptosis, loss of junctions, elongation or rounding, etc.

Although the present invention can, in theory, be practiced with a single cell, such a method is not efficient nor is it desirable. Preferably, the method of the present invention is used for high throughput screening of agents using a plurality of cells to simultaneously screen a variety of agents.

In such a large scale throughput screening approach the agent may be part of a library, such as an expression library including a plurality of expression constructs each having (i) a polynucleotide encoding one of a plurality of polypeptides which is tested for an ability to reverse an abnormal phenotype (an agent), and (ii) at least one cis acting regulatory element for directing expression of the polypeptides from the expression construct.

Alternatively, chemical libraries available, for example, from chemical companies including Merck, Glaxo, Novartis, and Bristol Meyers Squib can also be utilized for screening. Optionally, libraries of natural compounds in the form of bacterial, fungal, plant and animal extracts, which are available from, for example, Pan Laboratories or Mycosearch or are readily producible by methods known in the art can also be utilized by the present invention.

When performing large-scale screening, the cell population that is subjected to individual agents can be compartmentalized so as to facilitate identification of abnormal phenotype reversal. This may be effected by alliquoting the cell population into flat glass-bottom multiwell plates at a pre-calibrated density which allows the growth of just one or two clones per well.

In the step of screening a manual procedure can be followed, although automated screening using robots, such as multiwell attachment for the DeltaVision microscope, Cellomics automated microscope, are preferred.

Once identified, agents capable of at least partially reversing an abnormal cellular phenotype are recovered. If the agent is a polynucleotide or a polynucleotide expression product, cells are isolated and propagated and are used for isolating the polynucleotides agents, by, for example, PCR amplification, as discussed above.

The retrieved agents are further analyzed for their exact mechanism of action and adjusted for optimal effect, using various biochemical and cell-biology methods. Eventually, distinguishing which of the agent isolated is a potential a lead compound can be accomplished by testing the effect of the agent in pharmacological models of various diseases. Agents that affect disease progression or onset, constitute leads for drug development.

Such agents can be applied for treatment of many pathological states such as cancer and metabolic disorders such as, diabetes and obesity.

The following provides additional description of the present teachings.

Thus, the present invention provides a compound capable of distinguishing between a malignant and non-malignant cell by producing differential staining of the malignant and non-malignant cell, or by having differential fluorescence in the malignant and non-malignant cell. The compound of the present invention is further capable of distinguishing between a metabolically impaired cell and a metabolically normal cell by producing differential staining of the metabolically impaired cell and the metabolically normal cell, or by having differential fluorescence in the metabolically impaired cell and the metabolically normal cell. The present invention further provides compositions and kits comprising the compound, and methods of using the compound for a) identifying an agent which affects the phenotype of a malignant cell, a non-malignant cell, a metabolically impaired cell or a metabolically normal cell; b) determining whether the expression of an oncogene in a non-malignant cell affects the non-malignant phenotype of the cell; c) determining whether altering the expression or function of a tumor suppressor gene in a cell affects the phenotype of the cell; d) detecting the presence of a malignant cell and/or a cell having a metabolic disorder in a sample; e) diagnosing a condition or disease in a subject, wherein the condition or disease is a metabolic disorder or a condition characterized by the presence of at least one malignant cell; f) monitoring the progression of a condition or disease in a subject, wherein the condition or disease is a metabolic disorder or a condition characterized by the presence of at least one malignant cell; g) monitoring and/or regulating a therapy regimen for a subject undergoing therapy for a metabolic disorder or a condition or disease characterized by the presence of at least one malignant cell; h) in-vivo imaging for detecting the presence of at least one malignant cell in a subject; i) identifying an agent which induces neuronal or stem cell differentiation (embryonic and adult stem cells); and j) identifying an agent which histoprotects against organ/tissue damage. The methods of the present invention may be adapted to and performed using means for high output, thus providing efficient and reliable tools for drug discovery, target validation, diagnosis, drug therapy monitoring, and monitoring of disease progress.

As used herein, the term "differential staining" refers to a stain which can differentiate between the phenotype of two cell populations, for example between the phenotype of a malignant cell to the phenotype of a non-malignant cell, or the phenotype of a diseased versus healthy cell, for example the phenotype of a metabolically impaired cell and a metabolically normal cell. As used herein, the term "differential fluorescence" refers to a fluorescence which can differentiate between the phenotype of two cell populations, for example between the phenotype of a malignant cell to the phenotype of a non-malignant cell or the phenotype of a diseased versus a healthy cell, for example the phenotype of a metabolically impaired cell and a metabolically normal cell.

In one embodiment, the composition comprising the compound of the present invention is a plant extract. In another embodiment, the composition is a crude plant extract. In another embodiment, the composition is a purified plant extract.

In another embodiment, the compound of the present invention is extracted from a plant. In another embodiment, the plant is *Ficus Elastica*. In yet another embodiment, the compound is a synthetic compound, which may be synthesized by total or partial synthesis. In another embodiment, the compound is characterized by an NMR spectra as detailed in FIGS. 43-44. In another embodiment, the compound is fluorescent. In another embodiment, the compound emits fluorescence at 430 nm upon excitation at 375 nm. In another embodiment, the compound inhibits the staining of a malignant cell or a non-malignant cell.

In one embodiment, the agent is a physical agent. In another embodiment, the agent is a chemical agent. In another embodiment, the agent is a biological agent. In another embodiment, the agent is a gene. In another embodiment, the agent is a tumor suppressor gene. In another embodiment, the agent is an oncogene. In another embodiment, the agent is any combination of a physical agent, a chemical agent, a biological agent, a gene, a tumor suppressor gene or an oncogene.

In addition, in one embodiment, the present invention provides a method for identifying a composition comprising a compound capable of inhibiting the staining of a cell, the method comprising the steps of obtaining a sample comprising at least one cell, contacting the sample with the composition in the presence of a dye, and detecting the inhibition of staining of the cell by the dye as a function of the concentration of the composition; thereby identifying the composition. In one embodiment, the method further comprises the step of purifying the composition to obtain the compound.

As defined herein, "contacting" means that the compound, composition, dye or agent affecting a cell phenotype, is introduced into a sample comprising at least one cell in a test tube, flask, tissue culture, chip, array, plate, microplate, capillary, or the like, and incubated at a temperature and time sufficient to permit the desired effect, such as staining the cell, inhibiting the staining of a cell with a dye, conversion of a malignant phenotype to a non-malignant phenotype, conversion of a non-malignant phenotype to a malignant phenotype, and the like. Methods for contacting the samples with the compounds, compositions, dyes or agents are known to those skilled in the art and may be selected depending on the type of assay protocol to be run. Incubation methods are also standard and are known to those skilled in the art.

The term "obtaining", as used herein, refers interchangeably to providing, obtaining, procuring, or supplying a sample or specimen for the purpose of subjecting a biological sample contained therein to one or more of embodiments of the staining method of the present invention.

The term "detecting", as used herein, refers to the act of detecting, perceiving, uncovering, exposing, visualizing or identifying a cell.

The term "sample" as referred to herein encompasses, but is not limited to, a biological sample, for example any tissue, cell-comprising tissue, cell line, cell culture, a primary cell culture, arising from or derived from an organism and processes to form a specimen suitable for cell staining.

As used herein, the term "dye" refers to any substance that imparts color to a biological tissue, animal, plant, or otherwise, and which is useful for cytological or histological visualization of tissue, cells, or the parts that comprise them. The dyes which have been found to be of immediate utility for the purpose of implementing the present invention are disclosed herein, although other dyes not herein described may be useful as well for this purpose. Thus, although the description of the present invention provides dyes which manifest color in the visible range of the spectrum, it may easily be envisioned that, through the use of appropriate filters, illuminations, configurations, or means for detection, dyes which are invisible to direct observation may prove equivalent to the visible dyes described herein for implementing the present invention.

In one embodiment, the dye is an acidic dye. In another embodiment, the dye is a basic dye. In another embodiment, the dye is a triamnotriphenylmethane derivative. In another embodiment, the dye is a diazo derivative. In another embodiment, the dye is any combination of an acidic dye, a basic dye, a triaminotriphenylmethane derivative a diazo derivative.

In another embodiment, the dye is Hematoxylin Gill, Azure, A, Eosin Yellow, Phloxine, Light Green, New Fuchsin, Dahlia, Basic Fuchsin, Methyl Violet, Gentian Violet, Methyl Violet 6b, Crystal Violet, Pararosanilin, Rosanilin, Magenta I, Isorubin, Fuchsin NB, FIAT-764, Spiller's Purple, Bismark Brown R, Bismark Brown Y, Bismark Brown Eosine Conjugate, Bismark Brown Phloxine Conugate, Phoenix Brown A, or any combination thereof.

In one embodiment, the dye is a red dye. As used herein, the term "red" refers not only to the color red but as well to related shades and hues such as violet, pink or pinkish, purple or purplish, or magenta. In one embodiment, the red dye is New Fuchsin.

In one embodiment, the dye is a green dye. As used herein, the term "green" refers not only to the color green but as well to related shades and hues such as light green, dark green, emerald, olive and lime. In one embodiment, the green dye is Light Green dye.

The concentration of the dye will be determined empirically based on the need of the assay. A suitable concentration of a dye is one that enables the detection of the staining of the cell with the dye, using any of the detection methods as described herein.

In one embodiment, the composition comprising the compound capable of inhibiting the staining of a cell is a plant extract. In another embodiment, the composition is a crude plant extract. In another embodiment, the composition is a purified plant extract. In another embodiment, the compound which is capable of inhibiting the staining of a cell is extracted from a plant. In another embodiment, the plant is *Ficus Elastica*. In yet another embodiment, the compound is a synthetic compound. In another embodiment, the compound is characterized by an NMR spectra as detailed in FIGS. 43-44. In another embodiment, the compound is fluorescent. In another embodiment, the compound emits fluorescence at 430 nm upon excitation at 375 nm. In another embodiment, the compound has a molecular formula of $C_{23}H_{44}O_4$.

In addition, in one embodiment, the present invention provides a cytohistological staining method for identifying an agent which affects the phenotype of a malignant or a non-malignant cell, the method comprising the steps of obtaining a sample comprising more than one cell, aliquoting at least a first fraction and a second fraction from the sample, contacting the second fraction with a test agent, contacting the first fraction and the second fraction with a compound capable of distinguishing between a malignant cell and a non-malignant cell by producing differential staining of the malignant cell and the non-malignant cell as described hereinabove, contacting the first fraction and the second fraction with at least a first dye and a second dye, detecting the staining of the first fraction with the first dye and the second dye, detecting the staining of the second fraction with the first dye and the second dye, and comparing the staining of the first fraction and the second fraction, thereby identifying the agent which affects a malignant or non-malignant phenotype. In another embodiment, the method is adapted for identifying a combination of agents which affect a malignant or a non-malignant cell phenotype.

In one embodiment, a cell having a malignant phenotype stains substantially with one dye, and a cell having a non-malignant phenotype stains substantially with a second dye, which is different from the first dye. As used herein, the term "stains substantially" means that the cell stains with one particular dye to a larger extent than staining with the other dye. In one embodiment, a cell having a malignant phenotype stains substantially with a red dye. In another embodiment, a cell having a non-malignant phenotype stains substantially with a green dye.

In another embodiment, a cell having a malignant phenotype stains substantially with one dye, and a cell having a non-malignant phenotype stains differentially with the same dye. For example, the cell having a malignant phenotype stains substantially with one dye, and a cell having a non-malignant phenotype stains less intensively with the same dye.

In addition, in another embodiment, the present invention provides a method for identifying an agent which affects the phenotype of a malignant and non-malignant cells, the method comprising the steps of obtaining a sample comprising more than one cell, aliquoting at least a first fraction and a second fraction from the sample, contacting the second fraction with the agent, contacting the first fraction and the second fraction with a compound capable of distinguishing between a malignant cell and a non-malignant cell by having differential fluorescence in the malignant and non-malignant cell, detecting the fluorescence of the first fraction and the second fraction, and comparing the fluorescence of the first fraction and the second fraction, thereby identifying the agent affecting a malignant or non-malignant phenotype. In one embodiment, the method is repeated using different concentrations of the agent. In one embodiment, the fluorescent compound is the synthetic compound or the compound extracted from a plant, characterized by an NMR spectra as detailed in FIGS. 43-44, or having molecular formula of $C_{23}H_{44}O_4$, as described hereinabove. In another embodiment, the compound emits fluorescence at 430 nm upon excitation at 375 nm. In another embodiment, the method is used for identifying a combination of agents which affect a malignant or a non-malignant cell phenotype.

In another embodiment, the present invention provides a cytohistological staining method for identifying an agent which affects the phenotype of a metabolically impaired cell or a metabolically normal cell, the method comprising the steps of obtaining a sample comprising more than one, aliquoting at least a first fraction and a second fraction from the sample, contacting the second fraction with the agent, contacting the first fraction and the second fraction with a compound capable of distinguishing between the metabolically impaired cell and the metabolically normal cell by producing differential staining of the metabolically impaired and the metabolically normal cell, contacting the first fraction and the second fraction with at least one dye, detecting the staining of the first fraction with the dye; detecting the staining of the second fraction with the dye, and comparing the staining of the first fraction and said second fraction, thereby identifying the agent affecting the phenotype of the metabolically impaired cell or the metabolically normal cell.

In another embodiment, the present invention provides a method for identifying an agent which affects the phenotype of a metabolically impaired cell or a metabolically normal cell, the method comprising the steps of obtaining a sample comprising more than one cell, aliquoting at least a first fraction and a second fraction from the sample, contacting the second fraction with the agent, contacting the first fraction and the second fraction with a compound capable of distinguishing between the metabolically impaired cell and the metabolically normal cell by having differential fluorescence in the metabolically impaired cell and the metabolically normal cell, detecting the fluorescence of the first fraction and the second fraction, and comparing the fluorescence of the first fraction and the second fraction, thereby identifying the agent affecting the phenotype of the metabolically impaired cell or the metabolically normal cell.

In addition, in another embodiment, the present invention provides a cytohistological staining method for determining whether the expression of an oncogene in a non-malignant cell affects the non-malignant phenotype of the cell, the method comprising the steps of obtaining a sample comprising more than one non-malignant cell, aliquoting at least a first fraction and a second fraction from the sample, expressing an oncogene in the second fraction, contacting the first fraction and the second fraction with a compound capable of distinguishing between a malignant cell and a non-malignant cell by producing differential staining of the malignant cell and the non-malignant cell as described hereinabove, contacting the first fraction and the second fraction with at least a first dye and a second dye, detecting the staining of the first fraction with the first dye and the second dye, is detecting the staining of the second fraction with the first dye and the second dye, and comparing the staining of the first fraction and the second fraction, thereby determining whether the expression of the oncogene in the non-malignant cell affects the non-malignant phenotype of the cell.

In addition, in another embodiment, the present invention provides a method for determining whether the expression of an oncogene in a non-malignant cell affects the non-malignant phenotype of the cell the method comprising the steps of obtaining a sample comprising more than one non-malignant cell, aliquoting at least a first fraction and a second fraction from the sample, expressing an oncogene in the second fraction, contacting the first fraction and the second fraction with a compound capable of distinguishing between a malignant cell and a non-malignant cell by having differential fluorescence in the malignant and non-malignant cell, detecting the fluorescence of the first fraction and the second fraction, and comparing the fluorescence of the first fraction and the second fraction, thereby determining whether the expression of the oncogene in the non-malignant cell affects the non-malignant phenotype of the cell.

As used herein, the term "oncogene", used herein interchangeably with a "tumor-promoting" gene, has its commonly understood meaning in the art, i.e. is a gene whose expression correlates with tumor development.

In one embodiment, the oncogene promotes the conversion of the non-malignant cell to a cell having a malignant phenotype. In another embodiment, the oncogene is expressed by in the cell by chemically, biologically, virally or bacterially transfecting the oncogene into the cell.

In addition, in another embodiment, the present invention provides a cytohistological staining method for determining whether altering the expression or function of tumor suppressor gene in a cell affects the phenotype of the cell, the method comprising the steps of obtaining a sample comprising more than one cell, aliquoting at least a first fraction and a second fraction from the sample; altering the expression or function of a tumor suppressor gene in the second fraction; contacting the first fraction and the second fraction with a compound capable of distinguishing between a malignant cell and a non-malignant cell by producing differential staining of the malignant cell and the non-malignant cell as described hereinabove, contacting the first fraction and the second fraction with at least a first dye and a second dye, detecting the staining of the first fraction with the first dye and the second dye, detecting the staining of the second fraction with the first dye and the second dye; and comparing the staining of the first fraction and the second fraction, thereby determining whether altering the expression or function of the tumor suppressor gene in the cell affects the phenotype of the cell.

In addition, in another embodiment, the present invention provides a method for determining whether altering the expression or function of a tumor suppressor gene in a cell affects the phenotype of the cell, the method comprising the steps of obtaining a sample comprising more than one cell, aliquoting at least a first fraction and a second fraction from the sample, altering the expression or function of a tumor suppressor gene in the second fraction, contacting the first fraction and the second fraction with a compound capable of distinguishing between a malignant cell and a non-malignant cell by having differential fluorescence in the malignant and non-malignant cell, detecting the fluorescence of the first fraction and the second fraction, and comparing the fluorescence of the first fraction and the second fraction, thereby determining whether altering the expression or function of the tumor suppressor gene in the cell affects the phenotype of the cell.

As used herein, the term "tumor suppressor gene" has its commonly understood meaning in the art, i.e. a gene whose expression and normal function correlates with tumor suppressor activity.

In one embodiment, the cell is a malignant cell. In another embodiment, altering the expression or modifying the aberrant or abnormal function of the tumor suppressor gene comprises enhancing the expression/function of the tumor suppressor gene in the malignant cell. In another embodiment, enhancing the expression of the tumor suppressor gene comprises chemically, biologically, virally or bacterially transfecting the tumor suppressor gene in the cell. In another embodiment, normalizing the function of the tumor suppressor gene comprises chemically, biologically, virally or bacterially expressing the normal function of tumor suppressor gene in the cell. In another embodiment, enhancing the expression or normalizing the function of the tumor suppressor gene promotes the conversion of the malignant cell to a cell having a non-malignant phenotype. The term "aberrant" as used herein refers to a function that is abnormal, unusual, deviant, irregular or atypical.

In one embodiment, the cell is a non-malignant cell. In another embodiment, altering the expression/function of the tumor suppressor gene comprises functional silencing of the tumor suppressor gene in the non-malignant cell. In another embodiment, functional silencing of the tumor suppressor gene promotes the conversion of the non-malignant cell to a cell having a malignant phenotype.

In addition, in another embodiment, the present invention provides a cytohistological staining method for detecting the presence of a malignant cell in a sample, the method comprising the steps of obtaining a sample comprising at least one cell, contacting the sample with a compound capable of distinguishing between a malignant cell and a non-malignant cell by producing differential staining of the malignant cell and the non-malignant cell as described hereinabove, contacting the sample with at least a first dye and a second dye, and detecting the staining of the sample with the first and second dye, thereby detecting the presence of a malignant cell in the sample.

In addition, in another embodiment, the present invention provides a method for detecting the presence of a malignant cell in a sample, the method comprising the steps of obtaining a sample comprising at least one cell, contacting the sample with a compound capable of distinguishing between a malignant cell and a non-malignant cell by having differential fluorescence in the malignant and non-malignant cell, and detecting the fluorescence of the sample, thereby detecting the presence of a malignant cell in the sample.

Furthermore, in another embodiment, the present invention provides a method for detecting the presence of a metabolically impaired cell in a sample, the method comprising the steps of obtaining a sample comprising at least one cell, contacting the sample with a compound a compound capable of distinguishing between the metabolically impaired cell and the metabolically normal cell by producing differential staining of the metabolically impaired and the metabolically normal cell, contacting the sample with at least one dye, and detecting the staining of the sample with the dye, thereby detecting the presence of the metabolically impaired cell in the sample.

Furthermore, in another embodiment, the present invention provides a method for detecting the presence of a metabolically impaired cell in a sample, the method comprising the steps of obtaining a sample comprising at least one cell, contacting the sample with a compound capable of distinguishing between the metabolically impaired cell and a metabolically normal cell having differential fluorescence in the metabolically impaired cell and the metabolically normal cell, and detecting the fluorescence of the sample, thereby detecting the presence of the metabolically impaired cell in the sample.

In addition, in another embodiment, the present invention provides a method for diagnosing a condition or disease in a subject, wherein the condition or disease is characterized by the presence of at least one malignant cell, the method comprising the step of detecting at least one malignant cell in a sample obtained from the subject using any of the methods described hereinabove for detecting the presence of a malignant cell in a sample, wherein the presence of at least one malignant cell in the sample is indicative of the subject having the condition or disease. In one embodiment, the condition or disease is a cancer or a pre-cancerous condition or disease.

Furthermore, in one embodiment, the present invention provides a method for diagnosing a metabolic disorder in a subject, the method comprising the step of detecting at least one cell having a metabolic disorder in a sample obtained from the subject using any of the methods described hereinabove for detecting the presence of a cell having a metabolic disorder in a sample, wherein the presence of at least one cell having a metabolic disorder in the sample is indicative of the subject having the metabolic disorder.

In addition, in another embodiment, the present invention provides a method for monitoring the progression of a condition or disease in a subject, wherein the condition or disease is characterized by the presence of at least one malignant cell, the method comprising the steps of obtaining a first sample from the subject, determining the presence and/or number of malignant cells in the first sample using any of the methods described hereinabove for detecting the presence of a malignant cell in a sample, obtaining a second sample from the subject after a period of time, detecting the presence and/or number of malignant cells in the second sample using the method described hereinabove for detecting the presence of a malignant cell in a sample, and comparing the presence and/or number of malignant cells in the first sample and the second sample, thereby monitoring the progression of the condition or disease in the subject. In one embodiment, the condition or disease is a cancer or a pre-cancerous condition or disease.

Furthermore, in another embodiment, the present invention provides a method for monitoring the progression of a metabolic disorder in a subject, the method comprising the steps of obtaining a first sample from the subject, determining the presence and/or number of cells having the metabolic disorder in said first sample using any of the methods described hereinabove for detecting the presence of a cell having a metabolic disorder in a sample, obtaining a second sample from the subject after a period of time, detecting the presence and/or number of cells having the metabolic disorder in the second sample using any of the methods described hereinabove for detecting the presence of a cell having a metabolic disorder in a sample, and comparing the presence and/or number of cells having the metabolic disorder in the first sample and the second sample, thereby monitoring the progression of the metabolic condition or disease in the subject.

In addition, in another embodiment, the present invention provides a method for monitoring a therapy regimen for a subject undergoing therapy for condition or disease characterized by the presence of at least one malignant cell, the method comprising the steps of obtaining a first sample from the subject prior to initiation of the treatment regimen, determining the presence and/or number of malignant cells in the first sample using any of the methods described hereinabove for detecting the presence of a malignant cell in a sample, initiating the therapy regimen, obtaining a second sample from the subject after a period of time, determining the presence and/or number of malignant cells in the second sample using any of the methods described hereinabove for detecting the presence of a malignant cell in a sample, and comparing the presence and/or number of malignant cells in the first sample and the second sample, thereby monitoring the therapy regimen for the subject. In one embodiment, the condition or disease is a cancer or a pre-cancerous condition or disease.

Furthermore, in one embodiment, the present invention provides a method for monitoring a therapy regimen for a subject undergoing therapy for a metabolic disorder, said method comprises the steps of obtaining a first sample from the subject prior to initiation of the treatment regimen, determining the presence and/or number of cells having the metabolic disorder in the first sample using any of the methods described hereinabove for detecting the presence of a cell having a metabolic disorder in a sample, initiating the therapy regimen, obtaining a second sample from the subject after a period of time, determining the presence and/or number of cells having the metabolic disorder in the second sample using any of the methods described hereinabove for detecting the presence of a cell having a metabolic disorder in a sample, thereby monitoring the therapy regimen for the subject.

In one embodiment, the methods of monitoring the therapy regimen further comprise the step of regulating the therapy regimen by regulating a dosage amount, a dosage schedule, or a combination thereof of the therapy regimen. In one embodiment, the therapy regimen comprises radiotherapy. In another embodiment, the therapy regimen comprises chemotherapy. In another embodiment, the therapy regimen comprises immunotherapy. In another embodiment, the therapy regimen comprises viral therapy. In another embodiment, the therapy regimen comprises any combination of radiotherapy, chemotherapy, immunotherapy and viral therapy. In another embodiment, the therapy regimen comprises treatment with a chemical compound, a natural compound, a synthetic compound, a monomer, polymer, a protein, a glycoprotein, a lipid, a carbohydrate, a fatty acid, a nucleic acid, an antibody, a virus, a prion, a combinatorial library of synthetic compounds, a genomic library, a nucleic acid, a nucleic acid library, a protein, a protein library, a natural extract, a plant extract, an animal extract, or a mixture thereof.

In one embodiment, the step of detection of staining used in the methods described hereinabove comprises determining the ratio of staining with the first dye to the second dye in the first fraction and in the second fraction. In another embodiment, the step of detection of staining used in the methods described hereinabove further comprises determining the total number of cells in the sample by detecting the staining of the sample with the first dye, detecting the staining of the sample with the second dye, and summing the staining of the sample with the first dye and the second dye.

In another embodiment, the step of detection of staining used in any of the methods described hereinabove comprises detecting the absorption of the first dye or the second dye. In another embodiment, the step of detection staining comprises detecting the intensity of color of the first dye and the second dye. In another embodiment, the step of detection of staining comprises detecting the pattern of color of the first dye and the second dye. In another embodiment, the step of detection of staining comprises detecting the distribution of color of the first dye and the second dye. In another embodiment, the step of detection of staining comprises detecting the concentration of color of the first dye and the second dye. In another embodiment, the step of detection of staining comprises any combination of the detection methods described hereinabove.

In one embodiment, the methods of the present invention further comprise the step of fixing the cells. In another embodiment, the methods further comprise the step of air-fixing the cells.

In one embodiment, the methods are repeated using different concentrations of the agent, the oncogene, the tumor suppressor gene and the like.

In one embodiment, the methods of the present invention are adapted to and are performed using means for high output. In another embodiment, the means comprises an automated sampling device, a liquid handling equipment, an automated stainer, a dispenser, a robot, or any combination thereof.

In addition, in another embodiment, the present invention provides a kit for detecting the presence of a malignant cell in a sample, the kit comprising a compound capable of distinguishing between a malignant cell and a non-malignant cell by producing differential staining of the malignant cell and the non-malignant cell, or by having differential fluorescence in the malignant cell and the non-malignant cell as described hereinabove, and a member for holding a sample.

In addition, in another embodiment, the present invention provides a kit for detecting the presence of a metabolically impaired cell in a sample, the kit comprising a compound capable of distinguishing between a metabolically impaired cell and a metabolically normal cell by producing differential staining of the metabolically impaired cell and the metabolically normal cell, or by having differential fluorescence in the metabolically impaired cell and the metabolically normal cell as described hereinabove, and a member for holding a sample.

In one embodiment, the member is selected from the group consisting of slides, microscope slides, arrays of wells, microtiter plate assay trays, transparent vessels, coverslips, filters, membranes, tubes, or a combination thereof.

In another embodiment, the kit further comprises at least a first dye and a second dye. The dye may be any of the dyes described hereinabove, for example anacidic dye, a basic dye, atriaminotriphenylmethane derivative, a diazo derivative, or may combination thereof. In another embodiment, the kit further comprises at least one fixative. In another embodiment, the kit further comprises a buffer, a chelating agent, a preservative, or any combination thereof.

In addition, in another embodiment, the present invention provides a method of identifying the optimal working concentration of a composition comprising a compound capable of distinguishing between a malignant cell and a non-malignant cell by producing differential staining of the malignant cell and the non-malignant cell as described hereinabove, the method comprising the steps of obtaining a sample comprising more than one cell having a malignant phenotype, aliquoting at least a first fraction and a second fraction from the sample, contacting the second fraction with an agent which promotes the conversion of the malignant phenotype to a non-malignant phenotype, contacting the first fraction and the second fraction with one or more concentrations of the composition, contacting the first fraction and the second fraction with at least a first dye and a second dye, detecting the staining of the first fraction and the second fraction with the first dye and the second dye, measuring the ratio $R_1$ denoting staining with the first dye to the second dye the first fraction at each concentration of the composition; measuring the ratio $R_2$ denoting staining with the first dye to the second dye in the second fraction at each concentration of the composition, and calculating the ratio $R_1/R_2$ for each concentration of the composition, wherein the optimal working concentration of the composition is the concentration at which $R_1/R_2$ is at a maximum. In one embodiment, the malignant cell stains substantially with the first dye and the non-malignant cell stains substantially with the second dye.

In another embodiment, the present invention provides a method of identifying the optimal working concentration of a composition comprising a compound capable of distinguishing between a malignant cell and a non-malignant cell by producing differential staining of the malignant cell and the non-malignant cell as described hereinabove, the method comprising the steps of obtaining a sample comprising more than one cell having a non-malignant phenotype, aliquoting at least a first fraction and a second fraction from the sample, contacting the second fraction with an agent which promotes the conversion of the non-malignant phenotype to a malignant phenotype, contacting the first fraction and the second fraction with one or more concentrations of the composition, contacting the first fraction and the second fraction with at least a first dye and a second dye, detecting the staining of the first fraction and the second fraction with the first dye and the second dye, measuring the ratio $R_1$ denoting staining with the first dye to the second dye in the second fraction at each concentration of the composition, measuring the ratio $R_2$ denoting staining with the first dye to the second dye in the first fraction at each concentration of the composition; and calculating the ratio $R_1/R_2$ for each concentration of the composition; wherein the optimal working concentration of the composition is the concentration at which $R_1/R_2$ is at a maximum. In one embodiment, the malignant cell stains substantially with the first dye and the non-malignant cell stains substantially with the second dye.

In addition, in another embodiment, the present invention provides an in-vivo imaging method for detecting the presence of at least one malignant cell in a subject, the method comprising the steps of administering to the subject a composition comprising a compound is capable of distinguishing between a cell and a non-malignant cell by producing differential staining of the malignant cell and the non-malignant cell, administering to the subject at least a first dye and a second dye, and detecting the presence of the first and second dye in the subject, thereby detecting the presence of at least one malignant cell in the subject. In one embodiment, the malignant cell stains substantially with the first dye, wherein detecting the presence of the first dye in the subject is indicative of the subject having a malignant cell.

Malignant Disorders:

As used herein, the term "cancer" is used interchangeably with the terms malignancy, malignant or neoplasm, and refers to a disease of cells characterized by an abnormal growth of cells which tend to proliferate in an uncontrolled way and, in some cases, to metastasize.

A "cancer cell" or a "malignant cell" as used herein, is a cell which has been released from normal cell division control, is thus characterized by an abnormal growth and a tendency to proliferate in an uncontrolled way and, in some cases, to metastasize. In one embodiment, the term "malignant cell" refers to a cell having a malignant phenotype. The definition of a malignant cell includes a neoplastic cell, a pre-malignant cell, a metastatic cell, a malignant cell, a tumor cell, an oncogenic cell, a cell with a cancer genotype, a cell of malignant phenotype, a cell with a malignant genotype, an oncogene transfected cell, a virus transformed cell, a cell which expresses a marker for an oncogene, a cell which expresses a marker for cancer, or a combination thereof. Included in this definition are cell lines derived from any of these cells. Non-limiting examples of malignant cells/cell lines suitable for use in the present invention are: a human colorectal adenocarcinoma (HT29) cell line; a human breast carcinoma (MCF-7) cell line, a human leukemia K562 cell line, a human leukemic HL-60 cell line, a Ras V 12-transformed Rat1 (Rat1 Ras) cell line, a histiocytic lymphoma (U937) cell line, or a combination thereof.

A "non-malignant cell", as used herein, refers to a normal cell, a normal cell line, a malignant cell that has been induced to express a phenotype of anon-malignant cell, an immortalized cell line, a primary cell culture, or any combination thereof. Included in this definition are cell lines derived from any of these cells. In one embodiment, the term "non-malignant cell" refers to a cell having a malignant phenotype. Non-limiting examples of non-malignant cells/cell lines suitable for use in the present invention are: a human primary colonocytes (CCD-33C0), a rat1 fibroblasts an MCF-7 cell line treated with sodium butyrate, a HT29 cell line treated with sodium butyrate, a Rat1 Ras cell line treated with PD98058, a K562 cell line treated with sodium butyrate and/or gleevec, a U937 cell line treated with all-trans-retinoic acid (ATRA), or a combination thereof.

A "normal cell", as used herein, refers to a cell which does not have a malignant phenotype, and/or or cell which does not have a metabolic disorder.

In accordance with embodiments of the present invention, a malignant cell or a cancer cell is an adenocarcinoma cell, an adrenal gland tumor cell, an ameloblastoma cell, an anaplastic cell, anaplastic carcinoma of the thyroid cell, an angiofibroma cell, an angioma cell, an angiosarcoma cell, an apudoma cell, an argentaffmoma cell, an arrhenoblastoma cell, an ascites tumor cell, an ascitic tumor cell, an astroblastoma cell, an astrocytoma cell, an ataxia-telangiectasia cell, an atrial myxoma cell, a basal cell carcinoma cell, a benign tumor cell, a bone cancer cell, a bone tumor cell, a brainstem glioma cell, a brain tumor cell, a breast cancer cell, a Burkitt's lymphoma cell, a cancerous cell, a carcinoid cell, a carcinoma cell, a cerebellar astrocytoma cell, a cervical cancer cell, a cherry angioma cell, a cholangiocarcinoma cell, a cholangioma cell, a chondroblastoma cell, a chondroma cell, a chondrosarcoma cell, a chorioblastoma cell, a choriocarcinoma cell, a colon cancer cell, a common acute lymphoblastic leukemia cell, a craniopharyngioma cell, a cystocarcinoma cell, a cystofbroma cell, a cystoma cell, a cytoma cell, a ductal carcinoma in situ cell, a ductal papilloma cell, a dysgerminoma cell, an encephaloma cell, an endometrial carcinoma cell, an endothelioma cell, an ependymoma cell, an epithelioma cell, an erythroleukemia cell, an Ewing's sarcoma cell, an extra nodal lymphoma cell, a feline sarcoma cell, a fibro adenoma cell, a fibro sarcoma cell, a follicular cancer of the thyroid cell, a ganglioglioma cell, a gastrinoma cell, aglioblastoma multiform cell, a glioma cell, a gonadoblastoma cell, an haemangioblastoma cell, an haemangioendothelioblastoma cell, an haemangioendothelioma cell, an haemangiopericytoma cell, an haematolymphangioma cell, an haemocytoblastoma cell, an haemocytoma cell, a hairy cell leukemia cell, a hamartoma cell, an hepatocarcinoma cell, an hepatocellular carcinoma cell, an hepatoma cell, an histoma cell, a Hodgkin's disease cell, an hypernephroma cell, an infiltrating cancer cell, an infiltrating ductal cell carcinoma cell, an insulinoma cell, a juvenile angioforoma cell, a Kaposi sarcoma cell, a kidney tumor cell, a large cell lymphoma cell, a leukemia cell, a chronic leukemia cell, an acute leukemia cell, a lipoma cell, a liver cancer cell, a liver metastases cell, a Lucke carcinoma cell, a lymphadenoma cell, a lymphangioma cell, a lymphocytic leukemia cell, a lymphocytic lymphoma cell, a lymphoeytoma cell, a lymphoedema cell, a lymphoma cell, a lung cancer cell, a malignant mesothelioma cell, a malignant teratoma cell, a mastocytoma cell, a medulloblastome cell, a melanoma cell, a meningioma cell, a mesothelioma cell, a metastatic cell, a metastasis cell, a metastatic spread cell, a Morton's neuroma cell, a multiple myeloma cell, a myeloblastoma cell, a myeloid leukemia cell, a myelolipoma cell, a myeloma cell, a myoblastoma cell, a myxoma cell, a nasopharyngeal carcinoma cell, a neoplastic cell, a nephroblastoma cell, a neuroblastoma cell, a neurofibroma cell, a neurofibromatosis cell, a neuroglioma cell, a neuroma cell, a non-Hodgkin's lymphoma cell, an oligodendroglioma cell, an optic glioma cell, an osteochondroma cell, an osteogenic sarcoma cell, an osteosarcoma cell, an ovarian cancer cell, a Paget's disease of the nipple cell, a pancoast tumor cell, a pancreatic cancer cell, a phaeochromocytoma cell, a pheoehromocytoma cell, a plasmacytoma cell, a primary brain tumor cell, a progonoma cell, a prolactinoma cell, a renal cell carcinoma cell, a retinoblastoma cell, a rhabdomyosarcoma cell, a rhabdosarcoma cell, a solid tumor cell, sarcoma cell, a secondary tumor cell, a seminoma cell, a skin cancer cell, a small cell carcinoma cell, a squamous cell carcinoma cell, a strawberry haemangioma cell, a T-cell lymphoma cell, a teratoma cell, a testicular cancer cell, a thymoma cell, a trophoblastic tumor cell, a tumorigenic cell, a tumor initiation cell, a tumor progression cell, a vestibular schwannoma cell, a Wilm's tumor cell, or a combination thereof.

Neuronal or Stem Cell Differentiation

Furthermore, in accordance with another embodiment of the present invention, there is provided a cytohistological staining method for identifying an agent which induces neuronal or stem cell differentiation, the method comprising the steps of obtaining a sample comprising more than one undifferentiated neuronal or stem cell, aliquoting at least a first fraction and a second fraction from the sample, contacting the second fraction with the agent, contacting the first fraction and the second fraction with a compound capable of distinguishing between an undifferentiated and differentiated neuronal or stem cell by producing differential staining of the undifferentiated and differentiated neuronal or stem cell, contacting the first fraction and the second fraction with at least a first dye and a second dye, detecting the staining of the first fraction with the first dye and the second dye, detecting the staining of the second fraction with the first dye and the second dye; and comparing the staining of the first fraction and the second fraction, thereby identifying the agent which induces neuronal or stem cell differentiation. In another embodiment, the method is adapted for identifying a combination of agents which induce neuronal or stem cell differentiation.

Furthermore, in another embodiment, the present invention provides a method for identifying an agent which induces neuronal or stem cell differentiation, the method comprising the steps of obtaining a sample comprising more than one undifferentiated neuronal or stem cell, aliquoting at least a first fraction and a second fraction from the sample, contacting the second fraction with the agent, contacting the first fraction and the second fraction with a compound capable of distinguishing between an undifferentiated and differentiated neuronal or stem cell by having differential fluorescence in the undifferentiated and differentiated neuronal or stem cell, detecting the fluorescence of the first fraction and the second fraction; and comparing the fluorescence of the first fraction and the second fraction, thereby identifying the agent which induces neuronal or stem cell differentiation. In another embodiment, the method is adapted for identifying a combination of agents which induce neuronal or stem cell differentiation.

As used herein, the terms "undifferentiated" and "differentiated" neuronal or stem cell refer not only to a completely undifferentiated neuronal or stem cell versus a neuronal or stem cell that is completely differentiated, i.e. has completed the process of differentiation. Rather, these terms also include neuronal or stem cells at different stages in development and differentiation. For example, the compound of the present invention may produce differential staining in two neuronal or stem cells at different stages of differentiation. In another embodiment, the compound of the present invention may have differential fluorescence in two neuronal or stem cells at different stages of differentiation.

The potential connection between differentiation induction and the normalization of the diseased phenotype is established in the literature (Lindsell P, 2001). Moreover, the scientific foundation on the possibility to use the differentiation triggering agents as histoprotectors could be demonstrated by neuroprotectors in the case of the neuronal or stem cell damage and is well established (Cheung et al, 2000). *Ganoderma* extract (traditional Chinese medicine) induced the neuronal or stem cell differentiation of PC12 cells. The presence of neuroactive compounds that mediate the neuronal or stem cell differentiation and neuroprotection of the PC12 cells was documented (Cheung et al, 2000). Nerve growth factor (NGF), which has been shown to act as a morphological and neurochemical differentiating factor in PC12 cells, also protects PC12 cells from the toxicity of serum withdrawal and ischemia (Boniece et al, 1995). The neuroprotective effect of NGF requires some of the same signal transduction steps used by NGF to promote differentiation and neurite formation (Boniece et al, 1995). Furthermore, it was found that exposure of PC12 cells to retinoic acid, which promotes the differentiation and inhibits the growth of PC12 cells, also improves cell survival during ischemia. In addition, a combination of NGF and retinoic acid was more effective than either agent alone. It is likely that these two agents confer protection by independent pathways (Boniece et al, 1995), but these signals are differentiation-connected.

As contemplated herein, this invention provides a useful screening system to detect differentiation inducing agents. Base on the results described hereinbelow, showing the detection of NGF (not shown), Retinoic acid (FIGS. 36A-B) and sodium butyrate (FIGS. 22A-D and FIGS. 23A-C), the present invention further provides a method of neuroprotection against neuronal or stem cell damage, the method comprising the step of contacting a neuronal or stem cell with an agent which induces neuronal or stem cell differentiation, wherein the agent is identified according to any of the methods described hereinabove.

Metabolic Disorders

As defined herein, the term "metabolically impaired cell" refers to a cell having an aberrant, deficient or abnormal metabolic impairment as a result of the an abnormal metabolic activity. As defined herein, the term "metabolically normal cell" refers to a cell having a normal metabolic function and/or activity.

As contemplated herein, a non-limiting list of metabolic disorder which are within the scope of the present invention include carbohydrate metabolism disorders, disorders of steroid metabolism, connective tissue, muscle, bone, disorders of amino acid metabolism, disorders of purine/pyrimid. metabolism, blood disorders, disorders of lipid metabolism, disorders of metal metabolism, transport disorders, disorders of lysosomal enzymes and heme/porphyria metabolism disorders.

In one embodiment, the metabolic disorder is selected from the group consisting of a Carbohydrate Metabolism Disorder, a Disorder of Steroid Metabolism, a Connective Tissue Disorder, A Muscle Disorder of Amino Acid Metabolism, a Disorder of Purine/Pyrimidine. Metabolism, a Blood Disorder, a Disorder of Lipid Metabolism, a Disorder of Metal Metabolism, a Transport Disorder, a Disorder of Lysosomal Enzymes, and a Heme/Porphyrin Metabolism Disorder.

In another embodiment, the metabolic disorder is selected from the group consisting of Diabetes, Fructose Intolerance, Glycogen Storage Disease, Adrenal Hyperplasia, Muscular Dystrophy, Ehlers-Danlos syndromes Hypophosphatasia Phenylketonuria, Albinism, Goiter Gout, Lesch-Nyhan Syndrome, Xeroderma Pigmentosum, Hemophilia, β-Thalassemia, Sickle cell Anemia, Hypercholesterolemia, Wilson's Disease (copper excretion), Cystic Fibrosis, Rickets, Gaucher's Disease, Tay-Sachs Disease, Porphyria, and Niemann-Pick disease.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Differential Staining of Malignant and Non-Malignant Cells of Non-Cervical Biopsies Materials and Experimental Procedures The following materials and experimental procedures section relates to Examples 1 through Example 5 detailed hereinbelow.

Staining Procedures

Table 1b below provides step-by-step procedures for general staining according to the present invention. Please note that the air drying is preferably effected in accordance with the teachings of the present invention, improving the differential effect of the protocols. Multiwell plates could be stained following the drying: minimum 3 hours (hrs) with an optimum of 24 hours following staining.

TABLE 1b

A - Protocol for non-cervical air-dried smears

1. Air-dry slide or print
2. Fixation: 2 minutes in Fix-1
3. Clean in running distilled water
4. 1 minute in Fix-2
5. Clean in running distilled water
6. 1 minute in Dye-1
7. Clean in running distilled water
8. Ext-2 for 1 minute (min)
9. Clean vigorously 5-7 seconds in distilled water
10. 15 seconds in Ext-1
11. Clean vigorously 5-7 seconds in distilled water
12. 20 seconds in Ext-3
13. Clean vigorously 30 seconds in distilled water
14. PBS for 15 seconds
15. Clean in distilled water for 10 seconds
16. Dye-2 for 6 seconds
17. Clean in distilled water for 10 seconds
18. Dye-8 for 4 min.
19. Clean in distilled water for 10 seconds (sec)
20. Dehydration in 70%-96%-100% ethanol
21. Clear in Xylene
22. Mount in Eukitt B - Revised protocol for air-dried non-cervical smears 1. Air-dry slide or print
2. Fixation: 12 min. in Fix-3
3. Clean in running deionized water
4. 2 min. in Fix-4
5. Clean in running distilled water
6. 2 min. in Dye-3
7. Clean in running tap water
8. Ext-2 for 2 min.
9. Wash in deionized water for 1 min.
10. 10 sec. in Dye-5
11. Wash in distilled water
12. Incubate in Dye-23 for 5 min.
13. Clean in distilled water for 10 sec.
14. Dehydration in 70%-96%-100% ethanol
15. Clear in Xylene
16. Mount in Eukitt I - Protocol for histological section/paraffin-embedded tissue 1. Paraffin-embedded tissue on a slide (4 micron)
2. Deparaffination in two Xylene baths, 1 minute each
3. Clean in two consecutive ethanol baths, 1 minute each
4. Fix-5 for 3 min.
5. Wash in deionized water for 1 minute
6. Incubate in Dye-3 for 15 min.
7. Wash in running water for 1 min.
8. Incubate in Ext-2 for 3 min.
9. Wash in deionized water for 15 sec.
10. Incubate in Dye-22 for 3.5 min.

TABLE 1b-continued

11. Wash in deionized water for 15 sec.
12. Incubate in Dye-26 for 10 sec.-Rinse in distilled water
13. Incubate in Dye-27 for 1 minute 15 sec.-Rinse in distilled water
14. Incubate in Dye-25 for 30 sec.
15. Wash in deionized water for 15 sec.
16. Dehydration in 70%-70%-70% ethanol.
17. Clear in 9 consecutive baths of absolute ethanol, 5 seconds in each.
18. Clear in Xylene
19. Mount in Eukitt Reagents:

Hoechst N 33342, Sigma; 10 mg/ml in PBS; Dahlia Michrome 105, Color Index (CI) 42535, Edward Gurr LTD; New Fuchsin, SIGMA, Lot 37H3463, CI-42520; Pararosanilin acetate, Allied chemical, CI 42500; Rosaniline hydrochloride, BDH, Prod. 30024, CI 42510; Methyl Violet, Fluka, 69710, CI 42535L; Light Green, SF Yellowish, Lot 055H4405, CI 42095; Fast Green FCF, BDH, CI 42053; Eosin Yellow Shade, BDH Product No 34027, CI 45380; Bismark Brown R, SIGMA, Lot 111H3470, CI-21010; Toluidine Blue, Fluka, CI 52040; Methyl Green, MERCK, CI-42590; Picric Acid, Pyronin Y, Fluka, CI 45005; May-Grunwald Stain, SIGMA, Cat. No. M6901; Harris's Hematoxylin, Pioneer Research Chemicals; Hematoxylin Solution Gill No. 3, Sigma GHS-3-32; New Fuchsin, C.I. 42520, Sigma N-0638; Phloxine, C.I. 778, Hartman Leddon Co.; Azure A, Allied Chemical Cat. No. 442; Methyl Violet; Basic Fuchsin; PBS Tablets, SIGMA, P4417; trichloroacetic acid (TCA), methanol, glacial acetic acid (GAA); formaldehyde; ether; Carboxymethylcellulose resin, CM52, Whatman.

Screening Assay for Histomodulator Compound-Containing Fractions:

The screening assay was developed with the aim of screening purified fractions for activity. The assay is designed to assess whether a fraction is capable of simulating the activity of a crude extract or verified extract (labeled GS). A fraction is deemed active if it is capable of significantly inhibiting the first (green or red) staining of malignant cells, alternatively the histomodulatory activity was verified in histological staining.

Plant Extract:

Optimal leaves for the process are between 15 and 25 grams and their length is preferably 18-30 centimeter as measured from the base of the leaf until the edge. Leaves that were below these specifications tend to have a red pigment and tend to be over-active from the inhibition point of view, while leaves that are above these criteria are characterized by very strong green pigment and tend to show very little activity.

600 grams of leaves were cut into 1-2 cm pieces. The cut leaves were mixed with 1.5 liter of 70% ethanol (EtOH) and kept for 10 days (room temperature) in a sealed container. Thereafter, the liquid was separated from the solids and kept for further use in room temperature. For optimal purification yields, the liquid was allowed to age in the container for at least 10 days and up to one month at room temperature.

Alternative Preparation of Plant (*Ficus Elastica*) Extract for Use in the Staining Procedure of the Invention:

Input Material:

Leaf material was selected as described above in terms of leaf length and weight.

Alternative Preparation of Optimal Extract:

Leaves were cut into 1-2 cm pieces. The cut pieces were dried in an oven at 65° C. for 24 hours (hrs). At the beginning, wet content was 80%, while at the end it should have been 4%.

The material was blended into a powder (700-1000 micron). The powder was used in extraction in a reflux system: 1 hour (hr) per extraction, solvent: 70% ethanol, 40° C. Three sequential extractions were performed, each time the powder was re-extracted. Quantity of 70% ethanol in each extraction: first—1:5; second—1:4; third—1:3. The three resulting extracts were mixed, filtered in vacuum filter, paper No. 40. The mixed, filtered extract was evaporated in a rotor evaporator under vacuum at 60° C. until a steady weight was obtained.

The resulting powder (final humidity was 3%) was blended further in a grinder. The powder extract was reconstituted for use as a staining regent. The powder was taken up in 70% ethanol at TDS 1.3% w/v, pH 7.4. Shelf life of powdered extract: humidity 1%, after six months at room temperature in transparent glass—activity was equivalent to the initial level.

Staining Solutions and Fixatives:

Fixative No. 1 (Fix-1): Fixative No. 1 contained 0.3% trichloracetic acid (TCA), 20% ethanol, 2.5% methanol, 2.5% glacial acetic acid (GAA), 2.5% formaldehyde, 43% ether and 29.2% double distilled water. Ether was added ex tempera.

Fixative No. 2 (Fix-2): Fixative No. 2 contained 1.2% trichloracetic acid (TCA), 20% ethanol, 1.2% methanol, 2.5% glacial acetic acid (GAA), 0.5% formaldehyde, 40% ether and 34.6% double distilled water. Ether was added ex tempera.

Fixative No. 2B (Fix-2B): Fixative No. 2B contained 6.6% trichloracetic acid (TCA), 6.6% glacial acetic acid (GAA), 3.3% methanol, 3.3% formalin, 80.2% ether.

Fixative No. 3 (Fix-3): Fixative No. 3 contained 0.4% trichloroacetic acid (TCA), 1.2% methanol, 2.5% GAA, 2.5% formaldehyde, 93.4% double distilled water.

Fixative No. 4 (Fix-4): Fixative No. 4 contained 1.2% trichloracetic acid (TCA), 7% methanol, 9% GAA, 7% formaldehyde, 76.4% double distilled water.

Fixative No. 102-B (Fix-102-B): Fixative No. 102-B contained 6.6% trichloracetic acid (TCA), 7.5% glacial acetic acid (GAA), 5.8% methanol, 5.8% formalin, distilled water.

Additional Plant Extracts:

*Aloe arborescens* miller extract (Ext-1): 600 grams cut leaves were mixed with 1 liter of 96% ethanol and kept for 10 days (room temperature) in a sealed container. Thereafter, the liquid was separated from the solids and was kept for further use in room temperature.

*Ficus elastics* extract (Ext-2): Described above, but briefly: 600 grams cut leaves were mixed with 1.5 liter of 70% ethanol and kept for 10 days (room temperature) in a sealed container. Thereafter, the liquid was separated from the solids and was kept for further use in room temperature.

*Lantana Camara* extract (Ext-3): 300 grams cut leaves were mixed with 1 liter of 70% ethanol and kept for 10 days (room temperature) in a sealed container. Thereafter, the liquid was separated from the solids and was kept for further use in room temperature.

Dyes:

Phloxine (Dye-A): The aniline dye Phloxine was used for staining paraffin-embedded tissue. The dye was prepared by mixing 1.5 grams of Phloxine with 200 ml of double distilled water and 50 ml of ethanol.

BBr (Dye-B): The BBr dye was prepared by dissolving 2 grams of Bismark Brown R in 50 ml of ethanol and 200 ml of double distilled water.

Eosine (Dye-C): Yellow was prepared by dissolving 0.26 grams of Eosine Yellow shade in 15 ml of 100% ethanol and 35 ml of double distilled water.

Harris Hematoxylin dye (Dye-1): Commercially available Harris Hematoxylin dye, ready for use.

Light Green (Dye-2): The aniline dye Light Green served as a general stain in the staining procedures. The aniline dye was prepared by mixing 4 grams of Light Green with 50 ml 70% ethanol and 50 ml double distilled water.

Hematoxylin Gill (Dye-3): A ready for use solution of Hematoxylin Gill No. 3.

Bismark Brown Phloxine Conjugate (Dye-4): Dye-A and Dye-B were mixed, boiled for 20 min and cooled to room temperature. The dye was filtered through a filter paper, and 250 ml of absolute ethanol were added.

Light Green 50% (Dye-5): The aniline dye Light Green 50% was used as a general stain in some of the protocols. The aniline dye was prepared by mixing 4 grams of Light Green with 50 ml of ethanol and 50 ml of double distilled water.

New Fuchsin (Dye-6): 0.4% solution was prepared in 33% ethanol.

Azure (Dye-7): The aniline dye Azure A was used for staining paraffin-embedded tissue. The aniline dye was prepared by mixing 0.25 grams of Azure A with 50 ml of 100% ethanol and 50 ml of double distilled water.

Phosphate Buffer Saline (PBS): PBS, pH 7.4, was prepared using commercially available PBS tablets. One tablet per 200 ml double distilled water was used to achieve a working solution.

Dahlia dye (Dye-8): Dahlia dye served as a stain for non-cervical smears. The Dahlia dye was prepared by mixing 0.5 grams Dahlia in 20 ml of 70% ethanol and 80 ml of double distilled water.

Dahlia 99a (Dye-23): Dahlia 99A was an aniline dye used in the revised procedure for non-cervical smears. Dahlia 99A was prepared by mixing 1.5 grams of Basic Fuchsin, 1 gram of Methyl Violet, 0.5 gram of New Fuchsin with 100 ml of ethanol and 20 400 ml of double distilled water.

Light Green 20% (Dye-24): The aniline dye Light Green 20% was used as a general stain in the protocol for frozen sections. The aniline dye was prepared by mixing 4 grams of Light Green with 20 ml of ethanol and 80 ml of double distilled water.

Bismark Brown Eosine: Bismark Brown Eosine was prepared by dissolving 5 g Bismark Brown-R in 200 ml distilled water and 25 75 ml of 100% Ethanol, and set aside for 5 minutes (min). Next, 2.5 g of Eosine Yellow shade was dissolved in 150 ml distilled water and 50 ml of 100% ethanol, and set aside for 10 min. Both were mixed and boiled for 5 min, cooled to room-temperature and filtered through paper filter. Filter was allowed to dry and was washed in 300 ml of absolute ethanol.

May-Grunwald Stain: 0.25% May-Grunwald dye in methanol, diluted into Sorenson's Buffer, pH 6.8.

Giemsa Stain: 10% of Giemsa stain diluted in Sorenson's Buffer, pH 6.8.

Hematoxylin/Eosin Staining Protocol:

Paraffin-embedded 4 micron thick tissues on slides were deparaffinized in two Xylene baths, 3 min each, and washed in two consecutive ethanol baths, 3 min each, followed by two consecutive 95% ethanol baths, 3 min each, and a distilled water bath, for 3 min. Following deparaffinization, the slides were dipped in hematoxylin stain (Dye-1) for 1 min and washed in tap water (running in the container) until the water was clear. Then, slides were immersed in Eosin stain (Dye-C) for 1-2 min, and washed in tap water as described above. The slides were then dehydrated in ascending alcohol solutions (50%, 70%, 80%, 95%×2, 100%×2) and cleared with xylene (3-4 times). The dehydrated slides were mounted with Permount or another suitable organic mounting medium.

May Grunwald Giemsa Staining Protocol:

Slides were fixed in methanol for 15 min, and then stained in May-Grunwald Stain for 5 min. The slides were rinsed with water and stained in Giemsa Stain for 10 min. After staining, the slides were rinsed in Sorenson's buffer at pH 6.8 and rinsed again in 50/50 v/v buffer/acetone. Following rinse, the slides were dehydrated in two acetone washes and cleared in xylene. Finally, the slides were mounted with Permount or another suitable organic mounting medium.

Papanicolaou Staining Protocol:

Smears were dried and the following staining and washing steps were taken: Slides were washed with 70% ethanol for 2 minutes and then twice with tap water for 1 minute each. Slides were stained with Gill's hematoxylin for 4 minutes and rinsed with Scott's water for 2 minutes, washed with 70% ethanol for 1 minute, and then with 95% ethanol for 1 minute. Slides were then stained using Orange G for 2 minutes, and washed twice with 95% ethanol for 1 minute each. Slides were then stained for 10 minutes with Eosin A (Eosin Azure), which is a counterstain, comprising of three dyes Eosin Y, Light Green SF yellowish, and Bismarck brown Y. Slides were then washed twice with 95% ethanol for one minute each and treated twice with xylene for 5 minutes each. Slides were mounted and once dry, the slides were screened under the microscope.

Cells Lines:

Cell line cultures: The cell lines used herein are listed in Table 4 below. Cell lines were cultured in Dulbecco's modified Eagle's medium (4.5 g glucose/liter, DMEM) supplemented with 1% glutamine, penicillin (100 U/ml), streptomycin (100 mg/g) and 10% heat-inactivated (57° C., 30 min) fetal calf serum, FCS (Bio-Lab, Jerusalem, Israel). Cells were serially passaged (weekly) and cultured in 10 cm diameter Miniplast tissue culture plates (Miniplast, Israel). The cultures were maintained at 37° C. in a humid incubator with an air mixture containing 5% $CO_2$.

Cell line smears: Cell suspensions of all types were centrifuged, the pellet was re-suspended in a small volume of fresh DMEM-FCS medium. Small drops of the suspension were placed on glass slides, smeared, air-dried and used in staining experiments as further detailed hereinbelow.

Primary cell suspensions: Bone marrow cells were obtained by lavage of femurs and tibia of mice, placed on glass slides, smeared, air dried and used in staining experiments as further detailed hereinbelow.

Experimental Results

The staining procedures presented herein were developed using clinical cancer-positive and cancer-negative cytological smears, which were routinely received from and classified by a cytological laboratory. The presence of malignant cells was validated by standard cytological examination and in most cases by histopathological diagnosis.

About 3,000 peritoneal, pleural, pericardial aspirates were used for the development efforts of the staining procedure. The staining procedure was applicable to air-dried cytological smears of the type applicable for routine May-Grunwald-Giemsa staining.

The first step was specially designed fixation procedure involving the use of complex fixative reagents (Fix-1 and Fix-2) optimized for best subsequent staining results. These complex fixation reagents were, in most cases, essential for the effectiveness of the staining procedure. In addition to enabling effective staining, the fixation procedure described herein also provided superior morphological preservation, in particular of the nuclear features and details as compared to conventional fixation procedures. The second step included counterstaining with Harris-Hematoxylin which was introduced for better contrasting of nuclear details. The third step included treatment with plant extracts (*Aloe arborescens* miller, *Ficus elastica* and *Lantana camara* plant extracts), which was believed to change the binding capacities of the cells for dyes applied in subsequent steps. The fourth step comprises a sequential staining using biological dyes, first a short exposure to an acidic dye, e.g., Light Green and then a longer exposure to a basic dye, e.g., New Fuchsin or Dahlia.

In smears subjected to the above described staining procedure the cytoplasm of normal cells, namely mesothelial and epithelial cells, macrophages, granulocytes and various lymphocytes, turned green toned or remained unstained. In sharp contrast, the cytoplasm of cancer cells became red in color (FIGS. 1A-B and FIGS. 2A-B). The cell nuclei became blue-violet as a result of the Harris-Hematoxylin enforced by the Dahlia stain (FIG. 3). In part of the tumor cells, the red toning of the cytoplasm occurred together with distinct red toning of the nuclei (FIGS. 1A-B and FIG. 2B). Granulocytes may occasionally occur with red stained nuclei, which however, are clearly distinguishable from the red cytoplasm of cancer cells (FIGS. 1A-B).

The staining protocol described in this invention is applicable to air-dried cytological smears of the type applicable for routine May-Grunwald-Giemsa staining.

In a double blind test for the staining procedure, 128 samples were tested by three well-trained pathologists employed in a cytology laboratory of a hospital in Israel. Two slides were prepared from each specimen. One was conventionally stained with May-Grunwald-Giemsa (MGG), whereas the other was stained using the staining procedure according to the present invention and as described hereinabove. Each of the MGG stained slides was assessed by one of two pathologists and the slide stained according to the method of the present invention by the third.

The results, which are summarized in Table 2 hereinbelow, were striking. Of 40 pleural fluid samples tested, three were found positive and one suspected of including malignant cells by both staining methods employed. Of 10 peritoneal fluid samples, three were found positive and two suspected of including malignant cells by the MGG staining method, whereas all five were found to include such cells using the staining procedure according to the present invention. Of 75 bronchoalveolar lavage and brushing samples, four were found positive and three suspected of including malignant cells by the MGG staining method, whereas all seven were found to include such cells using the staining procedure according to the present invention. Of three pericardial fluid samples, one was found suspected of including malignant cells by the MGG staining method, whereas the same sample was found to include such cells using the staining procedure according to the present invention.

TABLE 2

| | | Cytological results | | | |
| --- | --- | --- | --- | --- | --- |
| | | Positive for malignancy | | Suspicious for malignancy | |
| Specimen | No. of cases | MGG | present invention | MGG | present invention |
| Pleural fluid | 40 | 3 | 3 | 1 | 1 |
| Peritoneal fluid | 10 | 3 | 5 | 2 | — |
| Bronchoalveolar lavage and Brushings | 75 | 4 | 7 | 3 | — |
| Pericardial fluid | 3 | — | 1 | 1 | — |

These results clearly showed that the staining procedure according to the present invention performed better than the MGG staining procedure, especially in diagnosis of malignancies in difficult cases. However, further efforts were aimed at improving the performances in terms of enhancing the color differentiation, contrast, and specificity of the staining procedure according to the present invention.

Thus, in another attempt, the staining procedure of the present invention was revalidated in a clinical pilot study. The results are summarized in Table 3 hereinbelow. This study was designed as a split-sample double-blind study in which the only data made available for the operator of the procedure was a coded reference and the type of clinical sample (e.g., pleural effusion, peritoneal effusion, etc.). Using the staining procedure of the present invention resulted in identification of 3 positive cases of cancer, 45 negative cases of cancer and 1 suspicious case. These results were identical to the results obtained by conventional cytological assessment. It should be emphasized that the staining procedure according to the present invention gave strong staining even when only a few scattered cancer cells were present on the slide (FIG. 4).

TABLE 3

| Histological validation | Present invention diagnosis | Clinical pathologist's diagnosis | No. | Specimen type |
| --- | --- | --- | --- | --- |
| Breast Adenocarcinoma | Positive | Positive | 1 | Pleural |
| Ovary Carcinoma | Positive | Positive | 1 | Pleural |
| Carcinoma Sp. | Positive Sp. | Positive Sp. | 1 1 | Pleural Pleural |
| Hematological Malignancy | Positive | Positive | | |
| | Negative | Negative | 25 | Pleural |
| | Negative | Negative | 1 | Stomach Effusion |
| | Negative | Negative | 2 | Retroperitoneum washing |
| | Negative | Negative | 3 | Peritoneal washing |
| | Negative | Negative | 5 | Ascites |
| | Negative | Negative | 9 | Peritoneal Fluids |
| | | | 49 | Total |

Various malignant cell lines of different origin, benign lines, primary cultures of normal tissues and suspensions prepared from adult and embryonic tissues were thereafter used to further validate the efficacy of differentiation of the staining procedure of the present invention (Table 4). This approach allowed the inquiry of separate cell components usually present in clinical smears. The results are summarized in Table 4 hereinbelow and presented in FIGS. 5A-G.

TABLE 4

| Cells | Origin | Present invention | Figure |
| --- | --- | --- | --- |
| Malignant and transformed lines | | | |
| 3LL Lewis lung carcinoma | Human | Positive | FIG. 5a(1) |
| CaCo2 Colon Adenocarcinoma | Human | Positive | |
| Fao Hepatoma | Rat | Positive | |
| Pc-12 Pheochromocytoma | Mouse | Positive | FIG. 5b(1) |
| Friend Erythroleukemia | Mouse | Positive | FIG. 5d(1) |
| Neuroblastoma SK-N-SH | Human | Positive | |
| Melanoma | Human | Positive | FIG. 5c(1) |
| Breast Carcinoma MDA435 | Human | Positive | |
| NIH3T3* | Mouse | Positive | FIG. 5e(1) |
| Rat1 | Rat | Negative | FIG. 33A |
| Rat1-Ras V12 | Rat | Positive | FIG. 33A |
| HF-1 | Human | Positive | FIG. 39 |
| Other lines and primary cultures | | | |
| Bone marrow and stromal fibroblasts | Mouse | Negative | |
| Fibroblasts from benign breast cyst | Human | Negative | |
| Cell suspensions | | | |
| Peritoneal inflammatory cells | Rat | Negative | FIG. 5f(1) |
| Normal hepatocytes | Rat | Negative | |

*This N1H3T3 clone was spontaneously transformed

All of the malignant cell lines tested were stained red, while all the non-malignant cell lines and primary cultures tested were stained green.

In order to improve the understanding of the procedure of the present invention, a set of experiments were performed in which certain components of the process were omitted (see Table 5). This procedure was tested employing both cell lines and clinical specimens for which cytopathological validation of the results was obtained prior to staining (Table 6 and FIGS. 5A-G).

TABLE 5

| Procedure no. | Extract | Light Green | Dahlia |
| --- | --- | --- | --- |
| 1 | + | + | + |
| 2 | + | − | + |
| 3 | − | + | + |
| 4 | − | − | + |
| 5 | + | + | − |
| 6 | − | + | − |

(+) present; (−) absent

TABLE 6

| | 1 | 2 | 3 | 4 | 5 | 6 |
| --- | --- | --- | --- | --- | --- | --- |
| Malignant and transformed cell lines: | | | | | | |
| 3LL Lewis lung carcinoma | Red | Red | Red Red background Effect | Strong Red | Green | Strong green |
| CaCo2 Colon | Red | Strong | RedRed | Strong | Green | Strong |

TABLE 6-continued

|  | 1 | 2 | 3 | 4 | 5 | 6 |
|---|---|---|---|---|---|---|
| Adenocarcinoma |  | Red | blurred background | Red |  | green |
| Fao Hepatoma | Strong Red | Strong Red | Strong Red, Red background effect | Strong Red | No marked stain | No marked stain |
| PC-12 Pheochromocytoma | Red | Red | Red background effect | Strong Red | Green | Green |
| C6 Astrocytoma | Red | Red | Red/Strong Red Background effect | Strong Red | Green | Strong green |
| Friend Erythroleukemia | Red | Strong Red | Red, green Shades in part of cells | Strong Red | Green | Strong green |
| Neuroblastoma SK-N-SH | Mild Red | Red | Mild Red | Strong red | Greenish | Green |
| Melanoma A375 | Red | Strong Red | Red, slight shift to violet | Strong Red (more than 2) | Green | Strong green |
| Breast Carcinoma MDA435 | Red | Strong Red | Red, green shades in part of cells | Strong red | Green | Green |
| N1H3T3 | Red | Strong red | Red, green shades in part of cells | Strong red | Green | Green |
| Non-malignant cell lines and primary cultures: | | | | | | |
| Bone marrow stromal fibroblasts | Green | Unstained | Green | Dirty red | Greenish | Green |
| Fibroblast from benign breast cyst | Green | Reddish | Violet | Red | Green | Strong green |
| Cell suspensions | | | | | | |
| Suspension of embryonic cells | No stain | No stain | Slightly dirty Violet | Dirty Red | Greenish | Green |
| Peritoneal inflammatory cells | Only mast cells stained red | Only mast cells stained red | Only mast cells stained red | Only mast cells stained red | Greenish | Green |
| Normal liver hepatocytes | No stain | No stain | No stain | Red | No stain | No stain |
| Peritoneal fluid from female patient with carcinoma of ovary: | | | | | | |
| Malignant Cells (Predominantly aggregated) | Red | Red | Red | Strong Red | Greenish | Green |
| Lymphocytes | Most of cells unstained, some with slight greentone | Unstained | Most of cells unstained, some with slight greentone | Reddish cytoplasmic color in most cells | Part of cells unstained, part with slight green tone | More cells with greenish tone, the tone is deeper |
| Monocytes and Macrophages | Largely unstained cycoplasmic stain | Unstained | Some of cells slight reddish | Various degrees of reddish color | Unstained, some greenish | More green stained cells |
| Mesothelial cells | Unstained | Unstained | Unstained, slight rose tone in some cells | From reddish to red color | Unstained | Greenish tone of cells |
| Erythrocytes | Very weak yellowish tone | Very weak yellowish tone | Unstained to greenish or rose tone | Unstained to dirty reddish | Unstained to very weak Yellowish | week greenish to greenish |
| Debris and diffuse background | Unstained | Unstained | Greenish and reddish | Red | Slight green | Prominent green |

Staining Situation (See Table 5)

The results from these experiments were indicative of the role of the various components of the staining procedure. While the full procedure resulted in red staining of malignant cells and green staining, or non-staining, of normal cells, omitting the Dahlia step demonstrated that there could be significant differences in the affinity of various tumors to Light Green, with hepatoma demonstrating low affinity (not shown), while astrocytoma (FIG. 5B5-6), 3LL carcinoma (FIG. 5A5-6) and CaCo2 carcinoma (not shown) demonstrating high affinity. On the other hand, all tumors studied exhibited strong affinity to Dahlia, as is emphasized by omitting the Light Green staining step (FIGS. 5A-G procedures 2 and 4 described in Table 5 hereinabove).

While many normal cells stain green, some normal cells failed to become significantly green-stained. This is the case, for example, for hepatocytes that showed very weak green-staining in all cases, even when both the extract and the Dahlia dye were omitted (not shown). Some leukocytes stained green, as well as macrophages and stromal cells.

The granules of mast cells present in rat peritoneum stained red, with the technique of the present invention (FIG. 5F). In the absence of Dahlia (i.e., procedures number 5 and 6 described in Table 5 hereinabove) there is no evidence of green staining of these granules (FIG. 5F).

Omitting the extracts from the procedure of the present invention changed the overall outcome. When staining only with Light Green one obtained a rather blurred and dirty background comprised mainly of non-specific binding of stain to erythrocytes and debris (procedure number 6 described in Table 5 hereinabove and FIGS. 5A6-G6). When staining with Light Green after treatment with the extract this background staining is suppressed (procedure number 5 described in 5 hereinabove and FIGS. 5A5-G5). Thus, the extract has a clearing effect.

Despite this clearing effect, the green staining of other normal elements or the green staining of some tumor populations was not prevented (i.e., in procedures number 5 described in Table 5 hereinabove), where the Dahlia staining is omitted.

When staining only with Dahlia (procedures number 4 described in Table 5 hereinabove and FIGS. 5A4-G4) one observed blurred and dirty background and strong red-staining of some normal cells (for example, hepatocytes). Pretreatment with plant extracts suppresses this staining both from the background and from non-malignant cells (procedures number 2 described in Table 5 hereinabove and FIGS. 5A2-G2).

The full staining procedure yielded results that could not have been obtained by using any of the partial protocols. The results of the full procedure included very high ability of differentiating between normal and malignant cells (FIGS. 5A1-G1). It should be noted that the intensity of red-staining in the complete procedure, has some variations between different tumors, but always provided best results within the same group. The strongest red staining was obtained for hepatoma and the mildest for neuroblastoma (not shown).

In order to analyze the effectiveness of the staining procedure according to the present invention in clinical specimens, eight representative cases were chosen as indicated in Table 7.

TABLE 7

| Patient | Sex and age | Source of cells | Diagnosis |
| --- | --- | --- | --- |
| Bar | M-70 | Pericardial effusion | Metastatic Carcinoma |
| Man | F-90 | Pleural effusion | Transitional Cell Carcinoma of Bladder |

TABLE 7-continued

| Patient | Sex and age | Source of cells | Diagnosis |
| --- | --- | --- | --- |
| Slu | M-65 | Pleural Effusion | Breast Carcinoma |
| Vin | F-71 | Ascites | Carcinoma |
| Eiz | F-50 | Pleural effusion | Carcinoma |
| Pel | F-40 | Pleural Effusion | Carcinoma of ovary, differentiation stage 4 |
| Zip | F-54 | Imprint of tumor | Sarcoma of Ovary |
| Zwe | F-7 | Pleural effusion | Carcinoma |

In all tested tumor cases, the staining procedure according to the present invention provided red labeling of all morphologically apparent tumor cells, single and clustered, on the slides. It should be stressed that in the case of Zwe large quantities of reactive mesothelium were present on the slide, but these were easily distinguished from the tumor cells. The cells of Zip are presented in FIG. 8.

The above-described results serve to support some important conclusions regarding the results obtained when implementing the staining procedure according to the present invention on various cell types. These conclusions are summarized in Table 8, hereinbelow.

TABLE 8

| | Nuclei | Cytoplasm |
| --- | --- | --- |
| | Malignant cells | |
| Malignant cells | Red/pink/blue | Red/Purple |
| | Non-Malignant Cells | |
| Lymphocytes | Blue | Blue/green |
| Monocytes | Blue | Green |
| Granulocytes | Blue/green | Green/Grey |
| Erythrocytes | — | From colorless to greenish |
| Macrophage | Blue/violet | Green/Colorless |
| Stromal Cells | Blue | Green |
| Reactive Mesothelium | Violet/green | Green/Colorless |
| Mast Cells | Red Granulocytes | |
| Erythrocytes | — | From colorless to greenish |
| | Degenerating Cells | |
| Degenerating Cells | | Pink/blue/violet |

As shown in FIGS. 6A-D, FIGS. 9B-D and FIG. 10, the staining procedure of the present invention is not limited to cytological smears prepared from fluids, but may also be applied to touch preparations (FIG. 10) and to other types of cell or tissue preparations such as paraffin embedded tissue (FIGS. 6A-D and FIGS. 9B-D).

The staining effect of the staining procedure of the present invention is sensitive to pH during all steps, including the fixative reagents, stains, extracts, and rinsing water.

The fixation procedure is preferably performed under low pH environment. The pH of fixative 1 and of fixative 2, as measured before addition of the ether, is 1.7 and 1.4, respectively. The pH of the plant extracts was found to be slightly acidic ranging from 5.5-6.0. In the staining procedure of the present invention, the optimum pH for the Light Green stain is within the range 3.5-5.0 and for the Dahlia stain in the range 3-4. It was observed that rinsing the slides after the Light Green step with PBS (pH 7.4) improved the final results. The pH of the distilled water used for rinsing was in the range 6.0-6.5.

The staining procedure of the present invention is not limited to the use of Dahlia, as many other basic stains with satisfactory contrast to green may also be considered. Most changes of the basic stain will require optimization of exposure times and concentrations. For example mixtures of Basic Fuchsin and Methyl Violet provided satisfactory results. A solution of 0.6% Basic Fuchsin and 0.3% of Methyl violet in 20% ethanol provided quite comparable results, without further changes in the staining procedure.

According to Gurr [Gurr, "Encyclopedia of Microscopic Stains" London: Leonard Hill (Books) Limited (1960)], the addition of further methyl (or ethyl) groups converts basic fuchsin and its components to violet dyes, which include Dahlia, Gentian Violet, Methyl violet 6b, Crystal Violet, etc. Consequently, the staining procedure could be performed with all these derivatives of basic fuchsins, with slight changes in performance.

Similarly, the effect of Fast Green as an alternative to the acidic stain Light Green was studied and the results were similar, albeit Light Green is superior. Other acidic stains could also be considered.

The order of the staining steps of the staining procedure of the present invention provided hereinabove (Table 1b) was found to yield optimal results. If in the course of staining, using the staining procedure for non-cervical cytological smears, the order of staining with the basic and acidic stains was reversed (e.g., Dahlia before Light Green) the heterochromatic effect below became less pronounced.

The two-step fixation process described above could be replaced by a one-step water based procedure. The water-based fixative comprised a solution of 1.2 grams trichloracetic acid (TCA), 4 ml glacial acetic acid (GAA), 3 ml formalin, 2 ml methanol, topped with double distilled water to 100 ml. Although the two-step procedure suggested above was superior to this fixative in terms of staining results, it was problematic for routine clinical practice because it was ether-based.

Time was of essence in this procedure, and under- and over-exposures could cause adverse results. The times suggested hereinabove (Table 1b) were selected as optimal for maximal differential staining. The most time sensitive step was the exposure to Light Green, as in many cases Light Green would predominate over the basic stain, even in tumor cells, if Light Green exposure was too long.

Example 2

Differential Staining of Malignant and Non-Malignant Cells in Cervical Smears and Breast Cancer Smears The procedures for cervical smears were developed in response to sub-optimal staining results of alcohol fixed smears by the protocol for non-cervical smears. These smears included both gynecological cervical pap-smears and non-cervical alcohol fixed breast cancer smears.

These staining procedures took advantage of the staining properties of conjugates of Bismark-Brown with Picric Acid, and Bismark Brown with Eosin, applying the effects of the plant extracts described in the protocol for non-cervical smears and the same fixation process. The protocols for cervical smears resulted in differential staining of normal cells in green tones and cancer cells in red tones (Flame red). In addition, both these staining procedures seemed capable of detecting most of the cellular changes, benign, malignant and pre-malignant, prevalent in cervical smears. These changes included: atypical squamous cells of undetermined significance (ASCUS), low grade squamous intraepithelial lesion (LGSIL), and high grade squamous intraepithelial lesion (HGSIL), as well as neoplasia as defended by the Bethesda System (FIGS. 12A-G).

In order to evaluate the advantages of the protocol for cervical smears according to the present invention, Pap-smears from a woman diagnosed with High Grade Squamous Interepithelial Lesion (HGSIL) were prepared and stained with either the conventional Papanicolaou stain (FIGS. 11A-D) or with the staining procedure according to the present invention (FIGS. 11E-H). The cells shown in FIGS. 11B and 11D, especially 11D, are non-atypical cells stained red by the conventional Papanicolaou stain, just like the atypical cells shown in FIGS. 11A and 11C, making the identification of atypical cells, especially in cases where they are low in number and "hiding" among red stained normal cells, very difficult. In sharp distinction, as clearly evident from FIGS. 11E-H, only atypical cells stained red using the staining procedure according to the present invention.

In a clinical trial encompassing 183 Pap-smear specimens the following results were obtained (Table 9):

TABLE 9

| | No. of cases | Conventional diagnosis included |
|---|---|---|
| Total | 183 | |
| Normal by both the procedure of the present invention and by conventional diagnosis | 150 | Normal, inflammatory, bloody smear, *trichomonas* and *coccobacilli* |
| Cell changes detected by both the procedure of the present invention and by conventional diagnosis | 25 | Squamous metaplasia, atypical squamous cells of undetermined significance (ASCUS), low grade squamous intraepithelial lesion (LGSIL), high grade squamous intraepithelial lesion (HGSIL) |
| Cell changes found only by the procedure of the present invention | 8 | Inflammation or normal |

The eight cases of discrepancy were reviewed; in all cases, the conventionally stained slides contained atypia that had been overlooked.

Some of the cases in which the procedure according to the present invention stained positive, while conventional diagnosis via cytopathological interpretation of slides stained with Papanicolaou stain yielded negative results are presented in FIGS. 13A-G.

It should be emphasized that the staining procedure according to the present invention does not grade the degree of atypia present on the slide. Rather, the staining procedure is used to highlight the presence of atypia on the slide.

In order to demonstrate the differences between the staining protocol for non-cervical smears, the staining protocol for cervical smears, and the May-Grunwald-Giemsa staining procedures, air-dried cytospin smears prepared from pleural fluid of a 65 year old male patient diagnosed with breast cancer, were stained (FIGS. 14A-C) according to these procedures. While the overall staining produced by using the protocols for cervical and non-cervical smears were quite similar, apart from apparent color differences, the protocol for cervical smears seemed to possess superior properties in single cells.

Table 10 below describes staining results using the protocol for cervical smears and non-cervical smears.

TABLE 10

|  | Nuclei | Cytoplasm |
| --- | --- | --- |
| Malignant | | |
| Malignant cells | Blue | Flaming Red |
| Non-Malignant Cells | | |
| Lymphocytes | Blue | Green/Grey |
| Monocytes | Blue | Green/Grey |
| Granulocytes | Blue | Green/Grey |
| Erythrocytes | Blue | Green/Grey |
| Macrophage | Blue | Green/Grey |
| Stromal Cells | Blue | Green/Grey |
| Reactive Mesothelium | Blue | Green/Grey |
| Mast Cells | Blue | Green/Grey |
| Erythrocytes | Blue | From colorless to greenish |
| Degenerating Cells | | |
| Degenerating Cells | | Grey/Green |

Example 3

Differential Staining of Malignant and Non-Malignant Cells in Paraffin-Embedded Histology Sections and Frozen Sections The results obtained with histological sections are consistent with those obtained with cytological smears. However, it should be emphasized that while cytological smears usually contain a very small variety of cells and tissue types, a histology section represents the entire scope of tissue and cell types and distinguishing malignant from normal structures present a more difficult task. FIGS. 9A-D show some comparative results.

Similarly, in FIGS. 6A-D, the colon cancer cells adjacent to normal tissue were successfully differentiated by a clear and distinctive red cytoplasmic color as opposed to a clear and distinctive green cytoplasmic color indicating normal cells.

The staining protocol for histological sections yielded red staining of malignant neoplastic cells as well as some neoplasia. Hyperplasia, as well as dysplasia stained distinctly from normal cells (see FIGS. 7A-C). FIGS. 6A-D and FIG. 7A demonstrated that colonic glands with normal morphology stained green, while colonic glands in the microscopic field of view stained red and pink (FIGS. 6A-D). Similarly, in FIGS. 15A-C and FIGS. 16A-D the colon cancer cells adjacent to normal tissue were successfully differentiated by a clear and distinctive red cytoplasmic color as opposed to a clear and distinctive green cytoplasmic color indicating normal cells.

Erythrocytes present on histological sections stained red due to the eosin component in Azure A. Other elements of the sections, such as fibroblasts, endothelial cells, muscle, and extracellular matrix components stained green, as so do normal epithelial, squamous, tissue surrounding the neoplasia.

In another example, a tissue section taken from a melanoma patient was stained by using conventional Hematoxylin-Eosin stain in comparison to the staining protocol of this invention. FIGS. 17A-B clearly demonstrates that although both methods enable visualization of the cells, cellular components and cell morphology, only the novel staining protocol was capable of differentiating between malignant and normal cells, staining the normal cells bluish-green and the malignant cells in distinctive red.

At present it is evident that sufficient differentiation between normal and malignant cells can be obtained by the revised protocol for non-cervical smears and the protocol for histological sections in which only one plant extract is used (*Ficus Elastica*).

Example 4

Boundary Detection of Malignant Tissues

The challenging task of boundary detection of a malignant tissue after surgical excision is of paramount importance to verify the complete removal of the tumor. It is preferable to conduct such diagnosis during the surgical procedure, particularly in cases of solid tumors including prostate and colon cancers, melanomas and the like. Usually conducted by microscopic visualization of a frozen section, there is a great need to improve the efficiency of the boundary detection process. The staining protocol of this invention can simplify and speed boundary detection, since the results obtained can be analyzed without the need for a specialist pathologist. FIGS. 18A-C demonstrates the ease of detection of a glioblastoma tumor in a rat brain using the methods of the present invention (FIG. 18C), compared to its visualization both with Giemsa stain (FIG. 18A) or with Hematoxylin Eosin (FIG. 18B) conventional methods.

Example 5

Discriminating Between Stages of Differentiation

Embryonic cells were selected as an example of tissue with rapid proliferation capacity associated with the normal developmental progression from the non-differentiated to the terminally differentiated phenotypical stage. FIGS. 19A-D show chick embryo retinal sections at different stages of differentiation and demonstrates that the staining using the novel protocol is associated with the general metabolic status of cells. The metabolic status is much higher in the non-differentiated cells and stain distinctively red, whereas terminally differentiated cells stain distinctively green. It is clearly shown that non-differentiating cells exhibit a red staining pattern and as the cells progress through differentiation and become less proliferative, they stain green.

Example 6

Use of the Teachings of the Present Invention to Distinguish Between Cells in In-Vitro Cell Systems Materials and Experimental Procedures The following materials and experimental procedures section relates to Example 6 through Example 12 detailed hereinbelow.

Staining Procedures:
Table 11 below provides procedures for general staining according to the present invention:

TABLE 11

I - Protocol for histological section/paraffin-embedded tissue

Paraffin-embedded tissue on a slide (4 micron)
Deparaffination in two Xylene baths, 1 minute each.
Clean in two consecutive ethanol baths, 1 minute each.
Incubate in Fix-2B for 10 min.

TABLE 11-continued

Incubate in Fix-102B for 5 min.
Wash in deionized water for 1 min.
Incubate in Dye-1 for 1.5 min.
Wash in running water for 1 min.
Incubate in Ext-2 for 3 min.
Wash in deionized water for 15 sec
Incubate in Dye-2 for 2 min.
Wash in deionized water for 30 sec
Incubate in 70% ethanol for 15 sec.
Incubate in Dye-3 for 5 min.
Wash in deionized water for 15 sec.
Incubate three times in 70% and three times 100% ethanol back and forth for total of 40 sec. Rinse in distilled water
Incubate in Dye-4 for 10 min.
Wash in deionized water for 15 sec.
Incubate three times in 70% and three times 100% ethanol back and forth for total of 30 sec. Rinse in distilled water.
Incubate in Dye-5 for 5 sec.
Wash in deionized water for 15 sec.
Dehydration in three times 70% ethanol, 10 seconds each
Clear in 9 consecutive baths of absolute ethanol, 5 seconds in each
Clear three times in Xylene, 1 minute each
Mount in Eukitt
II - Protocol for staining normal colonocytes and HT29 in chamber slides Plating to get confluent culture
Incubate with Extract 30 sec.
Wash in deionized water 30 sec.
Dye-6- 1 min.
Wash in running water
50% EtOH - 3 dips (short)
Wash in running water
Dye-7 1 min. 40 sec.
III - Basic protocol for HT29 staining in multiwell plates and HTS robot Extract (50%, bath-optimized as described below) 30 sec.
Wash in deionized water
Dye-8 - 7 min.
Wash in deionized water
Differentiation in 50% EtOH + 1 mM HCl - soak 1 min.
Wash in deionized water
Dye-7 - 9 min
Wash in deionized water twice
IV - Protocol for Rat2-Ras staining Incubate with Extract (40%, bath-optimized as described below) 30 sec. -
Wash in running water 3 times for 5 sec.
Dye-9 - 7 min.
Wash in running water 3 times
Dip in 50% EtOH - Wash in running water to repeat the cycle 3-5 times
V - Basic protocol for K562 cell staining Cells were prepared and plated according to the protocol
Extract - 1 min.
Wash in water, 4 times
Staining with Dye-9 - 4 min.
Differentiation, once in 50% ethanol
Wash in water, 4 times
Dye-7 - 6 min.
Wash in water, 3 times
VI - Basic protocol for HL-60 cell staining Cytospins were prepared at density 100 000 cells/ring
Incubate with extract (50%; bath-optimized as described below) 30 sec.
Wash in deionized 10 sec.
Dye-9 - 6 min.
Wash in running water 10 sec.
50% EtOH - 20 dips
Wash in water 10 sec,
Dye-7 - 6 min
Briefly wash in running water
VII - Basic protocol for U937 cell staining Cells were seeded at density 250 000 cells/chamber
Incubate with extract (40%; batch-optimized as described below) 30 sec.
Wash with running water 30 sec.
Dye-9 - 4 min.
Wash in running water 10 sec.
50% EtOH - 4 dips
Wash in running water 10 sec.

TABLE 11-continued

Dye-7 - 3 min.
Briefly wash in running water
VIII - LG rapid assay (for purification)

Plating cells in multiwell plates to get confluent culture
Incubate with Extract or fractions (100-0% in 70% EthOH) 4 min.
Wash in running water 4 times
Dye-7 - 1 min.
Wash in running water
The interpretation was done according to the procedure, described in the text
IX - Basic protocol for the extract fluorescence visualization in fixed cells Plate cells on the coverslip in medium without indicator, at the end of incubation period wash with medium without serum and indicator and air dry
2 min. incubation in 70% EtOH
1 min. incubation in 70% EtOH
Dry the extra EtOH with a absorbing paper
1 min. incubation with 100% crude extract or purified fraction
Wash the coverslip with tap water two times
Look under the microscope using FITC or TRITC filter.
X - Protocol 2 for histological section/paraffin- embedded tissue Paraffin-embedded tissue on a slide (4 micron)
Deparaffination in three Xylene baths, 5 minutes each
Clean in three consecutive ethanol baths, 5 minutes each
Incubate in Dye-1 for 3 min.
Wash in running water for 5 min.
Incubate in Ext-2 for 5 min.
Wash in deionized water for 30 sec.
Incubate in Dye-2 for 2 min.
Wash in deionized water for 1 min.
Incubate in 70% ethanol for 2 min.
Wash in deionized water for 15 sec.
Incubate in Dye-3 for 3 min.
Wash in deionized water for 15 sec.
Incubate three times in 70% and three times 100% ethanol back and forth for total of 1 min.
Rinse in distilled water
Incubate in Dye-10 for 2.5 min.
Wash in deionized water for 15 sec.
Dehydration in three times 70% ethanol, 5 seconds each
Clear in 9 consecutive baths of absolute ethanol, 5 seconds in each
Clear three times in Xylene, 1 minute each.
Mount in Eukitt Soft Agar Protocol:

20% serum media was warmed in 48° C. bath. 5% agar was melted in a microwave for 2 min, allowed to cool at RT for 10 min. and placed in 48° C. $H_2O$ bath. 1:5 agar dilution was prepared in pre-warmed media for a final concentration of 1% agar. 1.5 ml of agar was poured into 35×10 mm plates (Greiner, cat no. 627102) and plates were left to solidify at RT for 10 min. Plates were placed in an incubator (37° C., 5% $CO_2$) to adjust to the proper pH. Agar dilutions were prepared in prewarmed media for a final concentration of 0.3%. Treated cells were trypsinized and resuspended to a concentration of 10,000 cells/50-100 μl/plate. Cell viability was verified with Trypan Blue. Cell suspensions were quickly added to the agar, gently inverted 2-3 times (in order to suspend the cells evenly) and then poured (1.5 ml of agar+cell suspension) on top of each previously poured 1% agar plate. Plates were cooled to RT for approximately 10 min, placed in an incubator (37° C., 5% $CO_2$). 200 μl of 20% serum media was added to the cells every 3 days.

Nude Mice Experimental Protocol:

H29 cells were incubated for three days with 100 micro M Genistein, 10 micro M 5 FU, 5 nM Butyrate, 30 micro M N-methylformamide (NMF), 30 micro M Phytic acid or medium alone. On the fourth day, the cells were harvested and diluted to a final concentration of $5\times10^6$ cells in 0.2 ml PBS. Immediately following the dilution, HT29 cells from each test group were subcutaneously injected into the dorsal side of 10 nude mice (0.2 ml of $5 \times 10^6$ cells per mouse). During the assay period tumor size and mice body weight were recorded twice a week. Tumor volume (mm$^3$) was estimated according to the formula: Length (mm)×[Width (mm)]$^2$×0.5.

HTS Screening Procedure:

Day 1—Cell were Plated: Media prepared, cells were trypsinized, counted and diluted into media. Cell plating concentration was 5000 cells per well.

Day 2—Addition of library. Compound was diluted to a final working concentration: from DMSO stock to 30 micro Molar treatment concentration in the growth medium, "Day 2 medium".

Day 3—Cell media refreshment. The medium was replaced by "Day 2 medium":

Day 4—Cell media refreshment. The medium was replaced by "Day 2 medium":

Day 5—Cells were washed with medium and air dried

Stable Transfection of Rat1/Rat2 Cell Lines:

Rat1 cells or Rat2 cells (different clones of the same line) were plated 250 000 cells/well (6 well plate) on the day before the transfection. On the day of transfection, the density of the culture was 80-90% of confluency. Polyethylenimine (PEI) transfection was performed. PEI stock solution was prepared in water: 10 mM (4.5 mg/10 ml) pH 7.4. Solution I—micro L of PEI in 50 micro L of 150 mM NaCl was mixed and incubated in room temperature (RT) for 5 min. Solution II—2 micro g DNA in 50 micro L of 150 mM NaCl was prepared, mixed and incubated for 5 min at RT. Solutions I and II were mixed and incubated for 20 min at RT (transfection mixture). Volume of mixture was adjusted to 1 ml with transfection medium (antibiotic and serum-free medium). Rat cells were washed with transfection medium, transfection mixture was added to the cells for 4 hours. At the end of the incubation period, the medium was replaced with the complete growth medium.

K562 System Preparation:

K562 cells were seeded in 75 ml flask with 20 ml complete RPMI 1640 medium at a concentration of 50000 cells/ml for 4 days in an incubator. Cell medium was replaced after 48 hrs. After 96 hrs of incubation, K562 cells were centrifuged and resuspended in serum free medium at a concentration of 106 cells/ml. 100 micro Liters cells were plated in 96-well plates, preliminary coated with 0.01% poly-L-lysine, and incubated for 2 hrs until the cells attached to the bottom of the wells. Culture medium was aspirated and plates were air-dried opened for at least 12 hrs. Hemoglobin assay was accomplished with 105 cells washed in PBS, lysed in water by freezing and thawing 3 times. 100 micro L cell lysate was submitted to the Benzidine assay.

Nitrobluetetrazolium Test (NBT):

$1 \times 10^6$ cells in 1 ml of cell growth medium were incubated at 37° C. for 30 min in the presence of 0.1% nitroblue tetrazolium chloride (Merck) and 100 ng of phorbol myristate acetate (PMA, Sigma). After incubation, the cells were cytospinned and the slides stained with May-Grunwald-Giemsa stain (Sigma). Cells were scored for the presence of blue-black formazan granules.

Reagents:

Genistein, Sigma Cat. no. G-6649, Phytic acid, Sigma Cat. no. P-3168, SFU, Sigma Cat. no. F-6627, Butyric Acid, Sigma Cat. no. B-5887, NMF, Aldrich Cat. no. 473936, PD 98059, Calbiochem Cat. no. 513000
ChemBridge Corporation—http://www.chembridge.com
DNA constructs—Clontech Cat. no. K 6013-1 (Ras dominant negative vector set)
Polyethylenimine (PEI) Aldrich Cat. no. 40872-7,
3,3',5,5'-tetramethylbenzidine free base Sigma Cat. no. T2885
Gleevec™ Imatinib mesylate, Novartis
All-trans-retinoic acid (ATRA), Sigma Cat. no. R2625
Recombinant human IFN-gamma, Bender MedSystems. Stock solution 100 micro g/ml was prepared in distilled water. Specific activity of IFN-gamma is $2 \times 10_7$ NIH Gg 23-901-530 units/mg.
Hematoxylin Solution Gill No. 3, Surgipath Cat. no. 01540
Azure A, SIGMA, Cat. no. A-6270
Bismark Brown R, SIGMA Cat. no. B-7758
Eosin Yellow certified SIGMA Cat. no. E43 87
Phioxine, Phloxin-B Sigma P403 0
Light Green, SF Yellowish, Merck 1.15941
New Fuchsin (CI-42520; Basic Violet 2), Sigma N-0638
Lab-Tek Chamber slide system-Lab-Tek, Nalge Nunc International, 177402

Cell Lines:

All cell lines were purchased from ATCC and treated according to the ATCC instructions.
CCD-33CO, normal primary colonocytes, MEM Eagle medium:
450 ml MEM Eagle medium, Biological Industries (BI cat. no. 01-040-1A), 5 ml PSA/PS, 5 ml L-Glutamine, 5 ml Na-Pyruvate, 50 ml FCS.
HT-29 human colorectal adenocarcinoma, Mmloy's medium, 1.5 mM glutamine, 450 ml Mmloy's 5a medium, 5 ml PSA/PS, 50 ml FCS.
Rat2, DMEM medium: 450 ml DMEM HG medium (BI cat. no. 01-055-1A), 5 ml 20 PSA/PS, 5 ml L-Glutamine, 50 ml FCS.
K562, chronic myelogenous leukemia (CML), RPMI 1640 medium: 450 ml RPMI 1640 medium (BI cat. no. 01-104-1A), 5 ml PSA/PS, 5 ml L-Glutamine, 50 ml FCS.
HL-60, acute promyelocytic leukemia cells were maintained in Iscove's modified Dulbecco's medium (400 ml Isocove's modified Dulbecco's medium (BI cat. no. 01-058-1A), 5 ml PSA/PS, 4 mM glutamine, 100 ml FCS (20%).
U937, histiocytic lymphoma were maintained in RPMI 1640 supplemented with 10 mM HEPES, 1 mM sodium pyruvate, 2 mM L-glutamine, 4.5 g/L glucose and 10% fetal bovine serum.
MCF-7, adenocarcinoma; mammary gland. Cell line was maintained in DMEM medium.

Staining Solutions and Fixatives:

FIX 2B—8% trichloroacetic acid (TCA), 8% glacial acetic acid (GAA), 4% formaldehyde, 4% Methanol, 30% Ethanol and 46% Ether.
FIX 102B—8% trichloroacetic acid (TCA), 7% methanol, 9% GAA, 7% formaldehyde, and 69% double distilled water.

Dyes:

Hematoxylin Gill (Dye-1)—a ready for use solution of Hematoxylin Gill No. 3.
Azure (Dye-2)—the aniline dye Azure-A was prepared by mixing 0.25 grams of Azure with 50 ml of ethanol and 50 ml of double distilled water.
Bismark Brown Eosine Conjugate (Dye-3)—was prepared by mixing Dye-B and Dye-C. Mixture was boiled for 3 min and allowed to cool to room temperature. Mixture was filtered through filter paper. Filter was left to dry and washed with 250 ml absolute ethanol. Filter was removed and preparation was used.
Bismark Brown Phloxine Conjugate (Dye-4)—was prepared by mixing Dye-A and Dye-B. Mixture was boiled for 20 min, and allowed to cool to room temperature. Mixture was filtered through filter paper. Filter was left to dry and washed with 250 ml absolute ethanol. Filter was removed and preparation was used.

Light Green 4% (Dye-5)—the aniline dye Light Green 4% was used as a general stain in the protocol for histological sections. The aniline dye was prepared by mixing 4 gram Light Green with 70 ml ethanol and 30 ml double distilled water.

Phloxine (Dye-A)—the aniline dye Phloxine was used for staining paraffin-embedded tissue. The aniline dye was prepared by mixing 1.5 grams Phloxine with 200 ml double distilled water and 50 ml of ethanol.

BBr (Dye-B)—The BBr dye was prepared by dissolving 2 grams of Bismark Brown R in 50 ml ethanol and 200 ml double distilled water.

Eosine Yellow (Dye-C)—0.26 grams Eosine Yellow shade were mixed with 15 ml 100% ethanol and 35 ml double distilled water.

New Fuchsin (Dye-6)—0.4% solution was prepared in 33% EtOH

Light Green 4% (Dye-7)—4% solution was prepared in 20% EtOH

New Fuchsin (Dye-8)—0.4% solution was prepared in 33% EtOH

New Fuchsin (Dye-9)—0.5% solution was prepared in 20% EtOH. PH was adjusted to 5.7.

Light Green 4% (Dye-10)—the aniline dye Light Green 4% was used as a general stain in the protocol for histological sections. The aniline dye was prepared by mixing 4 gram Light Green with 100 ml double distilled water.

Experimental Results

This approach has been amended to support in vitro experiments where single fixed cells, rather than tissue samples were involved. A model system representing normal versus malignant tissue was constructed using primary normal colonocytes (CCD-33C0) and human colorectal adenocarcinoma (HT-29). In order to obtain the differential staining in this model system, certain amendments of the staining protocol used for histological samples were required (Protocol II). The resulting staining (FIGS. 20A-C) clearly discriminated between normal (Green, FIG. 20A) and malignant (Red, FIG. 20C) cellular phenotypes. A number of phenotype-related tests have been performed to verify the normal and abnormal phenotypes of these cells. Saturation density of normal cells was much lower than the malignant cells, probably due to the contact inhibition (FIGS. 20A-B and not shown), spreading of normal cells was more prominent compared to the malignant counterpart (FIGS. 20A-B) and in addition to this, the HT-29 possessed profound foci formation capabilities in soft agar (FIG. 21).

Example 7

Use of the Methods and Compounds Described by the Present Invention for Drug Discovery Having developed a staining protocol capable of differentially staining normal and transformed phenotypes, the present inventors demonstrated herein the ability to use this staining method to detect phenotypic changes of malignant cells. A number of chemical compounds were reported in the literature to cause normalization of cellular phenotype and representative different cellular activities/mechanisms were chosen. Examples of these chemicals are Sodium Butyrate [Newmark et al, Cancer Lett (1994) 78: 1-5] and Genistein [Barnes, J Nutr (1995) 125 (3 Suppl):77S-783S 1s].

Sodium Butyrate induces differentiation and normalization of the cellular phenotype by inhibiting activity of histone deacetylase [Parker et al., J Biol Chem (1986) 261: 2786-2790] while Genistein is a potent tyrosine kinase inhibitor [Barnes, J Nutr (1995) 125 (3 Suppl):77S-783S 1s]. As demonstrated herein, native HT-29 cells stained Red, while cells effectively treated with these compounds stained Green/blue but remained viable throughout the experiment (using Protocol II).

In order to facilitate quantification of the extent of color change, and since it is evident that cells contain a mixture of the Red and the Green dye, a measurement representing the ratio of optical density measured at the spectrum of the Red dye ($OD_{Red}$) and the optical density measured at the spectrum of the Green dye ($OD_{Green}$) was developed. This ratio, denoted R, proved to be a simple, useful tool: Malignant cells exhibit R values above or equal to 1, while normal cells exhibit R values below 1.

FIGS. 22A-D and FIGS. 23A-C show the phenotype drug screening result in HT29 (human colon carcinoma cells) treated with increasing concentrations of Sodium Butyrate to induce the malignant cell differentiation. Butyrate treatment resulted in reduction in cell number and morphological changes associated with differentiation and phenotype change. The phenotypic changes were detected by means of gradual, concentration and time-dependent color changes from red (malignant) to blue/green (normal). A similar color-change was obtained after treatment with Genistein (FIG. 24A). Three types of results were presented in FIGS. 24A-C: staining type (FIG. 24A), quantification of the staining results (FIG. 24B) and the effect of the treatment on the cell number (FIG. 24C). As demonstrated in FIGS. 24A-C, as a result of Genistein treatment, there was an evident dose-dependent shift in cellular staining type: from Red-staining to Green/Blue-staining, which could not be explained by the cell number reduction (FIG. 24C).

Example 8

Validation Using Functional Assays

Biochemical validations of cellular phenotype are highly valuable tools, albeit often they suffer from a lack of breadth across different cellular systems and across different differentiation pathways. While Alkaline Phoshphatase is a reasonable marker for Brush Border differentiation of colon cells [Matsumoto et al., Gastroenterology (1990) 98(5 Pt 1):1199-207], it has little value in other cell systems as well as in other differentiation pathways. Similarly, Hemoglobin production, which is a clear characteristic of normal hematopoietic cells [Clarke et al., Blood (1982) 60:346-351; Constantinou and Huberman, Proc Soc Exp Biol Med (1995) 208 (1):109-15] is highly inhibited in malignantly transformed hematopoietic cells. As valuable as this marker is in hematopoietic systems, it has no value as a marker in most other cell systems. Thus, while there is a lack of broad-scoped biochemical markers there are a number of classical approaches that allow for functional assessment of the transformed phenotype. Amongst the most commonly used classical approaches include soft agar, validating the anchorage independent growth of malignant cells, and animal models, assaying the tumor formation potential of malignant cells in immunosuppressed mice [Alberts et al, Molecular Biology of the Cell. 3rd ed. New York and London, c (1994)]. The present inventors used these classical approaches to validate the results reported above. The behavior in soft agar (FIG. 21) and nude mice (FIG. 25) was established by studying the function of cells pre-treated with different compounds. The compounds were classified according to their ability to generate different responses in the staining assay presented above. One group possessed the ability to affect a color change from Red to Green, while the other group did not possess this ability to change the type of staining from Red to Green. It was speculated that some compounds may affect a transient rather than a stable change of phenotype and that this would influence the results obtained in soft agar and in nude mice experiments. The present inventors tested these compounds ability to affect a stable sustainable change of phenotype by treating the cells and observing the cells after retraction of the sodium butyrate treatment (FIGS. 26A-E). In the case of Genistein the normal staining type was present for a long time after retraction of the compound from the cells and this behavior apparently contributed to the normal phenotype observed in soft agar (FIG. 21) and minimal tumorgenicity in the nude mice and even up to 30 days no tumors were detected in these animals (FIG. 25). By contrast, sodium butyrate caused a transient color-change-retraction caused a return of the Red staining within four days (FIGS. 26A-E). As expected, the cells treated with sodium butyrate behaved in a manner consistent with transformed phenotype both in soft agar and in the animal model (FIGS. 21 and 25, respectively). The correlation between these results is summarized in Table 12 below.

TABLE 12

| Treatment | Staining assay | Soft agar (colonies) | Tumorgenicity |
|---|---|---|---|
| Control | Negative (Red) | + | Tumors |
| PA Phytic acid | Negative (Red) | + | Not determined |
| 5FU | Positive (Green) | − | Partial inhibition |
| Genistein | Positive (Green, long duration) | − | No inhibition |
| Sodium Butyrate | Positive (Green, short duration/transient) | + | No inhibition |
| NMV N-methylformamide | Negative (Red) | + | No inhibition |

In summary, as demonstrated herein, while the staining results indicate that the phenotype has been affected, this change may be either transient or terminal. If the change is transient, the functionality of the cells in soft agar or in nude mice, may be somewhat hampered, but eventually the behavior will simulate that of the transformed phenotype.

Example 9

Use of the Methods and Compounds Described by the Present Invention in High Throughput Screening Based on the previous reports, the present inventors generated the conceptual possibility to use this approach as architecture for drug discovery; the industrial testing of large quantities of compounds for desired biological activity. The staining method suggested above allows for the detection of non-cytotoxic compounds, also commonly known as cancer regulating agents. These types of compounds lead to amelioration of the malignant/transformed cellular phenotype.

The practical implementation of this concept was completed using 384-well plates and a liquid handling system in the screening of large chemical collections. In order to deal with the possibility that some of these compounds could be cytotoxic and thus render the measurement of ratio (R) unreliable, the present inventors developed a measurement of the degree of cytotoxicity of the compound.

The use of two dyes within the staining protocol gave a distinct absorbance profile which made it feasible to read at two different wavelengths and use both output results for evaluation. The absorbance of the red dye New Fuchsin (NF) was read at 560 nm and the absorbance of the green dye Light Green (LG) was read at 630 nm. Both were read simultaneously in a spectrophotometer plate reader. The raw data output was automatically transformed and analyzed.

Since both the green and the red dyes contributed to the phenotypic color differentiation, an index of malignancy was created using the ratio of NF/LG. The quotient of 1 was used as the cutoff to distinguish between the malignant phenotype and the normal phenotype. Malignant cells stained red and therefore had an index of malignancy higher than 1. Normal cells or differentiated cells stained green and therefore had a malignancy index of less than 1 (see FIG. 23C).

The number of cells in each well also had significance in the evaluation of the results. In order to eliminate false interpretation, when very low number of cells give background read values, which can be misinterpreted when calculated as the malignancy index, an estimate of the cell number was necessary. Therefore the sum of NF+LG (i.e., $OD_{Red}$+$OD_{green}$) was used as an estimate for cell number in a well and normalized this, using untreated control. This was based on the fact that cells stained either red or green and the sum of both reflected the overall presence of cells in the well. Experiments in which cells in different densities were plated showed linearity of the sum of the dyes at the relevant range (data not shown).

Briefly, a small molecule chemical library (ChemBridge Corporation) was screened at 30 micro molar initial concentration of the compounds. HT-29 cells were plated, treated over 4 days with different compounds and at the end of the process were stained using protocol (II).

An automatic formatted Excel-based analysis tool analyzes the results. A phenotype change hit was pronounced when a compound gave a ratio of NF/LG of less than 1 but had a value of the sum of NF+LG higher than 0.2. A cytotoxic hit was pronounced when the sum of NF+LG was less than 0.2. The hits could be visualized even with a naked eye (FIG. 27A).

The screening of the ChemBridge library, of 55,120 small drug-like molecules, resulted with 248 (0.45%) hit at the primary screen, from which 32 hits (0.06%) were active in the nano-molar concentrations on the HT-29 cell line (FIG. 28). 6 of those compounds were chosen to be further validated. Although this library has been screened numerous times before, these compounds were never detected as anti-cancer leads in other assays. Hits activity was validated by a repeated assay. All hits were positive for the second time. The activity range was tested using a dose response curve using the same calorimetric assay (FIG. 27B).

The results of this screening are plotted in FIG. 28. As the results show, the screen gave rise to three distinct archetypes of responses for a given level of compound concentration: Toxic/static effect, change of phenotype (based on the Red-to-Green color change) and no obvious change of phenotype (Red staining). The subpopulation of compounds capable of affecting a change of color of cells, without inducing a highly toxic response as measured by cell number in the well, is of great interest as potential drug candidates, since the Green-staining has been shown correlated with tumorgenicity of cells. Compounds showing great static/toxic effect should be re-checked at lower concentration in order to determine whether there is a lower concentration at which the phenotype is changed at lower levels of cytotoxicity.

Example 10

Use of the Methods and Compounds of the Present Invention for Target Validation The results above demonstrate the ability of this staining method to determine changes of phenotype that have occurred in malignant cells. In addition, the results have also shown that this method has utility in determining phenotypic changes in normal cells; a highly desirable feature in the field of target validation. This system was constructed on the basis of Rat1 or Rat2 cells. Clones, stably expressing empty expression vector (Vec), wild type of Ras (Ras-vec) and oncogenic form of Ras (Ras-V12) (FIG. 29) were derived and characterized by western blotting (not shown), cytoskeletal organization (not shown) and the behavior in soft agar (according to Table 13 and FIGS. 30A-B). SVT2 cells were used as a positive control for the anchorage-independent growth [Simcha et al., J Cell Biol (1996) 133(1):199-209]. Thus, the previously reported ability of Ras-V12 to transform cells and induce colony formation in soft agar [Egozi et al., Int. J. Cancer (1999) 80:911-918] was confirmed.

TABLE 13

| | Rat2-based cell line | | | | | | | |
|---|---|---|---|---|---|---|---|---|
| | Vec | | Ras Vec | | Ras V12 | | SVT2 | |
| Cell number at plating | 250 | 1000 | 250 | 1000 | 250 | 1000 | 250 | 1000 |
| Number of colonies | 1 | 1 | 17 | 32 | 25 | 72 | 219 | ~800 |
| Size of colonies | Small (S) | | Small (S) | | Large (L) | | | |

The ability of the crude extract to stain Rat1 Ras cells was summarized in Table 14, where staining capacity is directly correlated with the concentration of the extract.

TABLE 14

| 70% EtOH | | 100% Ext | | 50% Ext | | 25% Ext | | 12% Ext | | 6% Ext | |
|---|---|---|---|---|---|---|---|---|---|---|---|
| 0.876 | 0.914 | 0.117 | 0.126 | 0.141 | 0.135 | 0.285 | 0.248 | 0.395 | 0.402 | 0.637 | |
| 0.861 | 1.017 | 0.114 | 0.133 | 0.180 | 0.185 | 0.365 | 0.286 | 0.517 | 0.479 | 0.671 | |
| 0.867 | 1.090 | 0.135 | 0.181 | 0.193 | 0.158 | 0.309 | 0.340 | 0.555 | 0.535 | 0.742 | |
| 0.848 | 1.081 | 0.126 | 0.140 | 0.155 | 0.159 | 0.282 | 0.272 | 0.514 | 0.589 | 0.681 | |
| 0.852 | 1.075 | 0.148 | 0.136 | 0.185 | 0.167 | 0.319 | 0.298 | 0.505 | 0.526 | 0.764 | |
| 0.870 | 1.075 | 0.141 | 0.177 | 0.182 | 0.188 | 0.296 | 0.333 | 0.556 | 0.478 | 0.754 | |
| 0.879 | 0.975 | 0.142 | 0.140 | 0.177 | 0.164 | 0.310 | 0.350 | 0.467 | 0.510 | 0.722 | |
| 0.840 | 0.852 | 0.130 | 0.142 | 0.141 | 0.125 | 0.247 | 0.291 | 0.372 | 0.412 | 0.510 | |
| 0.862 | 1.010 | 0.132 | 0.147 | 0.169 | 0.160 | 0.302 | 0.302 | 0.485 | 0.491 | 0.685 | Result |

Example 11

Use of the Methods and Compounds Described by the Present Invention in Development of Full Pathway Drug Discovery Systems The present inventors used the set of clones created to validate staining using protocol (IV). Expectedly, phenotypically normal cells appeared to be green (FIGS. 31A-B, Rat2) and phenotypically malignant/transformed cells appeared to be red (FIGS. 31C-D, Rat2 Ras-V12).

One of the best-elucidated signal transduction pathways is the one initiated by Ras, in which MAPKK plays a focal role. It has been reported [Duesbery et al., PNAS (2001) 98(7): 4089-4094] possible to stop Ras-induced transformation by preventing MAPKK activity. PD98059 is a potent chemical inhibitor possessing this activity. It was expected, based on previous reports [Duesbery et al., PNAS (2001) 98(7):4089-4094], that incubation of Ras-V12 cells with PD98059 would change the malignant phenotype to a normal cell phenotype. As shown in FIGS. 32A-D, the red staining of malignant/transformed cells (FIGS. 32A-B) was replaced by green staining in normalized cells (FIGS. 32C-D).

Other signaling pathways may involve Ras, therefore, signal transduction pathway sensitivity of phenotype drug screening was evaluated in Rat1-Ras system. Chemical interventions into the signaling pathway by farnesylation inhibitor (HR12, FIG. 33B) or by MAPK inhibitor (PD98059, FIGS. 33A and 33C) resulted in gradual dose-dependent changes of the phenotype from malignant to normal. A unique feature of the present invention is that no prior knowledge about the oncogenic target signaling is required for the drug screening, opposed to the standard practice. The inability of Genistein (tyrosine phosphorylation inhibitor, FIG. 33D) or LY294002 (PI3 kinase inhibitor, FIG. 33E) to change the type of staining clearly support this.

Using this model system, the present inventors have shown that an engineered cell-line, created by the malignant transformation of normal cells by transfection with an oncogene, may be used as a platform for drug discovery, since the transformation is reversible by a chemical compound.

Example 12

Use of the Methods and Compounds Described by the Present Invention in Development of Additional Systems In order to assess the utility of the drug discovery approach reported above, existing drugs and compounds with known abilities to affect cancer regulatory responses were tested. For validation purposes, cell systems for which biochemical markers or differentiation were available were used.

The present inventors established a model system for Chronic Myelogenous Leukemia (CML) based on K562 erythroleukemic cells. The advantage of this system is that Erythroid cell differentiation can be confirmed relatively easily by measuring the levels of hemoglobin synthesis (Benzidine staining method). As was previously described [Sutherland et al., J Biological Response Modifiers (1986) 5, 250-262], erythroid differentiation of K562 cells was induced by sodium butyrate (not shown), DMSO (not shown) and Gleevec™ (FIGS. 34A-C and FIGS. 35A-B). All of these differentiation inducers caused an evident change of staining phenotype, from Red to Blue/Green as was shown by Gleevec™ (FIGS. 34A-B and FIG. 35B).

ST1571 (Gleevec™, imatinib mesylate) is an example of a successful drug indicated for the treatment of CML. In the case of CML, disease progression is caused by accumulation of molecular abnormalities, which lead to a progressive loss of the capacity for terminal differentiation of the leukemic clone. Gleevec™ targets the kinase activity of Bcr-Abl and thus triggers terminal differentiation in CML and induces strong hematological and cytogenetic response in the clinic [Drucker, Trends in Molecular Medicine (2002) Vol. 8, No. 4 (Suppl.), S 14-S18].

Correlative studies on Gleevec™ effect on cell number and hemoglobin production were performed (FIGS. 34C and 35A). The detection level of K562 cell staining was found to be very sensitive and was able to detect the desired Gleevec activity at 30 nM concentration (FIG. 35B). At this concentration neither cell number nor hemoglobin production has yet been affected (FIG. 35A).

Two additional leukemia systems were established: HL-60 (human acute myeloid leukemia cell line) and U937 (monocytic leukemia/histiocytic lymphoma cell line). HL-60 cells exhibited strong Red-to-Green color change (FIGS. 36A-B) as a result of differentiation induced by ATRA, all-trans-retinoic acid [Alison et al., The Cancer Handbook. Nature publishing group (2002) Chapter 89, "Differentiation Therapy"]. U937 cells were treated with sodium butyrate (FIGS. 38C-D) or IFN-gamma to induce differentiation (FIGS. 37B-C and FIGS. 38E-H). Nitroblue Tetrazolium reduction (NBT) test was used as a biochemical marker indicative of the status of differentiation of these cells (FIGS. 37A-C). Treatment with increasing concentrations of IFN-gamma resulted in increased number of biochemically positive cells which is highly correlated with a shift in the color of cells from the malignant Red to the Normal Green (FIGS. 38A-B and FIGS. 38E-H). Similar results were obtained with sodium butyrate (FIGS. 38A-D).

Another system was established wherein HPV16 immortalized human keratinocytes were treated by different inhibitors (originated from the works of Dr. A Levitzki, Hebrew University, Jerusalem, Israel). FIG. 39 shows the lead optimization potential of phenotype drug screening approach. This experiment has shown the effect of different chemical scaffold changes on cellular phenotype which was visualized by the staining procedure of this invention. Note that AG555 does not work; however the chemical modification of the AG555 motif resulted in partial activity in AG494.

The present inventors have laid the foundations for a highly reliable and effective way of measuring the phenotype of cells. This method has been reduced to practice to applications such as drug discovery, target validation and diagnostics. Various systems have been developed covering both carcinomas and other tumors, and the results have been validated using various accepted methods and markers. The drug discovery platform has generic properties as it works not only with chemical compounds, but also with proteins ligands. The present inventors have shown that the system is readily used for target validation of oncogenes and have also been able to use it to for the screening of sense and anti-sense constructs (not shown). Testing of tumor suppressor genes has been trivial, simply starting the system with malignant cells and transfecting them with a tumor suppressor gene (not shown). The method suggested requires a quick adjustment to different cell systems, taking particular traits of the system into account in order to obtain optimal results. The generic nature of the method is partly connected with the fact that the staining is performed after treatment, wherefore the efficacy, not the nature, of the treatment administered to the cells is of importance.

Example 13

Purification of a New Staining Compound (CST 2001) from Plant Crude Extract Capable of Distinguishing Between Malignant and Non-Malignant Cells Materials and Experimental Procedures All of the procedures, protocols, cell lines, assays, reagents, staining solutions and fixatives for Examples 13 through Example 17 are as described in the materials and experimental procedures section for Examples 6 through Example 12 hereinabove.

Purification of CST-2001

1. Crude Ethanol Extract (50 ml) was prepared strongly basic (pH 12.0) with 1N NaOH, mixed and kept for 1 hr at 4° C.
2. Centrifuged at 4000 rpm for 15 min.
3. Washed once with 10 ml 70% ethanol, pH 12.
4. Pellet was centrifuged at 4000 rpm for 15 min.
5. Pellet was suspended in 20 ml distilled water.
6. Pellet was centrifuged at 4000 rpm for 15 min.
7. Pellet was suspended in 10 ml distilled water.
8. 1N HCl was added until pH reached 2.0 and suspension was kept for 1 hr at 4° C.
9. Pellet was collected by centrifugation at 4000 rpm for 15 min.
10. Pellet was dissolved in 10 ml 70% ethanol.
11. pH was adjusted to 6.2 with 1N NaOH.
12. Highly enriched extract was stored at room temperature in a dark bottle.
13. 10 ml of highly enriched extract was added to 5 ml of Chelating Sepharose Fast Flow (Pharmacia Biotech) and mixed.
14. Chelating Sepharose gel was sedimented by centrifugation at 500×g for 10 min.
15. Supernatant were carefully decanted (contained the active material).
16. Steps 1-3 were repeated two more times.
17. The supernatant (denoted as CST 2001) was used for analysis, e.g., fluorescence spectra, NMR and MS.

Experimental Results

Plant Extract:

The staining methods presented above involve the use of a plant extract, which empirically has been shown important for the phenotype-specific color discrimination of malignant versus non-malignant cells. The present inventors have successfully identified a composition which enables the same activity as the crude extract.

The starting point in this process is the crude extract preparation.

1. Crude Extract:

Leaves (*Ficus Elastica*) that were optimal for the process must have weight 15 to 25 grams and their length must have been 18 to 30 centimeter, as measured from the base of the leaf until the edge. 600 grams of leaves were cut into 1-2 cm pieces. The cut leaves were mixed with 1.5 liter 70% EtOH and kept for 10 days (at room temperature) in a sealed container. Thereafter, the liquid was separated from the solids and kept for further use at room temperature. Each batch required batch-optimization to determine the optimal working concentration. The batch-optimization procedure used pairs of cells (normal versus malignant cells, non-treated versus treated cells, normal versus oncogene transfected cells, malignant versus tumor suppressor gene transfected cells, etc.). The aim of the procedure was to maximize the ratio of $R_{malignant}/R_{normal}$ using a dilution curve changing the concentration of the working solution by adding 70% EtOH to the crude extract.

Alternatively, crude extracts have been prepared by the following protocol: Leaves (100 g) were extracted for 6 days at room temperature with 200 ml 90% (v/v) aqueous acetonitrile. Then acetonitrile was removed by rotary evaporation. After filtering (0.4 mm S&S) the aqueous fraction was reduced in volume in a rotary evaporator at 35° C. under reduced pressure. The remaining aqueous fraction—10 ml, was fractionated with size exclusion chromatography using Sephadex LH-20 (Pharmacia, Sweden).

II Purification and Properties of the Active Fraction CST-2001:

A multi-step purification protocol was designed to get an active fraction that exhibits similar activity to that of the crude extract. In order to make the process of assaying easier, a one-dye rapid assay (LG rapid assay, protocol VIII as detailed in the materials and experimental procedures section) was developed. The rapid assay tests the extract's ability to reduce staining by LG (FIG. 40) and many other dyes (not shown). The extent of inhibitory activity was measured using OD 630 nm of LG (FIG. 40).

CST-2001 was purified from the crude extract in accordance with the purification scheme as detailed in the materials and experimental procedures section. The presence of 2.5 micro mol $Mg^{2+}$ and/or $Ca^{2+}$ was found to be critical for the functional activity of CST-2001 in the one-dye rapid assay (protocol VIII).

CST-2001 was submitted to intensive chemical and functional validations, including fluorescence fingerprinting, elementary analysis and chemical structure information was collected in the process of structure elucidation.

Sephadex LH-20 Chromatography:

Crude Extract (2 ml in water) was applied to a 1.5×8 cm column of Sephadex LH-20 previously equilibrated with water. Then consecutive elution with 2×4 ml of 20%, 30%, 40%, 50%, 60%, 70% and 80% (v/v) methanol:water and then with 2×4 ml of 20%, 40%, 60% and 80% (v/v) acetone:water was performed. The resulting fractions were checked for their ability to inhibit LG and on the content of proanthocyanidins (FIG. 41). For these purposes, 200 ml of each fraction was evaporated and re-dissolved in 100 ml of 70% ethanol.

Acid Butanol Assay for Proanthocyanidins:

50 µl of the sample (chromatographic fraction in 70% ethanol), 300 µl of acid butanol (butanol:conc.HCl 95:5, v/v) and 10 µl of iron reagent (0.04 M $FeNH_4(SO_4)_2$ in 2N HCl) were mixed and incubated at 95° C. for 50 min, after cooling the absorbance at 540 nm was determined (FIG. 41).

Oligomeric and Polymeric Proanthocyanidins:

Oligomeric and polymeric proanthocyanidins (FIG. 41) were pooled, solvents evaporated in a rotary evaporator and the aqueous solution freeze-dried. The yield of the proanthocyanidins was 130 mg "Oligomer" and 83 mg of "Polymer" per 100 g of *ficus* leaves.

Fluorescence Spectra of CST 2001:

Fluorescence spectra investigation of CST 2001 was performed on a Perkin-Elmer Fluorometer LS50b. The spectra showed one peak, upon excitation at 375 nm and emission at 430 nm in acetic acid (FIG. 42). Upon testing, this fluorescent fingerprint was present in the different stages of CST 2001 purification.

HPLC of Oligomeric Proanthocyanidins:

Oligomeric proanthocyanidins were separated by HPLC method. Absorbance spectra were recorded for all peaks. Lichrosorb Si-60 250-4 (Merck) column was used.

Solvent System:

A - dichloromethane + 4% of 50%-aqueous acetic acid,
B - methanol + 4% of 50%-aqueous acetic acid,
All solvents were HPLC grade.
Gradient:

|  |  |  |  |
|---|---|---|---|
| 0 min | Flow: 0.8 ml/min | A %: 100 | B %: 0, |
| 10 min | Flow: 0.8 ml/min | A %: 70 | B %: 30, |
| 20 min | Flow: 0.8 ml/min | A %: 50 | B %: 50, |
| 25 min | Flow: 0.8 ml/min | A %: 14 | B %: 86, |
| 30 min | Flow: 0.8 ml/min | A %: 70 | B %: 0, |
| 34.8 min | Flow: 0.8 ml/min | A %: 70 | B %: 0, |
| 34.9 min | Flow: 0.1 ml/min | A %: 70 | B %: 0. |

Detection: Diode array 220-600 nm; 800 ms; 6 nm.

NMR and CST-2001 Structure Elucidation:

Additional information, describing the chemical properties and fingerprint of the CST 2001 was obtained by NMR (FIG. 43) and by NMR-$^1$H (FIG. 44). Purified proanthocyanidins were characterized by UV spectra (1 max=280 nm) and 13C NMR spectra. $^{13}$C NMR spectra confirmed that oligomeric and polymeric compounds were comprised of proanthocyanidins (condensed tannins). Two oligomeric forms are presented (FIG. 45 and FIG. 46). According to the NMR spectra analysis, CST 2001 was a derivative of the stearic acid, MW=384. The results of the NMR spectra analysis showed: $CH_3$—0.91 ppm; alpha-$CH_2$—2.39 ppm; beta-$CH_2$—1.65 ppm; $(CH_2)_{14}$—1.32 ppm; $CH_2$—dq, 3.75 ppm; CH—m, 4.06 ppm; and $CH_2$, CH=CH—4.2 ppm The proposed chemical formula of CST 2001 was $C_{23}H_{44}O_4$.

Example 14

Differential Interaction of Crude Plant Extract with Malignant and Normalized Cells The presence of a fluorescence signal in CST-2001 as well as in the crude extract, enabled the detection of this signal in cells that had been treated with the extract or with CST-2001 for traits of differential intracellular distribution. Observing post-incubational fluorescence, the present inventors found that the crude plant extract tends to interact differently with phenotypically normal or malignant cells. To ensure that the detected signal in fact originated in the extract and did not arise from any other involved component of the experiment, levels of background fluorescence of naive non-treated cells were tested. An example of fluorescent signal which originated from crude extract is shown in FIGS. 47A-C (according to Protocol IX). In this experiment human colorectal adenocarcinoma cells (HT-29, FIG. 47A) were treated with sodium butyrate in order to induce differentiation and phenotype normalization (FIG. 47B). Additionally, primary colonocytes (CCD-33C0) were tested as a normal control (FIG. 47C). A striking difference in the intensity of nuclear staining was observed (arrowheads).

Example 15

Differential Interactions of Enriched CST-2001 with Malignant and Normalized Cells While the phenotype-specific distribution of fluorescence in the nuclear compartment was the same for CST-2001 enriched with $Mg^{+2}$ or $Ca^{+2}$ (enriched CST-2001) and for the crude extract, the contrast and the intensity of the signal as well as the signal-to-background ratio were dramatically improved using the enriched CST-2001 rather than the crude extract. Using previously described protocol (IX), the present inventors again observed that the nuclei of the transformed or malignant cells were considerably less fluorescent than their respective normal or treated counterparts.

In order to address the breadth of the phenomenon, a large number of cell models using sets of malignant cells, normal cells and cells that had been normalized using sodium butyrate or ATRA (all-trans-retinoic acid) were established. These models included: Human breast carcinoma MCF-7 (FIGS. 48A-F), human colon carcinoma HT-29 (FIGS. 49A-B), normal human colonocytes (FIG. 47C and FIG. 49C), human leukemia K562 (FIGS. 50A-B), human leukemic HL-60 cell line (FIGS. 51A-B), human leukemic U937 cell-line (not shown), and the oncogene target-driven experimental system based on Rat1 fibroblasts and Ha-Ras V12-transformed Rat1 (Rat1-Ras) cells (FIGS. 52A-B). In the later system, the present inventors also tested the effect of treating the Rat1-Ras cells with PD98059, a MAPKK specific inhibitor, blocking the malignant transformation initiated by Ras V12 (FIG. 52C). In all cases, the air-fixed cells were incubated with either enriched CST-2001 or 70% ethanol as a solvent control (Protocol IX).

Following the treatment with enriched CST-2001, the CST-2001-originated fluorescence has been partitioned in different ways within the cytoplasm and nucleus of the cell. Localization of the fluorescent signal in malignant cells essentially differed from normal or reversion agent treated cells. In all studied phenotypically malignant cells the fluorescence was very weak in the nucleus (−), in comparison with phenotypically normal cells in which strong fluorescence of nucleus was observed (+). The results are summarized in Table 15 below.

TABLE 15

| Tissue | Cell Line | Treatment | Phenotype | CST-2001 in the nucleus |
|---|---|---|---|---|
| Breast | MCF | No treatment | Malignant | − |
| Breast | MCF | Butyrate | Normal | + |
| Colon | Primary CCD33Co | No treatment | Normal | + |
| Colon | HT29 | No treatment | Malignant | |
| Colon | HT29 | Butyrate | Normal | + |
| Fibroblast | Rat 1 | No treatment | Normal | + |
| Fibroblast | Rat1 Ras | No treatment | Malignant | |
| Fibroblast | Rat1 Ras | PD98058 | Normal | + |
| Blood | K562 | No treatment | Malignant | |
| Blood | K562 | Butyrate | Normal | + |
| Blood | HL60 | No treatment | Malignant | |
| Blood | HL60 | Butyrate | Normal | + |
| Blood | U937 | No treatment | Malignant | − |
| Blood | U937 | Butyrate | Normal | + |
| Blood | U937 | ATRA | Normal | + |

Example 16

Differential Interaction of CST-2001 with Living Cells

To demonstrate an ability of CST 2001 to discriminate between two phenotypes, U937 leukemia cells were incubated with 1.5 µM of ATRA for 72 h to induce phenotype normalization. At the end of the treatment, CST 2001 was added into the medium and incubated with ATRA-treated and solvent-treated U937 cells for 2 hours. The CST 2001-originated fluorescence was detected and the intensity level differentiated between the two phenotypes (by two folds, FIGS. 53A-B).

The autofluorescence of native CST 2001 was very weak, therefore a number of attempts were made to increase it by different modulations as described in the flow chart in FIG. 54: biotinylation [as described by Wilchek et al., Biochem. Biophys. Res. Comm. (1986) 138:872-879] and complex formation [as described by Karabourniotis et al., American Journal of Botany (1998) 85(7):1007). Biotinylation resulted in 10 folds increase in the specific signal detected by streptavidin-Cy3. FIGS. 55A-B illustrates the difference in signal intensity between native and biotinylated CST 2001.

Complex formation with diphenylboric acid-ethanolamine, Naturstoff reagent based on the work of Karabourniotis [Karabourniotis et al., Amer J of Bot (1998) 85(7):1007-1012] resulted in a strong fluorescence increase (26 folds) as was measured by FACS (FIGS. 56A-C).

CST 2001 was capable of forming complexes with proteins. Such complexation induced protein precipitation which was detected by radial diffusion assay. Briefly, BSA-containing agarose gel was loaded with decreasing concentrations of extract. BSA precipitated rings were visible (FIG. 57) indicating the dose-dependent precipitation process. This CST 2001 ability was successfully exploited for U937 cell visualization with biotinylated BSA (FIGS. 58A-C).

Three non-limiting examples of CST 2001-based staining of living cells were presented: MCF-7 untreated and treated cells (FIGS. 59A-B), Rat2 normal cells versus Rat2 Ras V12 malignant cells (FIGS. 60A-B) and placenta-originated cells (choriocarcinoma, FIGS. 61A-C).

Example 17

Differential Interactions of CST-2001 with Diabetic Versus Normal Gerbil Kidneys The Diabetes model has been established at the Diabetes Research Unit Hadassah University Hospital, Jerusalem, Israel (Kalman et al).

FIGS. 62A-D show histology section staining prepared from a diabetes type II-induced animal model. Sections of kidneys from normal (FIGS. 62A and 62C) and diabetic (FIGS. 62B and 62D) gerbils following CAMA staining are shown. High magnification images (lower panels) focus on glomerulus structures, and accentuate the green staining associated with diabetic tissue, visualized by this protocol. The experiment shows differential staining of normal and diabetic tissue with CST-2001.

It will be appreciated by a person skilled in the art that the present invention is not limited by what has been particularly shown and described hereinabove. Rather, the scope of the invention is defined by the claims section which follows.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications and GenBank Accession numbers mentioned in this specification are herein incorporated in their entirety by reference into the specification, to the same extent as if each individual publication, patent or patent application or GenBank Accession number was specifically and individually indicated to be incorporated herein by reference. In addition, citation or identification of any reference in this application shall not be construed as an admission that such reference is available as prior art to the present invention.

What is claimed is:

1. A method of staining or pre-staining a plurality of cells, the method comprising:
   (a) fixing the plurality of cells with a fixative to thereby obtain a plurality of fixed cells;
   (b) contacting the plurality of fixed cells with a staining agent consisting of an extract of a *Ficus elastica* plant, thereby staining or pre-staining the plurality of cells; and
   (c) contacting said plurality of fixed cells with at least one dye, wherein when:
      (i) said at least one dye is an acidic dye a staining intensity above a predetermined threshold is indicative of differentiated cells;
      (ii) said at least one dye is a basic dye a staining intensity above a predetermined threshold is indicative of undifferentiated cells;
      (iii) said at least one dye comprises said acidic dye and said basic dye a staining intensity above a predetermined threshold with said acidic dye is indicative of differentiated cells and a staining intensity above a predetermined threshold with said basic dye is indicative of undifferentiated cells.

2. The method of claim 1, wherein said plurality of cells comprises a heterogeneously differentiated population of cells.

3. The method of claim 1, wherein said at least one dye is a single dye.

4. The method of claim 2, wherein said heterogeneously differentiated population of cells comprises a solid tissue section.

5. The method of claim 2, wherein said heterogeneously differentiated population of cells comprises isolated cells.

6. The method of claim 2, wherein said heterogeneously differentiated population of cells comprises malignant or pre-malignant cells.

7. The method of claim 2, wherein said heterogeneously differentiated population of cells comprises fetal cells.

8. The method of claim 2, wherein said heterogeneously differentiated population of cells comprises metabolically impaired cells.

9. The method of claim 1, wherein said extract of *Ficus elastica* plant comprises a leaf extract.

10. The method of claim 1, wherein said extract of *Ficus elastica* plant comprises an ethanol extract.

11. The method of claim 1, wherein said extract of *Ficus elastica* plant comprises NMR spectra as detailed in FIGS. 43-44.

12. The method of claim 1, wherein said staining agent is fluorescent.

13. The method of claim 1, wherein said ethanol extract of *Ficus elastica* plant is supplemented with positively charged ions.

14. The method of claim 1, wherein said at least one dye comprises two dyes.

15. The method of claim 1, wherein said at least one dye is selected from the group consisting of a basic dye, an acidic dye, a triamnotriphenylmethane derivative, a diazo derivative and a combination of same.

16. The method of claim 14 wherein staining with said two dyes is effected sequentially.

17. The method of claim 15, wherein said basic dye is selected from the group consisting of Dahlia and new Fuchsin.

18. The method of claim 17, wherein said acidic dye is Light Green.

19. A method of staining or pre-staining a plurality of cells, the method comprising contacting the plurality of cells with an ethanol extract of a *Ficus elastica* plant, thereby staining or pre-staining the plurality of cells.

20. A method of staining a plurality of cells, the method comprising:
   (a) staining or pre-staining a plurality of cells according to the method of claim 19; and
   (b) contacting said pre-stained plurality of cells with at least one dye.

21. The method of claim 20, wherein when:
   (i) said at least one dye is an acidic dye a staining intensity above a predetermined threshold is indicative of differentiated cells;
   (ii) said at least one dye is a basic dye a staining intensity above a predetermined threshold is indicative of undifferentiated cells;
   (iii) said at least one dye comprises said acidic dye and said basic dye a staining intensity above a predetermined threshold with said acidic dye is indicative of differentiated cells and a staining intensity above a predetermined threshold with said basic dye is indicative of undifferentiated cells.

22. The method of claim 19, wherein said extract of *Ficus elastica* plant comprises a leaf extract.

23. A method of staining a plurality of cells, the method comprising:
   (a) contacting the plurality of cells with a staining agent consisting of an extract of a *Ficus elastica* plant, so as to obtain a pre-stained cell or cells; and
   (b) contacting said pre-stained cell or cells with at least one dye selected from the group consisting of a basic dye, an acidic dye, a triamnotriphenylmethane derivative, a diazo derivative and a combination of same,
   thereby staining the plurality of cells.

24. The method of claim 23, wherein when
   (i) said at least one dye is an acidic dye a staining intensity above a predetermined threshold is indicative of differentiated cells;
   (ii) said at least one dye is a basic dye a staining intensity above a predetermined threshold is indicative of undifferentiated cells;
   (iii) said at least one dye comprises said acidic dye and said basic dye a staining intensity above a predetermined threshold with said acidic dye is indicative of differentiated cells and a staining intensity above a predetermined threshold with said basic dye is indicative of undifferentiated cells.

25. The method of claim 23, wherein said extract of *Ficus elastica* plant comprises a leaf extract.

26. The method of claim 23, wherein said extract of *Ficus elastica* plant comprises an ethanol extract.